US010435462B2

(12) United States Patent
Bucher et al.

(10) Patent No.: US 10,435,462 B2
(45) Date of Patent: Oct. 8, 2019

(54) HYBRID INFLUENZA SEED VIRUSES, COMPOSITIONS THEREOF, AND USE THEREOF IN THE DIAGNOSIS OR THERAPY OF INFLUENZA

(71) Applicant: VIRO DYNAMICS CORPORATION, Hawthorne, NY (US)

(72) Inventors: Doris Bucher, Hawthorne, NY (US); Yu He, Malden, MA (US); Jianhua Le, Pleasantville, NY (US); Manojkumar Ramanunninair, Ossining, NY (US)

(73) Assignee: VIRO DYNAMICS CORPORATION, Hawthorne, NY (US)

( * ) Notice: Subject to any disclaimer, the term of this patent is extended or adjusted under 35 U.S.C. 154(b) by 263 days.

(21) Appl. No.: 15/085,343

(22) Filed: Mar. 30, 2016

(65) Prior Publication Data

US 2016/0289304 A1   Oct. 6, 2016

Related U.S. Application Data

(60) Provisional application No. 62/141,027, filed on Mar. 31, 2015.

(51) Int. Cl.
*C12N 7/00* (2006.01)
*C07K 16/10* (2006.01)

(52) U.S. Cl.
CPC ............ *C07K 16/1018* (2013.01); *C12N 7/00* (2013.01); *C07K 2317/52* (2013.01); *C07K 2317/55* (2013.01); *C07K 2317/56* (2013.01); *C07K 2317/565* (2013.01); *C07K 2317/76* (2013.01); *C07K 2317/92* (2013.01); *C12N 2760/16121* (2013.01); *C12N 2760/16134* (2013.01); *C12N 2760/16151* (2013.01)

(58) Field of Classification Search
None
See application file for complete search history.

(56) References Cited

PUBLICATIONS

Hung et al., Convalescent Plasma Treatment Reduced Mortality in Patients With Severe Pandemic Influenza A (H1N1) 2009 Virus Infection, 2011, CID, pp. 1-10.*
Kim et al., Preliminary Study about Sublingual Administration of Bacteriaexpressed Pandemic H1N1 Influenza Vaccine in Miniature Pigs, 2014, Journal of Microbiology, vol. 52, No. 9, pp. 794-800.*
ATCC Deposit, Viro Dynamics Corp, Received: Feb. 24, 2016, Strain: PR8-HA-39-3F2-2A6.
ATCC Deposit, Viro Dynamics Corp, Received: Feb. 24, 2016, Strain: PR8-HA-39-4D12-2D11.
ATCC Deposit, Viro Dynamics Corp, Received: Feb. 24, 2016, Strain: PR8-HA-56-2G9-1B3.

* cited by examiner

*Primary Examiner* — Benjamin P Blumel
(74) *Attorney, Agent, or Firm* — Millen, White, Zelano & Branigan, PC

(57) ABSTRACT

The invention provides antibody reagents for screening for seed viruses, in particular, antibodies that bind to one or more discontinuous epitopes in hemagglutinin (HA) polypeptide of human influenza virus (H1N1 strain). Additionally, the invention relates to compositions, kits, supports, and biologicals comprising the antibodies or fragments thereof. Also provided are nucleic acids encoding such antibodies or fragments, including, cells and/or hybridomas which generate such molecules. Additional embodiments relate to the immunogens useful in generating the antibodies, including nucleic acids encoding such immunogens, and compositions comprising such immunogens. Further embodiments relate to methods for screening for seed viruses, including human influenza type A virus seed viruses, using the antibodies or fragments thereof. Embodiments of the invention also provide for the prevention, reduction of incidence of, or therapy of subjects having influenza, via administration of the seed viruses, or vaccines and/or pharmaceutical compositions containing the seed viruses.

4 Claims, 16 Drawing Sheets
(16 of 16 Drawing Sheet(s) Filed in Color)
Specification includes a Sequence Listing.

```
MKANLLVLLCALAAADADTICIGYHANNSTDTVDTVLEKNVTVTHSVNLLEDSHNGKLCRLKGIA
PLQLGKCNIAGWLLGNPECDPLLPVRSWSYIVETPNSENGICYPGDFIDYEELREQLSSVSSFER
FEIFPKESSWPNHNTNGVTAACSHEGKSSFYRNLLWLTEKEGSYPNLKNSYVNKKGKEVLVLWGI
HHPSNSKEQQNLYQNENAYVSVVTSNYNRRFTPEIAERPKVRDQAGRMNYYWTLLKPGDTIIFEA
NGNLIAPMYAFALSRGFGSGIITSNASMHECNTKCQTPLGAINSSLPYQNIHPVTIGECPKYVRS
AKLRMVTGLRNIPSIQSRGLFGAIAGFIEGGWTGMIDGWYGYHHQNEQGSGYAADQKSTQNAING
ITNKVNTVIEKMNIQFTAVGKEFNKLEKRMENLNKKVDDGFLDIWTYNAELLVLLENERTLDFHD
SNVKNLYEKVKSQLKNNAKEIGNGCFEFYHKCDNECMESVRNGTYDYPKYSEESKLNREKVDGVK
LESMGIYQILAIYSTVASSLVLLVSLGAISFWMCSNGSLQCRICI
```

FIG. 18

```
MNPNQKIITIGSICLVVGLISLILQIGNIISIWISHSIQTGSQNHTGICNQNIITYKNSTWVKDT
TSVILTGNSSLCPIRGWAIYSKDNSIRIGSKGDVFVIREPFISCSHLECRTFFLTQGALLNDKHS
NGTVKDRSPYRALMSCPVGEAPSPYNSRFESVAWSASACHDGMGWLTIGISGPDNGAVAVLKYNG
IITETIKSWRKKILRTQESECACVNGSCFTIMTDGPSDGLASYKIFKIEKGKVTKSIELNAPNSH
YEECSCYPDTGKVMCVCRDNWHGSNRPWVSFDQNLDYQIGYICSGVFGDNPRPEDGTGSCGPVYV
DGANGVKGFSYRYGNGVWIGRTKSHSSRHGFEMIWDPNGWTETDSKFSVRQDVVAMTDWSGYSGS
FVQHPELTGLDCMRPCFWVELIRGRPKEKTIWTSASSISFCGVNSDTVDWSWPDGAELPFSIDK
```

FIG. 19

```
001 MKANLLVLLC ALAAADADTI CIGYHANNST DTVDTVLEKN VTVTHSVNLL EDSHNGKLCR
061 LKGIAPLQLG KCNIAGWLLG NPECDPLLPV RSWSYIVETP NSENGICYPG DFIDYEELRE
121 QLSSVSSFER FEIFPKESSW PNHNTNGVTA ACSHEGK░░░░░░░░░░░░░SYPNLKNS
181 ░░░░░░░░░PSN SKEQQNL░░░░░░░░░░NRRFTPEI AERPKVRDQA
241 GRMNYYWTLL KP░░░░░░░░░░░MYA FALSRGFGSG IITSNASMHE CNTKCQTPLG
301 AINSSLPYQN IHPVTIGECP KYVRSAKLRM VTGLRNIPSI QSRGLFGAIA GFIEGGWTGM
361 IDGWYGYHHQ NEQGSGYAAD QKSTQNAING ITNKVNTVIE KMNIQFTAVG KEFNKLEKRM
421 ENLNKKVDDG FLDIWTYNAE LLVLLENERT LDFHDSNVKN LYEKVKSQLK NNAKEIGNGC
481 FEFYHKCDNE CMESVRNGTY DYPKYSEESK LNREKVDGVK LESMGIYQIL AIYSTVASSL
541 VLLVSLGAIS FWMCSNGSLQ CRICI
```

FIG. 20

Antibody 39-3F2-2A6

Color code: Leader sequence-FR1-CDR1-FR2-CDR2-FR3-CDR3-FR4

Heavy chain: DNA sequence (408 bp)

ATGAACTTCGGGCTCAGATTGATTTTCCTTGTCCTTACTTTAAAAGGTGTCCAGTGTGACGTGAAGC
TGGTGGAGTCTGGGGGAGGCTTAGTGAAGCCTGGAGGGTCCCTGAAACTCTCCTGTGCAGCCTCTGG
ATTCACTTTCAGTAGCTATACCATGTCTTGGGTTCGCCAGACTCCGGAGAAGAGGCTGGAGTGGGTC
GCAACCATTAGTAGTGGTGGTATTTACACCTACTATCCAGACAGTGTGAAGGGCCGATTCACCATCT
CCAGAGACAATGCCAAGAACACCCTGTACCTGCAAATGAACAGTCTGAAGTCTGAGGACACAGCCAT
GTATTACTGTGTAAGATCTACGTCGTACTACTTTGACTACTGGGGCCAAGGCACCACTCTCACAGTC
TCCTCA

Heavy chain: Amino acids sequence (136 AA)

MNFGLRLIFLVLTLKGVQCDVKLVESGGGLVKPGGSLKLSCAASGFTFSSYTMSWVRQTPEKRLEWV
ATISSGGIYTYYPDSVKGRFTISRDNAKNTLYLQMNSLKSEDTAMYYCVRSTSYYFDYWGQGTTLTV
SS

Light chain: DNA sequence (399 bp)

ATGGAATCACAGACTCAGGTCCTCATGTCCCTGCTGTTCTGGGTATCTGGTACCTGTGGGGACATTG
TGATGACACAGTCTCCATCCTCCCTGACTGTGACAGCAGGAGAGAAGGTCACTATGAGCTGCAAGTC
CAGTCAGAGTCTGTTAAGCGATGGAAGTCAGAAGAACTACTTGACCTGGTGCCAGCAGAAACCAGGA
CAGCCTCCTAAACTGTTGATCTACTGGGCATCCACTAGGGAATCTGGGGTCCCTGATCGCTTCACAG
GCAGTGGATCTGGTACAGATTTCACTCTCACCATCAGCAGTGTGCAGGCTGAAGACCTGGGAGTTTA
TTACTGTCAGAATGATCATAGTTATCCGCTCACGTTCGGTGCTGGGACCAAACTGGAGCTGAAA

Light chain: Amino acids sequence (133 AA)

MESQTQVLMSLLFWVSGTCGDIVMTQSPSSLTVTAGEKVTMSCKSSQSLLSDGSQKNYLTWCQQKPG
QPPKLLIYWASTRESGVPDRFTGSGSGTDFTLTISSVQAEDLGVYYCQNDHSYPLTFGAGTKLELK

FIG. 21

Antibody 39-4D12-2D11

```
Color code: Leader sequence-FR1-CDR1-FR2-CDR2-FR3-CDR3-FR4
```

Heavy chain: DNA sequence (408 bp)

ATGAACTTCGGGCTCAGATTGATTTTCCTTGTCCTTACTTTAAAAGGTGTCCAGTGTGACGTGAAGC
TGGTGGAGTCTGGGGGAGGCTTAGTGAAGCCTGGAGGGTCCCCGAAACTCTCCTGTGCAGCCTCTGG
ATTCACTTTCAGTAGCTATACCATGTCTTGGGTTCGCCAGACTCCGGAGAAGAGGCTGGAGTGGGTC
GCAACCATTAGTAGTGGTGGTAGTTACACCTACTATCCAGACAGTTTGAAGGGCCGATTCACCATTT
CCAGAGACAATGCCAAGAACACCCTGTACCTGCAAATGAGCAGTCTGAAGTCTGAGGACACAGCCAT
CTATCACTGTGTAAGATCTACGTCGTACTATTTTGACTACTGGGGCCAAGGCACCACTCTCACAGTC
TCCTCT

Heavy chain: Amino acids sequence (136 AA)

MNFGLRLIFLVLTLKGVQCDVKLVESGGGLVKPGGSPKLSCAASGFTFSSYTMSWVRQTPEKRLEWV
ATISSGGSYTYYPDSLKGRFTISRDNAKNTLYLQMSSLKSEDTAIYHCVRSTSYYFDYWGQGTTLTV
SS

Light chain: DNA sequence (399 bp)

ATGGAATCACAGACTCAGGTCCTCATGTCCCTGCTGCTCTGGATATCTGGTACCTGTGGGGACATTG
TGATGACACAGTCTCCATCCTCCCTGACTGTGACAGCAGGAGAGAAGGTCACTATGAACTGCAAGTC
CAGTCAGAGTCTGTTAAGCGATGGAAGTCAAAAGAACTACTTGACCTGGTGCCAGCAGAAACCAGGA
CAGCCTCCTAAACTGTTGATCTACTGGGCATCCACTAGGGAATCTGGGGTCCCTGATCGCTTCACAG
GCAGTGGATCTGGTACAGATTTCACTCTCACCATCGACAGTGTGCAGGCTGAAGACCTGGGAATTTA
TTACTGTCAGAATGATCATAGTTATCCGCTCACGTTCGGTGCTGGGACCAAACTGGAGCTGAAA

Light chain: Amino acids sequence (133 AA)
MESQTQVLMSLLLWISGTCGDIVMTQSPSSLTVTAGEKVTMNCKSSQSLLSDGSQKNYLTWCQQKPG
QPPKLLIYWASTRESGVPDRFTGSGSGTDFTLTIDSVQAEDLGIYYCQNDHSYPLTFGAGTKLELK

FIG. 22

Antibody 56-2G9-1B3

Color code: Leader sequence-FR1-CDR1-FR2-CDR2-FR3-CDR3-FR4

Heavy chain: DNA sequence (408 bp)

ATGAACTTTGTGCTCAGCTTGATTTTCCTTGCCCTCATTTTAAAAGGTGTCCAGTGTGAAGTGCAGC
TGGTGGAGTCTGGGGGAGGCTTAGTGAAGCCTGGAGGGTCCCTGAAACTCTCCTGTGCAGCCTCTGG
ATTCATTTTCAGTAGCTATGTCATGTCTTGGGTTCGCCAGACTCCGGAGAAGAGGCTGGAGTGGGTC
GCAACCATTAGTAGTGGTGGTACTAACACCTACTATCCAGACAGTGTGAAGGGTCGATTCACCATCT
CCAGAGACAATGCCAAGAACACCCTGTACCTGCAAATGAGCAGTCTGAGGTCCGAGGACACGGCCAT
CTATTACTGTGTAAGATCCTATAGGTATTACTTTGACTACTGGGGCCAAGGCACCACTCTCACAGTC
TCCTCA

Heavy chain: Amino acids sequence (136 AA)

MNFVLSLIFLALILKGVQCEVQLVESGGGLVKPGGSLKLSCAASGFIFSSYVMSWVRQTPEKRLEWV
ATISSGGTNTYYPDSVKGRFTISRDNAKNTLYLQMSSLRSEDTAIYYCVRSYRYYFDYWGQGTTLTV
SS

Light chain: DNA sequence (399 bp)

ATGGAATCACAGACTCAGGTCCTCATGTCCCTGCTGTTCTGGGTATCTGGTACCTGTGGGGACATTG
TGATGACACAGTCTCCATCCTCCCTGACTGTGACAGCAGGAGAGAAGGTCACTATGAGCTGCAAGTC
CAGTCAGAGTCTGTTAAACAGTGGAAGTCAAAAGAATTACTTGACCTGGTTCCAGCAGAAACCAGGG
CAGTCTCCTAAATTGTTGATCTACTGGGCATCCAGTAGGGAATCTGGGGTCCCTGATCGCTTCACAG
GCAGTGGATCTGGAACAGATTTCACTCTCACCATCAGCAGTGTGCAGGCTGAAGACCTGGCAGTTTA
TTACTGTCAGAATGATTCTAATTATCCGCTCACGTTCGGTGCTGGGACCAAGCTGGAGCTGAAA

Light chain: Amino acids sequence (133 AA)
MESQTQVLMSLLFWVSGTCGDIVMTQSPSSLTVTAGEKVTMSCKSSQSLLNSGSQKNYLTWFQQKPG
QSPKLLIYWASSRESGVPDRFTGSGSGTDFTLTISSVQAEDLAVYYCQNDSNYPLTFGAGTKLELK

FIG. 23

SEQUENCE LISTING

```
<160> NUMBER OF SEQ ID NOS: 575

<210> SEQ ID NO 1
<211> LENGTH: 15
<212> TYPE: PRT
<213> ORGANISM: Influenza A virus

<400> SEQUENCE: 1

Gly Asp Thr Ile Ile Phe Glu Ala Asn Gly Asn Leu Ile Ala Pro
1               5                   10                  15

<210> SEQ ID NO 2
<211> LENGTH: 15
<212> TYPE: PRT
<213> ORGANISM: Influenza A virus

<400> SEQUENCE: 2

Ser Ser Phe Tyr Arg Asn Leu Leu Trp Leu Thr Glu Lys Glu Gly
1               5                   10                  15

<210> SEQ ID NO 3
<211> LENGTH: 15
<212> TYPE: PRT
<213> ORGANISM: Influenza A virus

<400> SEQUENCE: 3

Asn Lys Lys Gly Lys Glu Val Leu Val Leu Trp Gly Ile His His
1               5                   10                  15

<210> SEQ ID NO 4
<211> LENGTH: 15
<212> TYPE: PRT
<213> ORGANISM: Influenza A virus

<400> SEQUENCE: 4

Tyr Gln Asn Glu Asn Ala Tyr Val Ser Val Val Thr Ser Asn Tyr
1               5                   10                  15

<210> SEQ ID NO 5
<211> LENGTH: 60
<212> TYPE: PRT
<213> ORGANISM: Influenza A virus

<400> SEQUENCE: 5

Gly Arg Met Asn Tyr Tyr Trp Thr Leu Leu Lys Pro Gly Asp Thr Ile
1               5                   10                  15

Ile Phe Glu Ala Asn Gly Asn Leu Ile Ala Pro Met Tyr Ala Phe Ala
            20                  25                  30

Leu Ser Arg Gly Phe Gly Ser Gly Ile Ile Thr Ser Asn Ala Ser Met
        35                  40                  45

His Glu Cys Asn Thr Lys Cys Gln Thr Pro Leu Gly
    50                  55                  60

<210> SEQ ID NO 6
<211> LENGTH: 60
<212> TYPE: PRT
<213> ORGANISM: Influenza A virus

<400> SEQUENCE: 6

Gln Leu Ser Ser Val Ser Ser Phe Glu Arg Phe Glu Ile Phe Pro Lys
1               5                   10                  15

Glu Ser Ser Trp Pro Asn His Asn Thr Asn Gly Val Thr Ala Ala Cys
            20                  25                  30
```

Ser His Glu Gly Lys Ser Ser Phe Tyr Arg Asn Leu Leu Trp Leu Thr
         35                  40                  45

Glu Lys Glu Gly Ser Tyr Pro Lys Leu Lys Asn Ser
     50                  55                  60

<210> SEQ ID NO 7
<211> LENGTH: 23
<212> TYPE: PRT
<213> ORGANISM: Influenza A virus

<400> SEQUENCE: 7

His Glu Gly Lys Ser Ser Phe Tyr Arg Asn Leu Leu Trp Leu Thr Glu
1               5                   10                  15

Lys Glu Gly Ser Tyr Pro Lys
            20

<210> SEQ ID NO 8
<211> LENGTH: 31
<212> TYPE: PRT
<213> ORGANISM: Influenza A virus

<400> SEQUENCE: 8

His Glu Gly Lys Ser Ser Phe Tyr Arg Asn Leu Leu Trp Leu Thr Glu
1               5                   10                  15

Lys Glu Gly Ser Tyr Pro Lys Leu Lys Asn Ser Tyr Val Asn Lys
            20                  25                  30

<210> SEQ ID NO 9
<211> LENGTH: 13
<212> TYPE: PRT
<213> ORGANISM: Influenza A virus

<400> SEQUENCE: 9

Glu Pro Gly Asp Thr Ile Ile Phe Glu Ala Asn Gly Asn
1               5                   10

<210> SEQ ID NO 10
<211> LENGTH: 18
<212> TYPE: PRT
<213> ORGANISM: Influenza A virus
<220> FEATURE:
<221> NAME/KEY: MOD_RES
<222> LOCATION: (5)..(5)
<223> OTHER INFORMATION: Any amino acid

<400> SEQUENCE: 10

Leu Arg Met Lys Xaa Glu Pro Gly Asp Thr Ile Ile Phe Glu Ala Asn
1               5                   10                  15

Gly Asn

<210> SEQ ID NO 11
<211> LENGTH: 163
<212> TYPE: PRT
<213> ORGANISM: Influenza A virus

<400> SEQUENCE: 11

Ser Tyr Ile Val Glu Thr Pro Asn Ser Glu Asn Gly Ile Cys Tyr Pro
1               5                   10                  15

Gly Asp Phe Ile Asp Tyr Glu Glu Leu Arg Glu Gln Leu Ser Ser Val
            20                  25                  30

Ser Ser Phe Glu Arg Phe Glu Ile Phe Pro Lys Glu Ser Ser Trp Pro
         35                  40                  45

```
Asn His Asn Thr Asn Gly Val Thr Ala Ala Cys Ser His Glu Gly Lys
            50                  55                  60

Ser Ser Phe Tyr Arg Asn Leu Leu Trp Leu Thr Glu Lys Glu Gly Ser
 65                  70                  75                  80

Tyr Pro Lys Leu Lys Asn Ser Tyr Val Asn Lys Gly Lys Glu Val
                 85                  90                  95

Leu Val Leu Trp Gly Ile His His Pro Pro Asn Ser Lys Glu Gln Gln
            100                 105                 110

Asn Leu Tyr Gln Asn Glu Asn Ala Tyr Val Ser Val Val Thr Ser Asn
            115                 120                 125

Tyr Asn Arg Arg Phe Thr Pro Glu Ile Ala Glu Arg Pro Lys Val Arg
            130                 135                 140

Asp Gln Ala Gly Arg Met Asn Tyr Tyr Trp Thr Leu Leu Lys Pro Gly
145                 150                 155                 160

Asp Thr Ile

<210> SEQ ID NO 12
<211> LENGTH: 60
<212> TYPE: PRT
<213> ORGANISM: Influenza A virus

<400> SEQUENCE: 12

Tyr Val Asn Lys Lys Gly Lys Glu Val Leu Val Leu Trp Gly Ile His
 1               5                  10                  15

His Pro Pro Asn Ser Lys Glu Gln Gln Asn Leu Tyr Gln Asn Glu Asn
                20                  25                  30

Ala Tyr Val Ser Val Val Thr Ser Asn Tyr Asn Arg Arg Phe Thr Pro
                35                  40                  45

Glu Ile Ala Glu Arg Pro Lys Val Arg Asp Gln Ala
            50                  55                  60

<210> SEQ ID NO 13
<211> LENGTH: 176
<212> TYPE: PRT
<213> ORGANISM: Influenza A virus

<400> SEQUENCE: 13

Asn

-continued

Tyr Tyr Trp Thr Leu Leu Lys Pro Gly Asp Thr Ile Ile Phe Glu Ala
145                 150                 155                 160

Asn Gly Asn Leu Ile Ala Pro Met Tyr Ala Phe Ala Leu Ser Arg Gly
            165                 170                 175

<210> SEQ ID NO 14
<211> LENGTH: 176
<212> TYPE: PRT
<213> ORGANISM: Influenza A virus

<400> SEQUENCE: 14

Asn Ser Glu Asn Glu Ile Cys Tyr Pro Gly Asp Phe Ile Asp Lys Glu
1               5                   10                  15

Glu Leu Arg Glu Gln Leu Ser Ser Val Ser Ser Phe Glu Arg Phe Glu
            20                  25                  30

Ile Phe Pro Lys Glu Ser Ser Trp Pro Asn His Asn Thr Asn Gly Val
        35                  40                  45

Thr Ala Ala Cys Ser His Glu Gly Lys Ser Ser Phe Tyr Arg Asn Leu
    50                  55                  60

Leu Trp Leu Thr Glu Lys Glu Gly Ser Tyr Pro Lys Leu Lys Asn Ser
65                  70                  75                  80

Tyr Val Asn Lys Lys Gly Lys Glu Val Leu Val Leu Trp Gly Ile His
                85                  90                  95

His Pro Pro Asn Ser Lys Glu Gln Gln Asn Leu Tyr Gln Asn Glu Asn
            100                 105                 110

Ala Tyr Val Ser Val Val Thr Ser Asn Tyr Asn Arg Arg Phe Thr Pro
        115                 120                 125

Glu Ile Ala Glu Arg Pro Lys Val Arg Asp Gln Ala Gly Arg Met Asn
    130                 135                 140

Tyr Tyr Trp Thr Leu Leu Lys Pro Gly Asp Thr Ile Ile Phe Glu Ala
145                 150                 155                 160

Asn Gly Asn Leu Ile Ala Pro Met Tyr Ala Ala Ala Leu Ser Arg Gly
            165                 170                 175

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
agcgaaagca ggtcaattat att                                           23

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
agtagaaaca aggtcgtttt taa                                           23

<210> SEQ ID NO 17
<211> LENGTH: 23
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 17
agcgaaagca ggcaaaccat ttg                                            23

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
agtagaaaca aggcattttt tca                                            23

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
agcgaaagca ggtactgatc                                                20

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
agtagaaaca aggtactttt ttg                                            23

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gttcagaaaa agcagggg                                                  18

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
agtagaaaca agggtgtttt                                                20

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
```

-continued

```
      primer

<400> SEQUENCE: 23
agcaaaagac agggtagata atc                                              23

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
agtagaaaca agggtatttt tc                                               22

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
agcgaaagca ggagtttaaa at                                               22

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
agtagaaaca aggagttttt tg                                               22

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
agcgaaagca ggtagatatt ga                                               22

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
agtagaaaca aggtagtttt tt                                               22

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 29
agcaaaagca gggtgacaaa aa                                              22

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
agtagaaaca agggtgtttt tt                                              22

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Asp Thr Ile Cys Ile Gly Tyr His Ala Asn Asn Ser Thr Asp Thr
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Tyr His Ala Asn Asn Ser Thr Asp Thr Val Asp Thr Val Leu
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Asn Ser Thr Asp Thr Val Asp Thr Val Leu Glu Lys Asn Val Thr
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Val Asp Thr Val Leu Glu Lys Asn Val Thr Val Thr His Ser Val
1               5                   10                  15

<210> SEQ ID NO 35
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 35

Glu Lys Asn Val Thr Val Thr His Ser Val Asn Leu Leu Glu Asp
1               5                  10                  15

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Val Thr His Ser Val Asn Leu Leu Glu Asp Ser His Asn Gly Lys
1               5                  10                  15

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Asn Leu Leu Glu Asp Ser His Asn Gly Lys Leu Cys Arg Leu Lys
1               5                  10                  15

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ser His Asn Gly Lys Leu Cys Arg Leu Lys Gly Ile Ala Pro Leu
1               5                  10                  15

<210> SEQ ID NO 39
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Leu Cys Arg Leu Lys Gly Ile Ala Pro Leu Gln Leu Gly Lys Cys
1               5                  10                  15

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Ile Ala Pro Leu Gln Leu Gly Lys Cys Asn Ile Ala Gly Trp
1               5                  10                  15
```

<210> SEQ ID NO 41
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gln Leu Gly Lys Cys Asn Ile Ala Gly Trp Leu Leu Gly Asn Pro
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Asn Ile Ala Gly Trp Leu Leu Gly Asn Pro Glu Cys Asp Pro Leu
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Leu Leu Gly Asn Pro Glu Cys Asp Pro Leu Leu Pro Val Arg Ser
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Glu Cys Asp Pro Leu Leu Pro Val Arg Ser Trp Ser Tyr Ile Val
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Leu Pro Val Arg Ser Trp Ser Tyr Ile Val Glu Thr Pro Asn Ser
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 46

Trp Ser Tyr Ile Val Glu Thr Pro Asn Ser Glu Asn Gly Ile Cys
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Glu Thr Pro Asn Ser Glu Asn Gly Ile Cys Tyr Pro Gly Asp Phe
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Glu Asn Gly Ile Cys Tyr Pro Gly Asp Phe Ile Asp Tyr Glu Glu
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Tyr Pro Gly Asp Phe Ile Asp Tyr Glu Glu Leu Arg Glu Gln Leu
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ile Asp Tyr Glu Glu Leu Arg Glu Gln Leu Ser Ser Val Ser Ser
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Leu Arg Glu Gln Leu Ser Ser Val Ser Ser Phe Glu Arg Phe Glu
1               5                   10                  15

<210> SEQ ID NO 52
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 52

Ser Ser Val Ser Ser Phe Glu Arg Phe Glu Ile Phe Pro Lys Glu
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Phe Glu Arg Phe Glu Ile Phe Pro Lys Glu Ser Ser Trp Pro Asn
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ile Phe Pro Lys Glu Ser Ser Trp Pro Asn His Asn Thr Asn Gly
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ser Ser Trp Pro Asn His Asn Thr Asn Gly Val Thr Ala Ala Cys
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

His Asn Thr Asn Gly Val Thr Ala Ala Cys Ser His Glu Gly Lys
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Val Thr Ala Ala Cys Ser His Glu Gly Lys Ser Ser Phe Tyr Arg
1               5                   10                  15
```

<210> SEQ ID NO 58
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ser His Glu Gly Lys Ser Ser Phe Tyr Arg Asn Leu Leu Trp Leu
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ser Ser Phe Tyr Arg Asn Leu Leu Trp Leu Thr Glu Lys Glu Gly
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Asn Leu Leu Trp Leu Thr Glu Lys Glu Gly Ser Tyr Pro Asn Leu
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Thr Glu Lys Glu Gly Ser Tyr Pro Asn Leu Lys Asn Ser Tyr Val
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ser Tyr Pro Asn Leu Lys Asn Ser Tyr Val Asn Lys Lys Gly Lys
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 63

Lys Asn Ser Tyr Val Asn Lys Lys Gly Lys Glu Val Leu Val Leu
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Asn Lys Lys Gly Lys Glu Val Leu Val Leu Trp Gly Ile His His
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Glu Val Leu Val Leu Trp Gly Ile His His Pro Ser Asn Ser Lys
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Trp Gly Ile His His Pro Ser Asn Ser Lys Glu Gln Gln Asn Leu
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Pro Ser Asn Ser Lys Glu Gln Gln Asn Leu Tyr Gln Asn Glu Asn
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Glu Gln Gln Asn Leu Tyr Gln Asn Glu Asn Ala Tyr Val Ser Val
1               5                   10                  15

<210> SEQ ID NO 69
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Tyr Gln Asn Glu Asn Ala Tyr Val Ser Val Val Thr Ser Asn Tyr
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ala Tyr Val Ser Val Val Thr Ser Asn Tyr Asn Arg Arg Phe Thr
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Val Thr Ser Asn Tyr Asn Arg Arg Phe Thr Pro Glu Ile Ala Glu
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Asn Arg Arg Phe Thr Pro Glu Ile Ala Glu Arg Pro Lys Val Arg
1               5                   10                  15

<210> SEQ ID NO 73
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Pro Glu Ile Ala Glu Arg Pro Lys Val Arg Asp Gln Ala Gly Arg
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Arg Pro Lys Val Arg Asp Gln Ala Gly Arg Met Asn Tyr Tyr Trp
```

```
                1               5                  10                 15

<210> SEQ ID NO 75
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Asp Gln Ala Gly Arg Met Asn Tyr Tyr Trp Thr Leu Leu Lys Pro
1               5                   10                  15

<210> SEQ ID NO 76
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Met Asn Tyr Tyr Trp Thr Leu Leu Lys Pro Gly Asp Thr Ile Ile
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Thr Leu Leu Lys Pro Gly Asp Thr Ile Ile Phe Glu Ala Asn Gly
1               5                   10                  15

<210> SEQ ID NO 78
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Asp Thr Ile Ile Phe Glu Ala Asn Gly Asn Leu Ile Ala Pro
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Phe Glu Ala Asn Gly Asn Leu Ile Ala Pro Met Tyr Ala Phe Ala
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 80

Asn Leu Ile Ala Pro Met Tyr Ala Phe Ala Leu Ser Arg Gly Phe
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Met Tyr Ala Phe Ala Leu Ser Arg Gly Phe Gly Ser Gly Ile Ile
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Leu Ser Arg Gly Phe Gly Ser Gly Ile Ile Thr Ser Asn Ala Ser
1               5                   10                  15

<210> SEQ ID NO 83
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gly Ser Gly Ile Ile Thr Ser Asn Ala Ser Met His Glu Cys Asn
1               5                   10                  15

<210> SEQ ID NO 84
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Thr Ser Asn Ala Ser Met His Glu Cys Asn Thr Lys Cys Gln Thr
1               5                   10                  15

<210> SEQ ID NO 85
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Met His Glu Cys Asn Thr Lys Cys Gln Thr Pro Leu Gly Ala Ile
1               5                   10                  15

<210> SEQ ID NO 86

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Thr Lys Cys Gln Thr Pro Leu Gly Ala Ile Asn Ser Ser Leu Pro
1               5                   10                  15

<210> SEQ ID NO 87
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Pro Leu Gly Ala Ile Asn Ser Ser Leu Pro Tyr Gln Asn Ile His
1               5                   10                  15

<210> SEQ ID NO 88
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Asn Ser Ser Leu Pro Tyr Gln Asn Ile His Pro Val Thr Ile Gly
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Tyr Gln Asn Ile His Pro Val Thr Ile Gly Glu Cys Pro Lys Tyr
1               5                   10                  15

<210> SEQ ID NO 90
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Pro Val Thr Ile Gly Glu Cys Pro Lys Tyr Val Arg Ser Ala Lys
1               5                   10                  15

<210> SEQ ID NO 91
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91
```

Glu Cys Pro Lys Tyr Val Arg Ser Ala Lys Leu Arg Met Val Thr
1               5                   10                  15

<210> SEQ ID NO 92
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Val Arg Ser Ala Lys Leu Arg Met Val Thr Gly Leu Arg Asn Ile
1               5                   10                  15

<210> SEQ ID NO 93
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Leu Arg Met Val Thr Gly Leu Arg Asn Ile Pro Ser Ile Gln Ser
1               5                   10                  15

<210> SEQ ID NO 94
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gly Leu Arg Asn Ile Pro Ser Ile Gln Ser Arg
1               5                   10

<210> SEQ ID NO 95
<211> LENGTH: 565
<212> TYPE: PRT
<213> ORGANISM: Influenza A virus

<400> SEQUENCE: 95

Met Lys Ala Asn Leu Leu Val Leu Leu Cys Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

```
Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Asn
            165                 170                 175

Leu Lys Asn Ser Tyr Val Asn Lys Lys Gly Lys Glu Val Leu Val Leu
            180                 185                 190

Trp Gly Ile His His Pro Ser Asn Ser Lys Glu Gln Gln Asn Leu Tyr
        195                 200                 205

Gln Asn Glu Asn Ala Tyr Val Ser Val Val Thr Ser Asn Tyr Asn Arg
    210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
                260                 265                 270

Leu Ser Arg Gly Phe Gly Ser Gly Ile Ile Thr Ser Asn Ala Ser Met
        275                 280                 285

His Glu Cys Asn Thr Lys Cys Gln Thr Pro Leu Gly Ala Ile Asn Ser
    290                 295                 300

Ser Leu Pro Tyr Gln Asn Ile His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
                340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Thr Val Ile Glu
385                 390                 395                 400

Lys Met Asn Ile Gln Phe Thr Ala Val Gly Lys Glu Phe Asn Lys Leu
                405                 410                 415

Glu Lys Arg Met Glu Asn Leu Asn Lys Lys Val Asp Asp Gly Phe Leu
                420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
                485                 490                 495

Asn Gly Thr Tyr Asp Tyr Pro Lys Tyr Ser Glu Glu Ser Lys Leu Asn
                500                 505                 510

Arg Glu Lys Val Asp Gly Val Lys Leu Glu Ser Met Gly Ile Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560
```

-continued

Cys Arg Ile Cys Ile
            565

<210> SEQ ID NO 96
<211> LENGTH: 454
<212> TYPE: PRT
<213> ORGANISM: Influenza A virus

<400> SEQUENCE: 96

Met Asn Pro Asn Gln Lys Ile Ile Thr Ile Gly Ser Ile Cys Leu Val
1               5                   10                  15

Val Gly Leu Ile Ser Leu Ile Leu Gln Ile Gly Asn Ile Ile Ser Ile
            20                  25                  30

Trp Ile Ser His Ser Ile Gln Thr Gly Ser Gln Asn His Thr Gly Ile
        35                  40                  45

Cys Asn Gln Asn Ile Ile Thr Tyr Lys Asn Ser Thr Trp Val Lys Asp
    50                  55                  60

Thr Thr Ser Val Ile Leu Thr Gly Asn Ser Ser Leu Cys Pro Ile Arg
65                  70                  75                  80

Gly Trp Ala Ile Tyr Ser Lys Asp Asn Ser Ile Arg Ile Gly Ser Lys
                85                  90                  95

Gly Asp Val Phe Val Ile Arg Glu Pro Phe Ile Ser Cys Ser His Leu
            100                 105                 110

Glu Cys Arg Thr Phe Phe Leu Thr Gln Gly Ala Leu Leu Asn Asp Lys
        115                 120                 125

His Ser Asn Gly Thr Val Lys Asp Arg Ser Pro Tyr Arg Ala Leu Met
    130                 135                 140

Ser Cys Pro Val Gly Glu Ala Pro Ser Pro Tyr Asn Ser Arg Phe Glu
145                 150                 155                 160

Ser Val Ala Trp Ser Ala Ser Ala Cys His Asp Gly Met Gly Trp Leu
                165                 170                 175

Thr Ile Gly Ile Ser Gly Pro Asp Asn Gly Ala Val Ala Val Leu Lys
            180                 185                 190

Tyr Asn Gly Ile Ile Thr Glu Thr Ile Lys Ser Trp Arg Lys Lys Ile
        195                 200                 205

Leu Arg Thr Gln Glu Ser Glu Cys Ala Cys Val Asn Gly Ser Cys Phe
    210                 215                 220

Thr Ile Met Thr Asp Gly Pro Ser Asp Gly Leu Ala Ser Tyr Lys Ile
225                 230                 235                 240

Phe Lys Ile Glu Lys Gly Lys Val Thr Lys Ser Ile Glu Leu Asn Ala
                245                 250                 255

Pro Asn Ser His Tyr Glu Glu Cys Ser Cys Tyr Pro Asp Thr Gly Lys
            260                 265                 270

Val Met Cys Val Cys Arg Asp Asn Trp His Gly Ser Asn Arg Pro Trp
        275                 280                 285

Val Ser Phe Asp Gln Asn Leu Asp Tyr Gln Ile Gly Tyr Ile Cys Ser
    290                 295                 300

Gly Val Phe Gly Asp Asn Pro Arg Pro Glu Asp Gly Thr Gly Ser Cys
305                 310                 315                 320

Gly Pro Val Tyr Val Asp Gly Ala Asn Gly Val Lys Gly Phe Ser Tyr
                325                 330                 335

Arg Tyr Gly Asn Gly Val Trp Ile Gly Arg Thr Lys Ser His Ser Ser
            340                 345                 350

Arg His Gly Phe Glu Met Ile Trp Asp Pro Asn Gly Trp Thr Glu Thr
        355                 360                 365

Asp Ser Lys Phe Ser Val Arg Gln Asp Val Val Ala Met Thr Asp Trp
        370                 375                 380

Ser Gly Tyr Ser Gly Ser Phe Val Gln His Pro Glu Leu Thr Gly Leu
385                 390                 395                 400

Asp Cys Met Arg Pro Cys Phe Trp Val Glu Leu Ile Arg Gly Arg Pro
                405                 410                 415

Lys Glu Lys Thr Ile Trp Thr Ser Ala Ser Ser Ile Ser Phe Cys Gly
            420                 425                 430

Val Asn Ser Asp Thr Val Asp Trp Ser Trp Pro Asp Gly Ala Glu Leu
        435                 440                 445

Pro Phe Ser Ile Asp Lys
    450

<210> SEQ ID NO 97
<211> LENGTH: 408
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97
atgaacttcg ggctcagatt gatttccctt gtccttactt taaaaggtgt ccagtgtgac    60
gtgaagctgg tggagtctgg gggaggctta gtgaagcctg agggtccct gaaactctcc   120 tgtgcagcct ctggattcac tttcagtagc tataccatgt cttgggttcg ccagactccg   180
gagaagaggc tggagtgggt cgcaaccatt agtagtggtg gtatttacac ctactatcca   240
gacagtgtga agggccgatt caccatctcc agagacaatg ccaagaacac cctgtacctg   300
caaatgaaca gtctgaagtc tgaggacaca gccatgtatt actgtgtaag atctacgtcg   360
tactactttg actactgggg ccaaggcacc actctcacag tctcctca              408

<210> SEQ ID NO 98
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Met Asn Phe Gly Leu Arg Leu Ile Phe Leu Val Leu Thr Leu Lys Gly
1               5                   10                  15

Val Gln Cys Asp Val Lys Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Ser Tyr Thr Met Ser Trp Val Arg Gln Thr Pro Glu Lys Arg Leu
    50                  55                  60

Glu Trp Val Ala Thr Ile Ser Ser Gly Gly Ile Tyr Thr Tyr Tyr Pro
65                  70                  75                  80

Asp Ser Val Lys Gly Arg Phe Thr Ile Ser Arg Asp Asn Ala Lys Asn
                85                  90                  95

Thr Leu Tyr Leu Gln Met Asn Ser Leu Lys Ser Glu Asp Thr Ala Met
            100                 105                 110

Tyr Tyr Cys Val Arg Ser Thr Ser Tyr Tyr Phe Asp Tyr Trp Gly Gln
        115                 120                 125

```
Gly Thr Thr Leu Thr Val Ser Ser
    130                 135
```

<210> SEQ ID NO 99
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 99

```
atggaatcac agactcaggt cctcatgtcc ctgctgttct gggtatctgg tacctgtggg     60
gacattgtga tgacacagtc tccatcctcc ctgactgtga cagcaggaga gaaggtcact    120
atgagctgca agtccagtca gagtctgtta agcgatggaa gtcagaagaa ctacttgacc    180
tggtgccagc agaaaccagg acagcctcct aaactgttga tctactgggc atccactagg    240
gaatctgggg tccctgatcg cttcacaggc agtggatctg gtacagattt cactctcacc    300
atcagcagtg tgcaggctga agacctggga gtttattact gtcagaatga tcatagttat    360
ccgctcacgt tcggtgctgg gaccaaactg gagctgaaa                           399
```

<210> SEQ ID NO 100
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

```
Met Glu Ser Gln Thr Gln Val Leu Met Ser Leu Leu Phe Trp Val Ser
1               5                   10                  15

Gly Thr Cys Gly Asp Ile Val Met Thr Gln Ser Pro Ser Ser Leu Thr
            20                  25                  30

Val Thr Ala Gly Glu Lys Val Thr Met Ser Cys Lys Ser Ser Gln Ser
        35                  40                  45

Leu Leu Ser Asp Gly Ser Gln Lys Asn Tyr Leu Thr Trp Cys Gln Gln
    50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Gly Val Tyr
            100                 105                 110

Tyr Cys Gln Asn Asp His Ser Tyr Pro Leu Thr Phe Gly Ala Gly Thr
        115                 120                 125

Lys Leu Glu Leu Lys
    130
```

<210> SEQ ID NO 101
<211> LENGTH: 408
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101

```
atgaacttcg ggctcagatt gattttcctt gtccttactt taaaggtgt ccagtgtgac     60
```

```
gtgaagctgg tggagtctgg gggaggctta gtgaagcctg gagggtcccc gaaactctcc    120
tgtgcagcct ctggattcac tttcagtagc tataccatgt cttgggttcg ccagactccg    180
gagaagaggc tggagtgggt cgcaaccatt agtagtggtg gtagttacac ctactatcca    240
gacagtttga agggccgatt caccatttcc agagacaatg ccaagaacac cctgtacctg    300
caaatgagca gtctgaagtc tgaggacaca gccatctatc actgtgtaag atctacgtcg    360
tactattttg actactgggg ccaaggcacc actctcacag tctcctct                 408
```

<210> SEQ ID NO 102
<211> LENGTH: 136
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 102

```
Met Asn Phe Gly Leu Arg Leu Ile Phe Leu Val Leu Thr Leu Lys Gly
1               5                   10                  15

Val Gln Cys Asp Val Lys Leu Val Glu Ser Gly Gly Gly Leu Val Lys
            20                  25                  30

Pro Gly Gly Ser Pro Lys Leu Ser Cys Ala Ala Ser Gly Phe Thr Phe
        35                  40                  45

Ser Ser Tyr Thr Met Ser Trp Val Arg Gln Thr Pro Glu Lys Arg Leu
    50                  55                  60

Glu Trp Val Ala Thr Ile Ser Ser Gly Gly Ser Tyr Thr Tyr Tyr Pro
65                  70                  75                  80

Asp Ser Leu Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Ile
            100                 105                 110

Tyr His Cys Val Arg Ser Thr Ser Tyr Tyr Phe Asp Tyr Trp Gly Gln
        115                 120                 125

Gly Thr Thr Leu Thr Val Ser Ser
    130                 135
```

<210> SEQ ID NO 103
<211> LENGTH: 399
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 103

```
atggaatcac agactcaggt cctcatgtcc ctgctgctct ggatatctgg tacctgtggg    60
gacattgtga tgacacagtc tccatcctcc ctgactgtga cagcaggaga gaaggtcact    120
atgaactgca gtccagtca gagtctgtta agcgatggaa gtcaaaagaa ctacttgacc    180
tggtgccagc agaaaccagg acagcctcct aaactgttga tctactgggc atccactagg    240
gaatctgggg tccctgatcg cttcacaggc agtggatctg gtacagattt cactctcacc    300
atcgacagtg tgcaggctga agacctggga atttattact gtcagaatga tcatagttat    360
ccgctcacgt tcggtgctgg gaccaaactg gagctgaaa                           399
```

<210> SEQ ID NO 104
<211> LENGTH: 133
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 104

```
Met Glu Ser Gln Thr Gln Val Leu Met Ser Leu Leu Leu Trp Ile Ser
1               5                   10                  15

Gly Thr Cys Gly Asp Ile Val Met Thr Gln Ser Pro Ser Ser Leu Thr
                20                  25                  30

Val Thr Ala Gly Glu Lys Val Thr Met Asn Cys Lys Ser Ser Gln Ser
            35                  40                  45

Leu Leu Ser Asp Gly Ser Gln Lys Asn Tyr Leu Thr Trp Cys Gln Gln
        50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Asp Ser Val Gln Ala Glu Asp Leu Gly Ile Tyr
                100                 105                 110

Tyr Cys Gln Asn Asp His Ser Tyr Pro Leu Thr Phe Gly Ala Gly Thr
            115                 120                 125

Lys Leu Glu Leu Lys
        130
```

<210> SEQ ID NO 105
<211> LENGTH: 408
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 105

```
atgaactttg tgctcagctt gattttcctt gccctcattt taaaaggtgt ccagtgtgaa     60
gtgcagctgg tggagtctgg gggaggctta gtgaagcctg gagggtccct gaaactctcc   120
tgtgcagcct ctggattcat tttcagtagc tatgtcatgt cttgggttcg ccagactccg   180
gagaagaggc tggagtgggt cgcaaccatt agtagtggtg gtactaacac ctactatcca   240
gacagtgtga agggtcgatt caccatctcc agagacaatg ccaagaacac cctgtacctg   300
caaatgagca gtctgaggtc cgaggacacg gccatctatt actgtgtaag atcctatagg   360
tattactttg actactgggg ccaaggcacc actctcacag tctcctca              408
```

<210> SEQ ID NO 106
<211> LENGTH: 136
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 106

```
Met Asn Phe Val Leu Ser Leu Ile Phe Leu Ala Leu Ile Leu Lys Gly
1               5                   10                  15

Val Gln Cys Glu Val Gln Leu Val Glu Ser Gly Gly Gly Leu Val Lys
                20                  25                  30

Pro Gly Gly Ser Leu Lys Leu Ser Cys Ala Ala Ser Gly Phe Ile Phe
            35                  40                  45
```

Ser Ser Tyr Val Met Ser Trp Val Arg Gln Thr Pro Glu Lys Arg Leu
 50                  55                  60

Glu Trp Val Ala Thr Ile Ser Ser Gly Gly Thr Asn Thr Tyr Tyr Pro
 65                  70                  75                  80

Asp Ser Val Lys Gly Arg Phe Thr Ile Ser Arg Asp Asn Ala Lys Asn
                 85                  90                  95

Thr Leu Tyr Leu Gln Met Ser Ser Leu Arg Ser Glu Asp Thr Ala Ile
             100                 105                 110

Tyr Tyr Cys Val Arg Ser Tyr Arg Tyr Phe Asp Tyr Trp Gly Gln
         115                 120                 125

Gly Thr Thr Leu Thr Val Ser Ser
     130                 135

<210> SEQ ID NO 107
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 107
atggaatcac agactcaggt cctcatgtcc ctgctgttct gggtatctgg tacctgtggg      60
gacattgtga tgacacagtc tccatcctcc ctgactgtga cagcaggaga gaaggtcact     120
atgagctgca agtccagtca gagtctgtta acagtggaa gtcaaaagaa ttacttgacc      180
tggttccagc agaaaccagg gcagtctcct aaattgttga tctactgggc atccagtagg     240
gaatctgggg tccctgatcg cttcacaggc agtggatctg gaacagattt cactctcacc     300
atcagcagtg tgcaggctga agacctggca gtttattact gtcagaatga ttctaattat     360
ccgctcacgt tcggtgctgg gaccaagctg gagctgaaa                            399

<210> SEQ ID NO 108
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Met Glu Ser Gln Thr Gln Val Leu Met Ser Leu Leu Phe Trp Val Ser
  1               5                  10                  15

Gly Thr Cys Gly Asp Ile Val Met Thr Gln Ser Pro Ser Ser Leu Thr
                 20                  25                  30

Val Thr Ala Gly Glu Lys Val Thr Met Ser Cys Lys Ser Ser Gln Ser
             35                  40                  45

Leu Leu Asn Ser Gly Ser Gln Lys Asn Tyr Leu Thr Trp Phe Gln Gln
 50                  55                  60

Lys Pro Gly Gln Ser Pro Lys Leu Leu Ile Tyr Trp Ala Ser Ser Arg
 65                  70                  75                  80

Glu Ser Gly Val Pro Asp Arg Phe Thr Gly Ser Gly Ser Gly Thr Asp
                 85                  90                  95

Phe Thr Leu Thr Ile Ser Ser Val Gln Ala Glu Asp Leu Ala Val Tyr
             100                 105                 110

Tyr Cys Gln Asn Asp Ser Asn Tyr Pro Leu Thr Phe Gly Ala Gly Thr
         115                 120                 125

Lys Leu Glu Leu Lys

<210> SEQ ID NO 109
<211> LENGTH: 10
<212> TYPE: PRT
<213> ORGANISM: Influenza A virus

<400> SEQUENCE: 109

Ala Asp Gln Lys Ser Thr Gln Asn Ala Ile
1               5                   10

<210> SEQ ID NO 110
<211> LENGTH: 20
<212> TYPE: PRT
<213> ORGANISM: Influenza A virus

<400> SEQUENCE: 110

Ala Asp Tyr Glu Glu Leu Arg Glu Gln Leu Ser Ser Val Ser Ser Phe
1               5                   10                  15

Glu Arg Phe Glu
            20

<210> SEQ ID NO 111
<211> LENGTH: 10
<212> TYPE: PRT
<213> ORGANISM: Influenza A virus

<400> SEQUENCE: 111

Ala Gly Arg Met Asn Tyr Tyr Trp Thr Leu
1               5                   10

<210> SEQ ID NO 112
<211> LENGTH: 19
<212> TYPE: PRT
<213> ORGANISM: Influenza A virus

<400> SEQUENCE: 112

Ala Ile Tyr His Thr Glu Asn Ala Tyr Val Ser Val Val Ser Ser His
1 5 10 15

Tyr Asn Arg

<210> SEQ ID NO 113
<211> LENGTH: 10
<212> TYPE: PRT
<213> ORGANISM: Influenza A virus

<400> SEQUENCE: 113

Ala Ser Ser Leu Val Leu Leu Val Ser Leu
1 5 10

<210> SEQ ID NO 114
<211> LENGTH: 9
<212> TYPE: PRT
<213> ORGANISM: Influenza A virus

<400> SEQUENCE: 114

Ala Ser Ser Asn Tyr Asn Arg Arg Phe
1 5

<210> SEQ ID NO 115
<211> LENGTH: 10
<212> TYPE: PRT
<213> ORGANISM: Influenza A virus

```
<400> SEQUENCE: 115

Ala Thr Gly Asn Leu Ile Ala Pro Trp Tyr
1               5                   10

<210> SEQ ID NO 116
<211> LENGTH: 9
<212> TYPE: PRT
<213> ORGANISM: Influenza A virus

<400> SEQUENCE: 116

Cys Ser His Arg Gly Lys Ser Ser Phe
1               5

<210> SEQ ID NO 117
<211> LENGTH: 10
<212> TYPE: PRT
<213> ORGANISM: Influenza A virus

<400> SEQUENCE: 117

Cys Ser His Arg Gly Lys Ser Ser Phe Tyr
1               5                   10

<210> SEQ ID NO 118
<211> LENGTH: 14
<212> TYPE: PRT
<213> ORGANISM: Influenza A virus

<400> SEQUENCE: 118

Glu Gly Ser Tyr Pro Lys Leu Lys Asn Ser Tyr Glu Asn Lys
1               5                   10

<210> SEQ ID NO 119
<211> LENGTH: 10
<212> TYPE: PRT
<213> ORGANISM: Influenza A virus

<400> SEQUENCE: 119

Glu Ile Gly Asn Gly Cys Phe Glu Phe Tyr
1               5                   10

<210> SEQ ID NO 120
<211> LENGTH: 9
<212> TYPE: PRT
<213> ORGANISM: Influenza A virus

<400> SEQUENCE: 120

Glu Ser Met Gly Val Tyr Gln Ile Leu
1               5

<210> SEQ ID NO 121
<211> LENGTH: 9
<212> TYPE: PRT
<213> ORGANISM: Influenza A virus

<400> SEQUENCE: 121

Glu Ser Ser Trp Pro Asn His Thr Phe
1               5

<210> SEQ ID NO 122
<211> LENGTH: 9
<212> TYPE: PRT
<213> ORGANISM: Influenza A virus

<400> SEQUENCE: 122
```

```
Phe Glu Ala Thr Gly Asn Leu Ile Ala
1               5

<210> SEQ ID NO 123
<211> LENGTH: 10
<212> TYPE: PRT
<213> ORGANISM: Influenza A virus

<400> SEQUENCE: 123

Phe Glu Ser Gly Ile Ile Thr Ser Asn Ala
1               5                   10

<210> SEQ ID NO 124
<211> LENGTH: 9
<212> TYPE: PRT
<213> ORGANISM: Influenza A virus

<400> SEQUENCE: 124

Phe His Asp Ser Asn Val Lys Asn Leu
1               5

<210> SEQ ID NO 125
<211> LENGTH: 8
<212> TYPE: PRT
<213> ORGANISM: Influenza A virus

<400> SEQUENCE: 125

Phe Thr Ala Val Gly Lys Glu Phe
1               5

<210> SEQ ID NO 126
<211> LENGTH: 9
<212> TYPE: PRT
<213> ORGANISM: Influenza A virus

<400> SEQUENCE: 126

Gly Ile Ile Thr Ser Asn Ala Ser Met
1               5

<210> SEQ ID NO 127
<211> LENGTH: 10
<212> TYPE: PRT
<213> ORGANISM: Influenza A virus

<400> SEQUENCE: 127

Gly Leu Phe Gly Ala Ile Ala Gly Phe Ile
1               5                   10

<210> SEQ ID NO 128
<211> LENGTH: 11
<212> TYPE: PRT
<213> ORGANISM: Influenza A virus

<400> SEQUENCE: 128

Gly Leu Phe Gly Ala Ile Ala Gly Phe Ile Glu
1               5                   10

<210> SEQ ID NO 129
<211> LENGTH: 10
<212> TYPE: PRT
<213> ORGANISM: Influenza A virus

<400> SEQUENCE: 129

Gly Leu Arg Asn Ile Pro Ser Ile Gln Ser
1               5                   10
```

<210> SEQ ID NO 130
<211> LENGTH: 10
<212> TYPE: PRT
<213> ORGANISM: Influenza A virus

<400> SEQUENCE: 130

Gly Leu Arg Asn Ile Pro Ser Ile Gln Tyr
1               5                   10

<210> SEQ ID NO 131
<211> LENGTH: 8
<212> TYPE: PRT
<213> ORGANISM: Influenza A virus

<400> SEQUENCE: 131

Gly Thr Tyr Asp Tyr Pro Lys Tyr
1               5

<210> SEQ ID NO 132
<211> LENGTH: 10
<212> TYPE: PRT
<213> ORGANISM: Influenza A virus

<400> SEQUENCE: 132

Gly Val Lys Leu Glu Ser Met Gly Val Tyr
1               5                   10

<210> SEQ ID NO 133
<211> LENGTH: 9
<212> TYPE: PRT
<213> ORGANISM: Influenza A virus

<400> SEQUENCE: 133

Gly Val Tyr Gln Ile Leu Ala Ile Tyr
1               5

<210> SEQ ID NO 134
<211> LENGTH: 13
<212> TYPE: PRT
<213> ORGANISM: Influenza A virus

<400> SEQUENCE: 134

His Asn Thr Asn Gly Val Thr Ala Ala Cys Ser His Glu
1               5                   10

<210> SEQ ID NO 135
<211> LENGTH: 9
<212> TYPE: PRT
<213> ORGANISM: Influenza A virus

<400> SEQUENCE: 135

Ile Ala Gly Phe Ile Glu Gly Gly Trp
1               5

<210> SEQ ID NO 136
<211> LENGTH: 9
<212> TYPE: PRT
<213> ORGANISM: Influenza A virus

<400> SEQUENCE: 136

Ile Ala Pro Trp Tyr Ala Phe Ala Leu
1               5

```
<210> SEQ ID NO 137
<211> LENGTH: 9
<212> TYPE: PRT
<213> ORGANISM: Influenza A virus

<400> SEQUENCE: 137

Ile Glu Gly Gly Trp Thr Gly Met Ile
1               5

<210> SEQ ID NO 138
<211> LENGTH: 10
<212> TYPE: PRT
<213> ORGANISM: Influenza A virus

<400> SEQUENCE: 138

Ile Glu Lys Met Asn Thr Gln Phe Thr Ala
1               5                   10

<210> SEQ ID NO 139
<211> LENGTH: 20
<212> TYPE: PRT
<213> ORGANISM: Influenza A virus

<400> SEQUENCE: 139

Ile Phe Glu Ala Asn Gly Asn Leu Ile Ala Pro Trp Tyr Ala Phe Ala
1               5                   10                  15

Leu Ser Arg Gly
            20

<210> SEQ ID NO 140
<211> LENGTH: 9
<212> TYPE: PRT
<213> ORGANISM: Influenza A virus

<400> SEQUENCE: 140

Ile Gly Asn Gly Cys Phe Glu Phe Tyr
1               5

<210> SEQ ID NO 141
<211> LENGTH: 20
<212> TYPE: PRT
<213> ORGANISM: Influenza A virus

<400> SEQUENCE: 141

Ile Gly Asn Gln Arg Ala Leu Tyr His Thr Glu Asn Ala Tyr Val Ser
1               5                   10                  15

Val Val Ser Ser
            20

<210> SEQ ID NO 142
<211> LENGTH: 8
<212> TYPE: PRT
<213> ORGANISM: Influenza A virus

<400> SEQUENCE: 142

Ile Leu Ala Ile Tyr Ser Thr Val
1               5

<210> SEQ ID NO 143
<211> LENGTH: 12
<212> TYPE: PRT
<213> ORGANISM: Influenza A virus

<400> SEQUENCE: 143
```

Ile Leu Ala Ile Tyr Ser Thr Val Ala Ser Ser Leu
1               5                   10

<210> SEQ ID NO 144
<211> LENGTH: 9
<212> TYPE: PRT
<213> ORGANISM: Influenza A virus

<400> SEQUENCE: 144

Ile Thr Asn Lys Val Asn Ser Val Ile
1               5

<210> SEQ ID NO 145
<211> LENGTH: 9
<212> TYPE: PRT
<213> ORGANISM: Influenza A virus

<400> SEQUENCE: 145

Ile Trp Thr Tyr Asn Ala Glu Leu Leu
1               5

<210> SEQ ID NO 146
<211> LENGTH: 15
<212> TYPE: PRT
<213> ORGANISM: Influenza A virus

<400> SEQUENCE: 146

Ile Tyr Gln Ile Leu Ala Ile Tyr Ser Thr Val Ala Ser Ser Leu
1               5                   10                  15

<210> SEQ ID NO 147
<211> LENGTH: 9
<212> TYPE: PRT
<213> ORGANISM: Influenza A virus

<400> SEQUENCE: 147

Ile Tyr Ser Thr Val Ala Ser Ser Leu
1               5

<210> SEQ ID NO 148
<211> LENGTH: 11
<212> TYPE: PRT
<213> ORGANISM: Influenza A virus

<400> SEQUENCE: 148

Ile Tyr Ser Thr Val Ala Ser Ser Leu Val Leu
1               5                   10

<210> SEQ ID NO 149
<211> LENGTH: 10
<212> TYPE: PRT
<213> ORGANISM: Influenza A virus

<400> SEQUENCE: 149

Lys Glu Phe Asn Asn Leu Glu Lys Arg Met
1               5                   10

<210> SEQ ID NO 150
<211> LENGTH: 8
<212> TYPE: PRT
<213> ORGANISM: Influenza A virus

<400> SEQUENCE: 150

Lys Glu Gly Ser Tyr Pro Lys Leu
1               5

<210> SEQ ID NO 151
<211> LENGTH: 10
<212> TYPE: PRT
<213> ORGANISM: Influenza A virus

<400> SEQUENCE: 151

Lys Glu Ile Gly Asn Gly Cys Phe Glu Phe
1               5                   10

<210> SEQ ID NO 152
<211> LENGTH: 10
<212> TYPE: PRT
<213> ORGANISM: Influenza A virus

<400> SEQUENCE: 152

Lys Glu Ser Ser Trp Pro Asn His Thr Phe
1               5                   10

<210> SEQ ID NO 153
<211> LENGTH: 9
<212> TYPE: PRT
<213> ORGANISM: Influenza A virus

<400> SEQUENCE: 153

Lys Glu Val Leu Val Leu Trp Gly Val
1               5

<210> SEQ ID NO 154
<211> LENGTH: 9
<212> TYPE: PRT
<213> ORGANISM: Influenza A virus

<400> SEQUENCE: 154

Lys Leu Arg Met Val Thr Gly Leu Arg
1               5

<210> SEQ ID NO 155
<211> LENGTH: 8
<212> TYPE: PRT
<213> ORGANISM: Influenza A virus

<400> SEQUENCE: 155

Lys Ser Ser Phe Tyr Arg Asn Leu
1               5

<210> SEQ ID NO 156
<211> LENGTH: 9
<212> TYPE: PRT
<213> ORGANISM: Influenza A virus

<400> SEQUENCE: 156

Lys Ser Ser Phe Tyr Arg Asn Leu Leu
1               5

<210> SEQ ID NO 157
<211> LENGTH: 10
<212> TYPE: PRT
<213> ORGANISM: Influenza A virus

<400> SEQUENCE: 157

Lys Ser Thr Gln Asn Ala Ile Asn Gly Ile
1               5                   10

<210> SEQ ID NO 158
<211> LENGTH: 9
<212> TYPE: PRT
<213> ORGANISM: Influenza A virus

<400> SEQUENCE: 158

Lys Val Asn Ser Val Ile Glu Lys Met
1               5

<210> SEQ ID NO 159
<211> LENGTH: 9
<212> TYPE: PRT
<213> ORGANISM: Influenza A virus

<400> SEQUENCE: 159

Leu Glu Asn Glu Arg Thr Leu Asp Phe
1               5

<210> SEQ ID NO 160
<211> LENGTH: 9
<212> TYPE: PRT
<213> ORGANISM: Influenza A virus

<400> SEQUENCE: 160

Leu Glu Pro Gly Asp Thr Ile Ile Phe
1               5

<210> SEQ ID NO 161
<211> LENGTH: 9
<212> TYPE: PRT
<213> ORGANISM: Influenza A virus

<400> SEQUENCE: 161

Leu Glu Ser Met Gly Val Tyr Gln Ile
1               5

<210> SEQ ID NO 162
<211> LENGTH: 10
<212> TYPE: PRT
<213> ORGANISM: Influenza A virus

<400> SEQUENCE: 162

Leu Glu Ser Met Gly Val Tyr Gln Ile Leu
1               5                   10

<210> SEQ ID NO 163
<211> LENGTH: 10
<212> TYPE: PRT
<213> ORGANISM: Influenza A virus

<400> SEQUENCE: 163

Leu Leu Glu Pro Gly Asp Thr Ile Ile Phe
1               5                   10

<210> SEQ ID NO 164
<211> LENGTH: 10
<212> TYPE: PRT
<213> ORGANISM: Influenza A virus

<400> SEQUENCE: 164

Leu Leu Pro Ala Arg Ser Trp Ser Tyr Ile
1               5                   10

<210> SEQ ID NO 165
<211> LENGTH: 10

```
<212> TYPE: PRT
<213> ORGANISM: Influenza A virus

<400> SEQUENCE: 165

Leu Leu Val Ser Leu Gly Ala Ile Ser Phe
1               5                   10

<210> SEQ ID NO 166
<211> LENGTH: 9
<212> TYPE: PRT
<213> ORGANISM: Influenza A virus

<400> SEQUENCE: 166

Leu Arg Asn Ile Pro Ser Ile Gln Ser
1               5

<210> SEQ ID NO 167
<211> LENGTH: 10
<212> TYPE: PRT
<213> ORGANISM: Influenza A virus

<400> SEQUENCE: 167

Leu Arg Asn Ile Pro Ser Ile Gln Ser Arg
1               5                   10

<210> SEQ ID NO 168
<211> LENGTH: 9
<212> TYPE: PRT
<213> ORGANISM: Influenza A virus

<400> SEQUENCE: 168

Leu Ser Arg Gly Phe Glu Ser Gly Ile
1               5

<210> SEQ ID NO 169
<211> LENGTH: 10
<212> TYPE: PRT
<213> ORGANISM: Influenza A virus

<400> SEQUENCE: 169

Leu Ser Arg Gly Phe Glu Ser Gly Ile Ile
1               5                   10

<210> SEQ ID NO 170
<211> LENGTH: 10
<212> TYPE: PRT
<213> ORGANISM: Influenza A virus

<400> SEQUENCE: 170

Leu Ser Ser Val Ser Ser Leu Glu Arg Phe
1               5                   10

<210> SEQ ID NO 171
<211> LENGTH: 9
<212> TYPE: PRT
<213> ORGANISM: Influenza A virus

<400> SEQUENCE: 171

Leu Val Ser Leu Gly Ala Ile Ser Phe
1               5

<210> SEQ ID NO 172
<211> LENGTH: 9
<212> TYPE: PRT
<213> ORGANISM: Influenza A virus
```

```
<400> SEQUENCE: 172

Leu Tyr Glu Lys Val Lys Ser Gln Leu
1               5

<210> SEQ ID NO 173
<211> LENGTH: 10
<212> TYPE: PRT
<213> ORGANISM: Influenza A virus

<400> SEQUENCE: 173

Met Gly Val Tyr Gln Ile Leu Ala Ile Tyr
1               5                   10

<210> SEQ ID NO 174
<211> LENGTH: 8
<212> TYPE: PRT
<213> ORGANISM: Influenza A virus

<400> SEQUENCE: 174

Met Asn Ile Gln Phe Thr Ala Val
1               5

<210> SEQ ID NO 175
<211> LENGTH: 8
<212> TYPE: PRT
<213> ORGANISM: Influenza A virus

<400> SEQUENCE: 175

Met Asn Tyr Tyr Trp Thr Leu Leu
1               5

<210> SEQ ID NO 176
<211> LENGTH: 10
<212> TYPE: PRT
<213> ORGANISM: Influenza A virus

<400> SEQUENCE: 176

Asn Glu Arg Thr Leu Asp Phe His Asp Leu
1               5                   10

<210> SEQ ID NO 177
<211> LENGTH: 9
<212> TYPE: PRT
<213> ORGANISM: Influenza A virus

<400> SEQUENCE: 177

Asn Gly Thr Tyr Asp Tyr Pro Lys Tyr
1               5

<210> SEQ ID NO 178
<211> LENGTH: 11
<212> TYPE: PRT
<213> ORGANISM: Influenza A virus

<400> SEQUENCE: 178

Asn His Asn Thr Asn Gly Val Thr Ala Ala Cys
1               5                   10

<210> SEQ ID NO 179
<211> LENGTH: 9
<212> TYPE: PRT
<213> ORGANISM: Influenza A virus

<400> SEQUENCE: 179
```

Asn Ser Thr Asp Thr Val Asp Thr Ile
1               5

<210> SEQ ID NO 180
<211> LENGTH: 9
<212> TYPE: PRT
<213> ORGANISM: Influenza A virus

<400> SEQUENCE: 180

Pro Glu Ile Ala Ala Arg Pro Lys Val
1               5

<210> SEQ ID NO 181
<211> LENGTH: 10
<212> TYPE: PRT
<213> ORGANISM: Influenza A virus

<400> SEQUENCE: 181

Pro Ser Ser Ser Asp Glu Gln Gln Ser Leu
1               5                   10

<210> SEQ ID NO 182
<211> LENGTH: 9
<212> TYPE: PRT
<213> ORGANISM: Influenza A virus

<400> SEQUENCE: 182

Gln Leu Lys Asn Asn Ala Lys Glu Ile
1               5

<210> SEQ ID NO 183
<211> LENGTH: 15
<212> TYPE: PRT
<213> ORGANISM: Influenza A virus

<400> SEQUENCE: 183

Gln Leu Ser Ser Val Ser Ser Phe Glu Arg Phe Glu Ile Phe Pro
1               5                   10                  15

<210> SEQ ID NO 184
<211> LENGTH: 20
<212> TYPE: PRT
<213> ORGANISM: Influenza A virus

<400> SEQUENCE: 184

Gln Leu Ser Ser Val Ser Ser Phe Glu Arg Phe Glu Ile Phe Pro Lys
1               5                   10                  15

Glu Ser Ser Trp
            20

<210> SEQ ID NO 185
<211> LENGTH: 10
<212> TYPE: PRT
<213> ORGANISM: Influenza A virus

<400> SEQUENCE: 185

Gln Ser Leu Tyr Ser Asn Gly Asn Ala Tyr
1               5                   10

<210> SEQ ID NO 186
<211> LENGTH: 9
<212> TYPE: PRT
<213> ORGANISM: Influenza A virus

```
<400> SEQUENCE: 186

Arg Glu Lys Ile Asp Gly Val Lys Leu
1               5

<210> SEQ ID NO 187
<211> LENGTH: 10
<212> TYPE: PRT
<213> ORGANISM: Influenza A virus

<400> SEQUENCE: 187

Arg Glu Gln Leu Ser Ser Val Ser Ser Leu
1               5                   10

<210> SEQ ID NO 188
<211> LENGTH: 8
<212> TYPE: PRT
<213> ORGANISM: Influenza A virus

<400> SEQUENCE: 188

Arg Met Asn Tyr Tyr Trp Thr Leu
1               5

<210> SEQ ID NO 189
<211> LENGTH: 8
<212> TYPE: PRT
<213> ORGANISM: Influenza A virus

<400> SEQUENCE: 189

Arg Ser Thr Lys Leu Arg Met Val
1               5

<210> SEQ ID NO 190
<211> LENGTH: 10
<212> TYPE: PRT
<213> ORGANISM: Influenza A virus

<400> SEQUENCE: 190

Arg Thr Leu Asp Phe His Asp Leu Asn Val
1               5                   10

<210> SEQ ID NO 191
<211> LENGTH: 11
<212> TYPE: PRT
<213> ORGANISM: Influenza A virus

<400> SEQUENCE: 191

Ser Phe Glu Arg Phe Glu Ile Phe Pro Lys Glu
1               5                   10

<210> SEQ ID NO 192
<211> LENGTH: 9
<212> TYPE: PRT
<213> ORGANISM: Influenza A virus

<400> SEQUENCE: 192

Ser Phe Tyr Arg Asn Leu Leu Trp Leu
1               5

<210> SEQ ID NO 193
<211> LENGTH: 10
<212> TYPE: PRT
<213> ORGANISM: Influenza A virus

<400> SEQUENCE: 193
```

-continued

```
Ser Gly Ile Ile Thr Ser Asn Ala Ser Met
1               5                   10

<210> SEQ ID NO 194
<211> LENGTH: 9
<212> TYPE: PRT
<213> ORGANISM: Influenza A virus

<400> SEQUENCE: 194

Ser Leu Gly Ala Ile Ser Phe Trp Met
1               5

<210> SEQ ID NO 195
<211> LENGTH: 10
<212> TYPE: PRT
<213> ORGANISM: Influenza A virus

<400> SEQUENCE: 195

Ser Leu Leu Pro Ala Arg Ser Trp Ser Tyr
1               5                   10

<210> SEQ ID NO 196
<211> LENGTH: 10
<212> TYPE: PRT
<213> ORGANISM: Influenza A virus

<400> SEQUENCE: 196

Ser Leu Pro Phe Gln Asn Ile His Pro Val
1               5                   10

<210> SEQ ID NO 197
<211> LENGTH: 20
<212> TYPE: PRT
<213> ORGANISM: Influenza A virus

<400> SEQUENCE: 197

Ser Leu Pro Phe Gln Asn Val His Pro Val Thr Ile Gly Glu Cys Pro
1               5                   10                  15

Lys Tyr Val Arg
            20

<210> SEQ ID NO 198
<211> LENGTH: 8
<212> TYPE: PRT
<213> ORGANISM: Influenza A virus

<400> SEQUENCE: 198

Ser Met Gly Ile Tyr Gln Ile Leu
1               5

<210> SEQ ID NO 199
<211> LENGTH: 10
<212> TYPE: PRT
<213> ORGANISM: Influenza A virus

<400> SEQUENCE: 199

Ser Asn Val Lys Asn Leu Tyr Glu Lys Val
1               5                   10

<210> SEQ ID NO 200
<211> LENGTH: 10
<212> TYPE: PRT
<213> ORGANISM: Influenza A virus

<400> SEQUENCE: 200
```

Ser Gln Leu Lys Asn Asn Ala Lys Glu Ile
1               5                   10

<210> SEQ ID NO 201
<211> LENGTH: 9
<212> TYPE: PRT
<213> ORGANISM: Influenza A virus

<400> SEQUENCE: 201

Ser Ser Asp Glu Gln Gln Ser Leu Tyr
1               5

<210> SEQ ID NO 202
<211> LENGTH: 10
<212> TYPE: PRT
<213> ORGANISM: Influenza A virus

<400> SEQUENCE: 202

Ser Ser Phe Tyr Arg Asn Leu Leu Trp Leu
1               5                   10

<210> SEQ ID NO 203
<211> LENGTH: 9
<212> TYPE: PRT
<213> ORGANISM: Influenza A virus

<400> SEQUENCE: 203

Ser Ser Leu Glu Arg Phe Glu Ile Phe
1               5

<210> SEQ ID NO 204
<211> LENGTH: 8
<212> TYPE: PRT
<213> ORGANISM: Influenza A virus

<400> SEQUENCE: 204

Ser Ser Leu Pro Phe Gln Asn Ile
1               5

<210> SEQ ID NO 205
<211> LENGTH: 9
<212> TYPE: PRT
<213> ORGANISM: Influenza A virus

<400> SEQUENCE: 205

Ser Ser Leu Val Leu Leu Val Ser Leu
1               5

<210> SEQ ID NO 206
<211> LENGTH: 10
<212> TYPE: PRT
<213> ORGANISM: Influenza A virus

<400> SEQUENCE: 206

Ser Ser Ser Asp Glu Gln Gln Ser Leu Tyr
1               5                   10

<210> SEQ ID NO 207
<211> LENGTH: 9
<212> TYPE: PRT
<213> ORGANISM: Influenza A virus

<400> SEQUENCE: 207

Ser Ser Val Ser Ser Phe Glu Arg Phe

<210> SEQ ID NO 208
<211> LENGTH: 9
<212> TYPE: PRT
<213> ORGANISM: Influenza A virus

<400> SEQUENCE: 208

Ser Ser Val Ser Ser Leu Glu Arg Phe
1               5

<210> SEQ ID NO 209
<211> LENGTH: 10
<212> TYPE: PRT
<213> ORGANISM: Influenza A virus

<400> SEQUENCE: 209

Ser Thr Lys Leu Arg Met Val Thr Gly Leu
1               5                   10

<210> SEQ ID NO 210
<211> LENGTH: 9
<212> TYPE: PRT
<213> ORGANISM: Influenza A virus

<400> SEQUENCE: 210

Ser Thr Val Ala Ser Ser Leu Val Leu
1               5

<210> SEQ ID NO 211
<211> LENGTH: 10
<212> TYPE: PRT
<213> ORGANISM: Influenza A virus

<400> SEQUENCE: 211

Ser Thr Val Ala Ser Ser Leu Val Leu Leu
1               5                   10

<210> SEQ ID NO 212
<211> LENGTH: 10
<212> TYPE: PRT
<213> ORGANISM: Influenza A virus

<400> SEQUENCE: 212

Ser Val Ile Glu Lys Met Asn Thr Gln Phe
1               5                   10

<210> SEQ ID NO 213
<211> LENGTH: 13
<212> TYPE: PRT
<213> ORGANISM: Influenza A virus

<400> SEQUENCE: 213

Ser Val Ser Ser Phe Glu Arg Phe Glu Ile Phe Pro Lys
1               5                   10

<210> SEQ ID NO 214
<211> LENGTH: 10
<212> TYPE: PRT
<213> ORGANISM: Influenza A virus

<400> SEQUENCE: 214

Ser Tyr Pro Lys Leu Thr Asn Ser Tyr Val
1               5                   10

```
<210> SEQ ID NO 215
<211> LENGTH: 9
<212> TYPE: PRT
<213> ORGANISM: Influenza A virus

<400> SEQUENCE: 215

Thr Gly Leu Arg Asn Ile Pro Ser Ile
1               5

<210> SEQ ID NO 216
<211> LENGTH: 9
<212> TYPE: PRT
<213> ORGANISM: Influenza A virus

<400> SEQUENCE: 216

Thr Gly Asn Leu Ile Ala Pro Trp Tyr
1               5

<210> SEQ ID NO 217
<211> LENGTH: 8
<212> TYPE: PRT
<213> ORGANISM: Influenza A virus

<400> SEQUENCE: 217

Val Gly Lys Glu Phe Asn Lys Leu
1               5

<210> SEQ ID NO 218
<211> LENGTH: 9
<212> TYPE: PRT
<213> ORGANISM: Influenza A virus

<400> SEQUENCE: 218

Val Ile Glu Lys Met Asn Thr Gln Phe
1               5

<210> SEQ ID NO 219
<211> LENGTH: 8
<212> TYPE: PRT
<213> ORGANISM: Influenza A virus

<400> SEQUENCE: 219

Val Lys Asn Leu Tyr Glu Lys Val
1               5

<210> SEQ ID NO 220
<211> LENGTH: 9
<212> TYPE: PRT
<213> ORGANISM: Influenza A virus

<400> SEQUENCE: 220

Val Leu Leu Glu Asn Glu Arg Thr Leu
1               5

<210> SEQ ID NO 221
<211> LENGTH: 9
<212> TYPE: PRT
<213> ORGANISM: Influenza A virus

<400> SEQUENCE: 221

Val Leu Leu Val Ser Leu Gly Ala Ile
1               5

<210> SEQ ID NO 222
```

```
<211> LENGTH: 9
<212> TYPE: PRT
<213> ORGANISM: Influenza A virus

<400> SEQUENCE: 222

Val Ser Leu Gly Ala Ile Ser Phe Trp
1               5

<210> SEQ ID NO 223
<211> LENGTH: 10
<212> TYPE: PRT
<213> ORGANISM: Influenza A virus

<400> SEQUENCE: 223

Val Ser Leu Gly Ala Ile Ser Phe Trp Met
1               5                   10

<210> SEQ ID NO 224
<211> LENGTH: 10
<212> TYPE: PRT
<213> ORGANISM: Influenza A virus

<400> SEQUENCE: 224

Val Ser Ser Leu Glu Arg Phe Glu Ile Phe
1               5                   10

<210> SEQ ID NO 225
<211> LENGTH: 10
<212> TYPE: PRT
<213> ORGANISM: Influenza A virus

<400> SEQUENCE: 225

Val Thr Gly Leu Arg Asn Ile Pro Ser Ile
1               5                   10

<210> SEQ ID NO 226
<211> LENGTH: 13
<212> TYPE: PRT
<213> ORGANISM: Influenza A virus

<400> SEQUENCE: 226

Val Thr Gly Leu Arg Asn Ile Pro Ser Ile Gln Ser Arg
1               5                   10

<210> SEQ ID NO 227
<211> LENGTH: 25
<212> TYPE: PRT
<213> ORGANISM: Influenza A virus

<400> SEQUENCE: 227

Val Thr Gly Leu Arg Asn Ile Pro Ser Ile Gln Ser Arg Gly Leu Phe
1               5                   10                  15

Gly Ala Ile Ala Gly Phe Ile Glu Gly
            20                  25

<210> SEQ ID NO 228
<211> LENGTH: 9
<212> TYPE: PRT
<213> ORGANISM: Influenza A virus

<400> SEQUENCE: 228

Val Thr Ile Gly Glu Cys Pro Lys Tyr
1               5
```

```
<210> SEQ ID NO 229
<211> LENGTH: 10
<212> TYPE: PRT
<213> ORGANISM: Influenza A virus

<400> SEQUENCE: 229

Val Thr Ile Gly Glu Cys Pro Lys Tyr Val
1               5                   10

<210> SEQ ID NO 230
<211> LENGTH: 20
<212> TYPE: PRT
<213> ORGANISM: Influenza A virus

<400> SEQUENCE: 230

Val Val Ser Ser His Tyr Ser Arg Arg Phe Thr Pro Glu Ile Ala Lys
1               5                   10                  15

Arg Pro Lys Val
            20

<210> SEQ ID NO 231
<211> LENGTH: 9
<212> TYPE: PRT
<213> ORGANISM: Influenza A virus

<400> SEQUENCE: 231

Trp Leu Thr Lys Lys Gly Asp Ser Tyr
1               5

<210> SEQ ID NO 232
<211> LENGTH: 9
<212> TYPE: PRT
<213> ORGANISM: Influenza A virus

<400> SEQUENCE: 232

Trp Thr Gly Met Ile Asp Gly Trp Tyr
1               5

<210> SEQ ID NO 233
<211> LENGTH: 9
<212> TYPE: PRT
<213> ORGANISM: Influenza A virus

<400> SEQUENCE: 233

Tyr Ala Phe Ala Leu Ser Arg Gly Phe
1               5

<210> SEQ ID NO 234
<211> LENGTH: 20
<212> TYPE: PRT
<213> ORGANISM: Influenza A virus

<400> SEQUENCE: 234

Tyr Arg Asn Leu Leu Trp Leu Thr Gly Lys Asn Gly Leu Tyr Pro Asn
1               5                   10                  15

Leu Ser Lys Ser
            20

<210> SEQ ID NO 235
<211> LENGTH: 10
<212> TYPE: PRT
<213> ORGANISM: Influenza A virus

<400> SEQUENCE: 235
```

Tyr Ser Asn Gly Asn Ala Tyr Val Ser Val
1               5                   10

<210> SEQ ID NO 236
<211> LENGTH: 9
<212> TYPE: PRT
<213> ORGANISM: Influenza A virus

<400> SEQUENCE: 236

Tyr Ser Thr Val Ala Ser Ser Leu Val
1               5

<210> SEQ ID NO 237
<211> LENGTH: 10
<212> TYPE: PRT
<213> ORGANISM: Influenza A virus

<400> SEQUENCE: 237

Tyr Ser Thr Val Ala Ser Ser Leu Val Leu
1               5                   10

<210> SEQ ID NO 238
<211> LENGTH: 9
<212> TYPE: PRT
<213> ORGANISM: Influenza A virus

<400> SEQUENCE: 238

Tyr Val Arg Ser Thr Lys Leu Arg Met
1               5

<210> SEQ ID NO 239
<211> LENGTH: 9
<212> TYPE: PRT
<213> ORGANISM: Influenza A virus

<400> SEQUENCE: 239

Tyr Val Ser Val Ala Ser Ser Asn Tyr
1               5

<210> SEQ ID NO 240
<211> LENGTH: 13
<212> TYPE: PRT
<213> ORGANISM: Influenza A virus

<400> SEQUENCE: 240

Asp Thr Ile Ile Phe Glu Ala Asn Gly Asn Leu Ile Ala
1               5                   10

<210> SEQ ID NO 241
<211> LENGTH: 13
<212> TYPE: PRT
<213> ORGANISM: Influenza A virus

<400> SEQUENCE: 241

Glu Lys Met Asn Thr Gln Phe Thr Ala Val Gly Lys Glu
1               5                   10

<210> SEQ ID NO 242
<211> LENGTH: 13
<212> TYPE: PRT
<213> ORGANISM: Influenza A virus

<400> SEQUENCE: 242

Glu Leu Leu Val Leu Leu Glu Asn Glu Arg Thr Leu Asp
1               5                   10

```
<210> SEQ ID NO 243
<211> LENGTH: 13
<212> TYPE: PRT
<213> ORGANISM: Influenza A virus

<400> SEQUENCE: 243

Ile Ile Phe Glu Ala Asn Gly Asn Leu Ile Ala Pro Trp
1               5                   10

<210> SEQ ID NO 244
<211> LENGTH: 13
<212> TYPE: PRT
<213> ORGANISM: Influenza A virus

<400> SEQUENCE: 244

Pro Trp Tyr Ala Phe Ala Leu Ser Arg Gly Phe Gly Ser
1               5                   10

<210> SEQ ID NO 245
<211> LENGTH: 13
<212> TYPE: PRT
<213> ORGANISM: Influenza A virus

<400> SEQUENCE: 245

Ser Ser Leu Pro Phe Gln Asn Val His Pro Val Thr Ile
1               5                   10

<210> SEQ ID NO 246
<211> LENGTH: 13
<212> TYPE: PRT
<213> ORGANISM: Influenza A virus

<400> SEQUENCE: 246

Ser Val Ile Glu Lys Met Asn Thr Gln Phe Thr Ala Val
1               5                   10

<210> SEQ ID NO 247
<211> LENGTH: 13
<212> TYPE: PRT
<213> ORGANISM: Influenza A virus

<400> SEQUENCE: 247

Thr Gly Leu Arg Asn Ile Pro Ser Ile Gln Ser Arg Gly
1               5                   10

<210> SEQ ID NO 248
<211> LENGTH: 13
<212> TYPE: PRT
<213> ORGANISM: Influenza A virus

<400> SEQUENCE: 248

Val Leu Leu Glu Asn Glu Arg Thr Leu Asp Phe His Asp
1               5                   10

<210> SEQ ID NO 249
<211> LENGTH: 13
<212> TYPE: PRT
<213> ORGANISM: Influenza A virus

<400> SEQUENCE: 249

Tyr Ala Phe Ala Leu Ser Arg Gly Phe Gly Ser Gly Ile
1               5                   10
```

```
<210> SEQ ID NO 250
<211> LENGTH: 9
<212> TYPE: PRT
<213> ORGANISM: Influenza A virus

<400> SEQUENCE: 250

Trp Thr Gly Met Val Asp Gly Trp Tyr
1               5

<210> SEQ ID NO 251
<211> LENGTH: 18
<212> TYPE: PRT
<213> ORGANISM: Influenza A virus

<400> SEQUENCE: 251

Ala Asp Gln Lys Ser Thr Gln Asn Ala Ile Asn Gly Ile Thr Asn Lys
1               5                   10                  15

Val Asn

<210> SEQ ID NO 252
<211> LENGTH: 18
<212> TYPE: PRT
<213> ORGANISM: Influenza A virus

<400> SEQUENCE: 252

Ala Asp Tyr Glu Glu Leu Arg Glu Gln Leu Ser Ser Val Ser Ser Phe
1               5                   10                  15

Glu Arg

<210> SEQ ID NO 253
<211> LENGTH: 18
<212> TYPE: PRT
<213> ORGANISM: Influenza A virus

<400> SEQUENCE: 253

Ala Asn Gly Asn Leu Ile Ala Pro Trp Tyr Ala Phe Ala Leu Ser Arg
1               5                   10                  15

Gly Phe

<210> SEQ ID NO 254
<211> LENGTH: 18
<212> TYPE: PRT
<213> ORGANISM: Influenza A virus

<400> SEQUENCE: 254

Cys Gln Thr Pro Gln Gly Ala Ile Asn Ser Ser Leu Pro Phe Gln Asn
1               5                   10                  15

Val His

<210> SEQ ID NO 255
<211> LENGTH: 18
<212> TYPE: PRT
<213> ORGANISM: Influenza A virus

<400> SEQUENCE: 255

Glu Leu Leu Ile Ser Lys Glu Ser Trp Ser Tyr Ile Val Glu Thr Pro
1               5                   10                  15

Asn Pro

<210> SEQ ID NO 256
<211> LENGTH: 18
<212> TYPE: PRT
```

<213> ORGANISM: Influenza A virus

<400> SEQUENCE: 256

Glu Asn Ala Tyr Val Ser Val Val Ser Ser His Tyr Ser Arg Arg Phe
1 5 10 15

Thr Pro

<210> SEQ ID NO 257
<211> LENGTH: 18
<212> TYPE: PRT
<213> ORGANISM: Influenza A virus

<400> SEQUENCE: 257

Glu Gln Leu Ser Ser Val Ser Ser Phe Glu Arg Phe Glu Ile Phe Pro
1 5 10 15

Lys Glu

<210> SEQ ID NO 258
<211> LENGTH: 18
<212> TYPE: PRT
<213> ORGANISM: Influenza A virus

<400> SEQUENCE: 258

Phe Pro Lys Glu Ser Ser Trp Pro Asn His Thr Val Thr Gly Val Ser
1 5 10 15

Ala Ser

<210> SEQ ID NO 259
<211> LENGTH: 18
<212> TYPE: PRT
<213> ORGANISM: Influenza A virus

<400> SEQUENCE: 259

Gly Asp Thr Ile Ile Phe Glu Ala Asn Gly Asn Leu Ile Ala Pro Trp
1 5 10 15

Tyr Ala

<210> SEQ ID NO 260
<211> LENGTH: 18
<212> TYPE: PRT
<213> ORGANISM: Influenza A virus

<400> SEQUENCE: 260

Gly Lys Asn Gly Leu Tyr Pro Asn Leu Ser Lys Ser Tyr Val Asn Asn
1 5 10 15

Lys Glu

<210> SEQ ID NO 261
<211> LENGTH: 18
<212> TYPE: PRT
<213> ORGANISM: Influenza A virus

<400> SEQUENCE: 261

His Pro Pro Asn Ile Gly Asn Gln Arg Ala Leu Tyr His Thr Glu Asn
1 5 10 15

Ala Tyr

<210> SEQ ID NO 262
<211> LENGTH: 18
<212> TYPE: PRT
<213> ORGANISM: Influenza A virus

```
<400> SEQUENCE: 262

Ile Ala Pro Leu Gln Leu Gly Asn Cys Ser Val Ala Gly Trp Ile Leu
1               5                   10                  15

Gly Asn

<210> SEQ ID NO 263
<211> LENGTH: 18
<212> TYPE: PRT
<213> ORGANISM: Influenza A virus

<400> SEQUENCE: 263

Ile Gly Glu Cys Pro Lys Tyr Val Arg Ser Ala Lys Leu Arg Met Val
1               5                   10                  15

Thr Gly

<210> SEQ ID NO 264
<211> LENGTH: 18
<212> TYPE: PRT
<213> ORGANISM: Influenza A virus

<400> SEQUENCE: 264

Ile Gly Tyr His Ala Asn Asn Ser Thr Asp Thr Val Asp Thr Val Leu
1               5                   10                  15

Glu Lys

<210> SEQ ID NO 265
<211> LENGTH: 18
<212> TYPE: PRT
<213> ORGANISM: Influenza A virus

<400> SEQUENCE: 265

Ile Ile Thr Ser Asn Ala Pro Met Asp Glu Cys Asp Ala Lys Cys Gln
1               5                   10                  15

Thr Pro

<210> SEQ ID NO 266
<211> LENGTH: 18
<212> TYPE: PRT
<213> ORGANISM: Influenza A virus

<400> SEQUENCE: 266

Ile Leu Gly Asn Pro Glu Cys Glu Leu Leu Ile Ser Lys Glu Ser Trp
1               5                   10                  15

Ser Tyr

<210> SEQ ID NO 267
<211> LENGTH: 18
<212> TYPE: PRT
<213> ORGANISM: Influenza A virus

<400> SEQUENCE: 267

Ile Asn Ser Ser Leu Pro Phe Gln Asn Val His Pro Val Thr Ile Gly
1               5                   10                  15

Glu Cys

<210> SEQ ID NO 268
<211> LENGTH: 18
<212> TYPE: PRT
<213> ORGANISM: Influenza A virus
```

<400> SEQUENCE: 268

Lys Leu Cys Leu Leu Lys Gly Ile Ala Pro Leu Gln Leu Gly Asn Cys
1               5                   10                  15

Ser Val

<210> SEQ ID NO 269
<211> LENGTH: 18
<212> TYPE: PRT
<213> ORGANISM: Influenza A virus

<400> SEQUENCE: 269

Lys Arg Pro Lys Val Arg Asp Gln Glu Gly Arg Ile Asn Tyr Tyr Trp
1               5                   10                  15

Thr Leu

<210> SEQ ID NO 270
<211> LENGTH: 18
<212> TYPE: PRT
<213> ORGANISM: Influenza A virus

<400> SEQUENCE: 270

Leu Glu Asp Ser His Asn Gly Lys Leu Cys Leu Leu Lys Gly Ile Ala
1               5                   10                  15

Pro Leu

<210> SEQ ID NO 271
<211> LENGTH: 18
<212> TYPE: PRT
<213> ORGANISM: Influenza A virus

<400> SEQUENCE: 271

Leu Leu Cys Thr Phe Thr Ala Thr Tyr Ala Asp Thr Ile Cys Ile Gly
1               5                   10                  15

Tyr His

<210> SEQ ID NO 272
<211> LENGTH: 18
<212> TYPE: PRT
<213> ORGANISM: Influenza A virus

<400> SEQUENCE: 272

Leu Val Leu Leu Glu Asn Glu Arg Thr Leu Asp Phe His Asp Ser Asn
1               5                   10                  15

Val Lys

<210> SEQ ID NO 273
<211> LENGTH: 18
<212> TYPE: PRT
<213> ORGANISM: Influenza A virus

<400> SEQUENCE: 273

Leu Val Leu Leu Val Ser Leu Gly Ala Ile Ser Phe Trp Met Cys Ser
1               5                   10                  15

Asn Gly

<210> SEQ ID NO 274
<211> LENGTH: 18
<212> TYPE: PRT
<213> ORGANISM: Influenza A virus

<400> SEQUENCE: 274

Met Asp Glu Cys Asp Ala Lys Cys Gln Thr Pro Gln Gly Ala Ile Asn
1               5                   10                  15

Ser Ser

<210> SEQ ID NO 275
<211> LENGTH: 18
<212> TYPE: PRT
<213> ORGANISM: Influenza A virus

<400> SEQUENCE: 275

Met Lys Ala Lys Leu Leu Val Leu Leu Cys Thr Phe Thr Ala Thr Tyr
1               5                   10                  15

Ala Asp

<210> SEQ ID NO 276
<211> LENGTH: 18
<212> TYPE: PRT
<213> ORGANISM: Influenza A virus

<400> SEQUENCE: 276

Met Val Thr Gly Leu Arg Asn Ile Pro Ser Ile Gln Ser Arg Gly Leu
1               5                   10                  15

Phe Gly

<210> SEQ ID NO 277
<211> LENGTH: 18
<212> TYPE: PRT
<213> ORGANISM: Influenza A virus

<400> SEQUENCE: 277

Asn Cys Ser Val Ala Gly Trp Ile Leu Gly Asn Pro Glu Cys Glu Leu
1               5                   10                  15

Leu Ile

<210> SEQ ID NO 278
<211> LENGTH: 18
<212> TYPE: PRT
<213> ORGANISM: Influenza A virus

<400> SEQUENCE: 278

Asn Gly Lys Ser Ser Phe Tyr Arg Asn Leu Leu Trp Leu Thr Gly Lys
1               5                   10                  15

Asn Gly

<210> SEQ ID NO 279
<211> LENGTH: 18
<212> TYPE: PRT
<213> ORGANISM: Influenza A virus

<400> SEQUENCE: 279

Asn Lys Val Asn Ser Val Ile Glu Lys Met Asn Thr Gln Phe Thr Ala
1               5                   10                  15

Val Gly

<210> SEQ ID NO 280
<211> LENGTH: 18
<212> TYPE: PRT
<213> ORGANISM: Influenza A virus

<400> SEQUENCE: 280

Asn Leu Ser Lys Ser Tyr Val Asn Asn Lys Glu Lys Glu Val Leu Val
1               5                   10                  15

Leu Trp

<210> SEQ ID NO 281
<211> LENGTH: 18
<212> TYPE: PRT
<213> ORGANISM: Influenza A virus

<400> SEQUENCE: 281

Asn Asn Lys Glu Lys Glu Val Leu Val Leu Trp Gly Val His His Pro
1               5                   10                  15

Pro Asn

<210> SEQ ID NO 282
<211> LENGTH: 18
<212> TYPE: PRT
<213> ORGANISM: Influenza A virus

<400> SEQUENCE: 282

Pro Asn His Thr Val Thr Gly Val Ser Ala Ser Cys Ser His Asn Gly
1               5                   10                  15

Lys Ser

<210> SEQ ID NO 283
<211> LENGTH: 18
<212> TYPE: PRT
<213> ORGANISM: Influenza A virus

<400> SEQUENCE: 283

Pro Trp Tyr Ala Phe Ala Leu Ser Arg Gly Phe Gly Ser Gly Ile Ile
1               5                   10                  15

Thr Ser

<210> SEQ ID NO 284
<211> LENGTH: 18
<212> TYPE: PRT
<213> ORGANISM: Influenza A virus

<400> SEQUENCE: 284

Gln Glu Gly Arg Ile Asn Tyr Tyr Trp Thr Leu Leu Glu Pro Gly Asp
1               5                   10                  15

Thr Ile

<210> SEQ ID NO 285
<211> LENGTH: 18
<212> TYPE: PRT
<213> ORGANISM: Influenza A virus

<400> SEQUENCE: 285

Gln Asn Val His Pro Val Thr Ile Gly Glu Cys Pro Lys Tyr Val Arg
1               5                   10                  15

Ser Ala

<210> SEQ ID NO 286
<211> LENGTH: 18
<212> TYPE: PRT
<213> ORGANISM: Influenza A virus

<400> SEQUENCE: 286

Gln Arg Ala Leu Tyr His Thr Glu Asn Ala Tyr Val Ser Val Val Ser

<210> SEQ ID NO 287
<211> LENGTH: 18
<212> TYPE: PRT
<213> ORGANISM: Influenza A virus

<400> SEQUENCE: 287

Arg Phe Thr Pro Glu Ile Ala Lys Arg Pro Lys Val Arg Asp Gln Glu
1               5                   10                  15

Gly Arg

<210> SEQ ID NO 288
<211> LENGTH: 18
<212> TYPE: PRT
<213> ORGANISM: Influenza A virus

<400> SEQUENCE: 288

Arg Asn Leu Leu Trp Leu Thr Gly Lys Asn Gly Leu Tyr Pro Asn Leu
1               5                   10                  15

Ser Lys

<210> SEQ ID NO 289
<211> LENGTH: 18
<212> TYPE: PRT
<213> ORGANISM: Influenza A virus

<400> SEQUENCE: 289

Ser Phe Glu Arg Phe Glu Ile Phe Pro Lys Glu Ser Ser Trp Pro Asn
1               5                   10                  15

His Thr

<210> SEQ ID NO 290
<211> LENGTH: 18
<212> TYPE: PRT
<213> ORGANISM: Influenza A virus

<400> SEQUENCE: 290

Ser Arg Gly Phe Gly Ser Gly Ile Ile Thr Ser Asn Ala Pro Met Asp
1               5                   10                  15

Glu Cys

<210> SEQ ID NO 291
<211> LENGTH: 18
<212> TYPE: PRT
<213> ORGANISM: Influenza A virus

<400> SEQUENCE: 291

Ser Thr Asp Thr Val Asp Thr Val Leu Glu Lys Asn Val Thr Val Thr
1               5                   10                  15

His Ser

<210> SEQ ID NO 292
<211> LENGTH: 18
<212> TYPE: PRT
<213> ORGANISM: Influenza A virus

<400> SEQUENCE: 292

Ser Trp Ser Tyr Ile Val Glu Thr Pro Asn Pro Glu Asn Gly Thr Cys
1               5                   10                  15

Tyr Pro

<210> SEQ ID NO 293
<211> LENGTH: 18
<212> TYPE: PRT
<213> ORGANISM: Influenza A virus

<400> SEQUENCE: 293

Thr Cys Tyr Pro Gly Tyr Phe Ala Asp Tyr Glu Glu Leu Arg Glu Gln
1               5                   10                  15

Leu Ser

<210> SEQ ID NO 294
<211> LENGTH: 18
<212> TYPE: PRT
<213> ORGANISM: Influenza A virus

<400> SEQUENCE: 294

Thr Gly Met Val Asp Gly Trp Tyr Gly Tyr His His Gln Asn Glu Gln
1               5                   10                  15

Gly Ser

<210> SEQ ID NO 295
<211> LENGTH: 18
<212> TYPE: PRT
<213> ORGANISM: Influenza A virus

<400> SEQUENCE: 295

Thr Pro Asn Pro Glu Asn Gly Thr Cys Tyr Pro Gly Tyr Phe Ala Asp
1               5                   10                  15

Tyr Glu

<210> SEQ ID NO 296
<211> LENGTH: 18
<212> TYPE: PRT
<213> ORGANISM: Influenza A virus

<400> SEQUENCE: 296

Thr Tyr Ala Asp Thr Ile Cys Ile Gly Tyr His Ala Asn Asn Ser Thr
1               5                   10                  15

Asp Thr

<210> SEQ ID NO 297
<211> LENGTH: 18
<212> TYPE: PRT
<213> ORGANISM: Influenza A virus

<400> SEQUENCE: 297

Val Leu Glu Lys Asn Val Thr Val Thr His Ser Val Asn Leu Leu Glu
1               5                   10                  15

Asp Ser

<210> SEQ ID NO 298
<211> LENGTH: 18
<212> TYPE: PRT
<213> ORGANISM: Influenza A virus

<400> SEQUENCE: 298

Val Arg Ser Ala Lys Leu Arg Met Val Thr Gly Leu Arg Asn Ile Pro
1               5                   10                  15

Ser Ile

<210> SEQ ID NO 299
<211> LENGTH: 18
<212> TYPE: PRT
<213> ORGANISM: Influenza A virus

<400> SEQUENCE: 299

Val Ser Ala Ser Cys Ser His Asn Gly Lys Ser Ser Phe Tyr Arg Asn
1               5                   10                  15

Leu Leu

<210> SEQ ID NO 300
<211> LENGTH: 18
<212> TYPE: PRT
<213> ORGANISM: Influenza A virus

<400> SEQUENCE: 300

Val Ser Ser His Tyr Ser Arg Arg Phe Thr Pro Glu Ile Ala Lys Arg
1               5                   10                  15

Pro Lys

<210> SEQ ID NO 301
<211> LENGTH: 18
<212> TYPE: PRT
<213> ORGANISM: Influenza A virus

<400> SEQUENCE: 301

Val Thr His Ser Val Asn Leu Leu Glu Asp Ser His Asn Gly Lys Leu
1               5                   10                  15

Cys Leu

<210> SEQ ID NO 302
<211> LENGTH: 18
<212> TYPE: PRT
<213> ORGANISM: Influenza A virus

<400> SEQUENCE: 302

Trp Thr Tyr Asn Ala Glu Leu Leu Val Leu Leu Glu Asn Glu Arg Thr
1               5                   10                  15

Leu Asp

<210> SEQ ID NO 303
<211> LENGTH: 18
<212> TYPE: PRT
<213> ORGANISM: Influenza A virus

<400> SEQUENCE: 303

Tyr His Lys Cys Asn Asn Glu Cys Met Glu Ser Val Lys Asn Gly Thr
1               5                   10                  15

Tyr Asp

<210> SEQ ID NO 304
<211> LENGTH: 18
<212> TYPE: PRT
<213> ORGANISM: Influenza A virus

<400> SEQUENCE: 304

Tyr Trp Thr Leu Leu Glu Pro Gly Asp Thr Ile Ile Phe Glu Ala Asn
1               5                   10                  15

Gly Asn

<210> SEQ ID NO 305
<211> LENGTH: 14
<212> TYPE: PRT
<213> ORGANISM: Influenza A virus

<400> SEQUENCE: 305

Gly Leu Phe Gly Ala Ile Ala Gly Phe Ile Glu Gly Gly Trp
1               5                   10

<210> SEQ ID NO 306
<211> LENGTH: 15
<212> TYPE: PRT
<213> ORGANISM: Influenza A virus

<400> SEQUENCE: 306

Gly Asn Leu Ile Ala Pro Trp Tyr Ala Phe Ala Leu Ser Arg Gly
1               5                   10                  15

<210> SEQ ID NO 307
<211> LENGTH: 8
<212> TYPE: PRT
<213> ORGANISM: Influenza A virus

<400> SEQUENCE: 307

Arg Phe Thr Pro Glu Ile Ala Lys
1               5

<210> SEQ ID NO 308
<211> LENGTH: 15
<212> TYPE: PRT
<213> ORGANISM: Influenza A virus

<400> SEQUENCE: 308

Asp Gly Phe Leu Asp Ile Trp Thr Tyr Asn Ala Glu Leu Leu Val
1               5                   10                  15

<210> SEQ ID NO 309
<211> LENGTH: 13
<212> TYPE: PRT
<213> ORGANISM: Influenza A virus

<400> SEQUENCE: 309

Glu Gln Leu Ser Ser Val Ser Ser Phe Glu Arg Phe Glu
1               5                   10

<210> SEQ ID NO 310
<211> LENGTH: 13
<212> TYPE: PRT
<213> ORGANISM: Influenza A virus

<400> SEQUENCE: 310

Glu Arg Phe Glu Ile Phe Pro Lys Glu Ser Ser Trp Pro
1               5                   10

<210> SEQ ID NO 311
<211> LENGTH: 12
<212> TYPE: PRT
<213> ORGANISM: Influenza A virus

<400> SEQUENCE: 311

Lys Tyr Val Arg Ser Ala Lys Leu Arg Met Val Thr
1               5                   10

<210> SEQ ID NO 312
<211> LENGTH: 15
<212> TYPE: PRT
<213> ORGANISM: Influenza A virus

<400> SEQUENCE: 312

Arg Ala Leu Tyr His Thr Glu Asn Ala Tyr Val Ser Val Val Ser
1 5 10 15

<210> SEQ ID NO 313
<211> LENGTH: 14
<212> TYPE: PRT
<213> ORGANISM: Influenza A virus

<400> SEQUENCE: 313

Ser Ser Phe Glu Arg Phe Glu Ile Phe Pro Lys Glu Ser Ser
1 5 10

<210> SEQ ID NO 314
<211> LENGTH: 9
<212> TYPE: PRT
<213> ORGANISM: Influenza A virus

<400> SEQUENCE: 314

His Ala Gly Ala Lys Ser Phe Tyr Lys
1 5

<210> SEQ ID NO 315
<211> LENGTH: 8
<212> TYPE: PRT
<213> ORGANISM: Influenza A virus

<400> SEQUENCE: 315

Lys Leu Arg Gly Val Ala Pro Leu
1 5

<210> SEQ ID NO 316
<211> LENGTH: 9
<212> TYPE: PRT
<213> ORGANISM: Influenza A virus

<400> SEQUENCE: 316

Leu Pro Phe Gln Asn Ile His Pro Ile
1 5

<210> SEQ ID NO 317
<211> LENGTH: 11
<212> TYPE: PRT
<213> ORGANISM: Influenza A virus

<400> SEQUENCE: 317

Leu Pro Phe Gln Asn Ile His Pro Ile Thr Ile
1 5 10

<210> SEQ ID NO 318
<211> LENGTH: 9
<212> TYPE: PRT
<213> ORGANISM: Influenza A virus

<400> SEQUENCE: 318

Leu Ser Thr Ala Ser Ser Trp Ser Tyr
1 5

<210> SEQ ID NO 319
<211> LENGTH: 17

```
<212> TYPE: PRT
<213> ORGANISM: Influenza A virus

<400> SEQUENCE: 319

Glu Leu Leu Val Leu Leu Glu Asn Glu Arg Thr Leu Asp Phe His Asp
1               5                   10                  15
Ser

<210> SEQ ID NO 320
<211> LENGTH: 17
<212> TYPE: PRT
<213> ORGANISM: Influenza A virus

<400> SEQUENCE: 320

Glu Leu Leu Val Leu Leu Glu Asn Glu Arg Thr Leu Asp Tyr His Asp
1               5                   10                  15
Ser

<210> SEQ ID NO 321
<211> LENGTH: 17
<212> TYPE: PRT
<213> ORGANISM: Influenza A virus

<400> SEQUENCE: 321

Ile Ile Phe Glu Ala Asn Gly Asn Leu Ile Ala Pro Trp Tyr Ala Phe
1               5                   10                  15
Ala

<210> SEQ ID NO 322
<211> LENGTH: 17
<212> TYPE: PRT
<213> ORGANISM: Influenza A virus

<400> SEQUENCE: 322

Ile Thr Phe Glu Ala Thr Gly Asn Leu Val Val Pro Arg Tyr Ala Phe
1               5                   10                  15
Ala

<210> SEQ ID NO 323
<211> LENGTH: 16
<212> TYPE: PRT
<213> ORGANISM: Influenza A virus

<400> SEQUENCE: 323

Gln Gln Ser Leu Tyr Gln Asn Ala Asp Thr Tyr Val Phe Val Gly Ser
1               5                   10                  15

<210> SEQ ID NO 324
<211> LENGTH: 16
<212> TYPE: PRT
<213> ORGANISM: Influenza A virus

<400> SEQUENCE: 324

Gln Arg Ala Leu Tyr His Thr Glu Asn Ala Tyr Val Ser Val Ser Ser
1               5                   10                  15

<210> SEQ ID NO 325
<211> LENGTH: 16
<212> TYPE: PRT
<213> ORGANISM: Influenza A virus

<400> SEQUENCE: 325
```

Ser Val Ile Glu Lys Met Asn Thr Gln Phe Thr Ala Val Gly Lys Glu
1               5                   10                  15

<210> SEQ ID NO 326
<211> LENGTH: 19
<212> TYPE: PRT
<213> ORGANISM: Influenza A virus

<400> SEQUENCE: 326

Thr Gly Leu Arg Asn Ile Pro Ser Ile Gln Ser Arg Gly Leu Phe Gly
1               5                   10                  15

Ala Ile Ala

<210> SEQ ID NO 327
<211> LENGTH: 19
<212> TYPE: PRT
<213> ORGANISM: Influenza A virus

<400> SEQUENCE: 327

Ala Leu Tyr His Thr Glu Asn Ala Tyr Val Ser Val Val Ser Ser His
1               5                   10                  15

Tyr Ser Arg

<210> SEQ ID NO 328
<211> LENGTH: 17
<212> TYPE: PRT
<213> ORGANISM: Influenza A virus

<400> SEQUENCE: 328

Cys Phe Glu Phe Tyr His Lys Cys Asn Asn Glu Cys Met Glu Ser Val
1               5                   10                  15

Lys

<210> SEQ ID NO 329
<211> LENGTH: 17
<212> TYPE: PRT
<213> ORGANISM: Influenza A virus

<400> SEQUENCE: 329

Asp Asp Gly Phe Leu Asp Ile Trp Thr Tyr Asn Ala Glu Leu Leu Val
1               5                   10                  15

Leu

<210> SEQ ID NO 330
<211> LENGTH: 17
<212> TYPE: PRT
<213> ORGANISM: Influenza A virus

<400> SEQUENCE: 330

Asp Gln Glu Gly Arg Ile Asn Tyr Tyr Trp Thr Leu Leu Glu Pro Gly
1               5                   10                  15

Asp

<210> SEQ ID NO 331
<211> LENGTH: 17
<212> TYPE: PRT
<213> ORGANISM: Influenza A virus

<400> SEQUENCE: 331

Asp Gln Lys Ser Thr Gln Asn Ala Ile Asn Gly Ile Thr Asn Lys Val
1               5                   10                  15

Asn

<210> SEQ ID NO 332
<211> LENGTH: 17
<212> TYPE: PRT
<213> ORGANISM: Influenza A virus

<400> SEQUENCE: 332

Glu Ile Phe Pro Lys Glu Ser Ser Trp Pro Asn His Thr Val Thr Gly
1               5                   10                  15

Val

<210> SEQ ID NO 333
<211> LENGTH: 17
<212> TYPE: PRT
<213> ORGANISM: Influenza A virus

<400> SEQUENCE: 333

Glu Asn Glu Arg Thr Leu Asp Phe His Asp Ser Asn Val Lys Asn Leu
1               5                   10                  15

Tyr

<210> SEQ ID NO 334
<211> LENGTH: 17
<212> TYPE: PRT
<213> ORGANISM: Influenza A virus

<400> SEQUENCE: 334

Glu Gln Leu Ser Ser Val Ser Ser Phe Glu Arg Phe Glu Ile Phe Pro
1               5                   10                  15

Lys

<210> SEQ ID NO 335
<211> LENGTH: 17
<212> TYPE: PRT
<213> ORGANISM: Influenza A virus

<400> SEQUENCE: 335

Glu Ser Met Gly Val Tyr Gln Ile Leu Ala Ile Tyr Ser Thr Val Ala
1               5                   10                  15

Ser

<210> SEQ ID NO 336
<211> LENGTH: 17
<212> TYPE: PRT
<213> ORGANISM: Influenza A virus

<400> SEQUENCE: 336

Phe Ile Glu Gly Gly Trp Thr Gly Met Val Asp Gly Trp Tyr Gly Tyr
1               5                   10                  15

His

<210> SEQ ID NO 337
<211> LENGTH: 17
<212> TYPE: PRT
<213> ORGANISM: Influenza A virus

<400> SEQUENCE: 337

Gly Lys Glu Phe Asn Lys Leu Glu Arg Arg Met Glu Asn Leu Asn Lys
1               5                   10                  15

Lys

<210> SEQ ID NO 338
<211> LENGTH: 17
<212> TYPE: PRT
<213> ORGANISM: Influenza A virus

<400> SEQUENCE: 338

Gly Lys Ser Ser Phe Tyr Arg Asn Leu Leu Trp Leu Thr Gly Lys Asn
1               5                   10                  15

Gly

<210> SEQ ID NO 339
<211> LENGTH: 17
<212> TYPE: PRT
<213> ORGANISM: Influenza A virus

<400> SEQUENCE: 339

Gly Asn Leu Ile Ala Pro Trp Tyr Ala Phe Ala Leu Ser Arg Gly Phe
1               5                   10                  15

Gly

<210> SEQ ID NO 340
<211> LENGTH: 17
<212> TYPE: PRT
<213> ORGANISM: Influenza A virus

<400> SEQUENCE: 340

His Tyr Ser Arg Arg Phe Thr Pro Glu Ile Ala Lys Arg Pro Lys Val
1               5                   10                  15

Arg

<210> SEQ ID NO 341
<211> LENGTH: 17
<212> TYPE: PRT
<213> ORGANISM: Influenza A virus

<400> SEQUENCE: 341

Ile Gly Glu Cys Pro Lys Tyr Val Arg Ser Ala Lys Leu Arg Met Val
1               5                   10                  15

Thr

<210> SEQ ID NO 342
<211> LENGTH: 17
<212> TYPE: PRT
<213> ORGANISM: Influenza A virus

<400> SEQUENCE: 342

Ile Leu Gly Asn Pro Glu Cys Glu Leu Leu Ile Ser Lys Glu Ser Trp
1               5                   10                  15

Ser

<210> SEQ ID NO 343
<211> LENGTH: 17
<212> TYPE: PRT
<213> ORGANISM: Influenza A virus

<400> SEQUENCE: 343

Ile Gln Ser Arg Gly Leu Phe Gly Ala Ile Ala Gly Phe Ile Glu Gly
1               5                   10                  15

Gly

<210> SEQ ID NO 344
<211> LENGTH: 17
<212> TYPE: PRT
<213> ORGANISM: Influenza A virus

<400> SEQUENCE: 344

Ile Trp Thr Tyr Asn Ala Glu Leu Leu Val Leu Leu Glu Asn Glu Arg
1 5 10 15

Thr

<210> SEQ ID NO 345
<211> LENGTH: 17
<212> TYPE: PRT
<213> ORGANISM: Influenza A virus

<400> SEQUENCE: 345

Lys Glu Ser Trp Ser Tyr Ile Val Glu Thr Pro Asn Pro Glu Asn Gly
1 5 10 15

Thr

<210> SEQ ID NO 346
<211> LENGTH: 17
<212> TYPE: PRT
<213> ORGANISM: Influenza A virus

<400> SEQUENCE: 346

Lys Leu Asn Arg Glu Lys Ile Asp Gly Val Lys Leu Glu Ser Met Gly
1 5 10 15

Val

<210> SEQ ID NO 347
<211> LENGTH: 16
<212> TYPE: PRT
<213> ORGANISM: Influenza A virus

<400> SEQUENCE: 347

Lys Val Lys Ser Gln Leu Lys Asn Asn Ala Lys Glu Ile Gly Asn Gly
1 5 10 15

<210> SEQ ID NO 348
<211> LENGTH: 17
<212> TYPE: PRT
<213> ORGANISM: Influenza A virus

<400> SEQUENCE: 348

Leu Glu Lys Asn Val Thr Val Thr His Ser Val Asn Leu Leu Glu Asp
1 5 10 15

Ser

<210> SEQ ID NO 349
<211> LENGTH: 17
<212> TYPE: PRT
<213> ORGANISM: Influenza A virus

<400> SEQUENCE: 349

Leu Glu Pro Gly Asp Thr Ile Ile Phe Glu Ala Asn Gly Asn Leu Ile
1 5 10 15

Ala

<210> SEQ ID NO 350
<211> LENGTH: 17

```
<212> TYPE: PRT
<213> ORGANISM: Influenza A virus

<400> SEQUENCE: 350

Leu Glu Arg Arg Met Glu Asn Leu Asn Lys Lys Val Asp Asp Gly Phe
1               5                   10                  15

Leu

<210> SEQ ID NO 351
<211> LENGTH: 17
<212> TYPE: PRT
<213> ORGANISM: Influenza A virus

<400> SEQUENCE: 351

Leu Arg Met Val Thr Gly Leu Arg Asn Ile Pro Ser Ile Gln Ser Arg
1               5                   10                  15

Gly

<210> SEQ ID NO 352
<211> LENGTH: 17
<212> TYPE: PRT
<213> ORGANISM: Influenza A virus

<400> SEQUENCE: 352

Leu Arg Asn Ile Pro Ser Ile Gln Ser Arg Gly Leu Phe Gly Ala Ile
1               5                   10                  15

Ala

<210> SEQ ID NO 353
<211> LENGTH: 17
<212> TYPE: PRT
<213> ORGANISM: Influenza A virus

<400> SEQUENCE: 353

Leu Trp Gly Val His His Pro Pro Asn Ile Gly Asn Gln Arg Ala Leu
1               5                   10                  15

Tyr

<210> SEQ ID NO 354
<211> LENGTH: 17
<212> TYPE: PRT
<213> ORGANISM: Influenza A virus

<400> SEQUENCE: 354

Asn Ala Ile Asn Gly Ile Thr Asn Lys Val Asn Ser Val Ile Glu Lys
1               5                   10                  15

Met

<210> SEQ ID NO 355
<211> LENGTH: 17
<212> TYPE: PRT
<213> ORGANISM: Influenza A virus

<400> SEQUENCE: 355

Asn Leu Leu Glu Asp Ser His Asn Gly Lys Leu Cys Leu Leu Lys Gly
1               5                   10                  15

Ile

<210> SEQ ID NO 356
<211> LENGTH: 17
<212> TYPE: PRT
```

<213> ORGANISM: Influenza A virus

<400> SEQUENCE: 356

Asn Gln Arg Ala Leu Tyr His Thr Glu Asn Ala Tyr Val Ser Val Val
1 5 10 15

Ser

<210> SEQ ID NO 357
<211> LENGTH: 17
<212> TYPE: PRT
<213> ORGANISM: Influenza A virus

<400> SEQUENCE: 357

Asn Val His Pro Val Thr Ile Gly Glu Cys Pro Lys Tyr Val Arg Ser
1 5 10 15

Ala

<210> SEQ ID NO 358
<211> LENGTH: 17
<212> TYPE: PRT
<213> ORGANISM: Influenza A virus

<400> SEQUENCE: 358

Pro Pro Asn Ile Gly Asn Gln Arg Ala Leu Tyr His Thr Glu Asn Ala
1 5 10 15

Tyr

<210> SEQ ID NO 359
<211> LENGTH: 17
<212> TYPE: PRT
<213> ORGANISM: Influenza A virus

<400> SEQUENCE: 359

Arg Asn Leu Leu Trp Leu Thr Gly Lys Asn Gly Leu Tyr Pro Asn Leu
1 5 10 15

Ser

<210> SEQ ID NO 360
<211> LENGTH: 16
<212> TYPE: PRT
<213> ORGANISM: Influenza A virus

<400> SEQUENCE: 360

Ser Phe Trp Met Cys Ser Asn Gly Ser Leu Gln Cys Arg Ile Cys Ile
1 5 10 15

<210> SEQ ID NO 361
<211> LENGTH: 17
<212> TYPE: PRT
<213> ORGANISM: Influenza A virus

<400> SEQUENCE: 361

Ser Gly Tyr Ala Ala Asp Gln Lys Ser Thr Gln Asn Ala Ile Asn Gly
1 5 10 15

Ile

<210> SEQ ID NO 362
<211> LENGTH: 16
<212> TYPE: PRT
<213> ORGANISM: Influenza A virus

<400> SEQUENCE: 362

Ser Leu Gly Ala Ile Ser Phe Trp Met Cys Ser Asn Gly Ser Leu Gln
1               5                   10                  15

<210> SEQ ID NO 363
<211> LENGTH: 17
<212> TYPE: PRT
<213> ORGANISM: Influenza A virus

<400> SEQUENCE: 363

Ser Ser Phe Glu Arg Phe Glu Ile Phe Pro Lys Glu Ser Ser Trp Pro
1               5                   10                  15

Asn

<210> SEQ ID NO 364
<211> LENGTH: 17
<212> TYPE: PRT
<213> ORGANISM: Influenza A virus

<400> SEQUENCE: 364

Ser Ser Leu Pro Phe Gln Asn Val His Pro Val Thr Ile Gly Glu Cys
1               5                   10                  15

Pro

<210> SEQ ID NO 365
<211> LENGTH: 17
<212> TYPE: PRT
<213> ORGANISM: Influenza A virus

<400> SEQUENCE: 365

Ser Ser Trp Pro Asn His Thr Val Thr Gly Val Ser Ala Ser Cys Ser
1               5                   10                  15

His

<210> SEQ ID NO 366
<211> LENGTH: 17
<212> TYPE: PRT
<213> ORGANISM: Influenza A virus

<400> SEQUENCE: 366

Thr Asn Lys Val Asn Ser Val Ile Glu Lys Met Asn Thr Gln Phe Thr
1               5                   10                  15

Ala

<210> SEQ ID NO 367
<211> LENGTH: 17
<212> TYPE: PRT
<213> ORGANISM: Influenza A virus

<400> SEQUENCE: 367

Thr Gln Phe Thr Ala Val Gly Lys Glu Phe Asn Lys Leu Glu Arg Arg
1               5                   10                  15

Met

<210> SEQ ID NO 368
<211> LENGTH: 17
<212> TYPE: PRT
<213> ORGANISM: Influenza A virus

<400> SEQUENCE: 368

Thr Val Thr Gly Val Ser Ala Ser Cys Ser His Asn Gly Lys Ser Ser
1               5                   10                  15

Phe

<210> SEQ ID NO 369
<211> LENGTH: 17
<212> TYPE: PRT
<213> ORGANISM: Influenza A virus

<400> SEQUENCE: 369

Val Ile Glu Lys Met Asn Thr Gln Phe Thr Ala Val Gly Lys Glu Phe
1               5                   10                  15

Asn

<210> SEQ ID NO 370
<211> LENGTH: 17
<212> TYPE: PRT
<213> ORGANISM: Influenza A virus

<400> SEQUENCE: 370

Val Lys Asn Leu Tyr Glu Lys Val Lys Ser Gln Leu Lys Asn Asn Ala
1               5                   10                  15

Lys

<210> SEQ ID NO 371
<211> LENGTH: 16
<212> TYPE: PRT
<213> ORGANISM: Influenza A virus

<400> SEQUENCE: 371

Val Thr His Ser Val Asn Leu Leu Glu Asp Ser His Asn Gly Lys Leu
1 5 10 15

<210> SEQ ID NO 372
<211> LENGTH: 17
<212> TYPE: PRT
<213> ORGANISM: Influenza A virus

<400> SEQUENCE: 372

Tyr Gln Ile Leu Ala Ile Tyr Ser Thr Val Ala Ser Ser Leu Val Leu
1 5 10 15

Leu

<210> SEQ ID NO 373
<211> LENGTH: 17
<212> TYPE: PRT
<213> ORGANISM: Influenza A virus

<400> SEQUENCE: 373

Tyr Val Arg Ser Ala Lys Leu Arg Met Val Thr Gly Leu Arg Asn Ile
1 5 10 15

Pro

<210> SEQ ID NO 374
<211> LENGTH: 13
<212> TYPE: PRT
<213> ORGANISM: Influenza A virus

<400> SEQUENCE: 374

Glu Phe Tyr His Lys Cys Asn Asn Glu Cys Met Glu Ser
1 5 10

<210> SEQ ID NO 375

<211> LENGTH: 14
<212> TYPE: PRT
<213> ORGANISM: Influenza A virus

<400> SEQUENCE: 375

Thr Asn Lys Val Asn Ser Val Ile Glu Lys Met Asn Thr Gln
1               5                   10

<210> SEQ ID NO 376
<211> LENGTH: 4
<212> TYPE: PRT
<213> ORGANISM: Influenza A virus

<400> SEQUENCE: 376

Leu Val Lys Lys
1

<210> SEQ ID NO 377
<211> LENGTH: 20
<212> TYPE: PRT
<213> ORGANISM: Influenza A virus

<400> SEQUENCE: 377

Ile Asn Ser Ser Leu Pro Tyr Gln Asn Ile His Pro Val Thr Ile Gly
1               5                   10                  15

Glu Cys Pro Lys
            20

<210> SEQ ID NO 378
<211> LENGTH: 20
<212> TYPE: PRT
<213> ORGANISM: Influenza A virus

<400> SEQUENCE: 378

Glu Leu Leu Val Leu Leu Glu Asn Glu Arg Thr Leu Asp Tyr His Asp
1               5                   10                  15

Ser Asn Val Lys
            20

<210> SEQ ID NO 379
<211> LENGTH: 20
<212> TYPE: PRT
<213> ORGANISM: Influenza A virus

<400> SEQUENCE: 379

Ile Asp Tyr Glu Glu Leu Arg Glu Gln Leu Ser Ser Val Ser Ser Phe
1               5                   10                  15

Glu Arg Phe Glu
            20

<210> SEQ ID NO 380
<211> LENGTH: 23
<212> TYPE: PRT
<213> ORGANISM: Influenza A virus

<400> SEQUENCE: 380

Ile Tyr Gln Ile Leu Ala Ile Tyr Ser Thr Val Ala Ser Ser Leu Val
1               5                   10                  15

Leu Val Val Ser Leu Gly Ala
            20

<210> SEQ ID NO 381
<211> LENGTH: 20

-continued

```
<212> TYPE: PRT
<213> ORGANISM: Influenza A virus

<400> SEQUENCE: 381

Asn Leu Tyr Glu Lys Val Arg Ser Gln Leu Lys Asn Asn Ala Lys Glu
1               5                   10                  15

Ile Gly Asn Gly
            20

<210> SEQ ID NO 382
<211> LENGTH: 18
<212> TYPE: PRT
<213> ORGANISM: Influenza A virus

<400> SEQUENCE: 382

Val Leu Glu Lys Asn Val Thr Val Thr His Ser Val Asn Leu Leu Glu
1               5                   10                  15

Asp Lys

<210> SEQ ID NO 383
<211> LENGTH: 18
<212> TYPE: PRT
<213> ORGANISM: Influenza A virus

<400> SEQUENCE: 383

Val Thr His Ser Val Asn Leu Leu Glu Asp Lys His Asn Gly Lys Leu
1               5                   10                  15

Cys Lys

<210> SEQ ID NO 384
<211> LENGTH: 18
<212> TYPE: PRT
<213> ORGANISM: Influenza A virus

<400> SEQUENCE: 384

His Pro Pro Asn Ile Gly Asp Gln Arg Ala Leu Tyr His Thr Glu Asn
1               5                   10                  15

Ala Tyr

<210> SEQ ID NO 385
<211> LENGTH: 18
<212> TYPE: PRT
<213> ORGANISM: Influenza A virus

<400> SEQUENCE: 385

Leu Val Leu Trp Gly Val His His Pro Pro Asn Ile Gly Asp Gln Arg
1               5                   10                  15

Ala Leu

<210> SEQ ID NO 386
<211> LENGTH: 15
<212> TYPE: PRT
<213> ORGANISM: Influenza A virus

<400> SEQUENCE: 386

Ala Gly Ser Gly Ile Ile Ile Ser Asp Thr Pro Val His Asp Cys
1               5                   10                  15

<210> SEQ ID NO 387
<211> LENGTH: 15
<212> TYPE: PRT
<213> ORGANISM: Influenza A virus
```

<400> SEQUENCE: 387

Ala Ile Asp Glu Ile Thr Asn Lys Val Asn Ser Val Ile Glu Lys
1               5                   10                  15

<210> SEQ ID NO 388
<211> LENGTH: 15
<212> TYPE: PRT
<213> ORGANISM: Influenza A virus

<400> SEQUENCE: 388

Ala Lys Ser Phe Tyr Lys Asn Leu Ile Trp Leu Val Lys Lys Gly
1               5                   10                  15

<210> SEQ ID NO 389
<211> LENGTH: 15
<212> TYPE: PRT
<213> ORGANISM: Influenza A virus

<400> SEQUENCE: 389

Cys Asp Asn Thr Cys Met Glu Ser Val Lys Asn Gly Thr Tyr Asp
1               5                   10                  15

<210> SEQ ID NO 390
<211> LENGTH: 14
<212> TYPE: PRT
<213> ORGANISM: Influenza A virus

<400> SEQUENCE: 390

Cys Lys Leu Arg Gly Val Ala Pro Leu His Leu Gly Lys Cys
1               5                   10

<210> SEQ ID NO 391
<211> LENGTH: 15
<212> TYPE: PRT
<213> ORGANISM: Influenza A virus

<400> SEQUENCE: 391

Asp Thr Leu Cys Ile Gly Tyr His Ala Asn Asn Ser Thr Asp Thr
1               5                   10                  15

<210> SEQ ID NO 392
<211> LENGTH: 15
<212> TYPE: PRT
<213> ORGANISM: Influenza A virus

<400> SEQUENCE: 392

Glu Glu Ala Lys Leu Asn Arg Glu Glu Ile Asp Gly Val Lys Leu
1               5                   10                  15

<210> SEQ ID NO 393
<211> LENGTH: 15
<212> TYPE: PRT
<213> ORGANISM: Influenza A virus

<400> SEQUENCE: 393

Glu Lys Asn Val Thr Val Thr His Ser Val Asn Leu Leu Glu Asp
1               5                   10                  15

<210> SEQ ID NO 394
<211> LENGTH: 15
<212> TYPE: PRT
<213> ORGANISM: Influenza A virus

<400> SEQUENCE: 394

Glu Lys Arg Ile Glu Asn Leu Asn Lys Lys Val Asp Gly Phe
1               5                   10                  15

<210> SEQ ID NO 395
<211> LENGTH: 15
<212> TYPE: PRT
<213> ORGANISM: Influenza A virus

<400> SEQUENCE: 395

Glu Thr Pro Ser Ser Asp Asn Gly Thr Cys Tyr Pro Gly Asp Phe
1               5                   10                  15

<210> SEQ ID NO 396
<211> LENGTH: 15
<212> TYPE: PRT
<213> ORGANISM: Influenza A virus

<400> SEQUENCE: 396

Gly Ala Ile Ala Gly Phe Ile Glu Gly Gly Trp Thr Gly Met Val
1               5                   10                  15

<210> SEQ ID NO 397
<211> LENGTH: 15
<212> TYPE: PRT
<213> ORGANISM: Influenza A virus

<400> SEQUENCE: 397

Gly Lys Cys Pro Lys Tyr Val Lys Ser Thr Lys Leu Arg Leu Ala
1               5                   10                  15

<210> SEQ ID NO 398
<211> LENGTH: 15
<212> TYPE: PRT
<213> ORGANISM: Influenza A virus

<400> SEQUENCE: 398

Gly Asn Gly Cys Phe Glu Phe Tyr His Lys Cys Asp Asn Thr Cys
1               5                   10                  15

<210> SEQ ID NO 399
<211> LENGTH: 15
<212> TYPE: PRT
<213> ORGANISM: Influenza A virus

<400> SEQUENCE: 399

Gly Val Thr Ala Ala Cys Pro His Ala Gly Ala Lys Ser Phe Tyr
1               5                   10                  15

<210> SEQ ID NO 400
<211> LENGTH: 15
<212> TYPE: PRT
<213> ORGANISM: Influenza A virus

<400> SEQUENCE: 400

His Leu Gly Lys Cys Asn Ile Ala Gly Trp Ile Leu Gly Asn Pro
1               5                   10                  15

<210> SEQ ID NO 401
<211> LENGTH: 15
<212> TYPE: PRT
<213> ORGANISM: Influenza A virus

<400> SEQUENCE: 401

His Pro Ser Thr Ser Ala Asp Gln Gln Ser Leu Tyr Gln Asn Ala

```
1               5                  10                 15

<210> SEQ ID NO 402
<211> LENGTH: 15
<212> TYPE: PRT
<213> ORGANISM: Influenza A virus

<400> SEQUENCE: 402

Ile Leu Gly Asn Pro Glu Cys Glu Ser Leu Ser Thr Ala Ser Ser
1               5                  10                 15

<210> SEQ ID NO 403
<211> LENGTH: 15
<212> TYPE: PRT
<213> ORGANISM: Influenza A virus

<400> SEQUENCE: 403

Ile Pro Ser Ile Gln Ser Arg Gly Leu Phe Gly Ala Ile Ala Gly
1               5                  10                 15

<210> SEQ ID NO 404
<211> LENGTH: 15
<212> TYPE: PRT
<213> ORGANISM: Influenza A virus

<400> SEQUENCE: 404

Lys Glu Val Leu Val Leu Trp Gly Ile His His Pro Ser Thr Ser
1               5                  10                 15

<210> SEQ ID NO 405
<211> LENGTH: 13
<212> TYPE: PRT
<213> ORGANISM: Influenza A virus

<400> SEQUENCE: 405

Lys Leu Arg Gly Val Ala Pro Leu His Leu Gly Lys Cys
1               5                  10

<210> SEQ ID NO 406
<211> LENGTH: 15
<212> TYPE: PRT
<213> ORGANISM: Influenza A virus

<400> SEQUENCE: 406

Lys Pro Glu Ile Ala Ile Arg Pro Lys Val Arg Asp Gln Glu Gly
1               5                  10                 15

<210> SEQ ID NO 407
<211> LENGTH: 10
<212> TYPE: PRT
<213> ORGANISM: Influenza A virus

<400> SEQUENCE: 407

Leu Cys Lys Leu Arg Gly Val Ala Pro Leu
1               5                  10

<210> SEQ ID NO 408
<211> LENGTH: 11
<212> TYPE: PRT
<213> ORGANISM: Influenza A virus

<400> SEQUENCE: 408

Leu Cys Lys Leu Arg Gly Val Ala Pro Leu His
1               5                  10
```

```
<210> SEQ ID NO 409
<211> LENGTH: 12
<212> TYPE: PRT
<213> ORGANISM: Influenza A virus

<400> SEQUENCE: 409

Leu Cys Lys Leu Arg Gly Val Ala Pro Leu His Leu
1               5                   10

<210> SEQ ID NO 410
<211> LENGTH: 13
<212> TYPE: PRT
<213> ORGANISM: Influenza A virus

<400> SEQUENCE: 410

Leu Cys Lys Leu Arg Gly Val Ala Pro Leu His Leu Gly
1               5                   10

<210> SEQ ID NO 411
<211> LENGTH: 15
<212> TYPE: PRT
<213> ORGANISM: Influenza A virus

<400> SEQUENCE: 411

Leu Cys Lys Leu Arg Gly Val Ala Pro Leu His Leu Gly Lys Cys
1               5                   10                  15

<210> SEQ ID NO 412
<211> LENGTH: 15
<212> TYPE: PRT
<213> ORGANISM: Influenza A virus

<400> SEQUENCE: 412

Leu Arg Glu Gln Leu Ser Ser Val Ser Ser Phe Glu Arg Phe Glu
1               5                   10                  15

<210> SEQ ID NO 413
<211> LENGTH: 12
<212> TYPE: PRT
<213> ORGANISM: Influenza A virus

<400> SEQUENCE: 413

Leu Arg Gly Val Ala Pro Leu His Leu Gly Lys Cys
1               5                   10

<210> SEQ ID NO 414
<211> LENGTH: 15
<212> TYPE: PRT
<213> ORGANISM: Influenza A virus

<400> SEQUENCE: 414

Leu Ser Lys Ser Tyr Ile Asn Asp Lys Gly Lys Glu Val Leu Val
1               5                   10                  15

<210> SEQ ID NO 415
<211> LENGTH: 15
<212> TYPE: PRT
<213> ORGANISM: Influenza A virus

<400> SEQUENCE: 415

Leu Val Lys Lys Gly Asn Ser Tyr Pro Lys Leu Ser Lys Ser Tyr
1               5                   10                  15

<210> SEQ ID NO 416
```

```
<211> LENGTH: 15
<212> TYPE: PRT
<213> ORGANISM: Influenza A virus

<400> SEQUENCE: 416

Leu Tyr Gln Asn Ala Asp Thr Tyr Val Phe Val Gly Ser Ser Arg
1               5                   10                  15

<210> SEQ ID NO 417
<211> LENGTH: 15
<212> TYPE: PRT
<213> ORGANISM: Influenza A virus

<400> SEQUENCE: 417

Asn Glu Arg Thr Leu Asp Tyr His Asp Ser Asn Val Lys Asn Leu
1               5                   10                  15

<210> SEQ ID NO 418
<211> LENGTH: 15
<212> TYPE: PRT
<213> ORGANISM: Influenza A virus

<400> SEQUENCE: 418

Asn Gly Thr Tyr Asp Tyr Pro Lys Tyr Ser Glu Glu Ala Lys Leu
1               5                   10                  15

<210> SEQ ID NO 419
<211> LENGTH: 15
<212> TYPE: PRT
<213> ORGANISM: Influenza A virus

<400> SEQUENCE: 419

Asn Leu Leu Glu Asp Lys His Asn Gly Lys Leu Cys Lys Leu Arg
1               5                   10                  15

<210> SEQ ID NO 420
<211> LENGTH: 15
<212> TYPE: PRT
<213> ORGANISM: Influenza A virus

<400> SEQUENCE: 420

Asn Ser Thr Asp Thr Val Asp Thr Val Leu Glu Lys Asn Val Thr
1               5                   10                  15

<210> SEQ ID NO 421
<211> LENGTH: 15
<212> TYPE: PRT
<213> ORGANISM: Influenza A virus

<400> SEQUENCE: 421

Pro Phe Gln Asn Ile His Pro Ile Thr Ile Gly Lys Cys Pro Lys
1               5                   10                  15

<210> SEQ ID NO 422
<211> LENGTH: 15
<212> TYPE: PRT
<213> ORGANISM: Influenza A virus

<400> SEQUENCE: 422

Pro Arg Tyr Ala Phe Ala Met Glu Arg Asn Ala Gly Ser Gly Ile
1               5                   10                  15

<210> SEQ ID NO 423
<211> LENGTH: 15
<212> TYPE: PRT
```

-continued

<213> ORGANISM: Influenza A virus

<400> SEQUENCE: 423

Pro Val His Asp Cys Asn Thr Thr Cys Gln Thr Pro Lys Gly Ala
1               5                   10                  15

<210> SEQ ID NO 424
<211> LENGTH: 15
<212> TYPE: PRT
<213> ORGANISM: Influenza A virus

<400> SEQUENCE: 424

Arg Asp Gln Glu Gly Arg Met Asn Tyr Tyr Trp Thr Leu Val Glu
1               5                   10                  15

<210> SEQ ID NO 425
<211> LENGTH: 15
<212> TYPE: PRT
<213> ORGANISM: Influenza A virus

<400> SEQUENCE: 425

Ser Gln Leu Lys Asn Asn Ala Lys Glu Ile Gly Asn Gly Cys Phe
1               5                   10                  15

<210> SEQ ID NO 426
<211> LENGTH: 15
<212> TYPE: PRT
<213> ORGANISM: Influenza A virus

<400> SEQUENCE: 426

Ser Ser Trp Pro Asn His Asp Ser Asn Lys Gly Val Thr Ala Ala
1               5                   10                  15

<210> SEQ ID NO 427
<211> LENGTH: 15
<212> TYPE: PRT
<213> ORGANISM: Influenza A virus

<400> SEQUENCE: 427

Ser Thr Ala Ser Ser Trp Ser Tyr Ile Val Glu Thr Pro Ser Ser
1               5                   10                  15

<210> SEQ ID NO 428
<211> LENGTH: 15
<212> TYPE: PRT
<213> ORGANISM: Influenza A virus

<400> SEQUENCE: 428

Ser Val Ile Glu Lys Met Asn Thr Gln Phe Thr Ala Val Gly Lys
1               5                   10                  15

<210> SEQ ID NO 429
<211> LENGTH: 15
<212> TYPE: PRT
<213> ORGANISM: Influenza A virus

<400> SEQUENCE: 429

Thr Ala Val Gly Lys Glu Phe Asn His Leu Glu Lys Arg Ile Glu
1               5                   10                  15

<210> SEQ ID NO 430
<211> LENGTH: 15
<212> TYPE: PRT
<213> ORGANISM: Influenza A virus

<400> SEQUENCE: 430

Thr Phe Glu Ala Thr Gly Asn Leu Val Val Pro Arg Tyr Ala Phe
1               5                   10                  15

<210> SEQ ID NO 431
<211> LENGTH: 15
<212> TYPE: PRT
<213> ORGANISM: Influenza A virus

<400> SEQUENCE: 431

Thr Pro Lys Gly Ala Ile Asn Thr Ser Leu Pro Phe Gln Asn Ile
1               5                   10                  15

<210> SEQ ID NO 432
<211> LENGTH: 15
<212> TYPE: PRT
<213> ORGANISM: Influenza A virus

<400> SEQUENCE: 432

Val Asp Asp Gly Phe Leu Asp Ile Trp Thr Tyr Asn Ala Glu Leu
1               5                   10                  15

<210> SEQ ID NO 433
<211> LENGTH: 15
<212> TYPE: PRT
<213> ORGANISM: Influenza A virus

<400> SEQUENCE: 433

Val Gly Ser Ser Arg Tyr Ser Lys Lys Phe Lys Pro Glu Ile Ala
1               5                   10                  15

<210> SEQ ID NO 434
<211> LENGTH: 15
<212> TYPE: PRT
<213> ORGANISM: Influenza A virus

<400> SEQUENCE: 434

Trp Thr Gly Met Val Asp Gly Trp Tyr Gly Tyr His His Gln Asn
1               5                   10                  15

<210> SEQ ID NO 435
<211> LENGTH: 15
<212> TYPE: PRT
<213> ORGANISM: Influenza A virus

<400> SEQUENCE: 435

Trp Thr Leu Val Glu Pro Gly Asp Lys Ile Thr Phe Glu Ala Thr
1               5                   10                  15

<210> SEQ ID NO 436
<211> LENGTH: 15
<212> TYPE: PRT
<213> ORGANISM: Influenza A virus

<400> SEQUENCE: 436

Tyr Ala Ala Asp Leu Lys Ser Thr Gln Asn Ala Ile Asp Glu Ile
1               5                   10                  15

<210> SEQ ID NO 437
<211> LENGTH: 15
<212> TYPE: PRT
<213> ORGANISM: Influenza A virus

<400> SEQUENCE: 437

Tyr His His Gln Asn Glu Gln Gly Ser Gly Tyr Ala Ala Asp Leu
1               5                   10                  15

<210> SEQ ID NO 438
<211> LENGTH: 15
<212> TYPE: PRT
<213> ORGANISM: Influenza A virus

<400> SEQUENCE: 438

Tyr Asn Ala Glu Leu Leu Val Leu Leu Glu Asn Glu Arg Thr Leu
1               5                   10                  15

<210> SEQ ID NO 439
<211> LENGTH: 15
<212> TYPE: PRT
<213> ORGANISM: Influenza A virus

<400> SEQUENCE: 439

Tyr Pro Gly Asp Phe Ile Asp Tyr Glu Glu Leu Arg Glu Gln Leu
1               5                   10                  15

<210> SEQ ID NO 440
<211> LENGTH: 20
<212> TYPE: PRT
<213> ORGANISM: Influenza A virus

<400> SEQUENCE: 440

Glu Arg Phe Glu Ile Phe Pro Lys Thr Ser Ser Trp Pro Asn His Asp
1               5                   10                  15

Ser Asn Lys Gly
            20

<210> SEQ ID NO 441
<211> LENGTH: 20
<212> TYPE: PRT
<213> ORGANISM: Influenza A virus

<400> SEQUENCE: 441

Lys Lys Phe Lys Pro Glu Ile Ala Ile Arg Pro Lys Val Arg Asp Gln
1               5                   10                  15

Glu Gly Arg Met
            20

<210> SEQ ID NO 442
<211> LENGTH: 20
<212> TYPE: PRT
<213> ORGANISM: Influenza A virus

<400> SEQUENCE: 442

Gln Leu Ser Ser Val Ser Ser Phe Glu Arg Phe Glu Ile Phe Pro Lys
1               5                   10                  15

Thr Ser Ser Trp
            20

<210> SEQ ID NO 443
<211> LENGTH: 20
<212> TYPE: PRT
<213> ORGANISM: Influenza A virus

<400> SEQUENCE: 443

Ser Asn Val Lys Asn Leu Tyr Glu Lys Val Arg Ser Gln Leu Lys Asn
1               5                   10                  15

Asn Ala Lys Glu

<210> SEQ ID NO 444
<211> LENGTH: 20
<212> TYPE: PRT
<213> ORGANISM: Influenza A virus

<400> SEQUENCE: 444

Tyr Gln Asn Ala Asp Thr Tyr Val Phe Val Gly Ser Ser Arg Tyr Ser
1               5                   10                  15
Lys Lys Phe Lys
            20

<210> SEQ ID NO 445
<211> LENGTH: 10
<212> TYPE: PRT
<213> ORGANISM: Influenza A virus

<400> SEQUENCE: 445

Leu Leu Glu Asn Glu Arg Thr Leu Asp Tyr
1               5                   10

<210> SEQ ID NO 446
<211> LENGTH: 9
<212> TYPE: PRT
<213> ORGANISM: Influenza A virus

<400> SEQUENCE: 446

Asn Ala Asp Thr Leu Cys Ile Gly Tyr
1               5

<210> SEQ ID NO 447
<211> LENGTH: 16
<212> TYPE: PRT
<213> ORGANISM: Influenza A virus

<400> SEQUENCE: 447

Glu Leu Leu Val Leu Leu Glu Asn Glu Arg Thr Leu Asp Phe His Asp
1               5                   10                  15

<210> SEQ ID NO 448
<211> LENGTH: 34
<212> TYPE: PRT
<213> ORGANISM: Influenza A virus

<400> SEQUENCE: 448

Asn Ser Glu Asn Gly Thr Cys Tyr Pro Gly Asp Phe Ile Asp Tyr Glu
1               5                   10                  15
Glu Leu Arg Glu Gln Leu Ser Ser Val Ser Ser Phe Glu Lys Phe Glu
            20                  25                  30
Ile Phe

<210> SEQ ID NO 449
<211> LENGTH: 12
<212> TYPE: PRT
<213> ORGANISM: Influenza A virus

<400> SEQUENCE: 449

Arg Asn Leu Leu Trp Leu Thr Gly Lys Asn Gly Leu
1               5                   10

<210> SEQ ID NO 450
<211> LENGTH: 14

<212> TYPE: PRT
<213> ORGANISM: Influenza A virus

<400> SEQUENCE: 450

Ile Ala Ala Arg Pro Lys Val Lys Asp Gln His Gly Arg Met
1               5                   10

<210> SEQ ID NO 451
<211> LENGTH: 14
<212> TYPE: PRT
<213> ORGANISM: Influenza A virus

<400> SEQUENCE: 451

Ile Ala Ile Arg Pro Lys Val Arg Asp Gln Glu Gly Arg Met
1               5                   10

<210> SEQ ID NO 452
<211> LENGTH: 14
<212> TYPE: PRT
<213> ORGANISM: Influenza A virus

<400> SEQUENCE: 452

Ile Ala Lys Arg Pro Lys Val Arg Asp Gln Glu Gly Arg Ile
1               5                   10

<210> SEQ ID NO 453
<211> LENGTH: 14
<212> TYPE: PRT
<213> ORGANISM: Influenza A virus

<400> SEQUENCE: 453

Ile Ala Lys Arg Pro Lys Val Arg Gly Gln Ala Gly Arg Met
1               5                   10

<210> SEQ ID NO 454
<211> LENGTH: 18
<212> TYPE: PRT
<213> ORGANISM: Influenza A virus

<400> SEQUENCE: 454

Phe Ile Glu Gly Gly Trp Thr Gly Met Val Asp Gly Trp Tyr Gly Tyr
1               5                   10                  15

His His

<210> SEQ ID NO 455
<211> LENGTH: 9
<212> TYPE: PRT
<213> ORGANISM: Influenza A virus

<400> SEQUENCE: 455

His Ala Asn Asn Ser Thr Asp Thr Val
1               5

<210> SEQ ID NO 456
<211> LENGTH: 8
<212> TYPE: PRT
<213> ORGANISM: Influenza A virus

<400> SEQUENCE: 456

Asn Val Thr Val Thr His Ser Val
1               5

<210> SEQ ID NO 457
<211> LENGTH: 9

<212> TYPE: PRT
<213> ORGANISM: Influenza A virus

<400> SEQUENCE: 457

Ser Met Gly Val Tyr Gln Ile Leu Ala
1 5

<210> SEQ ID NO 458
<211> LENGTH: 9
<212> TYPE: PRT
<213> ORGANISM: Influenza A virus

<400> SEQUENCE: 458

Tyr Asn Ala Glu Leu Leu Val Leu Leu
1 5

<210> SEQ ID NO 459
<211> LENGTH: 20
<212> TYPE: PRT
<213> ORGANISM: Influenza A virus

<400> SEQUENCE: 459

Lys Ser Thr Gln Asn Ala Ile Asp Gly Ile Thr Asn Lys Val Asn Ser
1 5 10 15

Val Ile Glu Lys
20

<210> SEQ ID NO 460
<211> LENGTH: 52
<212> TYPE: PRT
<213> ORGANISM: Influenza A virus

<400> SEQUENCE: 460

Leu Lys Asn Asn Ala Lys Glu Ile Gly Asn Gly Cys Phe Glu Phe Tyr
1 5 10 15

His Lys Cys Asp Asn Thr Cys Met Glu Ser Val Lys Asn Gly Thr Tyr
20 25 30

Asp Tyr Pro Lys Tyr Ser Glu Glu Ala Lys Leu Asn Arg Glu Glu Ile
35 40 45

Asp Gly Val Lys
50

<210> SEQ ID NO 461
<211> LENGTH: 26
<212> TYPE: PRT
<213> ORGANISM: Influenza A virus

<400> SEQUENCE: 461

Ser Trp Ser Tyr Ile Val Glu Thr Ser Ser Ser Asp Asn Gly Thr Cys
1 5 10 15

Tyr Pro Gly Asp Phe Ile Asp Tyr Glu Glu
20 25

<210> SEQ ID NO 462
<211> LENGTH: 15
<212> TYPE: PRT
<213> ORGANISM: Influenza A virus

<400> SEQUENCE: 462

Ala Thr Gly Leu Arg Asn Ile Pro Ser Ile Gln Ser Arg Gly Leu
1 5 10 15

-continued

```
<210> SEQ ID NO 463
<211> LENGTH: 15
<212> TYPE: PRT
<213> ORGANISM: Influenza A virus

<400> SEQUENCE: 463

Gly Ala Ile Ser Phe Trp Met Cys Ser Asn Gly Ser Leu Gln Cys
1               5                   10                  15

<210> SEQ ID NO 464
<211> LENGTH: 15
<212> TYPE: PRT
<213> ORGANISM: Influenza A virus

<400> SEQUENCE: 464

Leu Val Leu Leu Glu Asn Glu Arg Thr Leu Asp Tyr His Asp Ser
1               5                   10                  15

<210> SEQ ID NO 465
<211> LENGTH: 15
<212> TYPE: PRT
<213> ORGANISM: Influenza A virus

<400> SEQUENCE: 465

Asn Lys Val Asn Ser Val Ile Glu Lys Met Asn Thr Gln Phe Thr
1               5                   10                  15

<210> SEQ ID NO 466
<211> LENGTH: 15
<212> TYPE: PRT
<213> ORGANISM: Influenza A virus

<400> SEQUENCE: 466

Arg Asn Ile Pro Ser Ile Gln Ser Arg Gly Leu Phe Gly Ala Ile
1               5                   10                  15

<210> SEQ ID NO 467
<211> LENGTH: 15
<212> TYPE: PRT
<213> ORGANISM: Influenza A virus

<400> SEQUENCE: 467

Ser Thr Val Ala Ser Ser Leu Val Leu Leu Val Ser Leu Gly Ala
1               5                   10                  15

<210> SEQ ID NO 468
<211> LENGTH: 15
<212> TYPE: PRT
<213> ORGANISM: Influenza A virus

<400> SEQUENCE: 468

Tyr Gln Ile Leu Ala Ile Tyr Ser Thr Val Ala Ser Ser Leu Val
1               5                   10                  15

<210> SEQ ID NO 469
<211> LENGTH: 8
<212> TYPE: PRT
<213> ORGANISM: Influenza A virus

<400> SEQUENCE: 469

Ser Ser Leu Pro Tyr Gln Asn Ile
1               5

<210> SEQ ID NO 470
<211> LENGTH: 20
```

```
<212> TYPE: PRT
<213> ORGANISM: Influenza A virus

<400> SEQUENCE: 470

Ala Val Gly Lys Glu Phe Asn His Leu Glu Lys Arg Ile Glu Asn Leu
1               5                   10                  15

Asn Lys Lys Val
            20

<210> SEQ ID NO 471
<211> LENGTH: 20
<212> TYPE: PRT
<213> ORGANISM: Influenza A virus

<400> SEQUENCE: 471

Glu Gly Arg Met Asn Tyr Tyr Trp Thr Leu Val Glu Pro Gly Asp Lys
1               5                   10                  15

Ile Thr Phe Glu
            20

<210> SEQ ID NO 472
<211> LENGTH: 20
<212> TYPE: PRT
<213> ORGANISM: Influenza A virus

<400> SEQUENCE: 472

Glu Lys Met Asn Thr Gln Phe Thr Ala Val Gly Lys Glu Phe Asn His
1               5                   10                  15

Leu Glu Lys Arg
            20

<210> SEQ ID NO 473
<211> LENGTH: 20
<212> TYPE: PRT
<213> ORGANISM: Influenza A virus

<400> SEQUENCE: 473

Phe Val Gly Ser Ser Arg Tyr Ser Lys Lys Phe Lys Pro Glu Ile Ala
1               5                   10                  15

Ile Arg Pro Lys
            20

<210> SEQ ID NO 474
<211> LENGTH: 20
<212> TYPE: PRT
<213> ORGANISM: Influenza A virus

<400> SEQUENCE: 474

Phe Tyr Lys Asn Leu Ile Trp Leu Val Lys Lys Gly Asn Ser Tyr Pro
1               5                   10                  15

Lys Leu Ser Lys
            20

<210> SEQ ID NO 475
<211> LENGTH: 20
<212> TYPE: PRT
<213> ORGANISM: Influenza A virus

<400> SEQUENCE: 475

His Pro Ile Thr Ile Gly Lys Cys Pro Lys Tyr Val Lys Ser Thr Lys
1               5                   10                  15

Leu Arg Leu Ala
```

<210> SEQ ID NO 476
<211> LENGTH: 20
<212> TYPE: PRT
<213> ORGANISM: Influenza A virus

<400> SEQUENCE: 476

Ile Thr Phe Glu Ala Thr Gly Asn Leu Val Val Pro Arg Tyr Ala Phe
1               5                   10                  15

Ala Met Glu Arg
            20

<210> SEQ ID NO 477
<211> LENGTH: 20
<212> TYPE: PRT
<213> ORGANISM: Influenza A virus

<400> SEQUENCE: 477

Lys Leu Cys Lys Leu Arg Gly Val Ala Pro Leu His Leu Gly Lys Cys
1               5                   10                  15

Asn Ile Ala Gly
            20

<210> SEQ ID NO 478
<211> LENGTH: 20
<212> TYPE: PRT
<213> ORGANISM: Influenza A virus

<400> SEQUENCE: 478

Lys Leu Glu Ser Thr Arg Ile Tyr Gln Ile Leu Ala Ile Tyr Ser Thr
1 5 10 15

Val Ala Ser Ser
20

<210> SEQ ID NO 479
<211> LENGTH: 20
<212> TYPE: PRT
<213> ORGANISM: Influenza A virus

<400> SEQUENCE: 479

Lys Val Arg Ser Gln Leu Lys Asn Asn Ala Lys Glu Ile Gly Asn Gly
1 5 10 15

Cys Phe Glu Phe
20

<210> SEQ ID NO 480
<211> LENGTH: 20
<212> TYPE: PRT
<213> ORGANISM: Influenza A virus

<400> SEQUENCE: 480

Leu Asp Ile Trp Thr Tyr Asn Ala Glu Leu Leu Val Leu Leu Glu Asn
1 5 10 15

Glu Arg Thr Leu
20

<210> SEQ ID NO 481
<211> LENGTH: 20
<212> TYPE: PRT
<213> ORGANISM: Influenza A virus

<400> SEQUENCE: 481

-continued

Leu Arg Leu Ala Thr Gly Leu Arg Asn Ile Pro Ser Ile Gln Ser Arg
1               5                   10                  15

Gly Leu Phe Gly
            20

<210> SEQ ID NO 482
<211> LENGTH: 20
<212> TYPE: PRT
<213> ORGANISM: Influenza A virus

<400> SEQUENCE: 482

Leu Val Val Pro Arg Tyr Ala Phe Ala Met Glu Arg Asn Ala Gly Ser
1               5                   10                  15

Gly Ile Ile Ile
            20

<210> SEQ ID NO 483
<211> LENGTH: 20
<212> TYPE: PRT
<213> ORGANISM: Influenza A virus

<400> SEQUENCE: 483

Met Lys Ala Ile Leu Val Val Leu Leu Tyr Thr Phe Ala Thr Ala Asn
1               5                   10                  15

Ala Asp Thr Leu
            20

<210> SEQ ID NO 484
<211> LENGTH: 20
<212> TYPE: PRT
<213> ORGANISM: Influenza A virus

<400> SEQUENCE: 484

Asn Arg Glu Glu Ile Asp Gly Val Lys Leu Glu Ser Thr Arg Ile Tyr
1               5                   10                  15

Gln Ile Leu Ala
            20

<210> SEQ ID NO 485
<211> LENGTH: 20
<212> TYPE: PRT
<213> ORGANISM: Influenza A virus

<400> SEQUENCE: 485

Pro Lys Tyr Val Lys Ser Thr Lys Leu Arg Leu Ala Thr Gly Leu Arg
1               5                   10                  15

Asn Ile Pro Ser
            20

<210> SEQ ID NO 486
<211> LENGTH: 20
<212> TYPE: PRT
<213> ORGANISM: Influenza A virus

<400> SEQUENCE: 486

Thr Leu Val Glu Pro Gly Asp Lys Ile Thr Phe Glu Ala Thr Gly Asn
1               5                   10                  15

Leu Val Val Pro
            20

<210> SEQ ID NO 487

```
<211> LENGTH: 20
<212> TYPE: PRT
<213> ORGANISM: Influenza A virus

<400> SEQUENCE: 487

Thr Asn Lys Val Asn Ser Val Ile Glu Lys Met Asn Thr Gln Phe Thr
1               5                   10                  15

Ala Val Gly Lys
            20

<210> SEQ ID NO 488
<211> LENGTH: 20
<212> TYPE: PRT
<213> ORGANISM: Influenza A virus

<400> SEQUENCE: 488

Thr Ser Leu Pro Phe Gln Asn Ile His Pro Ile Thr Ile Gly Lys Cys
1               5                   10                  15

Pro Lys Tyr Val
            20

<210> SEQ ID NO 489
<211> LENGTH: 20
<212> TYPE: PRT
<213> ORGANISM: Influenza A virus

<400> SEQUENCE: 489

Val Asp Thr Val Leu Glu Lys Asn Val Thr Val Thr His Ser Val Asn
1               5                   10                  15

Leu Leu Glu Asp
            20

<210> SEQ ID NO 490
<211> LENGTH: 20
<212> TYPE: PRT
<213> ORGANISM: Influenza A virus

<400> SEQUENCE: 490

Tyr Gln Asn Ala Asp Ala Tyr Val Phe Val Gly Ser Ser Arg Tyr Ser
1               5                   10                  15

Lys Lys Phe Lys
            20

<210> SEQ ID NO 491
<211> LENGTH: 46
<212> TYPE: PRT
<213> ORGANISM: Influenza A virus

<400> SEQUENCE: 491

Ser Gly Tyr Ala Ala Asp Leu Lys Ser Thr Gln Asn Ala Ile Asp Glu
1               5                   10                  15

Ile Thr Asn Lys Val Asn Ser Val Ile Glu Lys Met Asn Thr Gln Phe
                20                  25                  30

Thr Ala Val Gly Lys Glu Phe Asn His Leu Glu Lys Arg Ile
            35                  40                  45

<210> SEQ ID NO 492
<211> LENGTH: 16
<212> TYPE: PRT
<213> ORGANISM: Influenza A virus

<400> SEQUENCE: 492
```

```
Leu Lys Ser Thr Gln Asn Ala Ile Asp Glu Ile Thr Asn Lys Val Asn
1               5                   10                  15

<210> SEQ ID NO 493
<211> LENGTH: 20
<212> TYPE: PRT
<213> ORGANISM: Influenza A virus

<400> SEQUENCE: 493

Phe Gly Ala Ile Ala Gly Phe Ile Glu Gly Gly Trp Thr Gly Met Val
1               5                   10                  15

Asp Gly Trp Tyr
            20

<210> SEQ ID NO 494
<211> LENGTH: 20
<212> TYPE: PRT
<213> ORGANISM: Influenza A virus

<400> SEQUENCE: 494

Gly Ile Ile Asn Ser Asn Ala Pro Met Asp Glu Cys Asp Ala Lys Cys
1               5                   10                  15

Gln Thr Pro Gln
            20

<210> SEQ ID NO 495
<211> LENGTH: 16
<212> TYPE: PRT
<213> ORGANISM: Influenza A virus

<400> SEQUENCE: 495

Met Lys Ala Ile Leu Val Val Leu Leu Tyr Thr Phe Ala Thr Ala Asn
1               5                   10                  15

<210> SEQ ID NO 496
<211> LENGTH: 19
<212> TYPE: PRT
<213> ORGANISM: Influenza A virus

<400> SEQUENCE: 496

Arg Phe Glu Ile Phe Pro Lys Thr Ser Ser Trp Pro Asn His Asp Ser
1               5                   10                  15

Asn Lys Gly

<210> SEQ ID NO 497
<211> LENGTH: 15
<212> TYPE: PRT
<213> ORGANISM: Influenza A virus

<400> SEQUENCE: 497

Ala Ile Ser Phe Trp Met Cys Ser Asn Gly Ser Leu Gln Cys Arg
1               5                   10                  15

<210> SEQ ID NO 498
<211> LENGTH: 13
<212> TYPE: PRT
<213> ORGANISM: Influenza A virus

<400> SEQUENCE: 498

Ala Leu Asn Arg Gly Ser Gly Ser Gly Ile Ile Thr Ser
1               5                   10

<210> SEQ ID NO 499
```

```
<211> LENGTH: 15
<212> TYPE: PRT
<213> ORGANISM: Influenza A virus

<400> SEQUENCE: 499

Ala Met Glu Arg Asn Ala Gly Ser Gly Ile Ile Ile Ser Asp Thr
1               5                   10                  15

<210> SEQ ID NO 500
<211> LENGTH: 15
<212> TYPE: PRT
<213> ORGANISM: Influenza A virus

<400> SEQUENCE: 500

Ala Thr Gly Asn Leu Val Val Pro Arg Tyr Ala Phe Ala Met Glu
1               5                   10                  15

<210> SEQ ID NO 501
<211> LENGTH: 15
<212> TYPE: PRT
<213> ORGANISM: Influenza A virus

<400> SEQUENCE: 501

Cys Pro His Ala Gly Ala Lys Ser Phe Tyr Lys Asn Leu Ile Trp
1               5                   10                  15

<210> SEQ ID NO 502
<211> LENGTH: 15
<212> TYPE: PRT
<213> ORGANISM: Influenza A virus

<400> SEQUENCE: 502

Asp Ala Tyr Val Phe Val Gly Ser Ser Arg Tyr Ser Lys Lys Phe
1               5                   10                  15

<210> SEQ ID NO 503
<211> LENGTH: 15
<212> TYPE: PRT
<213> ORGANISM: Influenza A virus

<400> SEQUENCE: 503

Asp Asp Gly Phe Leu Asp Ile Trp Thr Tyr Asn Ala Glu Leu Leu
1               5                   10                  15

<210> SEQ ID NO 504
<211> LENGTH: 15
<212> TYPE: PRT
<213> ORGANISM: Influenza A virus

<400> SEQUENCE: 504

Asp Leu Lys Ser Thr Gln Asn Ala Ile Asp Glu Ile Thr Asn Lys
1               5                   10                  15

<210> SEQ ID NO 505
<211> LENGTH: 15
<212> TYPE: PRT
<213> ORGANISM: Influenza A virus

<400> SEQUENCE: 505

Asp Tyr His Asp Ser Asn Val Lys Asn Leu Tyr Glu Lys Val Arg
1               5                   10                  15

<210> SEQ ID NO 506
<211> LENGTH: 15
<212> TYPE: PRT
```

```
<213> ORGANISM: Influenza A virus

<400> SEQUENCE: 506

Glu Ala Lys Leu Asn Arg Glu Glu Ile Asp Gly Val Lys Leu Glu
1

-continued

<400> SEQUENCE: 513

Gly Ala Ile Asn Thr Ser Leu Pro Phe Gln Asn Ile His Pro Ile
1               5                   10                  15

<210> SEQ ID NO 514
<211> LENGTH: 15
<212> TYPE: PRT
<213> ORGANISM: Influenza A virus

<400> SEQUENCE: 514

Gly Ala Lys Ser Phe Tyr Lys Asn Leu Ile Trp Leu Val Lys Lys
1               5                   10                  15

<210> SEQ ID NO 515
<211> LENGTH: 15
<212> TYPE: PRT
<213> ORGANISM: Influenza A virus

<400> SEQUENCE: 515

Gly Ile Ile Ile Ser Asp Thr Pro Val His Asp Cys Asn Thr Thr
1               5                   10                  15

<210> SEQ ID NO 516
<211> LENGTH: 15
<212> TYPE: PRT
<213> ORGANISM: Influenza A virus

<400> SEQUENCE: 516

Gly Tyr Ala Ala Asp Leu Lys Ser Thr Gln Asn Ala Ile Asp Glu
1               5                   10                  15

<210> SEQ ID NO 517
<211> LENGTH: 15
<212> TYPE: PRT
<213> ORGANISM: Influenza A virus

<400> SEQUENCE: 517

His His Gln Asn Glu Gln Gly Ser Gly Tyr Ala Ala Asp Leu Lys
1               5                   10                  15

<210> SEQ ID NO 518
<211> LENGTH: 15
<212> TYPE: PRT
<213> ORGANISM: Influenza A virus

<400> SEQUENCE: 518

His Ser Val Asn Leu Leu Glu Asp Lys His Asn Gly Lys Leu Cys
1               5                   10                  15

<210> SEQ ID NO 519
<211> LENGTH: 10
<212> TYPE: PRT
<213> ORGANISM: Influenza A virus

<400> SEQUENCE: 519

Ile Ala Gly Trp Ile Leu Gly Asn Pro Glu
1               5                   10

<210> SEQ ID NO 520
<211> LENGTH: 15
<212> TYPE: PRT
<213> ORGANISM: Influenza A virus

<400> SEQUENCE: 520

Ile Asp Gly Val Lys Leu Glu Ser Thr Arg Ile Tyr Gln Ile Leu
1               5                   10                  15

<210> SEQ ID NO 521
<211> LENGTH: 15
<212> TYPE: PRT
<213> ORGANISM: Influenza A virus

<400> SEQUENCE: 521

Ile Asp Tyr Glu Glu Leu Arg Glu Gln Leu Ser Ser Val Ser Ser
1               5                   10                  15

<210> SEQ ID NO 522
<211> LENGTH: 15
<212> TYPE: PRT
<213> ORGANISM: Influenza A virus

<400> SEQUENCE: 522

Ile Glu Asn Leu Asn Lys Lys Val Asp Asp Gly Phe Leu Asp Ile
1               5                   10                  15

<210> SEQ ID NO 523
<211> LENGTH: 15
<212> TYPE: PRT
<213> ORGANISM: Influenza A virus

<400> SEQUENCE: 523

Ile Phe Pro Lys Thr Ser Ser Trp Pro Asn His Asp Ser Asn Lys
1               5                   10                  15

<210> SEQ ID NO 524
<211> LENGTH: 15
<212> TYPE: PRT
<213> ORGANISM: Influenza A virus

<400> SEQUENCE: 524

Ile Gly Asn Gly Cys Phe Glu Phe Tyr His Lys Cys Asp Asn Thr
1               5                   10                  15

<210> SEQ ID NO 525
<211> LENGTH: 15
<212> TYPE: PRT
<213> ORGANISM: Influenza A virus

<400> SEQUENCE: 525

Ile Thr Phe Glu Ala Thr Gly Asn Leu Val Val Pro Arg Tyr Ala
1               5                   10                  15

<210> SEQ ID NO 526
<211> LENGTH: 15
<212> TYPE: PRT
<213> ORGANISM: Influenza A virus

<400> SEQUENCE: 526

Ile Tyr Ser Thr Val Ala Ser Ser Leu Val Leu Val Val Ser Leu
1               5                   10                  15

<210> SEQ ID NO 527
<211> LENGTH: 15
<212> TYPE: PRT
<213> ORGANISM: Influenza A virus

<400> SEQUENCE: 527

Lys Leu Glu Ser Thr Arg Ile Tyr Gln Ile Leu Ala Ile Tyr Ser
1               5                   10                  15

```
<210> SEQ ID NO 528
<211> LENGTH: 15
<212> TYPE: PRT
<213> ORGANISM: Influenza A virus

<400> SEQUENCE: 528

Lys Asn Gly Thr Tyr Asp Tyr Pro Lys Tyr Ser Glu Glu Ala Lys
1               5                   10                  15

<210> SEQ ID NO 529
<211> LENGTH: 13
<212> TYPE: PRT
<213> ORGANISM: Influenza A virus

<400> SEQUENCE: 529

Lys Arg Asn Ser Gly Ser Gly Ile Ile Ile Ser Asp Thr
1               5                   10

<210> SEQ ID NO 530
<211> LENGTH: 15
<212> TYPE: PRT
<213> ORGANISM: Influenza A virus

<400> SEQUENCE: 530

Lys Val Arg Ser Gln Leu Lys Asn Asn Ala Lys Glu Ile Gly Asn
1               5                   10                  15

<210> SEQ ID NO 531
<211> LENGTH: 15
<212> TYPE: PRT
<213> ORGANISM: Influenza A virus

<400> SEQUENCE: 531

Lys Tyr Ser Glu Glu Ala Lys Leu Asn Arg Glu Glu Ile Asp Gly
1               5                   10                  15

<210> SEQ ID NO 532
<211> LENGTH: 15
<212> TYPE: PRT
<213> ORGANISM: Influenza A virus

<400> SEQUENCE: 532

Leu Glu Lys Asn Val Thr Val Thr His Ser Val Asn Leu Leu Glu
1               5                   10                  15

<210> SEQ ID NO 533
<211> LENGTH: 15
<212> TYPE: PRT
<213> ORGANISM: Influenza A virus

<400> SEQUENCE: 533

Leu Glu Lys Arg Ile Glu Asn Leu Asn Lys Lys Val Asp Asp Gly
1               5                   10                  15

<210> SEQ ID NO 534
<211> LENGTH: 15
<212> TYPE: PRT
<213> ORGANISM: Influenza A virus

<400> SEQUENCE: 534

Leu Val Leu Val Val Ser Leu Gly Ala Ile Ser Phe Trp Met Cys
1               5                   10                  15
```

```
<210> SEQ ID NO 535
<211> LENGTH: 15
<212> TYPE: PRT
<213> ORGANISM: Influenza A virus

<400> SEQUENCE: 535

Leu Val Val Pro Arg Tyr Ala Phe Ala Met Glu Arg Asn Ala Gly
1               5                   10                  15

<210> SEQ ID NO 536
<211> LENGTH: 15
<212> TYPE: PRT
<213> ORGANISM: Influenza A virus

<400> SEQUENCE: 536

Asn Ala Gly Ser Gly Ile Ile Ile Ser Asp Thr Pro Val His Asp
1               5                   10                  15

<210> SEQ ID NO 537
<211> LENGTH: 15
<212> TYPE: PRT
<213> ORGANISM: Influenza A virus

<400> SEQUENCE: 537

Asn Ala Lys Glu Ile Gly Asn Gly Cys Phe Glu Phe Tyr His Lys
1               5                   10                  15

<210> SEQ ID NO 538
<211> LENGTH: 15
<212> TYPE: PRT
<213> ORGANISM: Influenza A virus

<400> SEQUENCE: 538

Asn Lys Lys Val Asp Asp Gly Phe Leu Asp Ile Trp Thr Tyr Asn
1               5                   10                  15

<210> SEQ ID NO 539
<211> LENGTH: 15
<212> TYPE: PRT
<213> ORGANISM: Influenza A virus

<400> SEQUENCE: 539

Asn Leu Tyr Glu Lys Val Arg Ser Gln Leu Lys Asn Asn Ala Lys
1               5                   10                  15

<210> SEQ ID NO 540
<211> LENGTH: 15
<212> TYPE: PRT
<213> ORGANISM: Influenza A virus

<400> SEQUENCE: 540

Asn Arg Glu Glu Ile Asp Gly Val Lys Leu Glu Ser Thr Arg Ile
1               5                   10                  15

<210> SEQ ID NO 541
<211> LENGTH: 15
<212> TYPE: PRT
<213> ORGANISM: Influenza A virus

<400> SEQUENCE: 541

Asn Thr Thr Cys Gln Thr Pro Lys Gly Ala Ile Asn Thr Ser Leu
1               5                   10                  15

<210> SEQ ID NO 542
<211> LENGTH: 15
```

```
<212> TYPE: PRT
<213> ORGANISM: Influenza A virus

<400> SEQUENCE: 542

Pro Asn His Asp Ser Asn Lys Gly Val Thr Ala Ala Cys Pro His
1               5                   10                  15

<210> SEQ ID NO 543
<211> LENGTH: 15
<212> TYPE: PRT
<213> ORGANISM: Influenza A virus

<400> SEQUENCE: 543

Gln Ile Leu Ala Ile Tyr Ser Thr Val Ala Ser Ser Leu Val Leu
1               5                   10                  15

<210> SEQ ID NO 544
<211> LENGTH: 15
<212> TYPE: PRT
<213> ORGANISM: Influenza A virus

<400> SEQUENCE: 544

Gln Leu Lys Asn Asn Ala Lys Glu Ile Gly Asn Gly Cys Phe Glu
1               5                   10                  15

<210> SEQ ID NO 545
<211> LENGTH: 15
<212> TYPE: PRT
<213> ORGANISM: Influenza A virus

<400> SEQUENCE: 545

Gln Thr Pro Lys Gly Ala Ile Asn Thr Ser Leu Pro Phe Gln Asn
1               5                   10                  15

<210> SEQ ID NO 546
<211> LENGTH: 15
<212> TYPE: PRT
<213> ORGANISM: Influenza A virus

<400> SEQUENCE: 546

Arg Tyr Ala Phe Ala Met Glu Arg Asn Ala Gly Ser Gly Ile Ile
1               5                   10                  15

<210> SEQ ID NO 547
<211> LENGTH: 15
<212> TYPE: PRT
<213> ORGANISM: Influenza A virus

<400> SEQUENCE: 547

Ser Asp Thr Pro Val His Asp Cys Asn Thr Thr Cys Gln Thr Pro
1               5                   10                  15

<210> SEQ ID NO 548
<211> LENGTH: 15
<212> TYPE: PRT
<213> ORGANISM: Influenza A virus

<400> SEQUENCE: 548

Ser Asn Lys Gly Val Thr Ala Ala Cys Pro His Ala Gly Ala Lys
1               5                   10                  15

<210> SEQ ID NO 549
<211> LENGTH: 15
<212> TYPE: PRT
<213> ORGANISM: Influenza A virus
```

<400> SEQUENCE: 549

Ser Asn Val Lys Asn Leu Tyr Glu Lys Val Arg Ser Gln Leu Lys
1               5                   10                  15

<210> SEQ ID NO 550
<211> LENGTH: 13
<212> TYPE: PRT
<213> ORGANISM: Influenza A virus

<400> SEQUENCE: 550

Ser Arg Gly Phe Gly Ser Gly Ile Ile Thr Ser Asn Ala
1               5                   10

<210> SEQ ID NO 551
<211> LENGTH: 15
<212> TYPE: PRT
<213> ORGANISM: Influenza A virus

<400> SEQUENCE: 551

Ser Arg Tyr Ser Lys Lys Phe Lys Pro Glu Ile Ala Ile Arg Pro
1               5                   10                  15

<210> SEQ ID NO 552
<211> LENGTH: 15
<212> TYPE: PRT
<213> ORGANISM: Influenza A virus

<400> SEQUENCE: 552

Thr Arg Ile Tyr Gln Ile Leu Ala Ile Tyr Ser Thr Val Ala Ser
1               5                   10                  15

<210> SEQ ID NO 553
<211> LENGTH: 15
<212> TYPE: PRT
<213> ORGANISM: Influenza A virus

<400> SEQUENCE: 553

Thr Ser Ser Trp Pro Asn His Asp Ser Asn Lys Gly Val Thr Ala
1               5                   10                  15

<210> SEQ ID NO 554
<211> LENGTH: 15
<212> TYPE: PRT
<213> ORGANISM: Influenza A virus

<400> SEQUENCE: 554

Val Ala Ser Ser Leu Val Leu Val Val Ser Leu Gly Ala Ile Ser
1               5                   10                  15

<210> SEQ ID NO 555
<211> LENGTH: 15
<212> TYPE: PRT
<213> ORGANISM: Influenza A virus

<400> SEQUENCE: 555

Val Asp Thr Val Leu Glu Lys Asn Val Thr Val Thr His Ser Val
1               5                   10                  15

<210> SEQ ID NO 556
<211> LENGTH: 15
<212> TYPE: PRT
<213> ORGANISM: Influenza A virus

<400> SEQUENCE: 556

Val His Asp Cys Asn Thr Thr Cys Gln Thr Pro Lys Gly Ala Ile
1               5                   10                  15

<210> SEQ ID NO 557
<211> LENGTH: 15
<212> TYPE: PRT
<213> ORGANISM: Influenza A virus

<400> SEQUENCE: 557

Val Ser Leu Gly Ala Ile Ser Phe Trp Met Cys Ser Asn Gly Ser
1 5 10 15

<210> SEQ ID NO 558
<211> LENGTH: 15
<212> TYPE: PRT
<213> ORGANISM: Influenza A virus

<400> SEQUENCE: 558

Val Ser Ser Phe Glu Arg Phe Glu Ile Phe Pro Lys Thr Ser Ser
1 5 10 15

<210> SEQ ID NO 559
<211> LENGTH: 15
<212> TYPE: PRT
<213> ORGANISM: Influenza A virus

<400> SEQUENCE: 559

Val Thr Ala Ala Cys Pro His Ala Gly Ala Lys Ser Phe Tyr Lys
1 5 10 15

<210> SEQ ID NO 560
<211> LENGTH: 15
<212> TYPE: PRT
<213> ORGANISM: Influenza A virus

<400> SEQUENCE: 560

Val Thr Val Thr His Ser Val Asn Leu Leu Glu Asp Lys His Asn
1 5 10 15

<210> SEQ ID NO 561
<211> LENGTH: 14
<212> TYPE: PRT
<213> ORGANISM: Influenza A virus

<400> SEQUENCE: 561

Trp Met Cys Ser Asn Gly Ser Leu Gln Cys Arg Ile Cys Ile
1 5 10

<210> SEQ ID NO 562
<211> LENGTH: 15
<212> TYPE: PRT
<213> ORGANISM: Influenza A virus

<400> SEQUENCE: 562

Tyr Asp Tyr Pro Lys Tyr Ser Glu Glu Ala Lys Leu Asn Arg Glu
1 5 10 15

<210> SEQ ID NO 563
<211> LENGTH: 15
<212> TYPE: PRT
<213> ORGANISM: Influenza A virus

<400> SEQUENCE: 563

Tyr Gln Asn Ala Asp Ala Tyr Val Phe Val Gly Ser Ser Arg Tyr

```
1               5                   10                  15
```

<210> SEQ ID NO 564
<211> LENGTH: 19
<212> TYPE: PRT
<213> ORGANISM: Influenza A virus

<400> SEQUENCE: 564

```
Glu Asn Ala Tyr Val Ser Val Val Ser Ser His Tyr Ser Arg Lys Phe
1               5                   10                  15

Thr Pro Glu
```

<210> SEQ ID NO 565
<211> LENGTH: 19
<212> TYPE: PRT
<213> ORGANISM: Influenza A virus

<400> SEQUENCE: 565

```
Glu Pro Gly Asp Thr Ile Ile Phe Glu Ala Asn Gly Asn Leu Ile Ala
1               5                   10                  15

Pro Arg Tyr
```

<210> SEQ ID NO 566
<211> LENGTH: 19
<212> TYPE: PRT
<213> ORGANISM: Influenza A virus

<400> SEQUENCE: 566

```
Glu Ser Trp Ser Tyr Ile Val Glu Lys Pro Asn Pro Glu Asn Gly Thr
1               5                   10                  15

Cys Tyr Pro
```

<210> SEQ ID NO 567
<211> LENGTH: 19
<212> TYPE: PRT
<213> ORGANISM: Influenza A virus

<400> SEQUENCE: 567

```
Ile Gly Asp Gln Lys Ala Leu Tyr His Thr Glu Asn Ala Tyr Val Ser
1               5                   10                  15

Val Val Ser
```

<210> SEQ ID NO 568
<211> LENGTH: 19
<212> TYPE: PRT
<213> ORGANISM: Influenza A virus

<400> SEQUENCE: 568

```
Asn Cys Ser Val Ala Gly Trp Ile Leu Gly Asn Pro Glu Cys Glu Leu
1               5                   10                  15

Leu Ile Ser
```

<210> SEQ ID NO 569
<211> LENGTH: 19
<212> TYPE: PRT
<213> ORGANISM: Influenza A virus

<400> SEQUENCE: 569

```
Asn Pro Glu Cys Glu Leu Leu Ile Ser Lys Glu Ser Trp Ser Tyr Ile
1               5                   10                  15

Val Glu Lys
```

<210> SEQ ID NO 570
<211> LENGTH: 19
<212> TYPE: PRT
<213> ORGANISM: Influenza A virus

<400> SEQUENCE: 570

Ser His Asn Gly Lys Leu Cys Leu Leu Lys Gly Ile Ala Pro Leu Gln
1               5                   10                  15

Leu Gly Asn

<210> SEQ ID NO 571
<211> LENGTH: 19
<212> TYPE: PRT
<213> ORGANISM: Influenza A virus

<400> SEQUENCE: 571

Val Leu Trp Gly Val His His Pro Pro Asn Ile Gly Asp Gln Lys Ala
1               5                   10                  15

Leu Tyr His

<210> SEQ ID NO 572
<211> LENGTH: 19
<212> TYPE: PRT
<213> ORGANISM: Influenza A virus

<400> SEQUENCE: 572

Tyr Ala Asn Asn Lys Glu Lys Glu Val Leu Val Leu Trp Gly Val His
1               5                   10                  15

His Pro Pro

<210> SEQ ID NO 573
<211> LENGTH: 20
<212> TYPE: PRT
<213> ORGANISM: Influenza A virus

<400> SEQUENCE: 573

Glu Ile Thr Asn Lys Val Asn Ser Val Ile Glu Lys Met Asn Thr Gln
1               5                   10                  15

Phe Thr Ala Val
                20

<210> SEQ ID NO 574
<211> LENGTH: 15
<212> TYPE: PRT
<213> ORGANISM: Influenza A virus

<400> SEQUENCE: 574

Ala Lys Ser Phe Tyr Lys Asn Leu Ile Trp Leu Val Lys Lys Glu
1               5                   10                  15

<210> SEQ ID NO 575
<211> LENGTH: 11
<212> TYPE: PRT
<213> ORGANISM: Influenza A virus

<400> SEQUENCE: 575

Ser Phe Glu Arg Phe Glu Ile Phe Pro Lys Thr
1               5                   10

HYBRID INFLUENZA SEED VIRUSES, COMPOSITIONS THEREOF, AND USE THEREOF IN THE DIAGNOSIS OR THERAPY OF INFLUENZA

SEQUENCE LISTING

The instant application contains a Sequence Listing which has been submitted electronically in ASCII format and is hereby incorporated by reference in its entirety. Said ASCII copy, created on Mar. 25, 2016, is named BUCHER-003_SL.txt and is 142,834 bytes in size.

FIELD OF THE INVENTION

Embodiments relate to fields of virology and manufacturing or screening for viruses that serve as useful adjuvants or compositions. Embodiments additionally relate to reagents and methods for screening such viruses.

BIOLOGICAL DEPOSITS

Hybridoma cell lines producing monoclonal antibodies mAb-2A6, mAb-2D11 and mAb-1B3 were deposited on Feb. 24, 2016, with the American Type Tissue Culture Collection (ATCC), 10801 University Blvd, Manassas, Va. 20110 and given internal designation numbers 39-3F2-2A6, 39-4D12-2D11 and 56-2G9-1B3, respectively. The cell lines were deposited under the terms of the Budapest Treaty, and were given the following ATCC Accession Nos: PR8-HA-39-3F2-2A6 (ATCC Patent Deposit Designation PTA-122858), PR8-HA-39-4D12-2D11 (ATCC Patent Deposit Designation PTA-122859) and PR8-HA-56-2G9-1B3 (ATCC Patent Deposit Designation PTA-122860). All restrictions imposed by the depositor on the availability to the public of the deposited biological material be irrevocably removed upon the granting of the patent.

BACKGROUND

Influenza viruses are classified as A, B, and C genera within the family Orthomyxoviridae, which are enveloped, negative-sense (complementary to mRNA sequence), single-stranded RNA viruses with a segmented genome. Influenza A and B type viruses, which possess eight gene segments, evolutionarily diverged from each other more recently than influenza C viruses which only have seven discrete gene segments (Suzuki and Nei, 2002). Influenza A viruses (IAV) infect a variety of warm-blooded animals including humans, horses, pigs, etc., and aquatic birds serve as their natural reservoir (Webster et al., 1992).

Compared to IAV, influenza B and C viruses which mainly infect humans are less common and usually cause mild illness (Taubenberger and Morens, 2008). IAV can be further grouped into different subtypes based on the antigenicity of the two major surface glycoproteins: hemagglutinin (HA) and neuraminidase (NA). To date, there are 16 recognized HA subtypes and nine NA subtypes (Fouchier et al., 2005), and recently a new IAV has been discovered with both HA and NA which are divergent from all known influenza A subtypes (Tong et al., 2012). Each influenza virus strain is designated according to its type, the host of origin (if non-human), site of isolation, isolate number, year of isolation, and in the case of IAV, the subtype of HA and NA is given in parentheses (W.H.O., 1980). For example, A/Uruguay/716/2007 (H3N2) is the 716th isolate of a H3N2 subtype IAV isolated from a person in Uruguay in 2007.

The genome of IAV consists of eight RNA segments that typically encode a total of eleven proteins (Ghedin et al., 2005): polymerase basic protein 2 (PB2), polymerase basic protein 1 (PB1), PB1-F2, polymerase acidic protein (PA), hemagglutinin (HA), nucleoprotein (NP), neuraminidase (NA), the matrix protein (M1), the ion channel protein (M2), nonstructural protein 1 (NS1) and nuclear export protein/nonstructural protein 2 (NEP/NS2).

Among the eleven proteins, M2 and NEP/NS2 are encoded by spliced mRNAs from M and NS gene segments, respectively (Lamb and Horvath, 1991). PB1-F2 has been found to be encoded by an alternate open reading frame near the 5' end of the PB1 gene in most IAV (Chen et al., 2001). The PB1 gene recently has been reported to encode a third polypeptide expressed via differential AUG codon usage, termed N40 (Wise et al., 2009). Each viral segment contains noncoding regions at both 5' and 3' ends with promoter activity; the first 12 nucleotides at the 3' end and the last 13 at the 5' end are highly conserved among all segments, and these are followed by segment-specific noncoding regions (Fodor et al., 1995; Parvin et al., 1989). These conserved regions are also found to incorporate the RNA packaging signals for virus assembly (Gog et al., 2007).

The IAV particles are pleomorphic with spherical or filamentous morphology, or a mixture of both. Fresh clinical isolates are mostly seen as filamentous particles in contrast to the laboratory strains which have been extensively passaged in eggs or tissue culture are more in spherical shape (80-120 nm in diameter). The lipid envelope of the influenza virus particle is derived from the host cytoplasmic membrane embedded with two major integral membrane glycoproteins or spikes, HA and NA, projecting from the surface. The mean ratio of HA to NA spikes is about 4:1 and both protrude from the viral surface ranging from 10-12 nm in length (Nayak et al., 2009). The HA molecules are rod-shaped while NA spikes resemble 'mushroom' with a hydrophobic stalk. Indirect immunogold staining showed that the HA spikes are uniformly distributed on the virions (Murti and Webster, 1986) while the distribution of NA remains uncertain. It has been shown that if the HA spikes are removed with trypsin, then NA spikes became evenly distributed (Erickson and Kilbourne, 1980). However, earlier observations suggested that the NA spikes are clustered in discrete areas (Compans et al., 1969) as shown by immunoelectron microscopy with monoclonal antibodies, the NA proteins seem to be in patches (Amano et al., 1992; Murti and Webster, 1986). The third transmembrane protein, M2, serves as an ion channel to pump protons into the virion core during the uncoating process which releases the viral genome (Pinto et al., 1992; Sugrue et al., 1990).

Beneath the lipid membrane, the matrix protein M1 functions as a bridge between the envelope and the central virion core composed of eight ribonucleoprotein complexes (RNPs) (Nayak et al., 2004; Schmitt and Lamb, 2005). The M1 layer in opposition to the lipid membrane is believed to stabilize the virus particle (El Karadaghi et al., 1984).

Immunogold labeling with monoclonal antibodies to M1 failed to detect the protein in virions unless they were first treated with a protease or a detergent (Murti et al., 1992). It has been demonstrated that M1 directly binds lipid membrane (Bucher et al., 1980; Ruigrok et al., 2000) and associates with the transmembrane proteins: HA, NA, and M2 (Ali et al., 2000; Enami and Enami, 1996). M1 was also shown to interact with viral RNPs (vRNPs) and the M1-vRNP complex can be isolated from either infected cells or purified virions (Hara et al., 2003; Kawakami and Ishihama, 1983). The isolated vRNPs are rod-shaped, righthanded helices in various lengths ranging from 50 to 150 nm (Compans et al., 1972). Each RNP is comprised of one set of polymerase complex (PB1, PB2, and PA) and one viral RNA segment coated by NP with approximately one NP per 25 nucleotides and without sequence specificity (Compans et al., 1972; Ortega et al., 2000). The partially complementary 5' and 3' terminal ends of viral RNA form a panhandle-like structure (Hsu et al., 1987). NEP/NS2, an exporter for RNP complexes from the nucleus, is also found in purified virions, whereas NS1 and PB1-F2 proteins have not been detected (Richardson and Akkina, 1991).

Hemagglutinin (HA) and neuraminidase (NA) are the two major viral surface glycoproteins and the most important immunogens recognized by the host adaptive immune system. Accordingly, IAV can be further divided into 16 different HA subtypes (H1-H16) and 9 different NA subtypes (N1-N9) based on the differential antigenicity of HA and NA molecules (Fouchier et al., 2005). Phylogenetically, there are two groups of HAs: group 1 including H1, H2, H5, H6, H8, H9, H11, H12, H13, and H16 and, group 2 which contains H3, H4, H7, H10, H14, and H15. Similarly for NA, group 1 includes N1, N4, N5, and N8, and group 2 includes N2, N3, N6, N7 and N9 (FIG. 2).

The HA protein is a rod-shaped homotrimer with the carboxyl terminus integrated into the viral lipid membrane and the hydrophilic end extending as a spike away from the viral surface (Palese and Shaw, 2007). The monomeric HA molecule is initially synthesized as a single polypeptide chain (HA0) which undergoes posttranslational editing and modification, such as signal peptide cleavage, glycosylation, palmitoylation, and cleavage of the HA0 precursor (Klenk et al., 1975; Lazarowitz and Choppin, 1975; Porter et al., 1979). The resulting HA1 and HA2 subunits from HA0 cleavage are covalently linked by a single disulfide bond, while three HA1-HA2 monomers are associated via non-covalent forces. The HA molecule is structurally composed of two domains, a globular head and a fibrous stem (Stevens et al., 2004; Wang and Palese, 2011). The membrane-distal globular head region is exclusively composed of HA1 subunit and frames the receptor-binding site (RBS) (FIG. 3). The stem region, which is more proximal to the viral membrane, consists of residues from both HA1 and HA2 subunits. Receptor binding and membrane fusion activities are the two major functions of HA during the IAV life cycle, but it has been also suggested that HA may be involved in the virion assembly and budding steps. Initially, HA binds to the terminal sialic acid of oligosaccharides on glycoproteins or glycolipids of the host cells via a shallow depression at the globular head of HA1 subunit (Skehel and Wiley, 2000). After sialic acid receptor binding and endocytosis, the low pH in the endosomes triggers a dramatic conformational change of the HA2 subunit to execute the fusion activity (Stegmann, 2000). When it comes to the egress of progeny viruses, the HA is believed to incorporate the apical transport signals within its transmembrane domain and/or cytoplasmic tail (Brewer and Roth, 1991; Lin et al., 1998). The highly conserved transmembrane domain as well as the cytoplasmic tail of HA has also been shown to be important for efficient raft association which is believed to provide a platform for virion assembly and budding (Melkonian et al., 1999; Takeda et al., 2003).

The major protective immunity (i.e., neutralizing antibodies) against influenza viruses is induced by the HA glycoprotein. As mentioned above, the antigenicity of influenza A virus HA is subtype-specific and this feature is largely determined by the immune response to the globular head region (HA1 subunit). It is generally appreciated that influenza A virus HA possesses five different antigenic sites in the three-dimensional structure, although some overlap of these domains has been noted (Wiley and Wilson, 1981; Caton et al., 1982). For the H3 subtype, the five antigenic sites are A, B, C, D, and E (Wiley and Wilson, 1981), and for the H1 virus strains they are designated as Ca1, Ca2, Cb, Sa, and Sb (Caton et al., 1982). All these sites were identified from amino acid variations in escaping mutants selected with monoclonal antibodies and natural variants as well. These sites are also recognized as neutralizing epitopes, meaning monoclonal antibodies to each one of the five sites can neutralize the infectivity of the virus (Wiley and Skehel, 1987; Wiley and Wilson, 1981). It is notable that the gain or loss of N-linked glycosylation sites in the HA can also significantly affects the antigenicity of the molecule (Caton et al., 1982; Skehel et al., 1984).

NA is a type II transmembrane glycoprotein anchored into the viral membrane by the uncleaved signal/anchor domain at its N-terminus with a six amino-acid tail (Colman, 1994). The monomers of NA are synthesized in the ER and rapidly form a disulfide-linked dimer, which are then non-covalently oligomerized into tetramer. During the transport through Golgi apparatus, NA acquires a complex carbohydrate modification (Hogue and Nayak, 1992). The mature NA glycoprotein homotetramer is composed of a mushroom-shaped head and a slender stalk. The mushroom-shaped head is arranged with four identical coplanar and roughly spherical subunits in circular 4-fold symmetry and stabilized by calcium (Colman et al., 1983; Russell et al., 2006). Each monomeric subunit displays a symmetrical structure of six topologically identical anti-parallel β-sheets arranged as a propeller blade with the enzyme active site located in the center (Colman et al., 1983; Russell et al., 2006). The enzymatic activity on the surface of influenza viruses was first described by George Hirst (Hirst, 1942), who discovered that red blood cells turned out to be refractory to re-hemagglutination by influenza viruses after pre-treatment with the viruses. NA plays at least two major roles in the viral life cycle on the basis of its receptor-destroying activity. First, since the respiratory mucosal layer is also rich in sialic acid receptors for HA, the NA is needed to minimize the binding of HA to "decoy" receptors, thereby enabling the viruses to reach target cells on the respiratory epithelium (Palese et al., 1974). Another well-documented function of NA is to facilitate release of progeny virions by removing the sialic acid receptors from the viral particles and the infected cell surface. This role of NA was interpreted from the finding that intact virions were shown to aggregate on the surface of cells infected by mutants with defects in NA (Palese et al., 1974; Palese and Compans, 1976). Similar to HA, NA has also been reported to play a role in raft association and virion assembly. NA contains signals for apical transport in its transmembrane and cytoplasmic domains. The transmembrane domain also contains a signal for raft association which is separated from the apical sorting signal (Barman and Nayak, 2000). The highly conserved six amino-acid cytoplasmic tail of NA is also involved in virion assembly and budding (Jin et al., 1997).

The IAV NA generally has four antigenic sites consisting of multiple epitopes (Webster et al., 1984). Depending on their relationship with the enzymatic center, antibodies targeting some sites but not all of them can inhibit neuraminidase activity, and the mutations mainly occur in the distal surface loops connecting the various strands of β-sheets (Air et al., 1985). The site-specific mutagenesis indicates that only a few amino acids on five polypeptide loops surrounding the enzyme active site is critical for antibody recognition (Nuss et al., 1993).

Viral Life Cycle

IAV initiates infection by binding the cellular receptor through the HA glycoprotein. Although neuraminic acid serves as the ubiquitous receptor for IAV, viral Has isolated from different species do have differential binding specificity to the linkage between N-acetylneuraminic acid and the penultimate galactose sugar. Typically, human influenza viruses prefer the α-2,6 linkage whereas avian viruses are most likely to bind sialic acid with an α-2,3 linkage (Connor et al., 1994), however this specificity is not absolutely exclusive. After binding to the receptors, the attached virion undergoes a receptor-mediated endocytosis via different pathways (Lakadamyali et al., 2004). The low pH in the late endosome triggers a conformational change in the cleavage-activated HA to initiate fusion of the viral and vesicular membranes to release the core virion into the cytoplasm (Skehel et al., 1982). Meanwhile, M2 proteins channel protons into the core virion, which is believed to promote dissociation of the M1 from the ribonucleoprotein complexes (RNPs) and allow the RNPs to migrate to the nucleus (Pinto et al., 1992; Zhirnov, 1990). The proteins associated with RNPs including PB2, PB1, PA and NP all possess nuclear localization signals, which mediate the active nuclear import of RNPs via interactions with host nuclear import machinery (Kemler et al., 1994). When the RNPs reach the host cell nucleus, the associated polymerase complexes start primary transcription of mRNA from the viral genome by 'snatching' a 5'-capped primer from host cellular mRNA (Krug et al., 1979). The primary transcripts are then used in the production of viral proteins by the cellular translation machinery. The replication of viral RNAs occurs through a two-step primer-independent process. A full-length viral complementary RNA (cRNA) has to be synthesized first to serve as the template for the following production of viral RNAs. It was believed that the synthesis of cRNA was delayed until viral proteins had been produced (Beaton and Krug, 1986). However recent findings indicate that cRNA may start to be synthesized in early infection, but it is degraded rapidly by cellular nucleases until sufficient polymerases and NP proteins encapsidate it (Vreede et al., 2004). Newly synthesized polymerases (PB2, PB1, PA) and NP proteins are transported into the nucleus after their translation in the host cell cytosol to assemble new RNP complexes with progeny viral genomic RNAs in the nucleus. After their translation, viral membrane proteins HA, NA, and M2 are translocated into the lumen of the endoplasmic reticulum (ER) where they are further oligomerized, glycosylated and subsequently transported to the plasma membrane (Doms et al., 1993). The apical localization of viral membrane proteins in polarized cells determines the assembly and budding site for the progeny viral particles and the apical sorting signals have been identified within the transmembrane domains (TMD) of HA and NA (Nayak et al., 2004). M1 has been shown to be the only absolutely required viral protein during the virion assembly and budding process because of its interactions with other viral components (Gomez-Puertas et al., 2000). M1 and NEP/NS2 are proposed to cooperate with the cellular export factor (CRM1) to direct the nuclear export of viral RNPs (Neumann et al., 2000). After RNPs leave the nucleus, M1 may function as a molecular 'glue' to direct RNPs to the assembly site through its interaction with the cytoplasmic lipid membrane and cytosolic tails of integral viral proteins (Ali et al., 2000; Bucher et al., 1980; Enami and Enami, 1996; Ruigrok et al., 2000). Furthermore, M1 is vital for bud formation since budding cannot occur in the absence of M1, yet M1 alone can induce the formation of virus like particles (Gomez-Puertas et al., 2000). When a progeny viral particle is completely formed, the neuraminidase activity of the NA protein will cleave the sialic acid residues on the cellular receptor and those between the new virions to release the viruses for the next round of infection on neighboring cells (Palese et al., 1974).

Influenza is an acute viral infection caused by influenza viruses. It is one of the most common respiratory infections in humans and perhaps one of the most significant with its existence recorded in human history with high morbidity and mortality rate. Careful retrospective investigations of the historical records have revealed that outbreaks of influenza epidemics or pandemics can be traced back to at least the Middle Ages, if not earlier (Kilbourne, 1987). Seroarcheological studies have also shown that 90% of subjects born between 1857-1877 were found to have antibodies to 'Hong Kong' influenza virus (H3N2) prior to its epidemic reappearance in 1968 and 26% had pre-epidemic antibodies to the 'Asian' influenza virus (H2N2) that caused the pandemic of 1957 (Davenport, 1977; Masurel and Marine, 1973). Also, serological evidence for circulation of H1N1 viruses before the outbreak of 1918 'Spanish' influenza has been documented as well (Masurel and Heijtink, 1983; Rekart et al., 1982).

Seasonal influenza epidemics occur every year in temperate climates mostly from late autumn throughout the next spring with peak periods lasting 6-8 weeks. The seasonality of influenza activity is less established for tropical and sub-tropical regions. However, influenza viruses in the tropical and subtropical areas can circulate throughout the year at relatively low level with typical peaks of activity occurring in the summer months (Reichelderfer and Kendal, 1989). Although epidemics of influenza occur every year, the rates and severity of illness varies substantially from year to year. During a typical influenza epidemic, the overall infection rate is estimated to be 10-20%, but in selected populations or age groups, e.g., school-age children, a rate of primary influenza illness of 40-50% is not uncommon (Glezen, 1996). It is estimated that every year influenza epidemics result in about three to five million cases of severe illness, and about 250,000-500,000 deaths worldwide (W.H.O., 2009). In the United States, an annual average of more than 200,000 hospitalizations and about 36,000 deaths are caused by influenza-associated respiratory and circulatory illnesses (Thompson et al., 2003; Thompson et al., 2004).

In addition to annual seasonal influenza epidemics, pandemics of influenza have emerged at irregular intervals and varied in severity from mild to catastrophic. During the 20th century, there were at least three indisputable influenza pandemics: 1918 'Spanish' influenza, 1957 'Asian' influenza, and 1968 'Hong Kong' influenza. As the worst influenza pandemic in recorded history, the 1918 'Spanish' flu was estimated to cause approximately 675,000 total deaths in the United States and have killed up to 50 million people worldwide (Johnson and Mueller, 2002). In 1957, the 'Asian' influenza pandemic caused a total global excess mortality of over 1 million deaths, while the 1968 'Hong Kong' influenza pandemic also resulted in about 1 million excess deaths worldwide (Lipatov et al., 2004). In 2009, the world encountered the first influenza pandemic of the 21st century, which spread more rapidly across the continents than the previous pandemics, probably due to the sharp increase of individual travel. The illness caused by the 2009 H1N1pdm virus was relatively mild in most cases. According to the estimates by CDC from April 2009 to April 2010, more than 50 million people in the United States were infected by the 2009 H1N1pdm influenza virus, which resulted in about 195,000-403,000 hospitalizations and approximately 12,470 deaths in the United States (CDC, 2010). Influenza is generally accepted as an acute, prostrating, self-limited respiratory illness. The incubation period for influenza is relatively short with a typical 1-2 days from infection to onset of illness. The clinical expression of influenza infection is highly variable and largely influenced by the age, physiological status and pre-existing immunity of the host (Kilbourne, 1987). The typical symptoms of influenza infection in adults include fever, chills, headache, sore throat, dry cough, nasal discharge, myalgia, anorexia and malaise, while gastrointestinal symptoms such as vomiting, abdominal pain and diarrhea are also frequently observed in children. Generally influenza is a short-lived infection in healthy adults as most people recover from fever and other symptoms within a week without requiring medical attention, while cough and malaise may persist for one or more weeks after fever has subsided (Cox et al., 2010). Common complications of influenza infection include secondary bacterial pneumonia and exacerbation of underlying chronic cardiac, pulmonary, or metabolic diseases and otitis media in children (Nicholson, 1992). Secondary bacterial infections usually occur 5-10 days after initial onset of influenza symptoms and are responsible for most pneumonia during influenza epidemics. Typically *Streptococcus pneumoniae, Staphylcoccus aureus* and *Hemophilus influenzae* are the most common causative pathogens (Schwarzmann et al., 1971). Other uncommon complications of influenza include myositis, myocarditis and pericarditis, acute renal failure, encephalopathy, encephalitis, transverse myelitis, toxic-shock syndrome and Reye's syndrome. The Reye's syndrome is generally associated with the use of salicylate medications in children with influenza-like illness (Noble. 1982).

Currently there are two measures employed to reduce the impact of influenza: antiviral drugs and vaccination, antivirals and vaccines. Antiviral drugs are utilized as chemotherapy as well as chemoprophylaxis to control influenza. Based on the chemical properties and spectrum of activity against influenza, the currently licensed antiviral drugs can be classified into two categories, adamantine derivatives (amantadine and rimantadine) and neuraminidase inhibitors (oseltamivir and zanamivir). Both drugs have been shown to be effective in decreasing viral shedding and reducing the duration of symptoms of influenza infection by approximately one day if administered within 48 hours of the onset of illness compared with placebo administration (Burch et al., 2009). Adamantane only inhibits the replication of influenza A viruses, while the NA inhibitors are active against both type A and type B viruses, and the recommended treatment course for both antivirals is usually 5 days. Both adamantane derivatives and neuraminidase inhibitors are effective to be used as chemoprophylaxis. When used for chemoprophylaxis, amantadine and rimantadine are approximately 70-90% effective in preventing illnesses resulting from influenza type A infection (Hayden et al., 1996). Zanamivir and oseltamivir are approved to be used prophylactically for influenza A and B infections in individuals aged more than five years and one year old, respectively. Up to 82% of febrile, laboratory-confirmed influenza illnesses were prevented by zanamivir or oseltamivir prophylaxis (Hayden et al., 1999; Welliver et al., 2001). Studies also show that prophylactic treatment of household members with zanamivir or oseltamivir reduced secondary transmission by 79%-89% (Hayden et al., 2000; Welliver et al., 2001). The antiviral activity of amantadine and rimantadine is believed to be exerted through the M2 ion channel functions. At the early stage of the viral replication cycle, the blockage of the M2 transmembrane domain by the drugs prevents the import of protons into the viral core and in turn inhibits the dissociation of M1 from the ribonucleoprotein complex, a step which is essential for the initiation of viral transcription and replication (Pinto et al., 1992; Sugrue et al., 1990). In addition, for certain avian viruses these compounds can block a low pH-mediated maturation of the HA protein during its transport from ER to the cell surface, and as a result the viral assembly process is disrupted (Takeuchi and Lamb, 1994).

Oseltamivir and zanamivir are analogues of sialic acid that block the enzymatic activity of NA to impair the second round of infection by progeny viruses and consequently provide antiviral activity. Because NA activity is essential for newly assembled virions to be released from infected cells and prevent them from aggregating with each other, an effective level of NA activity is critical for multiple viral infectious cycles to generate a successful influenza infection (Gubareva et al., 2000); inhibition of NA activity would therefore attenuate secondary viral infection. The use of adamantane derivatives has been associated with the rapid selection and development of resistant virus strains. Resistant viruses can emerge when either of these drugs is administered for treatment in adults or children. The acquisition of resistance is not associated with attenuation since resistant mutants are equally pathogenic as their drug-sensitive counterparts (Hayden et al., 1996). The resistant strains are mostly found in the H3N2 subtype isolates rather than H1N1 isolates; in 2006, 92% of H3N2 isolates from the United States were shown to be drug-resistant (Bright et al., 2006). Most H5N1 isolates are resistant to the adamantane drugs, therefore neither amantadine nor rimantadine are recommended for prevention or treatment of the highly pathogenic avian influenza infections (Schünemann et al., 2007). Furthermore, all 2009 H1N1pdm viruses are also resistant to the adamantane derivatives, due to a single amino acid mutation at the transmembrane region of M2 (Dawood et al., 2009). Emergence of NA inhibitor resistant variants can be induced in vitro, but requires multiple passages in cell culture (Gubareva et al., 1997). In contrast to the adamantanes, the frequency of isolating naturally occurring NA inhibitor resistant mutants is relatively low (Gubareva et al., 2000), with most cases from children (Kiso et al., 2004). In 2008 a high percentage of seasonal H1N1 strains were found to be resistant to oseltamivir but still sensitive to zanamivir; however H3N2 and type B viruses are still sensitive to both neuraminidase inhibitors. Oseltamivir-resistant H5N1 viruses have also been reported in both recovered and fatal cases (De Jong et al., 2005). Although 2009 H1N1pdm viruses still remain sensitive to NA inhibitors, some oseltamivir-resistant viruses have been reported (Baz et al., 2009).

With the rapid emergence of antiviral drug-resistant influenza viruses, immunoprophylaxis with seasonal or pandemic vaccines still remains the most effective way to control influenza. Since the first inactivated influenza vaccine was used in the 1940s, the effectiveness of inactivated vaccine has been widely demonstrated in both military and civilian populations (Couch et al., 1986; Monto and Terpenning, 1996). Current inactivated vaccines can protect 70-90% of normal healthy adults against naturally occurring disease when the antigens of the vaccine match the circulating influenza viruses (Buxton Bridges et al., 2000; Nichol et al., 1995). Numerous studies have shown that seasonal vaccination reduces rates of hospitalization and death among nursing home residents whose average age is 85 years old (Ohmit et al., 1999; Patriarca et al., 1985). During the 2012-13 season, an interim estimate of the overall effectiveness of influenza vaccine was 56% (95% confidence interval [CI]=47%-63%)(CDC, 2013). Generally, vaccination is associated with reductions in: (a) influenza-related respiratory illnesses and physician visits; (b) hospitalizations and deaths among people at high risk; (c) Otitis media among children; and (d) work absenteeism levels in adults (WHO Global Influenza Surveillance Network, 2011).

Current seasonal influenza vaccines have a trivalent formulation which contains antigens of two influenza A subtypes (H1N1pdm and H3N2) and one or two representative type B strains. Since influenza viruses are highly mutable resulting in antigenic drift, the formulation of influenza vaccine needs to be updated annually. Typically, one or two components of the vaccine will be changed each year. Every February and September the World Health Organization (WHO) makes recommendations for northern and southern hemisphere vaccine formulations, respectively, about the influenza strains that should be included into the vaccine for the following influenza season (Gerdil, 2003). Such a recommendation is based on data collected within the WHO global influenza surveillance network to match the antigenicity of the influenza viruses that are likely emerging and circulating in the following influenza season (Cox et al., 2010). The inactivated influenza vaccines, i.e., flu shot, comprise the vast majority of vaccine doses distributed during annual vaccination campaigns. Since the 1970-1971 influenza season, the vaccine seeds used for production of type A components of the vaccine are high-yield reassortant (HYR) viruses instead of wild type (WT) field isolates (Kilbourne, 1969). By incorporating the "internal" genes from an egg-adapted laboratory strain, A/Puerto Rico/8/1934 (PR8), the reassortants achieve high-yield in eggs while preserving the antigenicity (HA and NA) of the target WT viruses.

Two types of influenza vaccines that are currently licensed in the United States are live attenuated influenza vaccine (LAIV) and inactivated influenza vaccine. The LAIV is composed of viruses that are avirulent and only produce mild or no symptoms on infections. The temperature-sensitive property of LAIV strains limits the replication in human lower respiratory airway since they are cold-adapted with efficient replication at 25 (Smith et al., 2006). In the United States, LAIV is currently only approved for use in healthy individuals aged 2-49 years who are not pregnant (Harper et al., 2004). The inactivated influenza vaccine can be further categorized into two types based on their effective components. The inactivated subvirion vaccine contains detergent-disrupted inactivated virus while surface antigen vaccine only contains isolated hemagglutinin (HA) and neuraminidase (NA) proteins, and both inactivated vaccines are approved for use in people aged more than 6 months old (Harper et al., 2004). Trivalent inactivated vaccine has been shown to be more effective than LAIV in the elderly (Treanor and Betts, 1998), whereas the reverse is true in young children (Belshe et al., 2007). The inactivated influenza vaccines comprise the majority of vaccine doses used during the annual vaccination campaign. Briefly, vaccine strains are grown individually in the allantoic cavity of embryonated chicken eggs, the allantoic fluid is harvested and then the virus is purified and concentrated by zonal centrifugation or column chromatography and finally inactivated with formalin or beta-propriolactone (Gerdil, 2003). For the current influenza vaccine only HA antigens are quantified by the single radial immuno-diffusion assay using standard antigens and specific sheep antiserum (Cox et al., 2010). Each vaccine dose must contain 15 μg HA per virus strain, while the quantity of NA may vary between vaccines.

Since the 1970-1971 influenza season, the vaccine seeds used for growth of type A components of the vaccine are high-yield reassortant viruses instead of wild type (WT) field isolates (Kilbourne, 1969). By incorporating the 'internal' genes from an egg-adapted laboratory strain, A/Puerto Rico/8/1934 (PR8), the reassortants achieve high-yield/growth in eggs while preserving the antigenicity (HA and NA) of the target WT viruses. Field isolates of representative type B influenza viruses with relatively high growth in eggs have been utilized usually utilized for production of the B component, however recently manufacturers have started to use type B reassortant viruses derived from reassorting HA and NA genes of WT viruses with 'internal' genes of a high growth egg-adapted B virus.

Reassortment generally refers to the "shuffling" of genetic material of a species into new combinations in different individuals. In particular, reassortment of influenza viruses is the rearrangement of viral RNA segments into progeny virus when two or more different influenza viruses infect the same cell. During the assembly of the new progeny virions, each of the RNA segments can derive from either parental virus to result in different gene combinations. Those progeny viruses with mixed-origin RNA segments are called 'reassortants'. Reassortment occurs in nature within the same type of influenza A, B and C viruses, but not across the different types (Wright, Neumann, Kawaoka, 2007a). The three latest influenza pandemics were all caused by reassortment within IAV. The 'Asian' influenza in 1957 and the 'Hong Kong' influenza in 1968 were caused by reassortment between human and avian viruses (Kawaoka et al., 1989), while the 2009 pandemic influenza strain was a "triple" reassortant of human, avian, and swine influenza viruses (Trifonov et al., 2009). Although reassortment has evolutionary benefits for the virus, it also provides us with a way to defend ourselves from influenza. In the 1960s, Dr. Edwin D. Kilbourne utilized reassortment as a genetic manipulation tool to quickly introduce desirable properties for vaccine production from a high-yield laboratory strain into a low-yield wild type virus (Kilbourne and Murphy, 1960). Since the application of reassortants to influenza vaccine production in 1971, reassortants have greatly improved the mass production of influenza vaccine. In brief, the seed viruses for the influenza A components are high-yield (hy) reassortants generated in embryonated chicken eggs (in ovo), which must contain two genes for the surface glycoproteins, hemagglutinin (HA) and neuraminidase (NA) from the currently circulating WT virus and up to six genes for the 'internal' proteins from the hy-donor virus, A/Puerto Rico/8/1934 (PR8) as the backbone (FIG. 1).

For the present classical reassortment method to generate seed viruses, the correct progeny viruses with WT HA and NA are selected for growth by using polyclonal antibodies (pAbs) against the high yield (hy) donor virus. Due to the uncertain effectiveness of pAbs, this negative selection process usually is repeated in 3 cycles and takes about 3-4 weeks or more. As a result, only the viruses with correct matching antigenicity (i.e., WT HA and NA genes) will comprise the selected virus population. With amplification, positive selection occurs with the reassortant variant with the best growth capability out-growing other reassortants. With cloning by limiting dilution the most abundant virus (indicating the virus with the best growth ability) will be readily cloned out from the virus population. The identity of the final cloned virus will be evaluated through molecular and serological tests.

Up to now the vaccine seed viruses prepared via the classical reassortment method are still being predominantly used for influenza A vaccine production because of their superior in ovo growth properties compared to seed viruses made by reverse genetics. Since classical reassortment develops seed viruses entirely in embryonated chicken eggs which are the predominant platform for producing influenza vaccines, the classically-made seed viruses are better adapted to in ovo growth than seed viruses prepared by other approaches.

Besides the established classical reassortment method, the reverse genetics (RG) method is widely recognized and employed as an alternative for developing influenza A vaccine seed viruses.

The RG technique provides an alternative way to make suitable vaccine seed viruses for the large scale production through direct molecular manipulations. The RG system was initiated when Palese and colleagues established a system that incorporates artificial viral RNA (vRNA) derived from cloned DNA into an influenza virus (Luytjes et at, 1989). However, the application of this system is limited by the reconstitution of the RNP complex and the selection of recombinant influenza virus from the helper virus background (Neumann and Kawaoka, 2002). The RG system, which only relies on DNA plasmids to generate vRNA and mRNA for the de novo synthesis of influenza virus, was independently developed by Neumann et al. and Fodor, et al. in 1999 (Fodor et al., 1999; Neumann et al., 1999). This system utilizes RNA polymerase I-driven plasmids to produce the complete set of eight influenza vRNA segments, and RNA polymerase II-driven plasmids for the generation of the three viral polymerases and NP proteins. Therefore, to successfully rescue a live influenza virus entirely from DNA plasmids, a total of 12 plasmids have to be simultaneously transfected into the same eukaryotic cell (e.g. 293T cells). The RG system was later refined by Hoffmann et al. (Hoffmann et al., 2000) to combine the vRNA and mRNA synthesis on one bi-directional plasmid which reduces the total number of plasmids that are required for rescue to eight. In 2005, Neumann and co-workers (Neumann et al., 2005) further reduced the total number of plasmids by combining eight RNA polymerase I transcription cassettes into one plasmid and the RNA polymerase II transcription cassettes of the three viral polymerases into another single plasmid. Several influenza inactivated vaccine seed viruses including highly pathogenic avian influenza virus, H5N1, have been generated by employing RG either through the 12 or eight plasmids system (Hoffmann et al., 2002; Nicolson et al., 2005; Webby et al., 2004). Following the same principle as classical reassortment, to acquire avirulent and high yield properties desired by vaccine manufactures, the HA and NA genes derived from circulating WT viruses are incorporated into a 'backbone' containing the six 'internal' genes from the by donor, PR8. The biggest advantage of RG over the classical reassortment method in making vaccine seed viruses is the capability of direct genetic modification of the viral genes. Because of the high virulence of the HA of highly pathogenic avian influenza virus (HPAI), the poly basic amino acid stretch at the HA cleavage site has to be removed to make vaccine seed virus attenuated for virus propagation in embryonated chicken eggs. This could only be achieved by RG but not by classical reassortment since the unmodified HPAI will kill the chicken embryo in the embryonated eggs. In addition, the RG technique does not need any selection process which theoretically should prepare the vaccine seed viruses more promptly than the classical reassortment method. However, during the response to 2009 H1N1pdm influenza pandemic the very first vaccine seed candidate was developed by classical reassortment instead of the RG method (Wanitchang et al., 2010). This suggests that although RG represents modern and advanced technology, the classical reassortment still remains as a standard and reliable method for generating seed viruses for influenza vaccine production. Therefore, improving the classical reassortment method will be of great interest to public health preparation against both annual influenza epidemics and potential pandemics.

Other than a few published articles (Kilbourne et al., 2004; Webster et al., 1988), the role of NA mAbs in countering influenza viruses remains to be further elucidated. In the aforementioned publications, NA mAbs were found to inhibit virus release from host cells resulting in size reduction of plaques, and some of these mAbs which inhibited catalytic activity of NA could neutralize the virus in embryonated chicken eggs. These studies merely postulated that mAbs to some epitopes on the NA protein may inhibit virus release more efficiently than others, depending on their relation to the enzymatic center (Webster et al., 1984). Subsequently, in the late 1990s, some mAbs prepared against the NA of A/Beijing/32/92 were shown to provide NA inhibition and also neutralize virus in infected cells (Aymard et al., 1998). In addition, in vivo protection of NA mAbs was demonstrated by treating influenza virus-infected SCID mice with non-neutralizing NA mAb that resulted in reduced pulmonary virus titer load (Mozdzanowska et al., 1999). However, there are few documented use of monoclonal antibodies in screening of seed viruses, particularly, seed viruses which can propagate and serve as immune compositions or vaccines for the prevention and treatment of influenza.

In this sense, polyclonal antibodies (pAbs), which have been traditionally employed in classical reassortment methods, are laden with problems. Firstly, classical methods involving pAbs are time-consuming and irreproducible due to the intrinsic disadvantage of using variably effective pAb. Additionally, polycloncal antibodies are problematic due to uncertainties of specificity and/or cross-reactivity. Due to time-sensitive nature of vaccine development and deployment, pAbs are not very useful as the selection by pAbs has to be performed three times or more to guarantee the elimination of donor virus' HA and NA genes (i.e., to ensure that the screened candidates only incorporate HA and NA genes from wild type (WT) viruses). This inherent disadvantage has led to increased interest in reverse genetics (RG) technique, which does not require such a selection process for vaccine seed virus preparation; the RG technique can directly manipulate and fix the gene composition for the resultant vaccine seed viruses. However, to date, HYRs prepared by classical reassortment have better growth properties than HYRs prepared by RG.

Monoclonal antibodies, which can be generated to meet predefined specificity requirements (see Kohler and Milstein, 1975), have been used in other research applications, e.g., immunostaining and immunoblotting; however, their application in the production of seed viruses has been discouraged in the art. For example, there are scientific reports of HA mAbs rendering viruses non-infective both in vitro and in vivo. There are only a few reports of non-neutralizing HA mAbs in literature (Cascino et al., 1986; Vanlandschoot et al., 1998); however, their use in screening of seed viruses, particularly, with respect to epitope mapping, was previously unknown in the field. Thus, there is an unmet need for novel antibody compositions which can be employed more efficiently to screen candidate viruses that serve as (or provide) immunotherapeutic compositions and vaccines, in particular monoclonal antibodies which can be used as reagents in classical reassortment for the generation of seed viruses, including seed viruses to fulfil the growing need for prophylactic or therapeutic vaccines against the influenza viruses, as well as serve as diagnostic and screening tools for the identification of new strains of viruses in circulation.

SUMMARY OF THE INVENTION

As described in detail below, embodiments of the instant invention provide for the isolation and characterization of suitable antibody candidates, such as, monoclonal antibodies targeting influenza virus surface glycoproteins (HA and NA) of the hy donor virus, A/Puerto Rico/8/1934 (PR8), which antibodies are then applied as selection reagents for the improving classical reassortment method and efficiently developing influenza A seed viruses. The implementation of these candidate antibodies in research and screening has also concomitantly led to the identification of many seed virus candidates, which are further optionally developed into immunological compositions, kits, and/or vaccines for the diagnosis, prophylaxis and therapy of influenza.

In contrast to heterogeneous pAbs of the art, monoclonal antibodies (mAbs) described herein are homogenous and highly specific to a particular antigen. MAbs with predetermined potent neutralizing activity to the hy donor virus can serve as a better selection reagent for classical reassortment. Since the mAbs recognize a defined epitope which provides high specificity to the hy donor virus, they enhance the selection efficiency by permitting minimal cross-reactivity to the HA and NA glycoproteins of WT viruses. Furthermore, the HA mAbs of the present invention have been intensively characterized including information of the epitopes to which they bind. The application of mAbs in the classical reassortment method greatly improves the speed and reliability of the generation of influenza A vaccine seed viruses, thereby allowing the production of influenza vaccines in a shorter time frame.

Embodiments of the instant invention also relate to methods for developing seed viruses that avoid cross-reactivity. As explained in detail below, during the antibody negative selection process, two hy donor viruses are used to provide the PR8 backbone (six 'internal' genes contribute to high growth in ovo). As a representative example, the first hy donor virus, e.g., PR8 (H1N1), is utilized for H3N2 subtype vaccine seed development; whereas a second H3N2 high yield reassortant (HYR) with all six 'internal' genes from PR8, NYMC X-157, is employed as the vehicle to deliver PR8 backbone genes into H1N1 and H1N1pdm subtypes. The reassorted strains are then negatively selected using antibody based reagents that bind to high yield donors' viral proteins (e.g. PR8, NYMC X-157). Preferably, monoclonal antibodies (mAbs) or antigen-binding fragments thereof are used in the selection process.

In this manner, the homogeneity of the mAbs will confer consistent selection activity as compared with the pAbs, thus improving the reproducibility of "classical reassortment" for generating the vaccine seed viruses. Also, the mAbs can be prepared in unlimited quantities using hybridomas, which is another advantage compared to pAbs, which can only be prepared in limited amounts using different antigen preparations and vary in efficacy from batch-to-batch, dependent on both the immunizing agent and the serologic response of the animal Thus, employing more potent and consistent selection reagents, such as monoclonal antibodies (mAbs), will significantly enhance the efficiency of the classical reassortment method. In contrast to unknown and variable components of pAbs, the more uniform and highly specific mAbs also serve better as selection reagents for developing vaccine seed viruses via the classical reassortment method.

Embodiments of the instant invention relate to candidate seed viruses for influenza A vaccine production. The seed viruses described are high yield reassortant (HYR) viruses generated in embryonated chicken eggs (in ovo), which contain two genes for the surface glycoproteins, hemagglutinin (HA) and neuraminidase (NA) from the currently circulating wild type (WT) virus and up to six genes for the 'internal' proteins from a highly egg adapted donor virus, A/Puerto Rico/8/1934 (PR8) and its derivatives. Art known classical reassortment method to generate candidate viruses rely on the use of reassortants having WT HA and NA genes that are then selected for growth by using polyclonal antibodies (pAbs) to inhibit progeny viruses with HA and NA from HYR donor virus. However, due to the variable efficacy and cross-reactivity of the non-homogenous pAbs, the selection process has to be repeated in multiple cycles and HYR donor viruses of a different subtype from WT viruses must be used. Embodiments of the instant invention thus provide efficient and reproducible reassortment methods via the use of monoclonal antibodies (mAbs) or antigen-binding fragments thereof, which not only provide high specificity against the HYR donor viruses, but can also be prepared as defined reagents with guaranteed activity in unlimited quantities. These monoclonal antibodies or antigen-binding fragments thereof are more potent and give consistent results as selection reagents compared to polyclonal antibodies. In this regard, the monoclonal antibodies and their antigen-binding fragments are useful as reagents for improving the efficiency of the classical reassortment method.

Embodiments of the instant invention further relate to methods for obtaining the monoclonal antibodies. From a panel of hybridoma clones developed for PR8 HA and NA proteins by a standard protocol, four HA mAbs and one NA mAb have been found highly specific in both in vitro and in ovo neutralization activity to the HYR donor virus, PR8. The epitopes of all four HA mAbs were mapped to the area around the receptor binding site (RBS) at the membrane-distal tip of HA. By utilizing mAb-1B3 (anti-HA) alone or combined with mAb-1G11 (anti-NA) as selection reagents, a more efficient mAb-based classical reassortment method for the preparation of influenza vaccine candidate seed viruses has been developed (10 day-turnaround). In contrast, the pAbs-based method requires about 21-28 days or more for generating seed viruses. Furthermore, in this novel mAb-based system, PR8 can be used as a universal HYR donor virus for the development of candidate vaccine viruses belonging to different influenza A subtypes Implementation of the new mAb-based reassortment method for vaccine seed preparation can significantly reduce the response time to influenza epidemics and will be of great value if the population encounters another pandemic.

Further embodiments of the instant invention relate to anti-NA antibodies. In contrast to HA antibodies, the antibodies directed against NA are usually non-neutralizing, but are capable of inhibiting or slowing down virus replication.

Embodiments of the instant invention further provide for immunological compositions based on one or more antigens expressed in the seed viruses. Insofar as the seed viruses for the influenza A components described herein are HYRs generated in embryonated chicken eggs (in ovo), which contain two genes for the surface glycoproteins, HA and NA from the currently circulating WT virus and up to six genes for the 'internal' proteins from the high-yield (hy) donor virus, PR8 as the backbone, the antigenic composition could contain, for example, one, two, three, four, five, six, seven or more of such antigens. Embodiments of the invention further relate to the antigenic and genetic identities of the final cloned viruses, which have been evaluated through molecular and serological tests.

Further embodiments of the instant invention provide unique mAbs, compositions thereof with other ingredients, including, the HA or NA antigens to which they bind, and kits comprising the same. Related embodiments relate to columns, tubes, plates, surfaces, etc. that contain the antibodies of the instant invention, including, kits comprising the same. Further embodiments of the invention relate to complementarity determining regions (CDR) domains of antibodies comprising variable heavy (VH) and/or variable light (VL) domains, antigen-binding fragments (e.g., Fab or $Fab_2$ fragments), $F_c$ subunits, and nucleic acids encoding the same. Also provided are phages, cells, hybridomas, tissues, and other biologicals containing such nucleic acids encoding the antibodies or fragments thereof. Embodiments of the instant invention further provide kits comprising such cells, hybridomas, and related biologicals and instructions, together with one or more further reagents for the propagation or maintenance of such cells, e.g., in a culture medium.

Embodiments of the instant invention further relate to pharmacological compositions and/or vaccines for the prevention and/or therapy of influenza in subjects, including, reduction of the incidence of influenza in subject populations.

Specific Embodiments

A few of the many embodiments encompassed by the present description are summarized in the following numbered paragraphs. The numbered paragraphs are self-referential. In particular, the phase "in accordance with any of the foregoing or the following" used in these paragraphs refers to the other paragraphs. The phrase means in the following paragraphs embodiments herein disclosed include both the subject matter described in the individual paragraphs taken alone and the subject matter described by the paragraphs taken in combination. In this regard, it is explicitly applicant's purpose in setting forth the following paragraphs to describe various aspects and embodiments particularly by the paragraphs taken in combination. That is, the paragraphs are a compact way of setting out and providing explicit written description of all the embodiments encompassed by them individually and in combination with one another and, accordingly, applicant specifically reserves the right at any time to claim any subject matter set out in any of the following paragraphs, alone or together with any other subject matter of any one or more other paragraphs, including any combination of any values therein set forth taken alone or in any combination with any other value set forth. Should it be required, applicant specifically reserves the right to set forth all of the combinations herein set forth in full in this application or in any successor applications having benefit of this application.

Antibodies, Nucleic Acids Encoding the Same, Hybridomas Expressing said Antibodies and Uses 1. An antibody which specifically binds to an influenza virus surface glycoprotein which is hemagglutinin (HA) or neuraminidase (NA) of the by donor virus
2. The antibody according to any of the foregoing or the following aspects, wherein the influenza virus is influenza A virus (IAV) or influenza B virus (IBV).
3. The antibody according to any of the foregoing or the following aspects, wherein the influenza virus is a human influenza A virus.
4. The antibody according to any of the foregoing or the following aspects, wherein the influenza virus is a human influenza A virus subtype H1N1 strain.
5. The antibody according to any of the foregoing or the following aspects, wherein the influenza virus is influenza A virus A/Puerto Rico/8/1934 (PR8).
6. The antibody according to any of the foregoing or the following aspects which is a monoclonal antibody or a polyclonal antibody.
7. The antibody according to any of the foregoing or the following aspects which is a monospecific, bispecific, or multispecific antibody.
8. The antibody according to any of the foregoing or the following aspects which is a human, humanized, or chimeric antibody.
9. A composition comprising a plurality of the antibodies according to any of the foregoing or the following aspects.
10. An antigen-binding fragment of an antibody of any of the foregoing or following aspects.
11. The antigen binding fragment according to any of the foregoing or following aspects which is an Fab, Fab', F(ab')$_2$, sdAb, scFv, di-scFv, each of which are optionally, recombinant molecules or a covalent a non-covalent conjugate of a plurality of said molecules.
12. The antibody according to any of the foregoing or the following aspects which is a single-chain variable fragment unibody (scFv), a diabody, a triabody, a tetrabody, or a pentabody.
13. The antibody according to any of the foregoing or the following aspects which binds to discontinuous epitopes in HA or NA.
14. The antibody according to any of the foregoing or the following aspects which binds to discontinuous epitopes in HA, as depicted in Table H.
15. A fusion protein or a chimeric protein comprising an antibody according to any of the foregoing or the following aspects.
16. The fusion protein according to any of the foregoing or the following aspects which comprises the antibody and a tag or a marker.
17. A composition, a kit or a vaccine comprising an antibody according to any of the foregoing or the following aspects and a carrier, adjuvant, excipient, emollient or stabilizer.
18. An antibody according to any of the foregoing or the following aspects which binds to Influenza A virus (A/Puerto Rico/8/1934(H1N1)) strain HA protein, comprising a polypeptide sequence accessioned in GENBANK with the accession #: CY033577.
19. An antibody according to any of the foregoing or the following aspects which binds to amino acid sequence GDTIIFEANGNLIAP (AMINO ACIDS: 240-254 of HA) (SEQ ID NO: 1) and/or the amino acid sequence SSFYRNLLWLTEKEG (AMINO ACIDS: 145-159 of HA) (SEQ ID NO: 2).
20. An antibody according to any of the foregoing or the following aspects which binds to amino acid sequence NKKGKEVLVLWGIHH (amino acids 170-184 of HA) (SEQ ID NO: 3) and/or the amino acids sequence YQNENAYVSVVTSNY (amino acids 195-209 of HA) (SEQ ID NO: 4).

21. An antibody according to any of the foregoing or the following aspects which binds with specificity to amino acids 145-159 of the HA polypeptide of an influenza A virus.
22. An antibody according to any of the foregoing or the following aspects which binds with specificity to amino acids 240-254 of the HA polypeptide of an influenza A virus.
23. An antibody according to any of the foregoing or the following aspects which binds with specificity to amino acids 170-184 of the HA polypeptide of the influenza A virus.
24. An antibody according to any of the foregoing or the following aspects which binds with specificity to amino acids 195-209 of the HA polypeptide of the influenza A virus.
25. A composition comprising an antibody which binds with specificity to amino acids 145-159 and an antibody which binds with specificity to amino acids 240-254 of hemagglutinin (HA) polypeptide of an influenza A virus.
26. A bispecific antibody which binds with specificity to amino acids 145-159 and amino acids 240-254 of hemagglutinin (HA) polypeptide of an influenza A virus.
27. A composition comprising an antibody which binds with specificity to amino acids 170-184 and an antibody which binds with specificity to amino acids 195-209 of the HA polypeptide of the influenza A virus.
28. A bispecific antibody which binds with specificity to amino acids 170-184 and amino acids 195-209 of the HA polypeptide of the influenza A virus.
29. A composition comprising an antibody which binds with specificity to amino acids 145-159, an antibody which binds with specificity to amino acids 240-254 and an antibody which binds with specificity to amino acids 170-184, optionally together with an antibody which binds with specificity to amino acids 195-209 of hemagglutinin (HA) polypeptide of an influenza A virus.
30. A multispecific antibody which binds with specificity to amino acids 145-159, amino acids 240-254 and amino acids 170-184 of HA polypeptide of IAV.
31. The antibody according to any of the foregoing or the following aspects which is monoclonal antibody mAb-1H6 or monoclonal antibody mAb-2A6, each of which, independently, binds to an epitope comprising HA residues #158-172, #183-197, and #253-267 (H1 numbering with signal sequence).
32. The antibody according to any of the foregoing or the following aspects which is monoclonal antibody mAb-2D11 which binds to an epitope comprising HA residues #158-172, #208-222 and #253-267.
33. The antibody according to any of the foregoing or the following aspects which is monoclonal antibody mAb-1B3 which binds to an epitope comprising HA residues #158-172 and #253-267.
34. The antibody according to any of the foregoing or the following aspects which binds to one or more of the HA epitopes depicted in FIG. 7.
35. The antibody according to any of the foregoing or the following aspects which is mAb-2D11 or mAb-1B3, each of which is deposited in ATCC and given the internal reference Nos. 39-3F2-2A6, 39-4D12-2D11 and 56-2G9-1B3, respectively
36. The antibody according to any of the foregoing or the following aspects which is an anti-neuraminidase antibody.
37. The anti-neuraminidase antibody according to any of the foregoing or the following aspects which is mAb-1G11.
38. The anti-neuraminidase antibody according to any of the foregoing or the following aspects which binds to epitopes comprising peptides in neuraminidase
39. The anti-neuraminidase antibody according to any of the foregoing or the following aspects which is deposited in ATCC
40. The composition according to any of the foregoing or the following aspects, which is a pharmaceutical composition.
41. A solid support comprising the compositions or antibodies according to any of the foregoing or following aspects.
42. The solid-support according to any of the foregoing or following aspects which is a sheet, a plate, a membrane, a tube, a column, a well, or a micro-array.
43. A nucleic acid encoding the antibody according to any of the foregoing or following aspects or the antigen-binding fragment thereof.
44. A vector comprising the nucleic acid according to any of the foregoing or the following aspects.
45. The vector according to any of the foregoing or the following aspects comprising a heterologous expression control system.
46. The vector according to any of the foregoing or the following aspects wherein the heterologous control system is a promoter, repressor, operator, initiator or a combination thereof.
47. A phage (e.g., bacteriophage of the family Myoviridae, Siphoviridae, Podoviridae, Lipothrixviridae, Rudiviridae, Ampullaviridae, Bicaudaviridae, Leviviridae or Microviridae), cell, cell-line, hybridoma, tissue, or tissue system, comprising the nucleic acid according to any of the foregoing or following aspects or a vector comprising the nucleic acid.
48. An immunogen (e.g., antigen sequence) which binds to any of the antibody of the foregoing or the following aspects.
49. An immunogen (e.g., antigen sequence) according to any of the foregoing or the following aspects which comprises the peptide sequence accessioned in GENBANK with the accession #: CY033577 or a fragment thereof.
50. An immunogen (e.g., antigen sequence) according to any of the foregoing or the following aspects which comprises the peptide sequence which is (a) GDTIIFEANGNLIAP (AMINO ACIDS: 240-254 of HA) (SEQ ID NO: 1) (b) SSFYRNLLWLTEKEG (AMINO ACIDS: 145-159 of HA) (SEQ ID NO: 2), NKKGKEVLVLWGIHH (amino acids 170-184 of HA) (SEQ ID NO: 3) and/or the amino acids sequence YQNENAYVSVVTSNY (amino acids 195-209 of HA) (SEQ ID NO: 4) or any antigenic fragment of said sequences.
51. A method for inhibiting human influenza A virus growth or replication, comprising, contacting the human influenza A virus with the antibody according to any of the foregoing or following aspects or a composition comprising the antibody.
52. Use of any of the antibody, composition, kit, solid-support, hybridoma according to any of the foregoing or following aspects for the screening and/or development of a seed virus.

Methods for Development of Seed Viruses
(i) A method for the development of influenza A strain seed viruses, comprising
a) generating high-yield reassortant (HYR) strains comprising hemagglutinin (HA) and neuraminidase (NA) genes of a circulating strain and genes encoding internal proteins of a high-yield donor virus as the backbone;

b) infecting a suitable host to generate viral progenies of the HYR strains of (a);

c) inhibiting the progenies of (b) having HA and NA of donor viruses with any of the foregoing or following anti-HA antibodies; and d) amplifying the reassortant variant of (c) comprising the best growth capability.

(ii) A method for the development of influenza A strain seed viruses according to any of the foregoing or the following aspects comprising inhibiting the progenies of HYR strains with one or more monoclonal antibodies which bind with specificity to amino acids 145-159, amino acids 240-254 of HA and optionally inhibiting the progenies with a monoclonal antibody that binds with specificity to NA.

(iii) A method for the development of influenza A strain seed viruses according to any of the foregoing or the following aspects comprising (e) cloning the amplified reassortant variant of (d) by limiting dilution; and (f) optionally evaluating the antigenic and/or genetic identity of the cloned virus of (e) via molecular and/or serological testing.

(iv) A hybrid influenza A strain seed virus developed according to any of the foregoing or the following method aspects.

Seed Viruses, Compositions and Kits Comprising the Same, and Use Thereof

A. An influenza A seed virus comprising HA and NA from human influenza A virus and the backbone sequences of Puerto Rico/8/1934 (PR8) human influenza A virus, and which further does not react with or is not neutralized by a plurality of monoclonal antibodies which bind with specificity to amino acids 145-159 and amino acids 240-254 of hemagglutinin (HA) polypeptide of an influenza A virus.

B. An influenza virus according to any of the foregoing or following aspects which is a hybrid, chimeric, or recombinant seed virus.

C. A hybrid human influenza A seed virus according to any of the foregoing or following aspects, wherein the backbone sequence comprises at least one of the genes encoding internal proteins from Puerto Rico/8/1934 (PR8) human influenza A virus selected from the group consisting of PB2, PB1, PA, NP, M and NS.

D. The hybrid human influenza A seed virus according to any of the foregoing or following aspects, wherein the backbone sequences comprise (a) at least two of the genes encoding internal proteins from Puerto Rico/8/1934 (PR8) human influenza A virus selected from the group consisting of PB2, PB1, PA, NP, M and NS; (b) at least three of the genes encoding internal proteins from Puerto Rico/8/1934 (PR8) human influenza A virus selected from the group consisting of PB2, PB1, PA, NP, M and NS; or (c) at least four of the genes encoding internal proteins from Peurto Rico/8/1934 (PR8) human influenza virus selected from the group consisting of PB2, PB1, PA, NP, M and NS.

E. The hybrid human influenza A seed virus according to any of the foregoing or following aspects, wherein the backbone sequences comprise at least 5 of the genes selected from the group consisting of PB2, PB1, PA, NP, M and NS.

F. The hybrid human influenza A seed virus according to any of the foregoing or following aspects, wherein the backbone sequences comprise all six genes selected from the group consisting of PB2, PB1, PA, NP, M and NS.

G. The hybrid human influenza A seed virus according to any of the foregoing or following aspects, which further does not react with a monoclonal antibody which binds with specificity to neuraminidase (NA) polypeptide of an influenza A virus, PR8.

H. The hybrid human influenza A seed virus according to any of the foregoing or following aspects, which further does not react with a monoclonal antibody which binds with specificity to amino acids 170-184 of the HA polypeptide of the influenza A virus.

I. The hybrid human influenza A seed virus according to any of the foregoing or following aspects, which further does not react with a monoclonal antibody which binds with specificity to amino acids 195-209 of the HA polypeptide of the influenza A virus.

J. The hybrid human influenza A seed virus according to any of the foregoing or following aspects, which further does not react with a plurality of monoclonal antibodies with specificity to amino acids 170-184 and amino acids 195-209 of the HA polypeptide.

K. A composition comprising the hybrid human influenza A seed virus according to any of the foregoing or following aspects and a carrier, adjuvant, excipient, emollient or stabilizer.

L. A composition comprising the seed viruses or compositions thereof according to any of the foregoing or following aspects and an anti-viral compound.

M. A hybrid human influenza A seed virus according to any of the foregoing or following aspects which is deposited in ATCC N. A hybrid human influenza A seed virus comprising HA and NA from a high yield (hy) donor human influenza A virus and the backbone sequences of Puerto Rico/8/1934 (PR8) human influenza A virus, and which further does not express two or more of the following epitopes (1)-(4):

(1) amino acids 145-159 of the HA polypeptide of the influenza A virus;

(2) amino acids 240-254 of the HA polypeptide of the influenza A virus;

(3) amino acids 170-184 of the HA polypeptide of the influenza A virus; and (4) amino acids 195-209 of the HA polypeptide of the influenza A virus.

O. The hybrid human influenza A seed virus according to any of the foregoing or following aspects, which further does not express (1) amino acids 145-159 of the HA polypeptide of the influenza A virus; and (2) amino acids 240-254 of the HA polypeptide of the influenza A virus.

P. The hybrid human influenza A seed virus according to any of the foregoing or following aspects, which further does not express (3) amino acids 170-184 of the HA polypeptide of the influenza A virus; and optionally (4) amino acids 195-209 of the HA polypeptide of the influenza A virus.

Q. A hybrid seed virus which is an hy reassortant R-2, R-3, R-6, R-8 or R-15, each of which comprises the following constellation of PB2, PB1, PA, HA, NP, NA, M and NS genes from H1N1 A/California/07/2009 strain (CA), H3N2 A/Uruguay/716/2007 wild-type strain (UY) or H1N1 A/South Dakota/06/2007 strain (SD) and A/Puerto Rico/8/1934 (PR8):

| Gene | R-2 (H3N2) | R-3 (H3N2) | R-6 (H1N1pdm) | R-8 (H1N1) | R-15 (H3N2) |
|---|---|---|---|---|---|
| PB2 | UY | UY | CA | PR8 | UY |
| PB1 | UY | PR8 | CA | PR8 | PR8 |
| PA | UY | PR8 | CA | PR8 | PR8 |
| HA | UY | UY | CA | SD | UY |
| NP | UY | PR8 | CA | PR8 | PR8 |
| NA | UY | UY | CA | SD | UY |
| M | PR8 | PR8 | CA | PR8 | PR8 |
| NS | UY | UY | PR8 | PR8 | UY |

R. The hybrid seed virus according to any of the foregoing or following aspects, which is:
  (1) the hy reassortant R-6 (H1N1pdm) comprising PB2 gene from CA strain; PB1 gene from CA strain; PA gene from CA strain; HA gene from CA strain; NP gene from CA strain; NA gene from CA strain; M gene from CA strain; and NS gene from PR8 strain; or
  (2) the hy reassortant R-8 (H1N1) comprising PB2 gene from PR8 strain; PB1 gene from PR8 strain; PA gene from PR8 strain; HA gene from SD strain; NP gene from PR8 strain; NA gene from SD strain; M gene from PR8 strain; and NS gene from PR8 strain.

S. The hybrid seed virus according to any of the foregoing or following aspects, which has a growth rate that is at least two-fold, at least five-fold, at least ten-fold, at least 20-fold, at least 30-fold, at least 40-fold, at least 100-fold or at least 1000-fold greater than the wild-type CA strain, as measured by HA titer.

T. The hybrid seed virus according to any of the foregoing or following aspects, which has a growth rate that is at least two-fold, at least three-fold, at least five-fold, at least eight-fold, at least ten-fold, at least 20-fold, at least 30-fold, at least 40-fold or at least 100-fold greater than the wild-type SD strain, as measured by HA titer.

U. A method for the prevention, reduction of the incidence of, or treatment of influenza in a patient in need thereof, comprising administering to said patient, a hybrid seed virus according to any of the foregoing or following aspects optionally together with a carrier, adjuvant, excipient, emollient or stabilizer and further optionally with an anti-viral compound.

V. Use of the seed virus according to any of the foregoing or following aspects, or a composition or combination comprising the same, for the prevention, reduction of the incidence of, or treatment of influenza in a patient in need thereof.

BRIEF DESCRIPTION OF THE DRAWINGS AND THE TABLES

Various features and advantages of the embodiments herein described can be fully appreciated as the same becomes better understood when considered in light of the accompanying drawings/tables, wherein:

The patent or application file contains at least one drawing executed in color. Copies of this patent or patent application publication with color drawing(s) will be provided by the Office upon request and payment of the necessary fee.

Drawings

Figure 3:
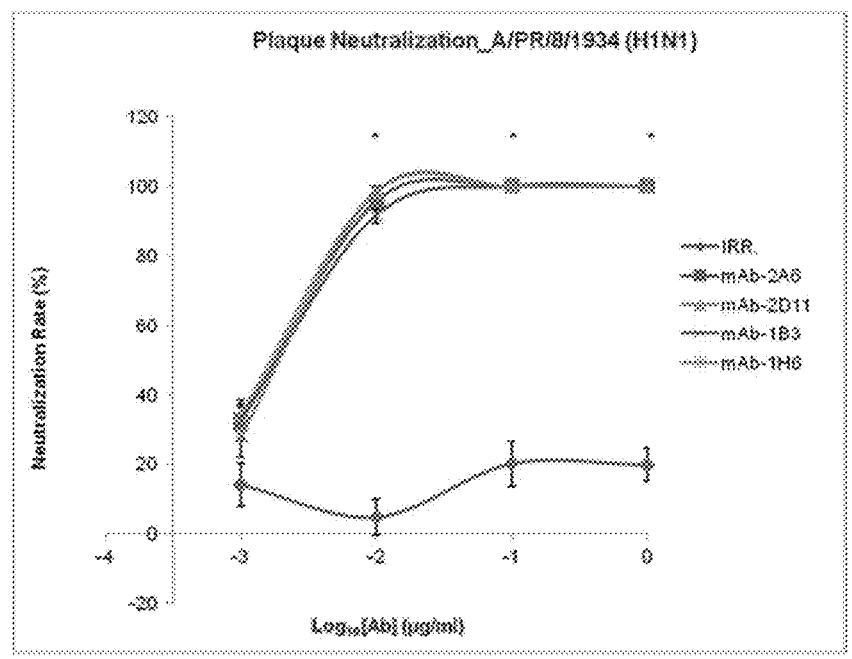

FIG. 3 shows in vitro neutralization activity of candidate HA neutralizing mAbs. IRR.: Irrelevant antibody. Values represent the means±SEM of duplicates of three independent experiments. * indicates p<0.005 compared to irrelevant control.

Figure 4:
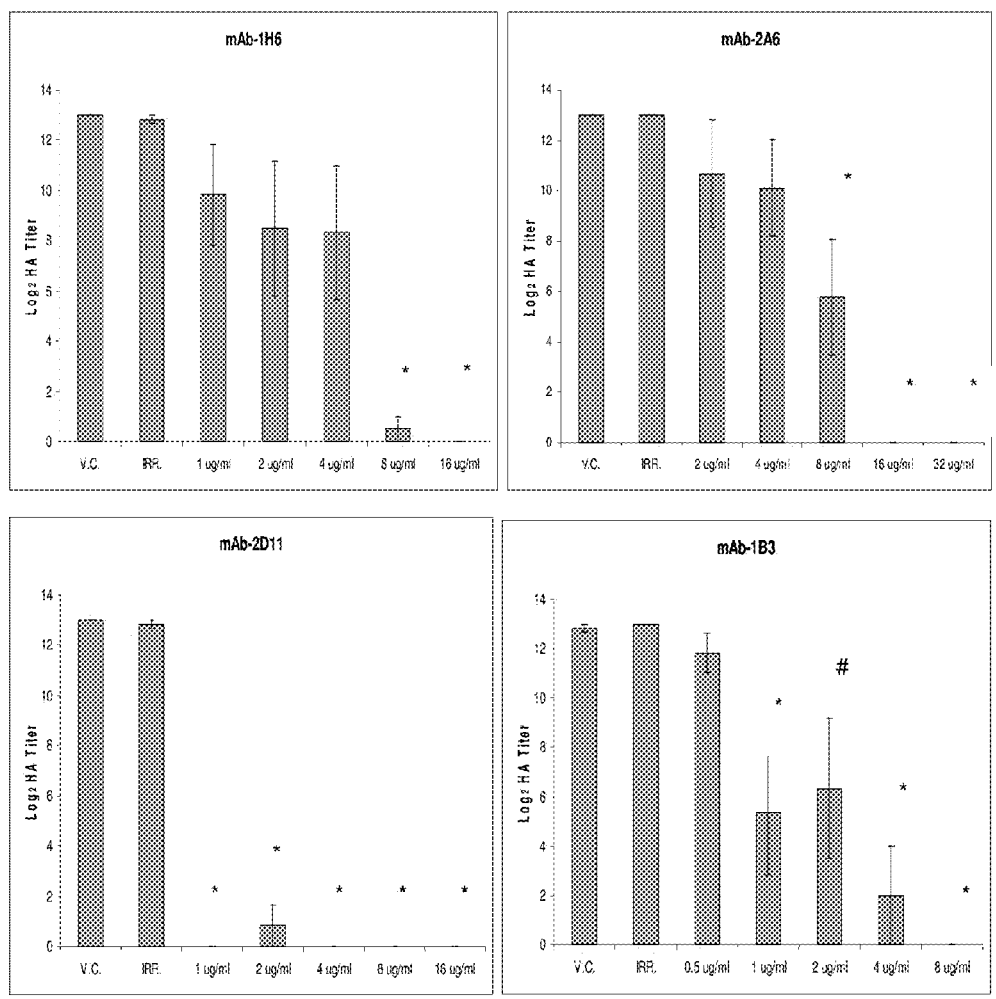

FIG. 4 shows in ovo neutralization activity of candidate HA mAbs. V.C.: Virus control; IRR.: Irrelevant antibody. Values represent the means±SEM of triplicates from two independent experiments. * indicates p<0.005 and # indicates p<0.05 compared to virus control.

Figure 5:
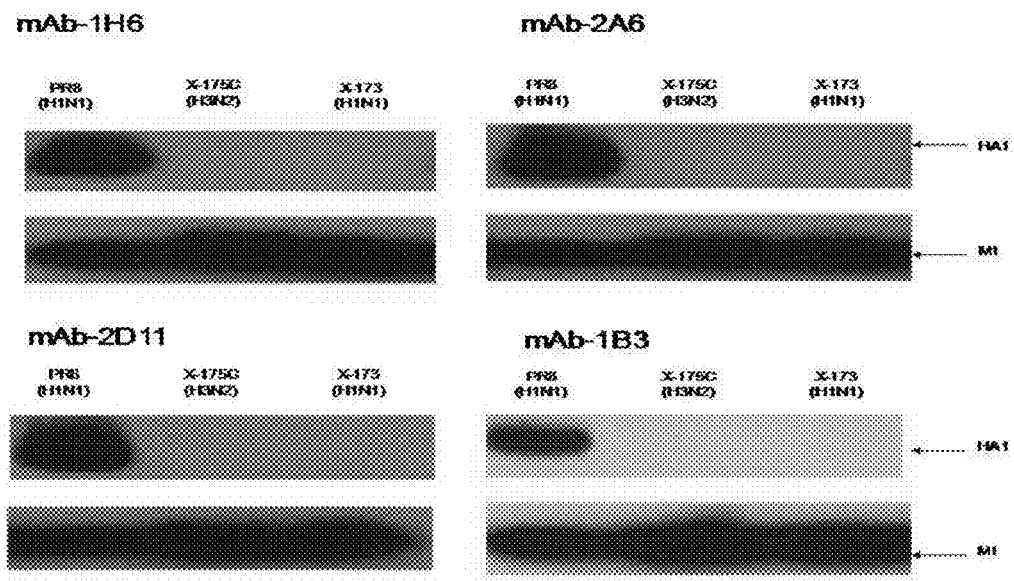

FIG. 5 shows Western blotting of PR8 (H1N1), X-175C (H3N2) and X-173 (H1N1) viral proteins by candidate HA mAbs under reducing conditions. Each lane was loaded with 1 µg total viral protein. M1 which is highly conserved among all type A influenza viruses was blotted as internal control.

Figure 6A:
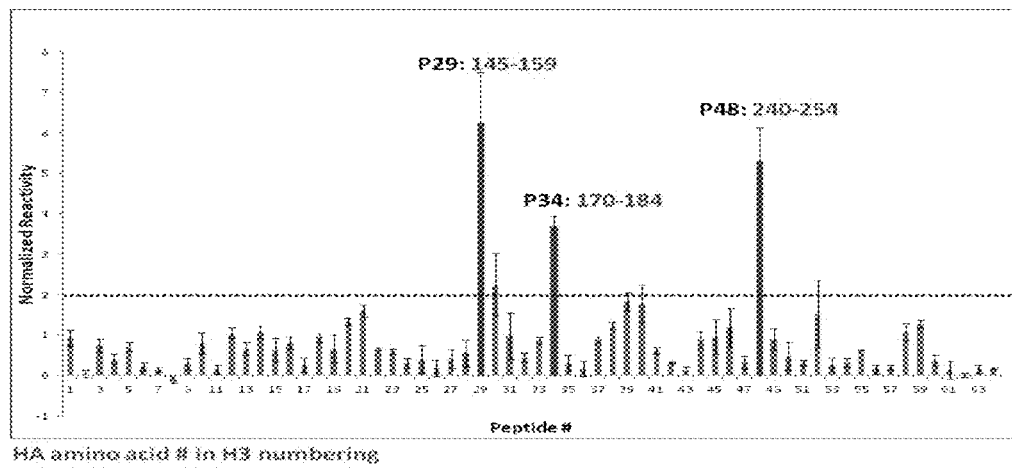
Figure 6A:
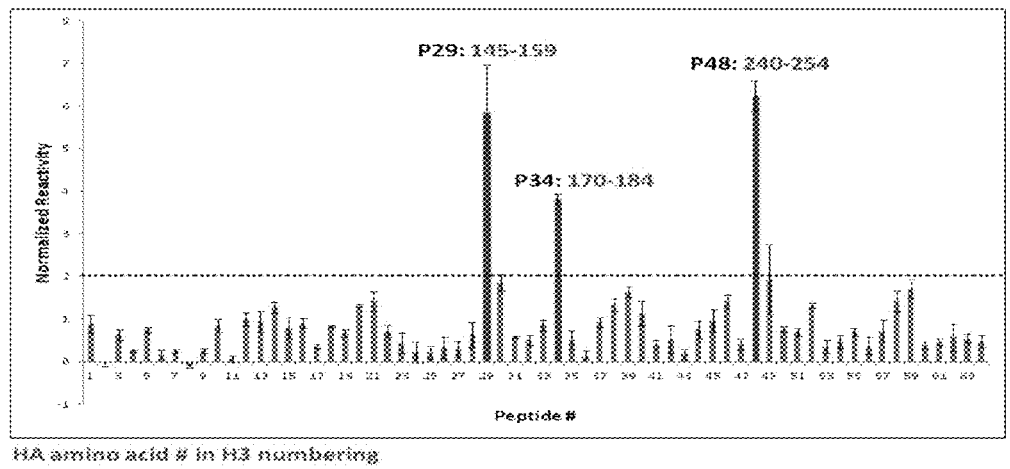

FIG. 6A shows peptide epitope for mAb-1H6 (top panel) and mAb-2A6 (bottom panel). The reactivity of each peptide was normalized to the mean of total peptide reactivity after subtracting background $A_{450}$ value given by isotype control. Any peptide with more than 2-fold normalized activity (shown in red) is considered positively reactive to testing antibody. Values represent the means±SEM of duplicates of three independent experiments.

Figure 6B:
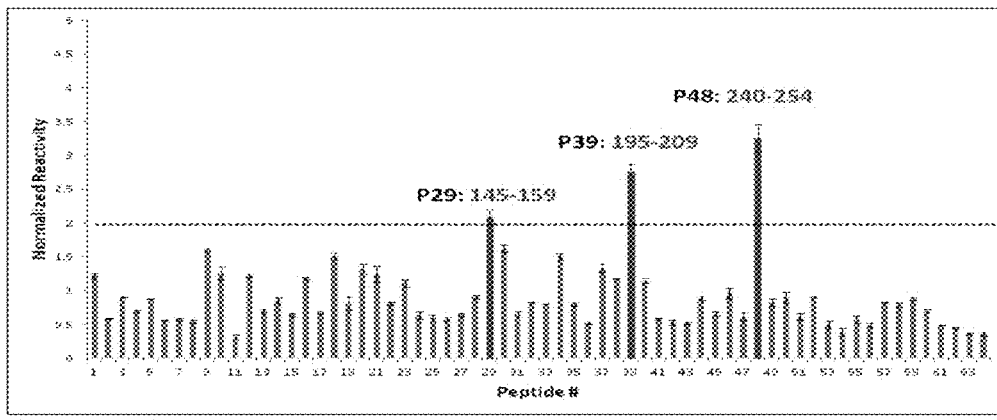
Figure 6B:
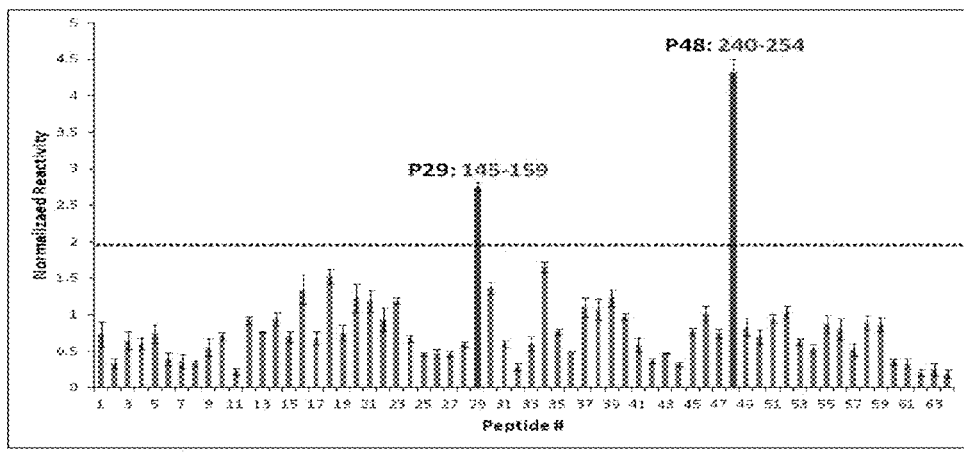

FIG. 6B shows peptide epitope for mAb-2D11 (top panel) and mAb-1B3 (bottom panel). The reactivity of each peptide was normalized to the mean of total peptide reactivity after subtracting background $A_{450}$ value given by isotype control. Any peptide with more than 2-fold normalized activity (shown in red) is considered positive reactive to testing antibody. Values represent the means±SEM of duplicates of three independent experiments.

Figure 7:
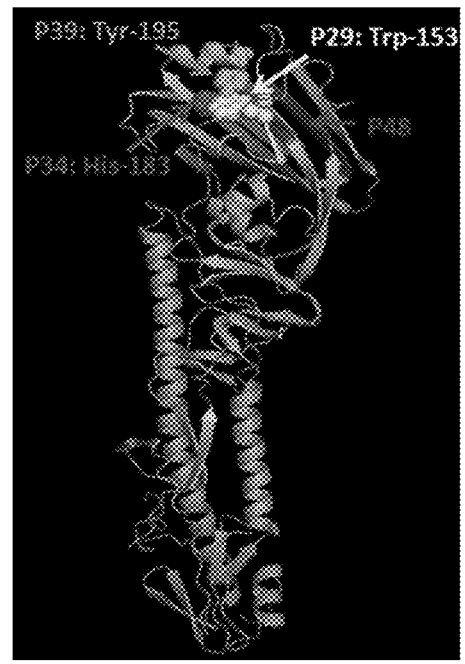

FIG. 7 shows epitopes for HA mAbs on the three-dimensional HA monomer structure. Peptide #29, #34, #39, #48 are shown in yellow, magenta, cyan and red, respectively. Conserved residues of receptor-binding site are labeled. The structure is adapted from PR8 H1 hemagglutinin (PDB ID: 1RVZ) in PyMOL.

Figure 8:
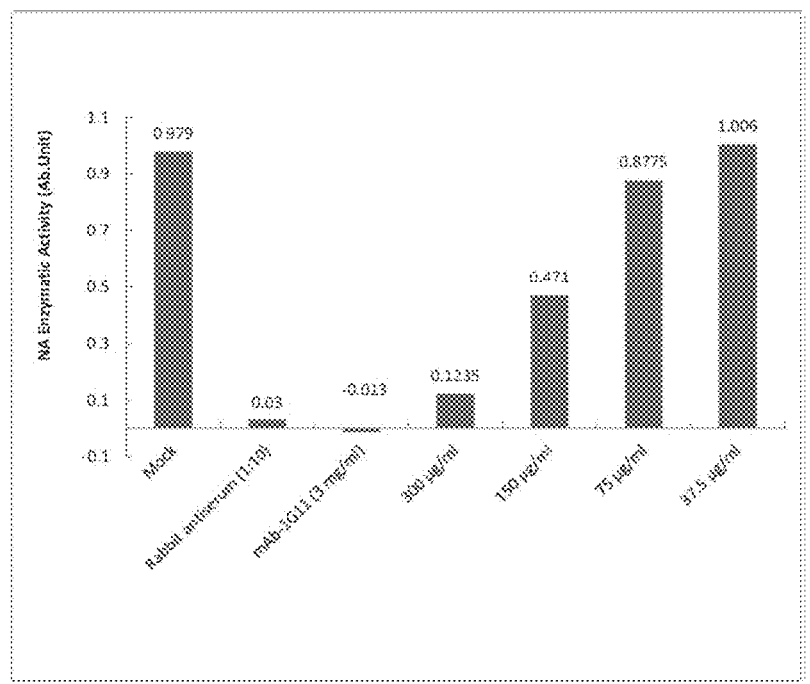

FIG. 8 shows NI activity of mAb-1G11 against PR8 NA. The numbers shown were normalized NA activity A549 as compared with fetuin substrate with no antibody or virus. Rabbit antiserum (1:10 dilution) raised against PR8 virus was used as the positive control.

Figure 9:
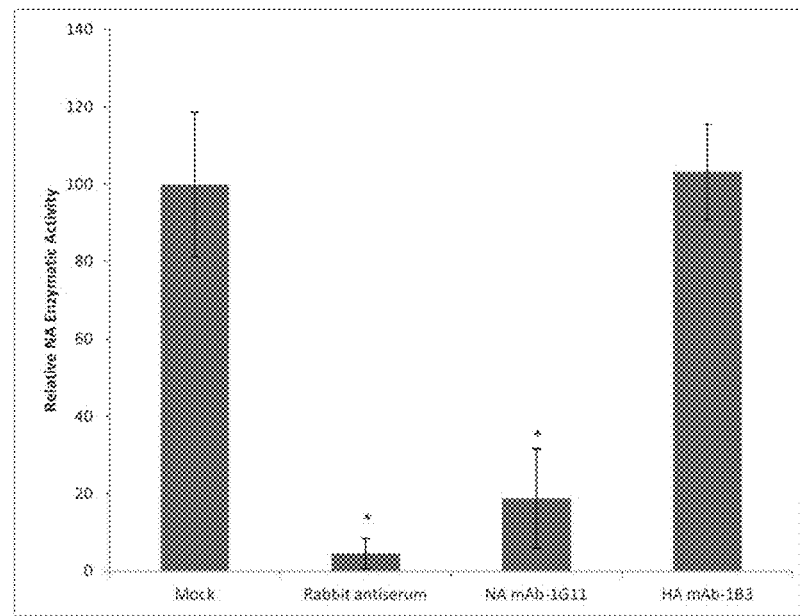

FIG. 9 shows NI activity of NA mAb-1G11 and HA mAb-1B3 to PR8. Both mAb-1G11 and mAb-1B3 were tested at 300 µg/ml. The NA activity was normalized to mock treatment which is assigned as 100% activity. * indicates p<0.05 compared to mock.

Figure 10:
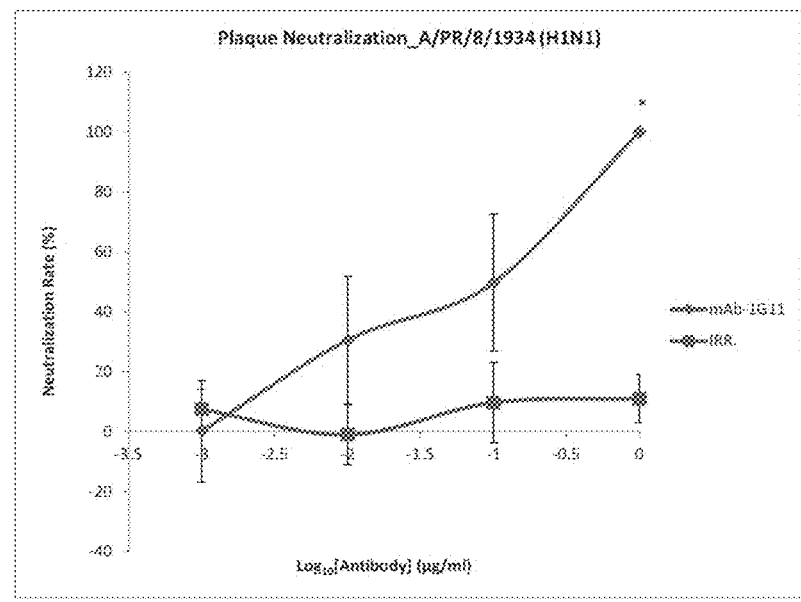

FIG. 10 shows in vitro neutralization activity of candidate NA mAb-1G11. IRR: Irrelevant antibody. Values represent the means+SEM of duplicates of three independent experiments. * indicates p<0.05 compared to irrelevant control.

Figure 11:
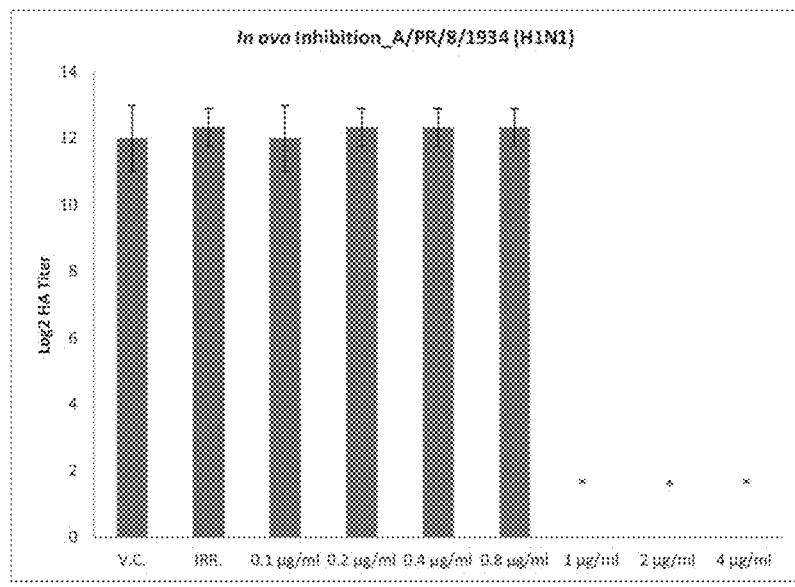

FIG. 11 shows in ovo neutralization activity of candidate NA mAb-1G11. V.C.: Virus control; IRR.: Irrelevant antibody. Values represent the means+SEM of triplicates from two independent experiments. * indicates p<0.05 compared to virus control.

Figure 12:
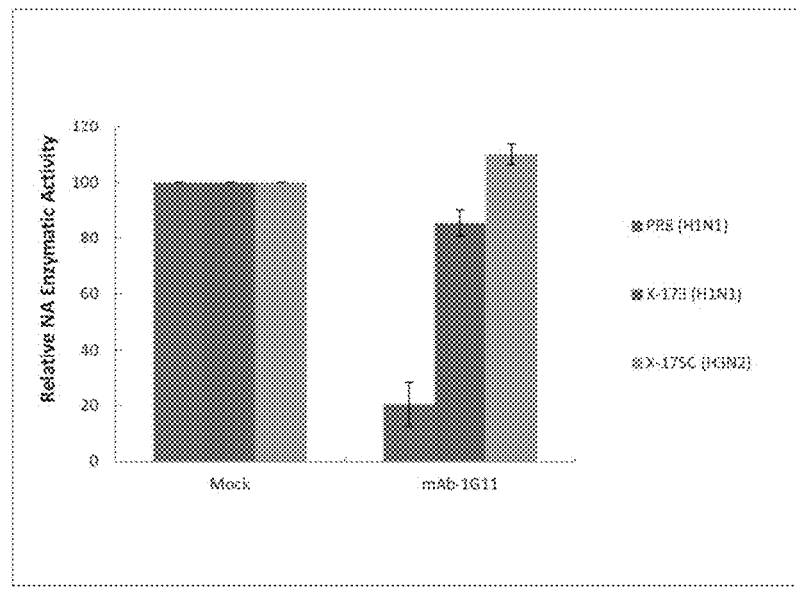

FIG. 12 shows cross-reactivity of mAb-1G11 as measured by NI. The NA mAb-1G11 was tested at 300 µg/ml. The NA activity was normalized to mock treatment for individual viruses.

Figure 13:
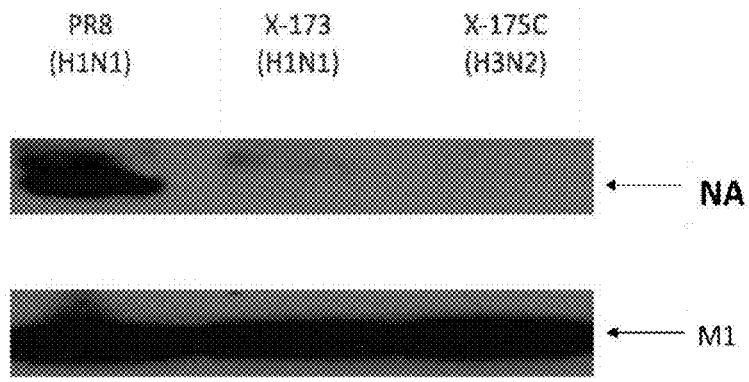
Figure 14:
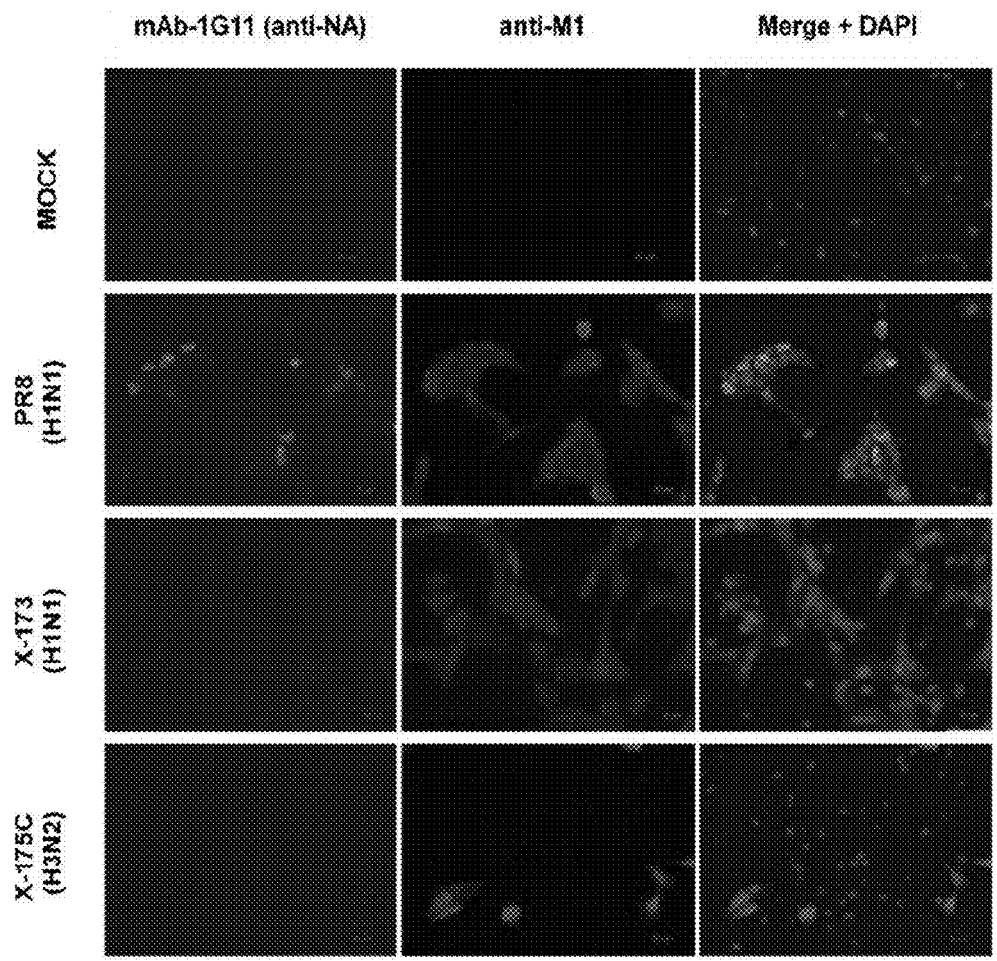

FIG. 13 shows Western blotting of PR8 (H1N1), X-173 (H1N1) and X-175C (H3N2) viral proteins by candidate NA mAb under reducing conditions. Each lane was loaded with 1 µg of total viral protein. The conserved M1 was blotted as internal control FIG. 14 shows immunofluorescence analysis of cross-recognition of mAb-1G11. MDCK cells were infected at MOI=1 with PR8, X-173 and X-175C. NA (green) was stained by mAb-1G11, and M1 (red) was stained by M1 rabbit antisera.

Figure 15:
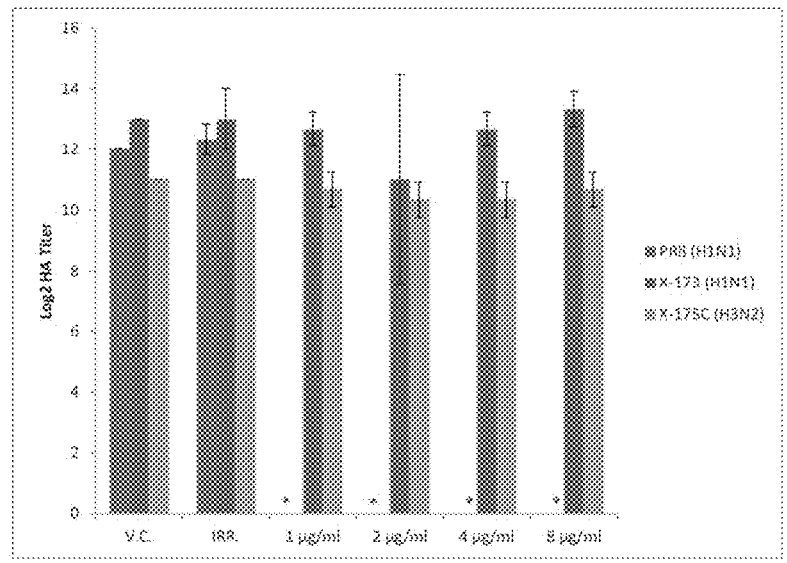

FIG. 15 shows in ovo neutralization cross-reactivity of mAb-1G11. V.C.: Virus control; IRR.: Irrelevant antibody. Values represent the means+SEM of triplicates from two independent experiments. * indicates p<0.05 compared to virus control.

Figure 16:
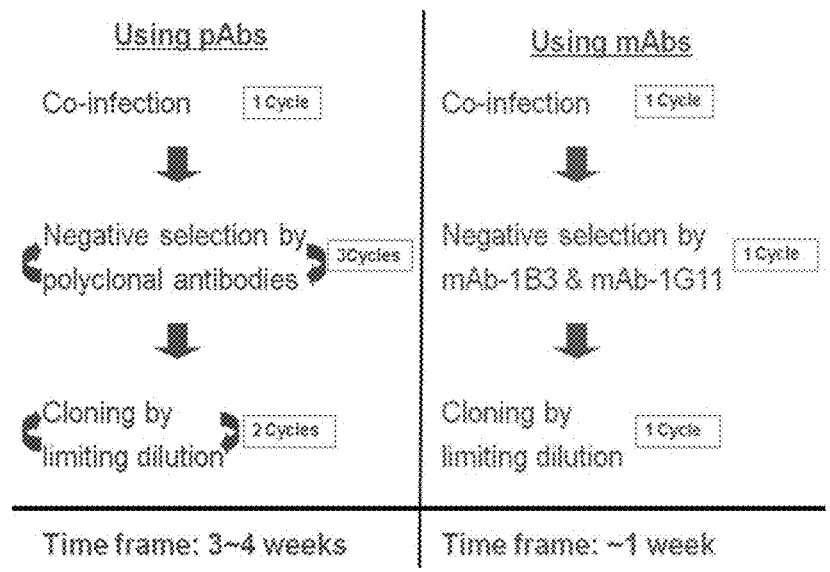

FIG. 16 shows a comparison between pAbs and mAbs-based classical reassortment.

Figure 17:
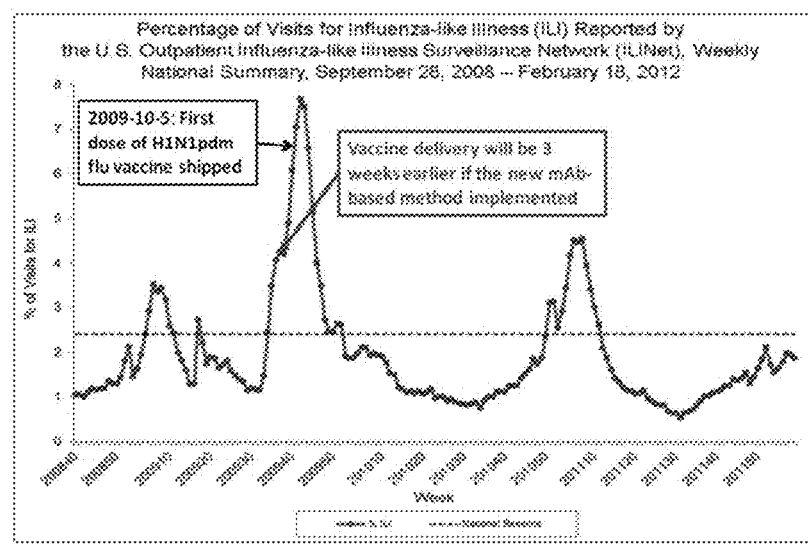

FIG. 17 shows the significance of mAb-based classical reassortment for future vaccine delivery. Data adapted from the information provided in the web-site of the United States Center for Disease Control (CDC).

FIG. 18 shows the sequence of hemagluttin (HA) of influenza virus having the GENBANK with the accession #CY033577 (accessioned: Jul. 17, 2008) (SEQ ID NO: 95).

FIG. 19 shows the sequence of neuraminidase (NA) of influenza virus having the GENBANK with the accession #ABD77678.1 (Accessioned: Mar. 15, 2006) (SEQ ID NO: 96)

FIG. 20 shows the epitopes in hemagluttin (SEQ ID NO: 95) to which the antibodies bind.

FIG. 21 shows the DNA and amino acid sequences of the heavy and light chains of the antibody produced by the hybridoma 39-3F2-2A6, with the subregions indicated in color, in the following order: Leader sequence (black)—Framework 1 (FR1) (red)—Complementarity Determining Region 1 (CDR-1) (blue)—FR2 (red)—CDR2 (blue)—FR3 (red)—CDR3 (blue)—FR4 (red). FIG. 21 discloses SEQ ID NOS 97-100, respectively, in order of appearance.

FIG. 22 shows the DNA and amino acid sequences of the heavy and light chains of the antibody produced by the hybridoma 39-4D12-2D11, with the subregions indicated in color, in the following order: Leader sequence (black)—Framework 1 (FR1) (red)—Complementarity Determining Region 1 (CDR-1) (blue)—FR2 (red)—CDR2 (blue)—FR3 (red)—CDR3 (blue)—FR4 (red). FIG. 22 discloses SEQ ID NOS 101-104, respectively, in order of appearance.

FIG. 23 shows the DNA and amino acid sequences of the heavy and light chains of the antibody produced by the hybridoma 56-2G9-1B3, with the subregions indicated in color, in the following order: Leader sequence (black)—Framework 1 (FR1) (red)—Complementarity Determining Region 1 (CDR-1) (blue)—FR2 (red)—CDR2 (blue)—FR3 (red)—CDR3 (blue)—FR4 (red). FIG. 23 discloses SEQ ID NOS 105-108, respectively, in order of appearance.

COLOR DRAWINGS

The patent or application file contains at least one drawing executed in color. Copies of this patent or patent application publication with color drawing(s) will be provided by the Office upon request and payment of the necessary fee.

Tables

Table A shows the structural characteristics of the various viral genes and the associated NCBI GENBANK accession numbers.

Table B shows oligonucleotide primers used in RT-PCR.

Table C shows restriction enzymes and corresponding conditions used for RFLP.

Table D shows synthetic Peptides used for Epitope Mapping.

Table E shows antigenic specificity for hybridoma clones. A total of 114 clones derived from 72 parental lines were tested either HA or NA positive. Hybridoma clones were named as "HANA" followed by mouse number, the well number of first screening, and the well number of subcloning. HA: Hemagglutinin; NA: Neuraminidase.

Table F shows hybridoma clones with neutralization activity by testing cell culture supernatants.

Table G shows HI activity and isotype of neutralizing HA mAb candidates. Neutralization titers are expressed as the reciprocal of the titration end-point to completely neutralize PR8. HI titers are expressed as the reciprocal of the titration end-point to completely block the hemagglutination of chicken erythrocytes. *The monoclonal antibodies are identified as indicated in the parentheses.

Table H shows the results of H1N1 HA epitope search. Legend: H=Human; M=Mouse; F=Ferret; C=Chicken.

Table I shows gene constellation of by reassortants developed in mAb-based classical reassortment.

DETAILED DESCRIPTION OF THE INVENTION

In some aspects, the invention provides antibodies which bind to influenza virus A-derived polypeptides. These polypeptides are gene products of the flu virus RNA, which sequences are known in the art. See, e.g., Ramanunninair et al., "Molecular Signature Residues of High Yield (Growth) Influenza A Virus Reassortants Prepared as Candidate Vaccine Seeds," PLoS One, 8(6), 2013. In short, the virus contains six internal genes, NS, M, NP, PA, basic polymerases (PB1 and PB2), and two surface genes, HA and NA. The eight viral genes and the functions can be summarized as follows:

The non-structural (NS) gene is the smallest RNA segment of influenza virus and codes for the two non-structural proteins (NS1 and NS2). NS1 is a RNA-binding non-structural protein of transport function. NS2 is a cellular and virion protein of unknown function. The matrix protein (M) is a membrane protein. M1 is a matrix type-specific antigen; M2 is a nonglycosylated membrane ion channel, found only in type A virus. The nucleoprotein (NP) specifically interacts with RNA molecules to form ribonucleoprotein complexes and has sequences that direct its migration into the nuclei of infected cells. This is a major nucleocapsid structural component and type-specific antigen. The polymerase acidic protein (PA) is a viral polymerase component involved in RNA replication. The polymerase basic 1 (PB1) protein is a viral polymerase component involved in RNA transcription; the polymerase basic 2 (PB2) is a second viral polymerase component involved in RNA transcription. The hemagglutinin gene (HA) and neuraminidase gene (NA) code for surface receptors. HA is the virion surface attachment and fusion glycoprotein, a major antigenic determinant; NA is the surface glycoprotein with receptor-destroying enzyme activity, a major antigenic determinant. The nucleic acid and protein sequences of these components are known in literature and have been accessioned in GENBANK.

TABLE A

Structural characteristics of the various viral genes and the associated NCBI GENBANK accession numbers.

| Seg | Protein Name | Accession# | Length | Strain Name |
|---|---|---|---|---|
| 6 | NA | CY033579 | 1367 | A/Puerto Rico/8/34 |
| 4 | HA | CY033577 | 1724 | A/Puerto Rico/8/34 |
| 1 | PB2 | CY033584 | 2281 | A/Puerto Rico/8/34 |
| 2 | PB1, PB1-F2, PB1-N40 | CY033583 | 2288 | A/Puerto Rico/8/34 |
| 7 | M1, M2, M42 | CY033578 | 984 | A/Puerto Rico/8/34 |
| 8 | NS1, NS2 | CY033581 | 840 | A/Puerto Rico/8/34 |
| 3 | PA, PA-N155, PA-N182, PA-X protein(+61) | CY033582 | 2193 | A/Puerto Rico/8/34 |
| 5 | NP | CY033580 | 1524 | A/Puerto Rico/8/34 |
| 3 | PA, PA-N155, PA-N182, PA-X, PA-X protein(+41) | CY121685 | 2192 | A/California/07/2009 |
| 1 | PB2 | CY121687 | 2316 | A/California/07/2009 |
| 4 | HA | CY121680 | 1752 | A/California/07/2009 |
| 5 | NP | CY121683 | 1541 | A/California/07/2009 |
| 8 | NS1, NS2 | CY121684 | 865 | A/California/07/2009 |
| 2 | PB1, PB1-N40 | CY121686 | 2317 | A/California/07/2009 |
| 6 | NA | CY121682 | 1432 | A/California/07/2009 |
| 7 | M1, M2 | CY121681 | 1002 | A/California/07/2009 |
| 8 | NS1, NS2 | CY121596 | 866 | A/South Dakota/06/2007 |
| 7 | M1, M2 | CY121593 | 1002 | A/South Dakota/06/2007 |
| 6 | NA | CY121594 | 1435 | A/South Dakota/06/2007 |
| 3 | PA, PA-N155, PA-N182, PA-X protein(+61) | CY121597 | 2151 | A/South Dakota/06/2007 |
| 1 | PB2 | CY121599 | 2314 | A/South Dakota/06/2007 |
| 4 | HA | CY121592 | 1750 | A/South Dakota/06/2007 |
| 2 | PB1, PB1-F2, PB1-N40 | CY121598 | 2317 | A/South Dakota/06/2007 |
| 5 | NP | CY121595 | 1541 | A/South Dakota/06/2007 |
| 6 | NA | CY121634 | 1443 | A/Uruguay/716/2007 |
| 8 | NS1, NS2 | CY121636 | 865 | A/Uruguay/716/2007 |
| 7 | M1, M2 | CY121633 | 997 | A/Uruguay/716/2007 |
| 2 | PB1, PB1-F2, PB1-N40 | CY121638 | 2316 | A/Uruguay/716/2007 |
| 1 | PB2 | CY121639 | 2308 | A/Uruguay/716/2007 |
| 3 | PA, PA-N155, PA-N182, PA-X protein(+61) | CY121637 | 2189 | A/Uruguay/716/2007 |
| 5 | NP | CY121635 | 1542 | A/Uruguay/716/2007 |
| 4 | HA | CY121632 | 1738 | A/Uruguay/716/2007 |

In particular, the antibodies described herein bind with specificity to Influenza A virus (A/Puerto Rico/8/1934 (H1N1); Taxonomy ID: 211044) strain HA protein, comprising a polypeptide sequence accessioned in GENBANK with the accession #: CY033577. The accession numbers and contents thereof are incorporated by reference in their entirety.

More specifically, the antibodies of the instant invention bind to the following epitopes in the aforementioned HA sequence:

| Reference # | Amino acids | Peptide sequence |
|---|---|---|
| 48 | 240-254: | GDTIIFEANGNLIAP (SEQ ID NO: 1) |
| 29 | 145-159 | SSFYRNLLWLTEKEG (SEQ ID NO: 2) |
| 34 | 170-184 | NKKGKEVLVLWGIHH (SEQ ID NO: 3) |
| 39 | 195-209 | YQNENAYVSVVTSNY (SEQ ID NO: 4) |

The term "antibody" or "antibody molecule" describes a functional component of serum and is often referred to either as a collection of molecules (antibodies or immunoglobulin) or as one molecule (the antibody molecule or immunoglobulin molecule). An antibody is capable of binding to or reacting with a specific antigenic determinant (the antigen or the antigenic epitope), which in turn may lead to induction of immunological effector mechanisms. An individual antibody is usually regarded as monospecific, and a composition of antibodies may be monoclonal (i.e., consisting of identical antibody molecules) or polyclonal (i.e., consisting of two or more different antibodies reacting with the same or different epitopes on the same antigen or even on distinct, different antigens). Each antibody has a unique structure that enables it to bind specifically to its corresponding antigen, and all natural antibodies have the same overall basic structure of two identical light chains and two identical heavy chains. Antibodies are also known collectively as immunoglobulins. Antibodies of the instant invention may include single chain antibodies as well as binding fragments of antibodies, such as Fab, F(ab')2, Fv fragments or single chain Fv (scFv) fragments, and multimeric forms such as dimeric igA molecules or pentavalent IgM. Antibodies further encompass, in particular, binding fragments and single chain antibodies.

Antibodies of the invention bind to an epitope that is linear or non-linear. In certain aspects of the invention, a non-linear epitope is a discontinuous epitope.

Each heavy chain of an antibody typically includes a heavy chain variable region (VH) and a heavy chain constant region. The heavy chain constant region typically includes three domains, referred to as CHI, CH2 and CHS. Each antibody light chain typically includes a light chain variable region (VL) and a light chain constant region. The light chain constant region typically includes a single domain, referred to as CL. The VH and VL regions may be further subdivided into regions of hypervariability ("hypervariable regions", which may be hypervariable in sequence and/or in structurally defined loops). The "hypervariable" regions found in the variable domains of an antibody that are primarily responsible for determining the antibody's binding specificity. These are also referred to as complementarity determining regions (CDRs), which are interspersed with regions that are more conserved, termed framework regions (FRs). Each of the heavy and light chains of an antibody contains three CDR regions, referred to as CDRi, CDR2 and CDRS, of which CDRS snows the greatest variability. Each VH and VL typically includes three CDRs and four FRs, arranged from the amino terminus to the carboxy terminus in the following order: FRi, CDRI, FR2, CDR2, FRS, CDRS, FR4. The amino acid residues in the variable regions are often numbered using a standardized numbering method known as the Kabat numbering scheme (Kabat et al. (1991) Sequences of Proteins of Immunological interest, 5th Ed. Public Health Service, National Institutes of Health, Bethesda, Md., USA), although other numbering schemes such as Chothia and IMGT also exist.

The specificity of an antibody's interaction with a target antigen resides primarily in the amino acid residues located in the six CDRs of the heavy and light chain. The amino acid sequences within CDRs are therefore much more variable between individual antibodies than sequences outside of CDRs. Because CDR sequences are responsible for most antibody-antigen interactions, it is possible to express recombinant antibodies that mimic the properties of a specific naturally occurring antibody, or more generally any specific antibody with a given amino acid sequence, by constructing expression vectors that express CDR sequences from the specific antibody grafted into framework sequences from a different antibody. As a result, it is possible to "humanize" a non-human antibody and still substantially maintain the binding specificity and affinity of the original antibody. A more detailed discussion of humanization is provided below.

A "chimeric antibody" refers in its broadest sense to an antibody that contains one or more regions from one antibody and one or more regions from one or more other antibodies, typically an antibody that is partially of human origin and partially of non-human origin, i.e., derived in part from a non-human animal, for example a mouse, rat or other rodent, or an avian such as a chicken. Chimeric antibodies are preferred over non-human antibodies in order to reduce the risk of a human anti-antibody response, e.g., a human anti-mouse antibody response in the case of a murine antibody. An example of a typical chimeric antibody is one in which the variable region sequences are murine sequences derived from immunization of a mouse, while the constant region sequences are human. In the case of a chimeric antibody, the non-human parts may be subjected to further alteration in order to humanize the antibody. As described elsewhere herein, the present invention is based on humanization of certain chimeric antibodies having murine variable region sequences.

The term "humanize" refers to the fact that where an antibody is wholly or partially of non-human origin, for example a murine antibody obtained from immunization of mice with an antigen of interest or a chimeric antibody based on such a murine antibody, it is possible to replace certain amino acids, in particular in the framework regions and constant domains of the heavy and light chains, in order to avoid or minimize an immune response in humans, it is known that ail antibodies have the potential for eliciting a human anti-antibody response, which correlates to some extent with the degree of "humanness" of the antibody in question. Although it is not possible to precisely predict the immunogenicity and thereby the human anti-antibody response of a particular antibody, non-human antibodies tend to be more immunogenic than human antibodies. Chimeric antibodies, where the foreign (usually rodent) constant regions have been replaced with sequences of human origin, have been shown to be generally less immunogenic than antibodies of fully foreign origin, and the trend in therapeutic antibodies is towards humanized or fully human antibodies. For chimeric antibodies or other antibodies of non-human origin, it is therefore preferred that they be humanized to reduce the risk of a human anti-antibody response.

For chimeric antibodies, humanization typically involves modification of the framework regions of the variable region sequences Amino acid residues that are part of a complementarity determining regions (CDRs) will most often not be altered in connection with humanization, although in certain cases it may be desirable to alter individual CDR amino acid residues, for example to remove a glycosylation site, a deamidation site, an aspartate isomerization site or an undesired cysteine or methionine residue. N-linked glycosylation occurs by attachment of an oligosaccharide chain to an asparagine residue in the tripeptide sequence Asn-X-Ser or Asn-X-Thr, where X may be any amino acid except Pro. Removal of an N-glycosylation site may be achieved by mutating either the Asn or the Ser/Thr residue to a different residue, preferably by way of conservative substitution. Deamidation of asparagine and glutamine residues can occur depending on factors such as pH and surface exposure. Asparagine residues are particularly susceptible to deamidation, primarily when present in the sequence Asn-Gly, and to a lesser extent in other dipeptide sequences such as Asn-Ala. When such a deamidation site, in particular Asn-Gly, is present in a CDR sequence, it may therefore be desirable to remove the site, typically by conservative substitution to remove one of the implicated residues.

Numerous methods for humanization of an antibody sequence are known in the art; see e.g. the review by Almagro & Fransson (2008) Front Biosci. 13: 1619-1633. One commonly used method is CDR grafting, which for e.g. a murine-derived chimeric antibody involves identification of human germline gene counterparts to the murine variable region genes and grafting of the murine CDR sequences into this framework. CDR grafting may be based on the Kabat CDR definitions, although a more recent publication (Agdeiaine-Beuzeiin et al. (2007) Crit Rev. Oncol Hematol. 64: 2.10-225) has suggested that the IMGT® definition [the international ImunoGeneTics information System®], worldwide-web URL at imgt(dot)org] may improve the result of the humanization (see Lefranc et al. (2003), IMGT unique numbering for immunoglobulin and T cell receptor variable domains and Ig superfamily V-like domains, Dev. Comp Immunol., 27, 55-77). Since CDR grafting may reduce the binding specificity and affinity, and thus the biological activity, of a CDR-grafted non-human antibody, back mutations (sometimes referred to as "framework repair") may be introduced at selected positions of the CDR-grafted antibody, typically in the framework regions, in order to reestablish the binding specificity and affinity of the parent antibody. Identification of positions for possible back mutations can be performed using information available in the literature and in antibody databases. Amino acid residues that are candidates for back mutations are typically those that are located at the surface of an antibody molecule, while residues that are buried or that have a low degree of surface exposure will not normally be altered. An alternative humanization technique to CDR grafting and back mutation is resurfacing, in which non-surface exposed residues of non-human origin are retained, while surface residues are altered to human residues.

In certain cases, it may also be desirable to alter one or more CDR amino acid residues in order to improve binding affinity to the target epitope. This is known as "affinity maturation" and may optionally be performed in connection with humanization, for example in situations where humanization of an antibody leads to reduced binding specificity or affinity and it is not possible to sufficiently improve the binding specificity or affinity by back mutations alone. Various affinity maturation methods are known in the art, for example the in vitro scanning saturation mutagenesis method described by Burks et al. (1997) PNAS USA, vol. 94, pp. 412-417 and the stepwise in vitro affinity maturation method of Wu et al. (1998) PNAS USA, vol. 95, pp. 6037-6042.

Amino acid residues herein may be indicated by either the one-letter code or the three-letter code Amino acid substitutions relative to a reference sequence may, for example, be indicated using the format "G44R", which indicates that a glycine residue in position 44 of a reference sequence has been mutated to an arginine residue. For example, "G44R" indicates a mutation of the glycine residue in a CDR-grafted antibody to an arginine residue. An amino acid residue written in the format "Arg44" indicates a particular residue in a particular position, i.e., in this case an arginine residue in position 44. Unless otherwise indicated, numbering of amino acid residues refers to the appended sequence listing.

As noted above, the present invention relates to humanized antibodies, more particularly to humanized antibodies based on certain chimeric parent antibodies described in WO 2012/059857. The humanized antibodies of the invention were developed using CDR grafting and back mutations, and in some cases alteration of unwanted sequence motifs, starting with selected chimeric anti-EGFR, anti-HER2 and anti-HER3 antibodies described in WO 2012/059857. The particular methods used to develop these humanized antibodies, as well as the results of functional evaluation of the humanized antibodies compared to the original chimeric antibodies from which they were developed, are described in the examples below.

Embodiments of the invention further include recombinant antibodies, which includes antibodies expressed from a cell or a cell-line transfected with a plurality of expression vectors comprising the coding sequence of the antibody, where said coding sequence is not naturally associated with the cell.

Thus, in one embodiment, the instant invention relates to antibodies which bind with specificity to amino acids 145-159 and/or amino acids 240-254 of hemagglutinin (HA) polypeptide of an influenza A virus, the numbering of the amino acids being deduced according to the H3 numbering system. The antibodies bind to amino acid sequences GDTIIFEANGNLIAP (AMINO ACIDS: 240-254) (SEQ ID NO: 1) and/or SSFYRNLLWLTEKEG (AMINO ACIDS: 145-159) (SEQ ID NO: 2), respectively.

In a related embodiment, the instant invention provides antibodies which bind to the aforementioned amino acids 240-254 of HA of HA, but do not bind to SEQ ID NO: 57 of U.S. Pat. No. 8,518,410 having the sequence GRMNYYWTLL KPGDTIIFEA NGNLIAPMYA FALSRGFGSG IITSNASMHE CNTKCQTPLG (SEQ ID NO: 5).

In a related embodiment, the instant invention provides antibodies which bind to the aforementioned amino acids 145-159 of HA, but do not bind to SEQ ID NO: 55 of U.S. Pat. No. 8,518,410 having the sequence QLSSVSSFER FEIFPKESSW PNHNTNGVTA ACSHEGKSSF YRNLLWLTEK EGSYPKLKNS (SEQ ID NO: 6); and/or SEQ ID NO: 202 or SEQ ID NO: 201, both of US patent app. pub. No. 2014/0206556 having the sequence HEGKSSFYRN LLWLTEKEGS YPK (SEQ ID NO: 7) and the sequence HEGKSSFYRN LLWLTEKEGS YPKLKNSYVN K (SEQ ID NO: 8), respectively.

Methods for screening antibodies that do not bind to a candidate sequence are known in the art. Such may include, for example, raising antibodies which first bind to the antigens of interest in a host animal, e.g., immunizing a rabbit with amino acids 240-254 of HA and/or 145-159 of HA; and contacting the antibodies harvested from the animal with a solid surface (e.g., a column) comprising the antigens used in the negative selection (e.g., SEQ ID NO: 57 of U.S. Pat. No. 8,518,410 or SEQ ID NO: 55 of U.S. Pat. No. 8,518,410) to remove the undesired antibodies. The desired antibodies, which do not bind to the negative selection marker, are then eluted using routine procedures and optionally concentrated using a lyophilizer.

In another related embodiments, the instant invention provides antibodies which bind to the aforementioned amino acids 240-254 of HA and/or 145-159 of HA, but do not bind to SEQ ID NO: 1386 having the sequence EPGDTIIFEA NGN (SEQ ID NO: 9) or SEQ ID NO: 1235 having the sequence LRMKXEPGDT IIFEANGN (SEQ ID NO: 10), both from U.S. Pat. No. 8,815,249; SEQ ID NO: 201 having the sequence HEGKSSFYRN LLWLTEKEGS YPKLKNSYVN K (SEQ ID NO: 8) or SEQ ID NO: 202 having the sequence HEGKSSFYRN LLWLTEKEGS YPK (SEQ ID NO: 7), both from U.S. Pat. No. 7,189,800; and/or SEQ ID NO: 25 having the sequence SYIVETPNSE NGICYPGDFI DYEELREQLS SVSSFERFEI FPKESSWPNH NTNGVTAACS HEGKSSFYRN LLWLTEKEGS YPKLKNSYVN KKGKEVLVLW GIHHPPNSKE QQNLYQNENA YVSVVTSNYN RRFTPEIAER PKVRDQAGRM NYYWTLLKPG DTI (SEQ ID NO: 11) from U.S. Pat. No. 8,815,522.

In another embodiment, the instant invention provides antibodies which bind to amino acids 170-184 of the HA polypeptide of the influenza A virus amino acid sequence: NKKGKEVLVLWGIHH (SEQ ID NO: 3). In more specific embodiment, the antibody binds to 170-184 of HA, but does not bind to SEQ ID NO: 56 having the sequence YVNKKGKEVLVLWGIHHPPNSKEQQNLYQNENAYVSVVTSNYNRRFTPEIAERPKVRDQA (SEQ ID NO: 12) from U.S. Pat. No. 8,518,410; SEQ ID NO: 25 having the sequence SYIVETPNSE NGICYPGDFI DYEELREQLS SVSSFERFEI FPKESSWPNH NTNGVTAACS HEGKSSFYRN LLWLTEKEGS YPKLKNSYVN KKGKEVLVLW GIHHPPNSKE QQNLYQNENA YVSVVTSNYN RRFTPEIAER PKVRDQAGRM NYYWTLLKPG DTI (SEQ ID NO: 11) from U.S. Pat. No. 8,815,522; or SEQ ID NO: 10 having the sequence NSENGICYPG DFIDYEELRE QLSSVSSFER FEIFPKESSW PNHNTNGVTA ACSHEGKSSF YRNLLWLTEK EGSYPKLKNS YVNKKGKEVL VLWGIHHPPN SKEQQNLYQN ENAYVSVVTS NYNRRFTPEI AERPKVRDQA GRMNYYWTLL KPGDTIIFEA NGNLIAPMYA FALSRG (SEQ ID NO: 13) or SEQ ID NO: 25 having the sequence NSENEICYPG DFIDKEELRE QLSSVSSFER FEIFPKESSW PNHNTNGVTA ACSHEGKSSF YRNLLWLTEK EGSYPKLKNS YVNKKGKEVL VLWGIHHPPN SKEQQNLYQN ENAYVSVVTS NYNRRFTPEI AERPKVRDQA GRMNYYWTLL KPGDTIIFEA NGNLIAPMYA AALSRG (SEQ ID NO: 14), both from U.S. Pat. No. 8,420,102.

In a related embodiment, the instant invention provides antibodies which bind to amino acids 195-209 of the HA polypeptide of the influenza A virus amino acid sequence: YQNENAYVSVVTSNY (SEQ ID NO: 4). In a specific aspect related thereto, the antibody binding to amino acids 195-209 of HA does not bind to SEQ ID NO: 56 from U.S. Pat. No. 8,518,410 having the sequence YVNKKGKEVL VLWGIHHPPN SKEQQNLYQN ENAYVSVVTS NYN-RRFTPEI AERPKVRDQA (SEQ ID NO: 12); SEQ ID NO: 25 of U.S. Pat. No. 8,815,522 having the sequence SYIV-ETPNSE NGICYPGDFI DYEELREQLS SVSSFERFEI FPKESSWPNH NTNGVTAACS HEGKSSFYRN LLWLTEKEGS YPKLKNSYVN KKGKEVLVLW GIHH-PPNSKE QQNLYQNENA YVSVVTSNYN RRFTPEIAER PKVRDQAGRM NYYWTLLKPG DTI (SEQ ID NO: 11); SEQ ID NO: 33 from US 2010/0239575 (or US 2014/0234344) having the sequence YVNKKGKEVLVLWGI-HHPPNSKEQQNLYQNENAYVSVVTSNYNRRFTPEI-AERPKV RDQA (SEQ ID NO: 12); or SEQ ID NO: 56 of US 2014/0127198 having the sequence YVNKKGKEVL VLWGIHHPPN SKEQQNLYQN ENAYVSVVTS NYN-RRFTPEI AERPKVRDQA (SEQ ID NO: 12).

Antibody Combinations and/or Compositions

Embodiments of the instant invention relate to combinations of the aforementioned antibodies in any ratio. Methods for formulating antibody combinations/compositions comprising two or more antibodies are also known in the art.

In a related embodiment, the instant invention provides antibodies which bind to amino acids 170-184 of the HA polypeptide of the influenza A virus amino acid sequence: NKKGKEVLVLWGIHH (SEQ ID NO: 3). This antibody may be combined with a first antibody binding to amino acids 240-254 of HA and/or a second antibody binding to amino acids 145-159 of HA. Optionally, the aforementioned antibody composition comprising a first antibody binding to amino acids 240-254 of HA and a second antibody binding to amino acids 145-159 of HA may be formulated into a first secondary composition further comprising antibodies which bind to amino acids 170-184 of HA.

In a related embodiment, the instant invention provides antibodies which bind to amino acids 195-209 of the HA polypeptide of the influenza A virus amino acid sequence: YQNENAYVSVVTSNY (SEQ ID NO: 4). This antibody may be combined with a first antibody binding to amino acids 240-254 of HA and/or a second antibody binding to amino acids 145-159 of HA. Optionally, the aforementioned antibody composition comprising a first antibody binding to amino acids 240-254 of HA and a second antibody binding to amino acids 145-159 of HA may be formulated into a tertiary composition comprising the antibody binding to amino acids 195-209 of HA. The tertiary composition comprising antibodies binding to amino acids 145-159, amino acids 240-254 and amino acids 195-209 of HA may be further formulated into a quaternary composition comprising the third antibody which binds to amino acids 170-184 of HA. Accordingly, any number of potential combinations may be formulated and each composition may contain the individual antibodies at any ratio.

In a related embodiment, the instant invention provides antibody composition comprising a first antibody which binds to the amino acid sequence GDTIIFEANGNLIAP (amino acids: 240-254 of HA) (SEQ ID NO: 1) and a second antibody which binds to the amino acid sequence SSFYRN-LLWLTEKEG (amino acids: 145-159 of HA) (SEQ ID NO: 2).

In a related embodiment, the instant invention provides a bispecific antibody which binds to the amino acid sequence GDTIIFEANGNLIAP (amino acids: 240-254 of HA) (SEQ ID NO: 1) and/or the amino acid sequence SSFYRNLL-WLTEKEG (amino acids: 145-159 of HA) (SEQ ID NO: 2).

In a related embodiment, the instant invention provides for multispecific antibodies which bind to amino acids 240-254 of HA and/or amino acids 145-159 of HA and/or amino acids 195-209 of HA and/or amino acids 170-184 of HA. Bispecific and/or multispecific antibodies have been characterized in literature.

Compositions

Embodiments of the instant invention further include antibody formulations comprising one or more of the aforementioned antibodies and a carrier or adjuvant. More specifically, the formulations or compositions consist, essentially, any two, any three, or all four of the antibodies which bind specifically to amino acids 240-254 of HA and/or amino acids 145-159 of HA and/or amino acids 195-209 of HA and/or amino acids 170-184 of HA. The instant invention further provides for kits comprising, in one or separate packages, at least one of the aforementioned antibodies and a carrier or adjuvant. More specifically, the kits consist, essentially, any two, any three, or all four of the antibodies which bind specifically to amino acids 240-254 of HA and/or amino acids 145-159 of HA and/or amino acids 195-209 of HA and/or amino acids 170-184 of HA and a carrier or adjuvant.

Another aspect of the invention is a pharmaceutical composition comprising as an active ingredient an antibody or antibody composition of the invention. Such compositions are intended for amelioration, prevention and/or treatment of influenza. The pharmaceutical composition may be administered to a human or to a domestic animal or pet, but will typically be administered to humans. In these compositions, the ratio between the individual antibodies in a therapeutic composition of the invention, or, in the case of individual antibodies of the invention being administered simultaneously, sequentially or separately, will often be such that the antibodies are administered in equal amounts, but this need not necessarily be the case. Depending on the characteristics of the individual antibodies, however, it may be possible to use non-equal amounts of the different antibodies, e.g., unequal amounts of anti-HA and anti-NA antibodies of the instant invention. Suitable ratios for the different anti-HER antibodies in compositions of the invention may be determined as described in WO 2010/040356 (incorporated herein by reference), which describes methods for identifying and selecting the optimal stoichiometric ratio between chemical entities in a combinatorial drug product to obtain a combinatorial drug with optimal potency and efficacy.

Embodiments of the instant invention further provide a solid support, e.g., plates, tubes, columns, gels, microarrays, etc. comprising one or more of the aforementioned antibodies. The solid supports may comprise, at least two, at least three, at least four or more of the aforementioned antibodies. More specifically, the solid supports consist, essentially, any two, any three, or all four of the antibodies which bind specifically to amino acids 240-254 of HA and/or amino acids 145-159 of HA and/or amino acids 195-209 of HA and/or amino acids 170-184 of HA.

Properties of the Antibodies and Antibody Compositions

The antibodies of the invention bind to the hemagluttin (HA) peptides human influenza virus family members, e.g., H1N1. The compositions may also comprise antibodies that bind to neuraminidase (NA) peptides of human influenza virus family members.

Epitopes of the antibodies of the invention are linear or non-linear. For instance, a non-linear epitope is discontinuous. Discontinuous epitopes are available for antibody binding, e.g., when the influenza HA protein is maintained in its native homotrimeric conformation. When an antibody binds to a discontinuous epitope, the antibody binds to a three-dimensional surface of the target protein, i.e. the influenza HA protein, upon which juxtaposed amino acids are alternatively exposed or masked.

The antibodies of the invention neutralize viruses at least 25%, at least 30%, at least 40%, at least 50%, at least 60%, at least 70%, at least 80%, at least 90%, at least 95%, at least 99%, or more compared to a control (e.g., irrelevant) antibody, as determined via an in ovo neutralization assay.

The antibodies of the invention neutralize viruses at a concentration from about 0.5 µg/ml-25 µg/ml, specifically at about 1 µg/ml-20 µg/ml, more specifically at about 2 µg/ml-16 µg/ml, particularly at about 4 µg/ml-12 µg/ml, more particularly at about 6 µg/ml-8 µg/ml, including all values in between, but not limited to, a concentration of about 6 µg/ml, preferably at about 7 µg/ml, more preferably at about 8 µg/ml, particularly preferably at about 10 µg/ml, and most preferably at about 12 µg/ml, or more. In these embodiments, the antibodies at a concentration of 0.5 µg/ml-25 µg/ml result in at least 25%, at least 30%, at least 40%, at least 50%, at least 60%, at least 70%, at least 80%, at least 90%, at least 95%, at least 99%, or greater neutralization of viral titers compared to a control (e.g., irrelevant) antibody, as determined via an in ovo neutralization assay.

Binding of one or more antibodies of the invention, in particular antibody composition of the invention, to influenza virus surface glycoprotein receptors preferably inhibits the growth and proliferation of viruses expressing the receptors (i.e., neutralizes the virus). The mechanism (s) involved may, for example, include one or more of the following: preventing the binding of viruses to cell-surface receptors, preventing internalization of the virus, promoting degradation of the virus, reducing internal signaling of the viral receptor, inducing phagocytosis, CDC and/or ADCC or a combination thereof.

As used herein, the term "neutralization" may be denoted in terms of sequestration of the virus by the antibodies of the invention, wherein about 10%, and preferably more, such as at least about 20% or 30%, more preferably at least about 40% or 50%, such as at least about 60%, 70%, 80%, 90%, 95% or 99%, or even about 100% of the virus in the mixture is sequestrated by the antibodies of the invention. Alternately, the term may be denoted in terms of reduction in the number of viral titers that are positive for the epitopes of interest, e.g., 10%, and preferably more, such as at least about 20% or 30%, more preferably at least about 40% or 50%, such as at least about 60%, 70%, 80%, 90%, 95% or 99%, or even about 100% reduction in the number of titers. The activity of the antibodies can determined in relevant cells or cell systems as described in the examples below.

Methods for testing antibodies or compositions, e.g., binding to an antigen of interest, such as, for example, HA and/or NA proteins, including fragments thereof, are known in the art, e.g., Western blots, radioimmunoassays, ELISA (enzyme linked immunosorbent assay), "sandwich" immunoassays, immunoprecipitation assays, gel diffusion precipitation reactions, immunodiffusion assays, agglutination assays, complement-fixation assays, immunoradiometric assays, fluorescent immunoassays, protein A immunoassays, etc.

Immunogens

The instant invention also provides for immunogens (e.g., antigen sequences) and nucleic acid sequences encoding such immunogens. Furthermore, the instant invention provides immunogenic compositions comprising two or more immunogens.

The immunogens further include antigenic fragments (or segments) which bind with specificity to the cognate antibodies, including, combinations of such partial sequences. Thus, in one embodiment, the instant invention relates to immunogens comprising amino acids 240-254 of HA and/or amino acids 145-159 of HA and/or amino acids 195-209 of HA and/or amino acids 170-184 of HA Immunogen compositions may consist, essentially, any one, any two, any three, or all four of the aforementioned immunogens and a carrier or adjuvant.

As is understood in the art, the aforementioned immunogens are useful in the generation of antibodies of the invention, e.g., a monoclonal antibody which is generated from a process comprising (a) immunizing a host animal with the immunogen; (b) obtaining B-cells from said host animal which secrete antibodies against said immunogen; (c) fusing said B-cells with a self-propagating (e.g., cancer) cell to generate a hybridoma; (d) obtaining a single clone of said hybridoma by using routine methods (e.g., serial dilution); and (e) culturing said single clone of said hybridoma to obtain the monoclonal antibody secreted by said hybridoma; and optionally (f) testing a monoclonal antibody secreted by said hybridoma for binding to said immunogen.

Immunogens of the instant invention, further relate to discontinuous epitopes. Representative examples are provided in Table H and/or in the enclosed Appendix A.

Nucleic Acids

Embodiments of the instant invention further relate to the nucleic acid sequences encoding the aforementioned reassortants, including nucleic acid sequences having significant sequence homology or identity thereto. Under one embodiment, significant sequence identity refers to at least 60%, at least 65%, at least 70%, at least 75%, at least 80%, at least 90%, at least 95%, at least 96%, at least 97%, at least 98%, at least 99%, at least 99.9% or greater than 99.9% sequence identity to the template sequence. Further embodiments relate to compositions comprising nucleic acids, including vectors, e.g., viral vector, bacterial vector, baculovirus vector, comprising heterologous expression control sequences, e.g., promoters, repressors, effectors, etc. for the expression of the gene products of such nucleic acids and genomes in a host, e.g., a bacteria, an insect cell, a cell-line, etc.

Embodiments of the instant invention also relate to nucleic acid variants containing one or more polymorphisms (e.g., wherein the encoded gene product is identical to the native sequence), or variants thereof which have significant structural similarity (e.g., >80%, specifically >90%, particularly >95%, preferably >97% or 99% sequence identity) to a template sequence. Methods for determining sequence identity to a template sequence are known in the art. A preferred pairwise alignment algorithm is the Needleman-Wunsch global alignment algorithm, using default parameters (e.g. with Gap opening penalty=10.0, and with Gap extension penalty=0.5, using the EBLOSUM62 scoring matrix). This algorithm is conveniently implemented in the needle tool in the EMBOSS package.

Further provided are compositions and kits comprising the aforementioned nucleic acids (or the genomes) and a carrier, optionally together with instructions for using the nucleic acids in transfection experiments or the like. In related embodiments, the invention provides for compositions and kits comprising the host cells comprising such nucleic acids together with a carrier or reagent for propagation of such host cells, e.g., in culture.

Reassortants

In the exemplified embodiment of the instant invention, the high yield donor strain is A/Puerto Rico/8/1934 (PR8, H1N1), which is highly egg-adapted influenza virus that has been continuously passaged in embryonated chicken eggs since 1934. The reassortants influenza viruses may comprise at least one backbone viral gene segment from PR8, i.e. PB2, PB1, PA, NP, M, NS and at least surface protein gene segments, i.e. HA, NA from current circulating wild type influenza A viruses including H1N1 subtype (e.g. SD), H3N2 (e.g. UY), H1N1pdm (e.g. CA) and other influenza A HA and NA subtypes, such as H2, H4, H5, H6, H7, H8, H9, H10, H11, H12, H13, H14, H15, H16, H17 and N3, N4, N5, N6, N7, N8, N9.

The reassortant influenza A viruses preferably comprise at least one backbone viral segment from the donor strain PR8. Thus, the influenza viruses of the invention may comprise one or more genome segments selected from: PB2 gene having the GenBank accession No. CY033584; PB1 gene having the GenBank accession No. CY033583; PA gene having the GenBank accession No. CY033582; NP gene having the GenBank accession No. CY033580; M gene having the GenBank accession No. CY033578; NS gene having the GenBank accession No. CY033581, the individual sequences which were accessioned on Aug. 18, 2008, are incorporated by reference herein The reassortant influenza A virus may comprise all of these backbone segments.

Alternatively, or in addition, the reassortant influenza A virus may comprise one or more backbone viral segments from other strains, e.g., H3N2.

The reassortant influenza viruses may comprise backbone segments from two or more influenza donor strains. The inventors have found that such reassortant influenza A viruses grow particularly well in culture hosts. Such reassortant influenza A viruses are particularly suitable for use in the methods of the invention because the increased rescue efficiency increases the speed further by which seed viruses for vaccine manufacture can be obtained.

The choice of high yield donor influenza virus for use in developing reassortants may include but not limit to PR8s (NYMC, CDC, St. Jude Children Hospital, Cambridge (UK), bioCSL (AU), NIBSC (UK)). The exemplified use of the monoclonal antibodies of the instant invention for practicing the methods involves use of PR8 as the high yield donor; however, other prospective/potential high yield influenza viruses (both influenza A and B types, e.g. A/WSN/1933, A/NWS/1933, A/WS/1933) may also be used in a manner that is analogous to the exemplified methods to develop reassortants by utilizing respective monoclonal antibodies that are developed according to the methods exemplified in the instant application. Such methods may include, for example, identifying homologous (or structurally identical) epitopes to those disclosed in Tables A-I in the viruses of interest; generating antibodies (e.g., monoclonal antibodies) which bind to such epitopes; and employing such antibodies in the selection procedure.

The egg isolate A/California/07/2009 (CA, H1N1pdm) is used to prepare the NYMC hy seed viruses for the 2009 H1N1 pandemic influenza vaccine. NYMC X-173 (H1N1) is a hy reassortant influenza A vaccine candidate virus incorporating six PR8 'internal' genes as 'backbone' and hemagglutinin (HA) and neuraminidase (NA) genes from wild type (WT) virus, SD (H1N1). NYMC X-175C (H3N2) is a hy reassortant virus which possesses HA and NA from the WT virus, UY (H3N2), together with the PR8 backbone. Other examples of such hy reassortant strains that are employable include, but are not limited to, A/South Dakota/06/2007 (SD, H1N1) and A/Uruguay/716/2007 (UY, H3N2), which are egg isolated wild type (WT) viruses receivable from the Center for Diseases Control and Prevention (CDC).

As reassortants between evolutionary distant strains might not replicate well in cell culture, it is possible that the donor strain and the vaccine strain have the same HA and/or NA subtype. In other embodiments, however, the vaccine strain and the donor strain can have different HA and/or NA subtypes, and this arrangement can facilitate selection for reassortant viruses that contain the HA and/or NA segment from the vaccine strain. Therefore, although other and PR8-X strains contain the H1 influenza subtype these donor strains can be used for vaccine strains which do not contain the H1 influenza subtype.

Reassortants of the donor strains wherein the HA and/or NA segment has been changed to another subtype can also be used. The H1 influenza subtype of other strain or PR8 strain may be changed, for example, to a H3 or H5 subtype.

Thus, an influenza A virus may comprises one, two, three, four, five, six or more viral segments from other or PR8 strains. See, for example, NYMC X-173 (H1N1) strain described above.

Methods for Generating Seed Viruses

In one embodiment, the invention provides a method for producing influenza viruses comprising steps of (a) infecting a culture host with a reassortant virus of the invention; (b) culturing the host from step (a) to produce the virus; and optionally (c) purifying the virus produced in step (b). The culture host may be cells or embryonated hen eggs, as described above. Where cells are used as a culture host in this aspect of the invention, it is known that cell culture conditions (e.g. temperature, cell density, pH value, etc.) are variable over a wide range subject to the cell line and the virus employed and can be adapted to the requirements of the application. The following information therefore merely represents guidelines. As mentioned above, cells are preferably cultured in serum-free or protein-free media.

Multiplication of the cells can be conducted in accordance with methods known to those of skill in the art. For example, the cells can be cultivated in a perfusion system using ordinary support methods like centrifugation or filtration. Moreover, the cells can be multiplied according to the invention in a fed-batch system before infection. In the context of the present invention, a culture system is referred to as a fed-batch system in which the cells are initially cultured in a batch system and depletion of nutrients (or part of the nutrients) in the medium is compensated by controlled feeding of concentrated nutrients. It can be advantageous to adjust the pH value of the medium during multiplication of cells before infection to a value between pH 6.6 and pH 7.8 and especially between a value between pH 7.2 and pH 7.3. Culturing of cells preferably occurs at a temperature between 30 and 40° C. When culturing the infected cells (step b), the cells are preferably cultured at a temperature of between 30° C. and 36° C. or between 32° C. and 34° C. or at 33° C. This is particularly preferred, as it has been shown that incubation of infected cells in this temperature range results in production of a virus that results in improved efficacy when formulated into a vaccine. Oxygen partial pressure can be adjusted during culturing before infection preferably at a value between 25% and 95% and especially at a value between 35% and 60%. The values for the oxygen partial pressure stated in the context of the invention are based on saturation of air. Infection of cells occurs at a cell density of preferably about $8-25\times10^5$ cells/mL in the batch system or preferably about $5-20\times10^6$ cells/mL in the perfusion system. The cells can be infected with a viral dose (MOI value, "multiplicity of infection"; corresponds to the number of virus units per cell at the time of infection) between 10-8 and 10, preferably between 0.0001 and 0.5.

Virus may be grown on cells in adherent culture or in suspension. Microcarrier cultures can be used. In some embodiments, the cells may thus be adapted for growth in suspension. The methods according to the invention also include harvesting and isolation of viruses or the proteins generated by them. During isolation of viruses or proteins, the cells are separated from the culture medium by standard methods like separation, filtration or ultrafiltration. The viruses or the proteins are then concentrated according to methods sufficiently known to those skilled in the art, like gradient centrifugation, filtration, precipitation, chromatography, etc., and then purified. It is also preferred according to the invention that the viruses are inactivated during or after purification. Virus inactivation can occur, for example, by β-propiolactone or formaldehyde at any point within the purification process. The culture host may be eggs. The current standard method for influenza virus growth for vaccines uses embryonated SPF hen eggs, with virus being purified from the egg contents (allantoic fluid). It is also possible to passage a virus through eggs and subsequently propagate it in cell culture and vice versa.

Propagating the Viruses

In some embodiments, viruses described herein are maintained and passaged in host cells. By way of example, but not by way of limitation, exemplary host cells appropriate for growth of influenza viral mutants, such as influenza A viral mutants include any number of eukaryotic cells, including, but not limited to Madin-Darby canine kidney cells (MDCK cells), simian cells such as African green monkey cells (e.g., Vero cells), CV-1 cells and rhesus monkey kidney cells (e.g., LLcomk.2 cells), bovine cells (e.g., MDBK cells), swine cells, ferret cells (e.g., mink lung cells) BK-1 cells, rodent cells (e.g., Chinese Hamster Ovary cells), human cells, e.g., embryonic human retinal cells (e.g., PER-C6®), 293T human embryonic kidney cells and avian cells including embryonic fibroblasts.

Additionally or alternatively, in some embodiments, the eukaryotic host cell is modified to enhance viral production, e.g., by enhancing viral infection of the host cell and/or by enhancing viral growth rate. For example, in some embodiments, the host cell is modified to express, or to have increased expression, of 2,6-linked sialic acid on the cell surface, allowing for more efficient and effective infection of these cells by mutant or wild-type influenza A viruses. See US 2010-0021499, and U.S. Pat. No. 7,176,021. Thus, in some illustrative embodiments, Chinese Hamster Ovary Cells (CHO cells) and/or Vero cells modified to express at least one copy of a 2,6-sialyltransferase gene (ST6GAL 1) are used. By way of example, but not by way of limitation, the Homo sapiens ST6 beta-galatosamide alpha-2,6-sialyltransferase gene sequence denoted by the accession number BC040009.1, is one example of a ST6Gal gene that can be integrated into and expressed by a CHO cell. One or more copies of a polynucleotide that encodes a functional ST6Gal I gene product can be engineered into a cell. That is, cells which have been stably transformed to express 1, 2, 3, 4, 5, 6, 7, 8, 9, 10, 11, 12, or more than 12 copies of a ST6Gal I gene may be used. A single expression cassette may include one or more copies of the ST6Gal I gene to be expressed, which is operably linked to regulatory elements, such as promoters, enhancers, and terminator and polyadenylation signal sequences, to facilitate the expression of the ST6Gal I gene or its copies. Alternatively, a single expression cassette may be engineered to express one copy of an ST6Gal I gene, and multiple expression cassettes integrated into a host cell genome. Accordingly, in some embodiments, at least one ST6Gal I gene is incorporated into the genome of a host cell, such that the cell expresses the ST6Gal I gene and its enzymatic protein product. Depending on the copy number, a single host cell may express many functional ST6Gal I gene proteins.

Suitable vectors for cloning, transfecting and producing stable, modified cell lines are well known in the art. One non-limiting example includes pcDNA3.1 (Invitrogen). Method for producing both expression vectors and modified host cells are well known in the art.

The viruses may be tested using the methods described below. In one embodiment, the virus has a growth rate that is at least two-fold, at least five-fold, at least ten-fold, at least 20-fold, at least 30-fold, at least 40-fold, at least 100-fold or at least 1000-fold greater than the wild-type CA strain, as measured by HA titer.

Vaccines

Embodiments of the invention further relate to the use of virus produced according to the methods of the instant invention to produce vaccines and other immunological compositions. Vaccines (particularly for influenza virus) are generally based either on live virus or on inactivated virus. Inactivated vaccines may be based on whole virions, split virions, or on purified surface antigens. Antigens can also be presented in the form of virosomes. The invention can be used for manufacturing any of these types of vaccine.

Where an inactivated virus is used, the vaccine may comprise whole virion, split virion, or purified surface antigens (for influenza, including hemagglutinin and, usually, also including neuraminidase). Chemical means for inactivating a virus include treatment with an effective amount of one or more of the following agents: detergents, formaldehyde, β-propiolactone, methylene blue, psoralen, carboxyfullerene (C60), binary ethylamine, acetyl ethyleneimine, or combinations thereof. Non-chemical methods of viral inactivation are known in the art, such as for example UV light or gamma irradiation.

Virions can be harvested from virus-containing fluids, e.g. allantoic fluid or cell culture supernatant, by various methods. For example, a purification process may involve zonal centrifugation using a linear sucrose gradient solution that includes detergent to disrupt the virions. Antigens may then be purified, after optional dilution, by diafiltration.

Split virions are obtained by treating purified virions with detergents (e.g. ethyl ether, polysorbate 80, deoxycholate, tri-N-butyl phosphate, Triton X-100, Triton N101, cetyltrimethylammonium bromide, Tergitol NP9, etc.) to produce subvirion preparations, including the 'Tween-ether' splitting process. Methods of splitting influenza viruses, for example are well known in the art e.g. see refs. 42-47, etc. Splitting of the virus is typically carried out by disrupting or fragmenting whole virus, whether infectious or non-infectious with a disrupting concentration of a splitting agent. The disruption results in a full or partial solubilisation of the virus proteins, altering the integrity of the virus. Preferred splitting agents are non-ionic and ionic (e.g. cationic) surfactants e.g. alkylglycosides, alkylthioglycosides, acyl sugars, sulphobetaines, betains, polyoxyethylenealkylethers, N,N-dialkyl-Glucamides, Hecameg, alkylphenoxy-polyethoxyethanols, NP9, quaternary ammonium compounds, sarcosyl, CTABs (cetyl trimethyl ammonium bromides), tri-N-butyl phosphate, Cetavlon, myristyltrimethylammonium salts, lipofectin, lipofectamine, and DOT-MA, the octyl- or nonylphenoxy polyoxyethanols (e.g. the Triton surfactants, such as Triton X-100 or Triton N101), polyoxyethylene sorbitan esters (the Tween surfactants), polyoxyethylene ethers, polyoxyethlene esters, etc. One useful splitting procedure uses the consecutive effects of sodium deoxycholate and formaldehyde, and splitting can take place during initial virion purification (e.g. in a sucrose density gradient solution). Thus a splitting process can involve clarification of the virion-containing material (to remove non-virion material), concentration of the harvested virions (e.g. using an adsorption method, such as CaHPO4 adsorption), separation of whole virions from non-virion material, splitting of virions using a splitting agent in a density gradient centrifugation step (e.g. using a sucrose gradient that contains a splitting agent such as sodium deoxycholate), and then filtration (e.g. ultrafiltration) to remove undesired materials. Split virions can usefully be resuspended in sodium phosphate-buffered isotonic sodium chloride solution. Examples of split influenza vaccines are the BEGRIVAC™, FLUARIX™, FLUZONE™ and FLUSHIELD™ products.

Methods of Making Vaccines

Purified influenza virus surface antigen vaccines comprise the surface antigens hemagglutinin and, typically, also neuraminidase. Processes for preparing these proteins in purified form are well known in the art. The FLUVIRIN™, AGRIPPAL™ and INFLUVAC™ products are influenza subunit vaccines.

Another form of inactivated antigen is the virosome (nucleic acid free viral-like liposomal particles). Virosomes can be prepared by solubilization of virus with a detergent followed by removal of the nucleocapsid and reconstitution of the membrane containing the viral glycoproteins. An alternative method for preparing virosomes involves adding viral membrane glycoproteins to excess amounts of phospholipids, to give liposomes with viral proteins in their membrane.

The methods of the invention may also be used to produce live vaccines. Such vaccines are usually prepared by purifying virions from virion-containing fluids. For example, the fluids may be clarified by centrifugation, and stabilized with buffer (e.g. containing sucrose, potassium phosphate, and monosodium glutamate). Various forms of influenza virus vaccine are currently available (e.g. see chapters 17 and 18 of reference 49). Live virus vaccines include MedImmune's FLUMIST™ product (trivalent live virus).

The virus may be attenuated. The virus may be temperature-sensitive. The virus may be cold-adapted. These three features are particularly useful when using live virus as an antigen. HA is the main immunogen in current inactivated influenza vaccines, and vaccine doses are standardized by reference to HA levels, typically measured by SRID. Existing vaccines typically contain about 15 μg of HA per strain, although lower doses can be used e.g. for children, or in pandemic situations, or when using an adjuvant. Fractional doses such as ½ (i.e., 7.5 μg HA per strain), ¼ and ⅛ have been used, as have higher doses (e.g. 3× or 9× doses). Thus vaccines may include between 0.1 and 150 of HA per influenza strain, preferably between 0.1 and 50 μg e.g. 0.1-10 m, 0.5-5 etc. Particular doses include e.g. about 45, about 30, about 15, about 10, about 7.5, about 5, about 3.8, about 3.75, about 1.9, about 1.5, etc. per strain.

For live vaccines, dosing is measured by median tissue culture infectious dose ($TCID_{50}$) rather than HA content, and a $TCID_{50}$ of between $10^6$ and $10^8$ (preferably between $10^6$-$10^7$) per strain is typical.

Viral Products

Embodiments of the invention further include viral products, e.g., antigens, proteins, peptides or nucleic acids, including genomes, of viruses obtained using the aforementioned methods. Influenza strains developed with the invention may have a natural HA as found in a wild-type virus, or a modified HA. For instance, it is known to modify HA to remove determinants (e.g. hyper-basic regions around the HA1/HA2 cleavage site) that cause a virus to be highly pathogenic in avian species. Reverse genetics can be used for the modification.

As well as being suitable for immunizing against interpandemic strains, the compositions of the invention are particularly useful for immunizing against pandemic or potentially-pandemic strains. The invention is suitable for vaccinating a subject.

Other strains whose antigens can usefully be included in the compositions are strains which are resistant to antiviral therapy (e.g. resistant to oseltamivir and/or zanamivir), including resistant pandemic strains.

Compositions of the invention may include antigen(s) from one or more (e.g. 1, 2, 3, 4 or more) influenza virus strains, including influenza A virus and/or influenza B virus provided that at least one influenza strain is a reassortant influenza strain of the invention. Compositions wherein at least two, at least three or all of the antigens are from reassortant influenza strains of the invention are also envisioned. Where a vaccine includes more than one strain of influenza, the different strains are typically grown separately and are mixed after the viruses have been harvested and antigens have been prepared. Thus a process of the invention may include the step of mixing antigens from more than one influenza strain. A trivalent vaccine is typical, including antigens from two influenza A virus strains and one influenza B virus strain. A tetravalent vaccine is also useful, including antigens from two influenza A virus strains and two influenza B virus strains, or three influenza A virus strains and one influenza B virus strain.

Pharmaceutical Compositions of Viral Vaccines or Products Derived from Viruses

Embodiments of the instant invention further provide compositions that are pharmaceutically acceptable or of pharmaceutical grade. They usually include components in addition to the antigens or viruses, e.g., they typically include one or more pharmaceutical carrier(s) and/or excipient(s). As described below, adjuvants may also be included. A thorough discussion of such components is available in U.S. Pat. No. 5,252,252, which is incorporated by reference. Further embodiments relate to vaccines comprising the viruses. Vaccine compositions will generally be in aqueous form. However, some vaccines may be in dry form, e.g. in the form of injectable solids or dried or polymerized preparations on a patch.

Vaccine compositions may include preservatives such as thiomersal or 2-phenoxyethanol. It is preferred, however, that the vaccine should be substantially free from (i.e., less than 5 μg/ml) mercurial material e.g. thiomersal-free. Vaccines containing no mercury are more preferred. An α-tocopherol succinate can be included as an alternative to mercurial compounds. Preservative-free vaccines are particularly preferred. To control tonicity, it is preferred to include a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride, calcium chloride, etc.

Vaccine compositions will generally have an osmolality of between 200 mOsm/kg and 400 mOsm/kg, preferably between 240-360 mOsm/kg, and will more preferably fall within the range of 290-310 mOsm/kg. Osmolality has previously been reported not to have an impact on pain caused by vaccination, but keeping osmolality in this range is nevertheless preferred.

Vaccine compositions may include one or more buffers. Typical buffers include: a phosphate buffer; a Tris buffer; a borate buffer; a succinate buffer; a histidine buffer (particularly with an aluminum hydroxide adjuvant); or a citrate buffer. Buffers will typically be included in the 5-20 mM range.

The pH of a vaccine composition will generally be between 5.0 and 8.1, and more typically between 6.0 and 8.0 e.g. 6.5 and 7.5, or between 7.0 and 7.8. A process of the invention may therefore include a step of adjusting the pH of the bulk vaccine prior to packaging.

The vaccine composition is preferably sterile. The vaccine composition is preferably non-pyrogenic e.g. containing <1 EU (endotoxin unit, a standard measure) per dose, and preferably <0.1 EU per dose. The vaccine composition is preferably gluten-free.

Vaccine compositions of the invention may include detergent e.g. a polyoxyethylene sorbitan ester surfactant (known as 'Tweens'), an octoxynol (such as octoxynol-9 (Triton X-100) or t-octylphenoxypolyethoxyethanol), a cetyl trimethyl ammonium bromide ('CTAB'), or sodium deoxycholate, particularly for a split or surface antigen vaccine. The detergent may be present only at trace amounts. Thus the vaccine may include less than 1 mg/ml of each of octoxynol-10 and polysorbate 80. Other residual components in trace amounts could be antibiotics (e.g. neomycin, kanamycin, polymyxin B).

A vaccine composition may include material for a single immunization, or may include material for multiple immunizations (i.e., a 'multidose' kit). The inclusion of a preservative is preferred in multidose arrangements. As an alternative (or in addition) to including a preservative in multidose compositions, the compositions may be contained in a container having an aseptic adaptor for removal of material.

Influenza vaccines are typically administered in a dosage volume of about 0.5 ml, although a half dose (i.e., about 0.25 ml) may be administered to children.

Compositions and kits are preferably stored at between 2° C. and 8° C. They should not be frozen. They should ideally be kept out of direct light.

Where virus has been isolated and/or grown on a cell line, it is standard practice to minimize the amount of residual cell line DNA in the final vaccine, in order to minimize any potential oncogenic activity of the DNA. Thus a vaccine composition prepared according to the invention preferably contains less than 10 ng (preferably less than 1 ng, and more preferably less than 100 pg) of residual host cell DNA per dose, although trace amounts of host cell DNA may be present. It is preferred that the average length of any residual host cell DNA is less than 500 bp e.g. less than 400 bp, less than 300 bp, less than 200 bp, less than 100 bp, etc. Contaminating DNA can be removed during vaccine preparation using standard purification procedures e.g. chromatography, etc. Removal of residual host cell DNA can be enhanced by nuclease treatment e.g. by using a DNase. A convenient method for reducing host cell DNA contamination is disclosed in the art, involving a two-step treatment, first using a DNase (e.g. Benzonase), which may be used during viral growth, and then a cationic detergent (e.g. CTAB), which may be used during virion disruption. Treatment with an alkylating agent, such as β-propiolactone, can also be used to remove host cell DNA, and advantageously may also be used to inactivate virions.

Compositions of the invention may advantageously include an adjuvant, which can function to enhance the immune responses (humoral and/or cellular) elicited in a subject who receives the composition. Preferred adjuvants comprise oil-in-water emulsions. Various such adjuvants are known, and they typically include at least one oil and at least one surfactant, with the oil(s) and surfactant(s) being biodegradable (metabolizable) and biocompatible. The oil droplets in the emulsion are generally less than 5 µm in diameter, and ideally have a sub-micron diameter, with these small sizes being achieved with a microfluidiser to provide stable emulsions. Droplets with a size less than 220 nm are preferred as they can be subjected to filter sterilization.

The emulsion can comprise oils such as those from an animal (such as fish) or vegetable source. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and may therefore be used in the practice of this invention. The procedures for separation, purification, saponification and other means necessary for obtaining pure oils from animal sources are well known in the art. Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoids known as squalene, 2,6,10,15,19,23-hexamethyl-2,6,10,14,18,22-tetracosahexaene, which is particularly preferred herein. Squalane, the saturated analog to squalene, is also a preferred oil. Fish oils, including squalene and squalane, are readily available from commercial sources or may be obtained by methods known in the art. Another preferred oil is α-tocopherol (see below). Mixtures of oils can also be used.

Surfactants can be classified by their 'HLB' (hydrophile/lipophile balance). Preferred surfactants of the invention have a HLB of at least 10, preferably at least 15, and more preferably at least 16. The invention can be used with surfactants including, but not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-630/NP-40); phospholipids such as phosphatidylcholine (lecithin); nonylphenol ethoxylates, such as the Tergitol™ NP series; polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. Non-ionic surfactants are preferred. Preferred surfactants for including in the emulsion are Tween 80 (polyoxyethylene sorbitan monooleate), Span 85 (sorbitan trioleate), lecithin and Triton X-100.

Mixtures of surfactants can be used e.g. Tween 80/Span 85 mixtures. A combination of a polyoxyethylene sorbitan ester such as polyoxyethylene sorbitan monooleate (Tween 80) and an octoxynol such as t-octylphenoxypolyethoxyethanol (Triton X-100) is also suitable. Another useful combination comprises laureth 9 plus a polyoxyethylene sorbitan ester and/or an octoxynol.

Preferred amounts of surfactants (% by weight) are: polyoxyethylene sorbitan esters (such as Tween 80) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

Where the vaccine contains a split virus, it is preferred that it contains free surfactant in the aqueous phase. This is advantageous as the free surfactant can exert a 'splitting effect' on the antigen, thereby disrupting any unsplit virions and/or virion aggregates that might otherwise be present. This can improve the safety of split virus vaccines.

Preferred emulsions have an average droplets size of <1 µm e.g. ≤750 nm, ≤500 nm, ≤400 nm, ≤300 nm, ≤250 nm, ≤220 nm, ≤200 nm, or smaller. These droplet sizes can conveniently be achieved by techniques such as microfluidization.

In some embodiments an emulsion may be mixed with antigen extemporaneously, at the time of delivery, and thus the adjuvant and antigen may be kept separately in a packaged or distributed vaccine, ready for final formulation at the time of use. In other embodiments an emulsion is mixed with antigen during manufacture, and thus the composition is packaged in a liquid adjuvanted form.

The antigen will generally be in an aqueous form, such that the vaccine is finally prepared by mixing two liquids. The volume ratio of the two liquids for mixing can vary (e.g. between 5:1 and 1:5) but is generally about 1:1 and this is most preferred. Where concentrations of components are given in the above descriptions of specific emulsions, these concentrations are typically for an undiluted composition, and the concentration after mixing with an antigen solution will thus decrease (e.g. it will be half the concentration where the antigen and the adjuvant are mixed at a ratio of 1:1).

Kits

Embodiments of the instant invention further relate to compositions containing any of the aforementioned products in one or more packages with instructions for use. Suitable containers for compositions of the invention (or kit components) include vials, syringes (e.g. disposable syringes), nasal sprays, etc. These containers should be sterile.

Where a composition/component is located in a vial, the vial is preferably made of a glass or plastic material. The vial is preferably sterilized before the composition is added to it. To avoid problems with latex-sensitive patients, vials are preferably sealed with a latex-free stopper, and the absence of latex in all packaging material is preferred. The vial may include a single dose of vaccine, or it may include more than one dose (a 'multidose' vial) e.g., 10 doses. Preferred vials are made of colorless glass. A vial can have a cap (e.g. a Luer lock) adapted such that a pre-filled syringe can be inserted into the cap, the contents of the syringe can be expelled into the vial (e.g. to reconstitute lyophilized material therein), and the contents of the vial can be removed back into the syringe. After removal of the syringe from the vial, a needle can then be attached and the composition can be administered to a patient. The cap is preferably located inside a seal or cover, such that the seal or cover has to be removed before the cap can be accessed. A vial may have a cap that permits aseptic removal of its contents, particularly for multidose vials. Where a component is packaged into a syringe, the syringe may have a needle attached to it. If a needle is not attached, a separate needle may be supplied with the syringe for assembly and use. Such a needle may be sheathed. Safety needles are preferred. 1-inch 23-gauge, 1-inch 25-gauge and ⅝-inch 25-gauge needles are typical. Syringes may be provided with peel-off labels on which the lot number, influenza season and expiration date of the contents may be printed, to facilitate record keeping. The plunger in the syringe preferably has a stopper to prevent the plunger from being accidentally removed during aspiration. The syringes may have a latex rubber cap and/or plunger. Disposable syringes contain a single dose of vaccine. The syringe will generally have a tip cap to seal the tip prior to attachment of a needle, and the tip cap is preferably made of a butyl rubber. If the syringe and needle are packaged separately then the needle is preferably fitted with a butyl rubber shield. Preferred syringes are those marketed under the trade name "Tip-Lok"™. Containers may be marked to show a half-dose volume e.g. to facilitate delivery to children. For instance, a syringe containing a 0.5 ml dose may have a mark showing a 0.25 ml volume. Where a glass container (e.g. a syringe or a vial) is used, then it is preferred to use a container made from a borosilicate glass rather than from a soda lime glass. A kit or composition may be packaged (e.g. in the same box) with a leaflet including details of the vaccine e.g. instructions for administration, details of the antigens within the vaccine, etc. The instructions may also contain warnings e.g. to keep a solution of adrenaline readily available in case of anaphylactic reaction following vaccination, etc.

Methods for Using the Vaccines and/or Immunological Compositions

An embodiment of invention provides for use of a vaccine manufactured according to the invention. These vaccine compositions are suitable for administration to human or non-human animal subjects, such as pigs or birds, and the invention provides a method of raising an immune response in a subject, comprising the step of administering a composition of the invention to the subject. The invention also provides a composition of the invention for use as a medicament, and provides the use of a composition of the invention for the manufacture of a medicament for raising an immune response in a subject.

The immune response raised by these methods and uses will generally include an antibody response, preferably a protective antibody response. Methods for assessing antibody responses, neutralizing capability and protection after influenza virus vaccination are well known in the art. Human studies have shown that antibody titers against hemagglutinin of human influenza virus are correlated with protection (a serum sample hemagglutination-inhibition titer of about 30-40 gives around 50% protection from infection by a homologous virus). Antibody responses are typically measured by hemagglutination inhibition, by microneutralization, by single radial immunodiffusion (SRID), and/or by single radial hemolysis (SRH). These assay techniques are well known in the art.

Compositions of the invention can be administered in various ways. The most preferred immunization route is by intramuscular injection (e.g. into the arm or leg), but other available routes include subcutaneous injection, intranasal, oral, intradermal, transcutaneous, transdermal, etc.

Vaccines prepared according to the invention may be used to treat both children and adults. Influenza vaccines are currently recommended for use in pediatric and adult immunization, from the age of 6 months. Thus a human subject may be less than 1 year old, 1-5 years old, 5-15 years old, 15-55 years old, or at least 55 years old. Preferred subjects for receiving the vaccines are the elderly (e.g. ≥50 years old, ≥60 years old, and preferably ≥65 years), the young (e.g. ≥5 years old), hospitalized subjects, healthcare workers, armed service and military personnel, pregnant women, the chronically ill, immunodeficient subjects, subjects who have taken an antiviral compound (e.g. an oseltamivir or zanamivir compound; see below) in the 7 days prior to receiving the vaccine, people with egg allergies and people travelling abroad. The vaccines are not suitable solely for these groups, however, and may be used more generally in a population. For pandemic strains, administration to all age groups is preferred.

Preferred compositions of the invention satisfy 1, 2 or 3 of the CPMP criteria for efficacy. In adults (18-60 years), these criteria are: (1) ≥70% seroprotection; (2) ≥40% seroconversion; and/or (3) a GMT increase of ≥2.5-fold. In elderly (>60 years), these criteria are: (1) ≥60% seroprotection; (2) ≥30% seroconversion; and/or (3) a GMT increase of ≥2-fold. These criteria are based on open label studies with at least 50 patients.

Treatment can be by a single dose schedule or a multiple dose schedule. Multiple doses may be used in a primary immunization schedule and/or in a booster immunization schedule. In a multiple dose schedule the various doses may be given by the same or different routes e.g. a parenteral prime and mucosal boost, a mucosal prime and parenteral boost, etc. Administration of more than one dose (typically two doses) is particularly useful in immunologically naïve patients e.g. for people who have never received an influenza vaccine before, or for vaccinating against a new HA subtype (as in a pandemic outbreak). Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.).

Vaccines produced by the invention may be administered to patients at substantially the same time as (e.g. during the same medical consultation or visit to a healthcare professional or vaccination center) other vaccines e.g. at substantially the same time as a measles vaccine, a mumps vaccine, a rubella vaccine, a MMR vaccine, a varicella vaccine, a MMRV vaccine, a diphtheria vaccine, a tetanus vaccine, a pertussis vaccine, a DTP vaccine, a conjugated *H. influenzae* type b vaccine, an inactivated poliovirus vaccine, a hepatitis B virus vaccine, a meningococcal conjugate vaccine (such as a tetravalent A-C-W135-Y vaccine), a respiratory syncytial virus vaccine, a pneumococcal conjugate vaccine, etc. Administration at substantially the same time as a pneumococcal vaccine and/or a meningococcal vaccine is particularly useful in elderly patients.

Similarly, vaccines of the invention may be administered to patients at substantially the same time as (e.g. during the same medical consultation or visit to a healthcare professional) an antiviral compound, and in particular an antiviral compound active against influenza virus (e.g. oseltamivir and/or zanamivir). These antivirals include neuraminidase inhibitors, such as (3R,4R,5S)-4-acetylamino-5-amino-3(1-ethylpropoxy)-1-cyclohexene-1-carboxylic acid or 5-(acetylamino)-4-[(aminoiminomethyl)-amino]-2,6-anhydro-3,4,5-trideoxy-D-glycero-D-galactonon-2-enonic acid, including esters thereof (e.g. the ethyl esters) and salts thereof (e.g. the phosphate salts). A preferred antiviral is (3R,4R,5S)-4-acetylamino-5-amino-3(1-ethylpropoxy)-1-cyclohexene-1-carboxylic acid, ethyl ester, phosphate (1:1), also known as oseltamivir phosphate (TAMIFLU™).

Whilst the invention has been described with reference to influenza viruses and influenza vaccines, the invention can also be used for the production of other viruses which can be produced by reverse genetics, as well as other viral vaccines. For example, the methods of the invention are particularly suitable for producing viruses such as dengue virus, rotaviruses, measles virus, rubella virus, coronaviruses. Other biologicals which can be produced recombinantly can also be produced by the methods of the invention. Suitable examples include antibodies, growth factors, cytokines, lymphokines, receptors, hormones, diagnostic antigens, etc.

The method steps described herein will apply mutatis mutandis to these viruses, vaccines or biologicals.

Definitions

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x is optional and means, for example, x±10%.

An "amino acid linker", or also just termed "linker" within this specification, as used herein, either associates the antigen or antigenic determinant with the second attachment site, or more preferably, already comprises or contains the second attachment site, typically—but not necessarily—as one amino acid residue, preferably as a cysteine residue. The term "amino acid linker" as used herein, however, does not intend to imply that such an amino acid linker consists exclusively of amino acid residues, even if an amino acid linker consisting of amino acid residues is a preferred embodiment of the present invention. The amino acid residues of the amino acid linker are, preferably, composed of naturally occurring amino acids or unnatural amino acids known in the art, all-L or all-D or mixtures thereof. However, an amino acid linker comprising a molecule with a sulfhydryl group or cysteine residue is also encompassed within the invention. Such a molecule comprise preferably a C1-C6 alkyl-, cycloalkyl (C5,C6), aryl or heteroaryl moiety. However, in addition to an amino acid linker, a linker comprising preferably a C1-C6 alkyl-, cycloalkyl-(C5, C6), aryl- or heteroaryl-moiety and devoid of any amino acid(s) shall also be encompassed within the scope of the invention. Association between the antigen or antigenic determinant or optionally the second attachment site and the amino acid linker is preferably by way of at least one covalent bond, more preferably by way of at least one peptide bond.

The term "animal" is meant to include, for example, humans, sheep, elks, deer, mule deer, minks, mammals, monkeys, horses, cattle, pigs, goats, dogs, cats, rats, mice, birds, chicken, reptiles, fish, insects and arachnids.

The term "antibody" refers to molecules which are capable of binding an epitope or antigenic determinant. The term is meant to include whole antibodies and antigen-binding fragments thereof, including single-chain antibodies. Such antibodies include human antigen binding antibody fragments and include, but are not limited to, fragments and domains described before. Preferably, the antibodies are mammalian e.g., human, murine, rabbit, goat, guinea pig, camel, horse and the like, or other suitable animals e.g. chicken. As used herein, "human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described, for example, in U.S. Pat. No. 5,939,598.

Term "antigen" refers to a molecule capable of being bound by an antibody or a T cell receptor (TCR) if presented by MHC molecules. The term "antigen", as used herein, also encompasses T-cell epitopes. A T-cell epitope is recognized by a T-cell receptor in the context of a MHC class I, present on all cells of the body except erythrocytes, or class II, present on immune cells and in particular antigen presenting cells. This recognition event leads to activation of T-cells and subsequent effector mechanisms such as proliferation of the T-cells, cytokine secretion, perforin secretion etc. An antigen is additionally capable of being recognized by the immune system and/or being capable of inducing a humoral immune response and/or cellular immune response leading to the activation of B- and/or T-lymphocytes. This may, however, require that, at least in certain cases, the antigen contains or is linked to a TH cell epitope and is given in adjuvant. An antigen can have one or more epitopes (B- and T-epitopes). The specific reaction referred to above is meant to indicate that the antigen will preferably react, typically in a highly selective manner, with its corresponding antibody or TCR and not with the multitude of other antibodies or TCRs which may be evoked by other antigens. Antigens as used herein may also be mixtures of several individual antigens. Antigens, as used herein, include but are not limited to allergens, self-antigens, haptens, cancer antigens and infectious disease antigens as well as small organic molecules such as drugs of abuse (like nicotine) and fragments and derivatives thereof. Furthermore, antigens used for the present invention can be peptides, proteins, domains, carbohydrates, alkaloids, lipids or small molecules such as, for example, steroid hormones and fragments and derivatives thereof.

The term "antigenic determinant" is meant to refer to that portion of an antigen that is specifically recognized by either B- or T-lymphocytes. B-lymphocytes respond to foreign antigenic determinants via antibody production, whereas T-lymphocytes are the mediator of cellular immunity. Thus, antigenic determinants or epitopes are those parts of an antigen that are recognized by antibodies, or in the context of an MHC, by T-cell receptors. An antigenic determinant contains one or more epitopes. Allergens also serve as antigens in vertebrate animals.

The term "association" as it applies to the first and second attachment sites, refers to the binding of the first and second attachment sites that is preferably by way of at least one non-peptide bond. The nature of the association may be covalent, ionic, hydrophobic, polar or any combination thereof, preferably the nature of the association is covalent.

The term "bound" refers to binding or attachment that may be covalent, e.g., by chemically coupling, or non-covalent, e.g., ionic interactions, hydrophobic interactions, hydrogen bonds, etc. Covalent bonds can be, for example, ester, ether, phosphoester, amide, peptide, imide, carbon-sulfur bonds, carbon-phosphorus bonds, and the like. The term "bound" is broader than and includes terms such as "coupled," "fused" and "attached."

The term "core particle" refers to a rigid structure with an inherent repetitive organization. A core particle as used herein may be the product of a synthetic process or the product of a biological process.

The terms "disease" or "disorder" refer to any adverse condition of an individual including tumors, cancer, allergies, addiction, autoimmunity, poisoning or impairment of optimal mental or bodily function. "Conditions" as used herein includes diseases and disorders but also refers to physiologic states. For example, fertility is a physiologic state but not a disease or disorder. Compositions of the invention suitable for preventing pregnancy by decreasing fertility would therefore be described as a treatment of a condition (fertility), but not a treatment of a disorder or disease. Other conditions are understood in the art.

The term "epitope" refers to basic element or smallest unit of recognition by an individual antibody or T-cell receptor, and thus the particular domain, region or molecular structure to which the antibody or T-cell receptor binds. An antigen may consist of numerous epitopes while a hapten, typically, possesses few epitopes.

The term "immune response" refers to any action by the immune system of an individual that is directed against a molecule or compound, such as an antigen. In mammals, the immune response includes both the activities of cells and the production of soluble molecules such as cytokines and antibodies. The term thus includes a humoral immune response and/or cellular immune response leading to the activation or proliferation of B- and/or T-lymphocytes. In some instances, however, the immune responses may be of low intensity and become detectable only when using at least one substance in accordance with the invention "Immunogenic" refers to an agent used to stimulate the immune system of a living organism, so that one or more functions of the immune system are increased and directed towards the immunogenic agent. An "immunogenic polypeptide" is a polypeptide that elicits a cellular and/or humoral immune response, whether alone or linked to a carrier in the presence or absence of an adjuvant.

The term "immunotherapeutic" refers to a composition for the treatment of diseases, disorders or conditions. More specifically, the term is used to refer to a method of treatment wherein a beneficial immune response is generated by vaccination.

The term "immunologically effective amount" refers to an amount of a composition sufficient to induce an immune response in an individual when introduced into that individual. The amount of a composition necessary to be immunologically effective varies according many factors including to the composition, the presence of other components in the composition (e.g. adjuvants), the antigen, the route of immunization, the individual, the prior immune or physiologic state etc.

The terms "individual," "subject" or "patient" are interchangeable and refer to multicellular organisms and includes both plants and animals Preferred multicellular organisms are animals, specifically vertebrates, particularly mammals, e.g., humans.

The phrase "low or undetectable," when used in reference to gene expression level, refers to a level of expression which is either significantly lower than that seen when the gene is maximally induced (e.g., at least five fold lower) or is not readily detectable by the methods used in examples herein.

The term "mimotope" refers to a substance which induces an immune response to an antigen or antigenic determinant. Generally, the term mimotope will be used with reference to a particular antigen. For example, a peptide which elicits the production of antibodies to a phospholipase A2 (PLA2) is a mimotope of the antigenic determinant to which the antibodies bind. A mimotope may or may not have substantial structural similarity to or share structural properties with an antigen or antigenic determinant to which it induces an immune response. Methods for generating and identifying mimotopes which induce immune responses to particular antigens or antigenic determinants are known in the art.

By "multispecific" antibody is meant herein an antibody having at least two distinct antibody specificities. Such an antibody can be a single antibody (or an antibody fragment) having multiple specificities, or an aggregate of two or more antibodies (or antibody fragments), each having one or more different specificities. By "bispecific" antibody is meant herein a single antibody or antibody fragment having two distinct binding specificities. That is, a bispecific antibody comprises two moieties, each of which comprises a binding region that is specific for a different antigenic target.

The term "mutein" refers to a protein or polypeptide differing by one or more amino acids from a given reference (e.g. natural, wild type, etc.) polypeptide, wherein such difference is caused by addition, substitution or deletion of at least one amino acid or a combination thereof. Preferred embodiments comprise mutations derived from substitution of at least one amino acid, preferably derived from conservative substitution of at least one amino acid. Conservative substitutions include isosteric substitutions, substitutions where the charged, polar, aromatic, aliphatic or hydrophobic nature of the amino acid is maintained. For example, substitution of a cysteine residue with a serine residue is a conservative substitution. In preferred embodiments of the present invention, the term "mutein" refers to a protein or polypeptide differing by three, preferably two and most preferably one amino acid from a given reference (e.g. natural, wild type, etc.) polypeptide, wherein such difference is caused by addition, substitution or deletion or a combination thereof. In further preferred embodiments of the present invention, the term "mutein" refers to a protein or polypeptide differing by three, preferably two and most preferably one amino acid from a given reference (e.g. natural, wild type, etc.) polypeptide, wherein such difference is derived from substitution of three, preferably two and most preferably one amino acid, preferably derived from conservative substitution of three, preferably two and most preferably one amino acid.

The term "natural origin" means that the whole or parts thereof are not synthetic and exist or are produced in nature. Preferably, as used herein, the term "natural origin" means that the whole is not synthetic and exist or is produced in nature. In contrast, "non-natural" generally means not from nature, more specifically, the term means from the hand of man.

The term "non-natural origin" generally means synthetic or not from nature; more specifically, the term means from the hand of man.

The term "polypeptide" refers to a polymer composed of amino acid residues, generally natural amino acid residues, linked together through peptide bonds. A polypeptide may not necessarily be limited in size, and include both proteins and peptides. A peptide is a polypeptide of a typical size of about five to about 50 amino acids, or any number amino acids within this general range. A peptide may, however, also be of longer length, for example up to 120-150 amino acids. "Protein" refers to a polypeptide generally of a size of above about 5 or more, 10 or more 20 or more, 25 or more, 50 or more, 75 or more, 100 or more, 200 or more, 500 or more, 1000 or more, 2000 or more amino acids. Proteins generally have a defined three dimensional structure although they do not necessarily need to, and are often referred to as folded, as opposed to peptides and polypeptides which often do not possess a defined three-dimensional structure, but rather can adopt a large number of different conformations, and are referred to as unfolded. Peptides may, however, also have a defined three-dimensional structure.

The term "purified" is used in reference to a molecule, it means that the concentration of the molecule being purified has been increased relative to molecules associated with it in its natural environment, or environment in which it was produced, found or synthesized. Naturally associated molecules include proteins, nucleic acids, lipids and sugars but generally do not include water, buffers, and reagents added to maintain the integrity or facilitate the purification of the molecule being purified. For example, even if mRNA is diluted with an aqueous solvent during oligo dT column chromatography, mRNA molecules are purified by this chromatography if naturally associated nucleic acids and other biological molecules do not bind to the column and are separated from the subject mRNA molecules. According to this definition, a substance may be 5% or more, 10% or more, 20% or more, 30% or more, 40% or more, 50% or more, 60% or more, 70% or more, 80% or more, 90% or more, 95% or more, 98% or more, 99% or more, or 100% pure when considered relative to its contaminants.

The term "receptor" refers to proteins or glycoproteins or fragments thereof capable of interacting with another molecule, called the ligand. The ligand may belong to any class of biochemical or chemical compounds. The receptor need not necessarily be a membrane-bound protein. Soluble proteins, like e.g., maltose binding protein or retinol binding protein, are receptors as well. The term "residue" is meant to mean a specific amino acid in a polypeptide backbone or side chain.

The term "recombinant host cell" refers to a host cell into which one or more nucleic acid molecules of the invention have been introduced. Host cells include eukaryotes include e.g. mammalian, insect, plant, avian, yeast; and prokaryotic e.g. *E. coli, B. subtilis*, etc.

The term "phage" or "RNA-phage" refers to viruses infecting bacteria, more specifically to RNA viruses, e.g., single-stranded positive-sense RNA viruses.

The term "self-antigen" refers to molecules or compounds capable of being encoded by the host's DNA. These include peptides, proteins, carbohydrates, nucleic acids, lipids and other biological molecules. More typically and preferably, the term "self-antigen" refers to polypeptides or proteins encoded by the host's DNA. Products generated by proteins or RNA encoded by the host's DNA are also defined as self.

"$TCID_{50}$" refers to "tissue culture infective dose" and is defined as that dilution of a virus required to infect 50% of a given batch of inoculated cell cultures. Various methods may be used to calculate $TCID_{50}$, including the Spearman-Karber method which is utilized throughout this specification. For a description of the Spearman-Karber method, see B. W. Mahy & H. O. Kangro, Virology Methods Manual 25-46 (1996).

"Therapeutic agent" refers to any molecule, compound, virus or treatment, preferably a virus attenuated or killed, or subunit or compound, that assists in the treatment of a viral infection or a disease or condition caused thereby.

"Therapeutically effective amount," in the context of this disclosure, refers to an amount of an antigen or vaccine that would induce an immune response in a subject (e.g., dog) receiving the antigen or vaccine which is adequate to prevent or ameliorate signs or symptoms of disease, including adverse health effects or complications thereof, caused by infection with a pathogen, such as a virus (e.g., H3N8), bacterium, parasite or fungus. Humoral immunity or cell-mediated immunity or both humoral and cell-mediated immunity may be induced. The immunogenic response of an animal to a vaccine may be evaluated, e.g., indirectly through measurement of antibody titers, lymphocyte proliferation assays, or directly through monitoring signs and symptoms after challenge with wild type strain. The protective immunity conferred by a vaccine can be evaluated by measuring, e.g., reduction in clinical signs such as mortality, morbidity, temperature number and overall physical condition and overall health and performance of the subject. The amount of a vaccine that is therapeutically effective may vary depending on the particular virus used, or the condition of the subject, and can be determined by one skilled in the art.

"Transmitted" means a virus that is capable of being passed from a first animal (dog) to a second animal (dog) where the second dog demonstrates seroconversion to the transmitted virus.

"Treating" refers to reversing, alleviating, inhibiting the progress of, or preventing a disorder, condition or disease to which such term applies, or of preventing one or more symptoms of such disorder, condition or disease.

"Treatment" refers to the act of "treating" as defined immediately above.

"Vaccine" refers to an immunogenic composition selected from a virus, either modified live, attenuated, or killed, or a subunit vaccine, or any combination of the aforementioned. Administration of the vaccine to a subject results in an immune response. The vaccine may be introduced directly into the subject by any known route of administration, including parenterally, perorally, and the like.

The term "vector" refers to an agent (e.g., a plasmid or virus) used to transmit genetic material to a host cell. A vector may be composed of either DNA or RNA.

The term "virus-like particle" refers to a structure resembling a virus particle. Moreover, a virus-like particle in accordance with the invention is non replicative and noninfectious since it lacks all or part of the viral genome, in particular the replicative and infectious components of the viral genome. A virus-like particle in accordance with the invention may contain nucleic acid distinct from their genome. A typical and preferred embodiment of a virus-like particle in accordance with the present invention is a viral capsid such as the viral capsid of the corresponding virus, bacteriophage, or RNA-phage. The terms "viral capsid" or "capsid", as interchangeably used herein, refer to a macromolecular assembly composed of viral protein subunits. Typically and preferably, the viral protein subunits assemble into a viral capsid and capsid, respectively, having a structure with an inherent repetitive organization, wherein said structure is, typically, spherical or tubular. For example, the capsids of RNA-phages have a spherical form of icosahedral symmetry. The term "capsid-like structure" as used herein, refers to a macromolecular assembly composed of viral protein subunits resembling the capsid morphology in the above defined sense but deviating from the typical symmetrical assembly while maintaining a sufficient degree of order and repetitiveness. The term "virus-like particle of a bacteriophage" refers to a virus-like particle resembling the structure of a bacteriophage, being non replicative and noninfectious, and lacking at least the gene or genes encoding for the replication machinery of the bacteriophage, and typically also lacking the gene or genes encoding the protein or proteins responsible for viral attachment to or entry into the host. This definition should, however, also encompass virus-like particles of bacteriophages, in which the aforementioned gene or genes are still present but inactive, and, therefore, also leading to non-replicative and noninfectious virus-like particles of a bacteriophage. "Virus particle" as used herein refers to the morphological form of a virus. In some virus types it comprises a genome surrounded by a protein capsid; others have additional structures (e.g., envelopes, tails, etc.).

One, a, or an: When the terms "one," "a," or "an" are used in this disclosure, they mean "at least one" or "one or more," unless otherwise indicated.

As used herein when referring to any numerical value, the term "about" means a value of ±10% of the stated value (e.g., "about 50° C." encompasses a range of temperatures from 45° C. to 55° C., inclusive; similarly, "about 100 mM" encompasses a range of concentrations from 90 mM to 110 mM inclusive).

Unless specifically stated, a process comprising a step of mixing two or more components does not require any specific order of mixing. Thus components can be mixed in any order. Where there are three components then two components can be combined with each other, and then the combination may be combined with the third component, etc.

The various steps of the methods may be carried out at the same or different times, in the same or different geographical locations, e.g. countries, and by the same or different people or entities.

Where animal (and particularly bovine) materials are used in the culture of cells, they should be obtained from sources that are free from transmissible spongiform encephalopathies (TSEs), and in particular free from bovine spongiform encephalopathy (BSE). Overall, it is preferred to culture cells in the total absence of animal-derived materials.

Where a compound is administered to the body as part of a composition then that compound may alternatively be replaced by a suitable prodrug.

References to a percentage sequence identity between two amino acid sequences means that, when aligned, that percentage of amino acids are the same in comparing the two sequences. This alignment and the percent homology or sequence identity can be determined using software programs known in the art. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is known in the art.

References to a percentage sequence identity between two nucleic acid sequences mean that, when aligned, that percentage of bases are the same in comparing the two sequences. This alignment and the percent homology or sequence identity can be determined using software programs known in the art. A preferred alignment program is GCG Gap (Genetics Computer Group, Wisconsin, Suite Version 10.1), preferably using default parameters, which are as follows: open gap=3; extend gap=1.

EXAMPLES

The following examples are provided by way of illustration only by means of various particular embodiments and are in no way exhaustive or exclusive.

Example 1

Materials and Methods

The high yield (hy) donor, A/Puerto Rico/8/1934 (PR8, H1N1) is a highly egg-adapted influenza virus which has been continuously passaged in embryonated chicken eggs since 1934. A/South Dakota/06/2007 (SD, H1N1) and A/Uruguay/716/2007 (UY, H3N2) are eggisolated wild type (WT) viruses received from the Center for Diseases Control and Prevention (CDC) as the vaccine target viruses fort the 2007-2008 flu season. A/California/07/2009 (CA, H1N1pdm) is an egg isolate used to prepare the NYMC hy seed viruses for the 2009 H1N1 pandemic influenza vaccine. NYMC X-173 (H1N1) is a hy reassortant influenza A vaccine candidate virus incorporating six PR8 'internal' genes as 'backbone' and hemagglutinin (HA) and neuraminidase (NA) genes from wild type (WT) virus, SD (H1N1). NYMC X-175C (H3N2) is a hy reassortant virus which possesses HA and NA from the WT virus, UY (H3N2), together with the PR8 backbone.

Madin-Darby canine kidney (MDCK) cells purchased from American Type Culture Collection (ATCC, Manassas, Va., USA) were grown in Eagle's Minimum Essential Medium (MEM, Invitrogen/GIBCO, Carlsbad, Calif., USA) supplemented with 10% fetal bovine serum (FBS) Invitrogen/GIBCO, Carlsbad, Calif., USA), 10 mM HEPES (Invitrogen/GIBCO, Carlsbad, Calif., USA), 10 units/ml penicillin (Sigma-Aldrich, St. Louis, Mo., USA) and 10 μg/ml streptomycin (Sigma-Aldrich, St. Louis, Mo., USA) at 5% $CO_2$ and 37° C. For subculture, the cells were grown to ~80% confluency and split at a ratio of 1:10-1:20 by using trypsin-EDTA (Sigma-Aldrich, St. Louis, Mo., USA). The viruses were amplified in 10-11 days old embryonated specific pathogen free (SPF) chicken eggs (Charles River, Conn., USA).

A virus dilution of 10-5 was prepared in phosphate buffered saline (PBS, Fisher Scientific, Pittsburgh, Pa., USA) with 25 μg/ml gentamicin (Sigma-Aldrich, St. Louis, Mo., USA), and 0.1 ml of the virus preparation per egg was injected. After incubation at 35° C. for 48 hours, the eggs were placed at −20° C. for 1 hour followed by at 4° C. for 2 hours and the allantoic fluid containing viruses was harvested. The titer of the virus was determined by hemagglutination (HA) assay.

The infectious virus titer was determined by plaque assay in terms of plaque forming units per ml (PFU/ml). The 50% egg infectious dose (EID50) of each virus was determined MDCK cells were inoculated in 6-well plates (Corning, Tewksbury, Mass., USA) at a density of 0.5-1.0×105 cells per well in 4 ml of growth medium. When approximately 90% confluency was achieved, the growth medium was removed and each well was washed with 2 ml PBS containing 0.2% bovine albumin (MP Biomedicals, Solon, Ohio, USA).

Viral inocula were prepared in 10-fold serial dilutions from stock and 0.2 ml of each dilution was inoculated into a single well. After incubation at 5% $CO_2$ and 37° C. for 30 minutes, the virus inoculum was removed and the cells were washed with PBS containing 0.2% bovine albumin and covered with agar overlay including MEM, 0.2% bovine albumin, 2 μg/ml trypsin (Worthington, Lakewood, N.J., USA), and 0.01% DEAE dextran. After 72 hours post infection, plaques were visualized by staining with 0.1% crystal violet. Each virus dilution was evaluated in duplicate and the PFU of the stock virus was calculated based on the virus dilution yielding 5-50 plaques. Serial 10-fold dilutions of the virus were made in PBS with 25 μg/ml gentamicin, and 0.1 ml of virus dilution was injected per embryonated chicken egg (10-11 days old). A total of six eggs were used for each virus dilution. After 48 hours of incubation at 35° C., the allantoic fluid containing virus was harvested and viral titer was determined by HA assay. The EID50 is defined as the virus dilution that confers viral growth in 50% eggs (WHO Global Influenza Surveillance Network, 2011).

MDCK cells were inoculated in 6-well plates at a density of 0.5-1.0×105 cells per well in 4 ml of growth medium. When approximately 90% confluency was achieved, the growth medium was removed and each well was washed with 2 ml PBS containing 0.2% bovine albumin and then inoculated with 0.2 ml virus at 125 PFU/ml.

After incubation at 5% $CO_2$ and 37° C. for 30 minutes, the virus inoculum was removed and the cells were washed with PBS with 0.2% bovine albumin and covered with agar overlay including MEM, 0.2% bovine albumin, 2 μg/ml trypsin, 0.01% DEAE dextran and 2-fold serially diluted hybridoma cell culture supernatant (CCS) or different concentrations of purified monoclonal antibodies (mAbs). Plaques were visualized by 0.1% crystal violet staining at 72 hours post infection. Each concentration of mAb was evaluated in duplicate in three independent experiments.

For inhibition assay, the virus dilution to provide 1000 EID50/ml was incubated with different concentrations of mAbs in PBS with 25 μg/ml gentamicin at 37° C. for 60 minutes and 0.1 ml of mixture was injected per embryonated chicken egg (10-11 days old). Following 42-48 hours incubation at 35° C., the virus titer of allantoic fluid from each egg was determined by HA assay. Each concentration of individual mAb was evaluated in triplicate in two independent experiments.

Antibody isotyping was performed utilizing a Pierce mouse antibody isotyping kit (Thermo Pierce, Rockford, Ill., USA) according to manufacturer's protocols. Each candidate hybridoma CCS was diluted 1:100 by adding 5 μl of supernatant to 0.5 ml of Sample Diluent and mixed by gentle vortexing. The diluted sample (150 μl) was added to the well of the testing cassette, and the result was read in 5-10 minutes. Successful test results appeared as a red band at the "C" or control location and a darker band at one of the isotypes on the cassette.

Antibodies were purified by protein G column chromatography. The CCS of candidate hybridomas was centrifuged at 6000 g for 5 minutes to remove cell debris. A protein G column (Sigma-Aldrich, St. Louis, Mo., USA) was equilibrated with 75 ml of PBS and the CCS diluted two fold with PBS and was directly applied to the column. The column was washed with 100 ml PBS. Bound mAbs were eluted from the column with 75 ml of 0.1 M glycine (pH 2.7, Fisher Scientific, Pittsburgh, Pa., USA) and approximately 3 ml per fraction was collected in 5 ml test-tubes with 40 μl neutralizing buffer, 1 M Tris-HCl (pH 9.0, Fisher Scientific, Pittsburgh, Pa., USA). A280 was measured for each fraction, and all fractions with A280 greater than 0.5 were pooled into 15 ml centrifuge tubes. The pH of the purified mAb was determined by pH paper and adjusted to 7.0 by neutralizing buffer.

The concentration of purified mAbs was performed by Bradford assay according to manufacturer's instruction (Bio-Rad, Hercules, Calif., USA). Five linear-range dilutions of the bovine gamma immunoglobulin standard and the appropriate dilution of purified mAb were prepared. 800 μl of each standard and the sample solution was incubated with 200 μl of dye reagent concentrate in a test-tube at room temperature for 5 minutes and the absorbance measured at 595 nm. The concentration of purified mAb was calculated from the standard curve. All protein solutions were assayed in duplicate.

The lyophilized receptor destroying enzyme (RDE, Lonza, Allendale, N.J., USA) was reconstituted with 5 ml sterile distilled water; then diluted to 100 units/ml in calcium saline solution (See Appendix) to be used as the working solution. Briefly, for the RDE treatment of antibodies one volume of antibody was mixed with four volumes of RDE working solution and incubated overnight (12-18 hours) in a 37° C. water bath. Three volumes of 2.5% sodium citrate solution were added and the reaction was heated in a 56° C. water bath to inactivate any remaining RDE. The final RDE-treated antibody dilution was raised to 1:10 by adding two volumes of PBS.

For hemagglutination (HA) assay, to each well of a V bottomed 96-well microtiter plate 50 µl PBS was added and 50 µl allantoic fluid of virus was added into the first well of each row. A 2-fold serial dilution (1:2, 1:4, 1:8, etc.) was made by carrying 50 µl mixture from well to well. Totally 50 µl solution was left in each well and incubated with 50 µl 10.5% chicken erythrocytes (Pocono Rabbit Farm & Laboratory, Canadensis, Pa., USA) suspension in PBS. The contents of the plate were mixed using a laboratory shaker for 30 seconds. After incubation at room temperature for 30 minutes, the virus titer was read as the reciprocal of the titration end-point which is defined as the highest dilution of virus that still cause complete agglutination of the chicken erythrocytes (WHO Global Influenza Surveillance Network, 2011).

For hemagglutination inhibition (HI) assay, a U bottomed 96-well microtiter plates were used. Each virus used in the HI assay was back titrated in PBS in order to get the final hemagglutinin units (HAU) to 4 HAU/25 µl. 25 µl PBS was added into all wells except the 2nd well of each row (i.e., A2, B2, C2, etc.). Each row was used to assay an individual mAb; the first three wells of each row (i.e., A1-A3, B1-B3, C1-C3, etc.) contained 25 µl RDE-treated testing mAb (1:10 dilution). A 2-fold serial dilution was started in the 3rd well by carrying 25 µl mixture from well to well (i.e., A3-A12, B3-B12, C3-C12, etc.), and the final 25 µl was discarded after well #12 to leave serial dilutions of mAb starting from 1:10 to 1:10240. A total of 25 µl standardized virus was then added into all wells except the 1st well of each row (i.e., A2-A12, B2-B12, C2-C12, etc.). The contents of the plates were mixed using a laboratory shaker for 10 seconds or by manually agitating the plates. The plate was incubated at room temperature for 15 minutes, and then 50 µl of 0.5% chicken erythrocyte suspension was added to all wells. The HI titer of individual mAb samples was read after additional 30 minutes incubation at room temperature. The HI titer was recorded as the reciprocal of the titration end-point which is defined as the highest dilution of mAb that prevents hemagglutination. (WHO Global Influenza Surveillance Network, 2011.)

For neuraminidase (NA) assay, serial 2-fold dilutions of viruses were made in PBS containing 2 mM Ca2+ from 1:2 to 1:128. If the virus had a higher level of NA activity, higher dilutions were used. A fetuin control reaction without virus but with all other reagents was set up as a blank. A total of 100 µl of each virus dilution was transferred into each of a series of labeled test-tubes (16 mm×125 mm) A total of 100 µl of a mixture of equal volume of phosphate buffer (pH 5.9) and fetuin (Sigma-Aldrich, St. Louis, Mo., USA) was added to all test-tubes. The test-tubes were then vortex-mixed and placed in a 37° C. water bath overnight (16-18 hours). After the incubation, test-tubes were cooled to room temperature and 0.1 ml periodate reagent (See Appendix) was added into each tube. The reaction was mixed thoroughly by vortex mixer and incubated at room temperature for exactly 20 minutes. Then, 1.0 ml arsenite reagent (See Appendix) was added and the tube was flicked until the brown color dissipates. 2.5 ml 2-Thiobarbituric acid reagent (2-TBA) (See Appendix) was then added. The reaction was mixed thoroughly and immediately incubated in a boiling water bath for 15 minutes. All test-tubes were cooled to room temperature and added with 4 ml Warrenoff reagent (See Appendix) per tube. To extract the color into the organic phase, the reaction was mixed vigorously using a vortex mixer and centrifuged at 1000 rpm for 5 minutes. A549 for each reaction was determined. The fetuin blank was used to equilibrate the spectrophotometric reading, and the dilution that gave an A549 of 0.4 to 0.8 was used as the working dilution for the neuraminidase inhibition assay.

For neuraminidase inhibition (NI) assay, serial 2-fold dilutions of mAbs were prepared in PBS containing 2 mM Ca2+ and 50 µl of each antibody dilution was transferred into a series of labeled test-tubes. Each virus was diluted to its proper working dilution (i.e., the dilution giving A549 readings of 0.4 to 0.8 in the NA assay) and 50 µl of diluted virus was added to the antibody and mixed. The reaction was incubated at 37° C. for 1 hour. Afterwards, 100 µl of a mixture of equal volume of phosphate buffer and fetuin was added to all test-tubes. The test-tubes were then vortexed and incubated overnight (16-18 hours) in a 37° C. water bath. The NA activity of each reaction was assayed by the same procedure used for the NA assay. The NI titer of an antibody is defined as the dilution giving 50% inhibition of NA activity (NI50) (WHO Global Influenza Surveillance Network, 2011).

Viral RNA (vRNA) was extracted from allantoic fluid containing viruses using a QIAmp® Viral RNA Mini Kit (Qiagen Inc., Valencia, Calif., USA) per manufacturer's recommendations with the modification that 280 µl of allantoic fluid was used instead of 140 µl was lysed thus providing a more concentrated RNA preparation. The concentration of extracted viral RNA was measured using the Nanodrop ND-1000 spectrophotometer (Thermo Scientific, Wilmington, Del., USA). The RNA samples were stored at −20 C until further use.

A set of primers used for RT-PCR were designed to amplify specific cDNAs from eight gene segments individually: in addition to the 3' and 5' conserved regions, 8-11 additional segment-specific nucleotides were also incorporated. All the primers were synthesized by Integrated DNA Technologies Inc. (Coralville, Iowa, USA). Forward and reverse primers used for PCR amplification of all eight gene segments are listed in Table B.

TABLE B

Oligonucleotide primers used in RT-PCR (SEQ ID NOS 15-30, respectively, in order of appearance).

| Gene | Primer Sequence | Primer Length (nt) | Annealing Temp. (°C.) | Site of the amplicon (nt) |
| --- | --- | --- | --- | --- |
| PB2 | F: AGCGAAAGCA GGTCAATTATATT | 23 | 61 | 2341 |
|  | R: AGTAGAAACA AGGTCGTTTTTAA | 23 |  |  |

TABLE B-continued

Oligonucleotide primers used in RT-PCR (SEQ ID NOS 15-30, respectively, in order of appearance).

| Gene | Primer Sequence | Primer Length (nt) | Annealing Temp. (°C.) | Site of the amplicon (nt) |
|---|---|---|---|---|
| PB1 | F: AGCGAAAGCA GGCAAACCATTTG | 23 | 61 | 2341 |
|  | R: AGTAGAAACA AGGCATTTTTCA | 23 |  |  |
| PA | F: AGCGAAAGCA GGTACTGATC | 20 | 61 | 2233 |
|  | R: AGTAGAAACA AGGTACTTTTTG | 23 |  |  |
| HA | F: GTTCAGAAAA AGCAGGGG | 18 | 55 | 1778 |
|  | R: AGTAGAAACA AGGGTGTTTT | 20 |  |  |
| NP | F: AGCAAAAGAC AGGGTAGATAATC | 23 | 55 | 1565 |
|  | R: AGTAGAAACA AGGGTATTTTTC | 22 |  |  |
| NA | F: AGCGAAAGCA GGAGTTTAAAAT | 22 | 55 | 1413 |
|  | R: AGTAGAAACA AGGAGTTTTTG | 22 |  |  |
| M | F: AGCGAAAGCA GGTAGATATTGA | 22 | 55 | 1027 |
|  | R: AGTAGAAACA AGGTAGTTTTTT | 22 |  |  |
| NS | F: AGTAGAAACA AGGGTGTTTTT | 22 | 55 | 890 |
|  | R: AGTAGAAACA AGGGTGTTTTT | 22 |  |  |

F: forward primers; R: reverse primers used for amplification.

RT-PCR was performed using a Takara One Step RNA PCR Kit (Takara Bio Inc., Otsu, Shiga, Japan) per the manufacturer's recommendations. Briefly, 2 µg of vRNA was added to the following mixture: 1× One Step RNA PCR Buffer, 5 mM MgCl2, 1 mM dNTP, 0.8 U/µl RNase Inhibitor, 0.1 U/µl AMV RTase XL, 0.1 U/µl AMV-Optimized Taq, 0.4 µM each of forward and reverse primers, and RNase free H2O up to a total volume of 50 µl. RT-PCR parameters used were as follows: 55° C. for 30 min, 94° C. for 2 min, followed by 35 cycles of 94° C. for 30 sec, 55° C. for 1 min (HA, NP, NA, M and NS gene segments) or 61° C. for 1 min (PB2, PB1 and PA gene segments), 70° C. for 4 min and a final extension at 72° C. for 10 min The reactions were performed on an Eppendorf Mastercycler®. The amplified RT-PCR products were visualized on a 2% agarose-TAE/EtBr gel.

For viral cDNA purification, PCR products were gel purified in a 2% low melt agarose gel using a QIAquick® Gel Extraction Kit (Qiagen Inc., Valencia, Calif., USA) per manufacturer's recommendations. The extracted PCR products were visualized for purity on a 2% agarose-TAE/EtBr gel. T. Restriction fragment length polymorphism (RFLP) was carried out by digesting purified segment specific DNA with their respective restriction enzymes (Table C). The digestion reactions were carried out in 10 µl volume with 10 units of the designated enzyme and incubated for 3 hours following reaction conditions recommended by the manufacturers (NEB, Ipswich, Mass., USA or Fermentas Inc., Glen Burnie, Md., USA). The DNA from the by donor virus, WT virus and their respective reassortants was digested concurrently. The digestion reactions were visualized on a 2% agarose-TAE/EtBr gel.

TABLE C

Restriction enzymes and corresponding conditions used for RFLP.

| Viral Protein | Reaction Mix | Volume (µl) | Reaction (water bath) (° C./hrs) | Inactivation (° C./min) |
|---|---|---|---|---|
| PB2/PB1 Enzyme 1 | PvuII | 2 | 37° C./3 hrs | 80° C./20 min |
|  | Buffer 2 | 1 |  |  |
|  | DNA sample | 6 |  |  |
|  | H2O | 1 |  |  |
| PA Enzyme 1 | HindIII | 2 | 37° C./3 hrs | 65° C./20 min |
|  | Buffer 2 | 1 |  |  |
|  | DNA sample | 6 |  |  |
|  | H2O | 1 |  |  |
| Enzyme 2 | XmnI | 2 |  |  |
|  | Buffer 2 | 1 |  |  |
|  | BSA | 1 |  |  |
|  | DNA sample | 5 |  |  |
|  | H2O | 1 |  |  |
| HA Enzyme 1 | PvuII | 2 | 37° C./3 hrs | 80° C./20 min |
|  | Buffer 2 | 1 |  |  |
|  | DNA sample | 6 |  |  |
|  | H2O | 1 |  |  |
| Enzyme 2 | HindIII | 2 |  | 65° C./20 min |
|  | Buffer 2 | 1 |  |  |
|  | DNA sample | 6 |  |  |
|  | H2O | 1 |  |  |
| NP Enzyme 1 | HindIII | 2 | 37° C./3 hrs | 65° C./20 min |
|  | Buffer 2 | 1 |  |  |
|  | DNA sample | 6 |  |  |
|  | H2O | 1 |  |  |
| Enzyme 2 | XmnI | 2 |  |  |
|  | Buffer 2 | 1 |  |  |
|  | DNA sample | 5 |  |  |
|  | BSA | 1 |  |  |
|  | H2O | 1 |  |  |
| NA Enzyme 1 | BsgI | 2 | 37° C./3 hrs | 65° C./20 min |
|  | SAM | 1 |  |  |
|  | Buffer 4 | 1 |  |  |
|  | DNA sample | 5 |  |  |
|  | H2O | 1 |  |  |
| Enzyme 2 | Eco57I | 2 |  |  |
|  | SAM | 1 |  |  |
|  | Buffer G | 1 |  |  |
|  | DNA sample | 5 |  |  |
|  | H2O | 1 |  |  |
| M Enzyme 1 Seasonal H1N1 & H3N2 | BsgI | 2 | 37° C./3 hrs | 65° C./20 min |
|  | SAM | 1 |  |  |
|  | Buffer 4 | 1 |  |  |
|  | DNA sample | 5 |  |  |
|  | H2O | 1 |  |  |
| M Enzyme 1 H1N1 pdm viruses | BamHI | 2 | 37° C./3 hrs | 65° C./20 min |
|  | Buffer 3 | 1 |  |  |
|  | BSA | 1 |  |  |
|  | DNA sample | 5 |  |  |
|  | H2O | 1 |  |  |
| NS Enzyme 1 | SmlI | 2 | 37° C./3 hrs | 65° C./20 min |
|  | Buffer 4 | 1 |  |  |
|  | BSA | 1 |  |  |
|  | DNA sample | 5 |  |  |
|  | H2O | 1 |  |  |
| Enzyme 2 | XmnI | 2 | 55° C./3 hrs |  |
|  | Buffer 2 | 1 |  |  |
|  | BSA | 1 |  |  |
|  | DNA sample | 5 |  |  |
|  | H2O | 1 |  |  |

For SDS-PAGE and Western blotting, a total amount of approximately 1 µg viral protein of each virus was mixed with 5 µl NuPAGE® LDS Sample Buffer (4×, Invitrogen, Carlsbad, Calif., USA), 2 µl NuPAGE® Sample Reducing Agent (10×, Invitrogen, Carlsbad, Calif., USA), and deionized H2O added up to 20 µl. For the non-reducing condition, no reducing agent was added. The samples were heated at 70° C. for 10 minute in a heating block, cooled to room temperature and then centrifuged before loading samples on SDS-polyacrylamide gels. The prepared samples were loaded onto NuPAGE® Novex 4-12% Bis-Tris precast gel (Invitrogen, Carlsbad, Calif., USA) and separated using the Invitrogen XCell SureLock Mini-Cell electrophoresis system at 200V constant for 35 minutes in the NuPAGE® MES SDS running buffer (Invitrogen, Carlsbad, Calif., USA). Upon completion of electrophoresis the proteins were transferred onto a polyvinylidene difluoride (PVDF) membrane for Western blot analysis. The Invitrogen XCell II Blot Module was used for gel transfer with NuPAGE® Transfer Buffer (Invitrogen, Carlsbad, Calif., USA). The transfer was conducted at 30 V constant for 1.5 hours. The membranes were blocked with 4% non-fat dry milk in TBST (10 mM Tris-HCl pH 7.5, 150 mM NaCl, 0.1% Tween-20) solution for 1 hour. After blocking the membranes were washed with TBST three times, 5 minutes each time, and then incubated overnight with primary antibodies diluted in TBST at 4° C. on the shaker. The next day the membranes were washed three times with TBST, 10 minutes each, and then incubated with the respective secondary antibody conjugated with horseradish peroxidase (HRP) diluted in TBST containing 2% non-fat dry milk for 1 hour. After incubation the membranes were washed 3 times with TBST for 10 minutes each, and subsequently developed with SuperSignal® West Pico Chemiluminescent Substrates (Thermo Scientific, Rockford, Ill., USA) using HyBlot CL autoradiography film (Denville Scientific, MD, USA).

For immunofluorescence analysis, the MDCK cells were plated in Labtek 8-well chamber slides (Nunc, Penfield, N.Y., USA) in EMEM growth medium at a density of 1×10⁴ cells per chamber. After 24 hours the growth medium was removed and the cells were washed with PBS and infected with a virus solution diluted to a multiplicity of infection of 1.0 (MOI=1.0) at 37° C. for 30 minutes. After the removal of the virus solution, the cells were washed with PBS and returned to a 37° C. incubator (5% CO2) with growth medium. Control and infected cells were washed twice with PBS and fixed with 3.7% formaldehyde in PBS at 24 hours post infection. After blocking with PBS containing 10% FBS and 0.2% Triton X-100 for 30 minutes, candidate mAbs (mouse) and the M1 control rabbit pAbs were applied to the cells. Respective fluorescence conjugated secondary antibodies were used to recognize mouse IgG (Alexa Flour 488) and rabbit IgG (Alexa Flour 594). The slides were mounted in Vectashield containing 4'-6'-diamidino-2-phenylindole (DAPI, Vector Laboratories, Burlingame, Calif., USA) and examined with a Zeiss Axiovert 200M fluorescent microscope.

To determine the epitope(s) for the identified HA mAb candidates, a peptide array was designed and synthesized by NEO Group Inc. (Cambridge, Mass., USA) to represent the linear epitopes on HA1 subunit (Table D). Each peptide was 15 amino acids long with 10 amino acids overlapping with the successive peptide. A total of 64 peptides were synthesized without modifications and included the free amino group and carboxyl group at their Nterminus and C-terminus, respectively. All the peptides were analyzed by high-performance liquid chromatography (HPLC) and mass spectrometry (MS) to ensure minimal 70% purity.

TABLE D

Synthetic Peptides used for Epitope Mapping

| Peptide Name | SEQ ID NO: | DESCRIPTION | Purity |
|---|---|---|---|
| 1 | 31 | DTICIGYHANNSTDT | 73.06% |
| 2 | 32 | GYHANNSTDTVDTVL | 95.20% |
| 3 | 33 | NSTDTVDTVLEKNVT | 75.64% |
| 4 | 34 | VDTVLEKNVTVTHSV | 71.90% |
| 5 | 35 | EKNVTVTHSVNLLED | 85.50% |
| 6 | 36 | VTHSVNLLEDSHNGK | 83.63% |
| 7 | 37 | NLLEDSHNGKLCRLK | 84.09% |
| 8 | 38 | SHNGKLCRLKGIAPL | 92.94% |
| 9 | 39 | LCRLKGIAPLQLGKC | 90.60% |
| 10 | 40 | GIAPLQLGKCNIAGW | 86.38% |
| 11 | 41 | QLGKCNIAGWLLGNP | 85.44% |
| 12 | 42 | NIAGWLLGNPECDPL | 85.79% |
| 13 | 43 | LLGNPECDPLLPVRS | 92.91% |
| 14 | 44 | ECDPLLPVRSWSYIV | 73.24% |
| 15 | 45 | LPVRSWSYIVETPNS | 70.51% |
| 16 | 46 | WSYIVETPNSENGIC | 73.06% |
| 17 | 47 | ETPNSENGICYPGDF | 86.25% |
| 18 | 48 | ENGICYPGDFIDYEE | 90.79% |
| 19 | 49 | YPGDFIDYEELREQL | 91.98% |
| 20 | 50 | IDYEELREQLSSVSS | 92.44% |
| 21 | 51 | LREQLSSVSSFERFE | 91.53% |
| 22 | 52 | SSVSSFERFEIFPKE | 83.11% |
| 23 | 53 | FERFEIFPKESSWPN | 82.44% |
| 24 | 54 | IFPKESSWPNHNTNG | 91.87% |
| 25 | 55 | SSWPNHNTNGVTAAC | 94.43% |
| 26 | 56 | HNTNGVTAACSHEGK | 91.70% |
| 27 | 57 | VTAACSHEGKSSFYR | 86.59% |
| 28 | 58 | SHEGKSSFYRNLLWL | 85.37% |
| 29 | 59 | SSFYRNLLWLTEKEG | 87.41% |
| 30 | 60 | NLLWLTEKEGSYPNL | 84.17% |
| 31 | 61 | TEKEGSYPNLKNSYV | 89.61% |
| 32 | 62 | SYPNLKNSYVNKKGK | 78.60% |
| 33 | 63 | KNSYVNKKGKEVLVL | 91.43% |
| 34 | 64 | NKKGKEVLVLWGIHH | 92.02% |
| 35 | 65 | EVLVLWGIHHPSNSK | 86.88% |
| 36 | 66 | WGIHHPSNSKEQQNL | 71.66% |
| 37 | 67 | PSNSKEQQNLYQNEN | 83.18% |

TABLE D-continued

Synthetic Peptides used for Epitope Mapping

| Peptide Name | SEQ ID NO: | DESCRIPTION | Purity |
|---|---|---|---|
| 38 | 68 | EQQNLYQNENAYVSV | 73.32% |
| 39 | 69 | YQNENAYVSVVTSNY | 73.16% |
| 40 | 70 | AYVSVVTSNYNRRFT | 82.03% |
| 41 | 71 | VTSNYNRRFTPEIAE | 82.05% |
| 42 | 72 | NRRFTPEIAERPKVR | 79.40% |
| 43 | 73 | PEIAERPKVRDQAGR | 82.15% |
| 44 | 74 | RPKVRDQAGRMNYYW | 83.40% |
| 45 | 75 | DQAGRMNYYWTLLKP | 88.02% |
| 46 | 76 | MNYYWTLLKPGDTII | 75.34% |
| 47 | 77 | TLLKPGDTIIFEANG | 82.47% |
| 48 | 78 | GDTIIFEANGNLIAP | 87.47% |
| 49 | 79 | FEANGNLIAPMYAFA | 81.18% |
| 50 | 80 | NLIAPMYAFALSRGF | 82.97% |
| 51 | 81 | MYAFALSRGFGSGII | 74.60% |
| 52 | 82 | LSRGFGSGIITSNAS | 73.72% |
| 53 | 83 | GSGIITSNASMHECN | 76.36% |
| 54 | 84 | TSNASMHECNTKCQT | 71.21% |
| 55 | 85 | MHECNTKCQTPLGAI | 83.00% |
| 56 | 86 | TKCQTPLGAINSSLP | 79.47% |
| 57 | 87 | PLGAINSSLPYQNIH | 83.18% |
| 58 | 88 | NSSLPYQNIHPVTIG | 82.69% |
| 59 | 89 | YQNIHPVTIGECPKY | 84.39% |
| 60 | 90 | PVTIGECPKYVRSAK | 78.69% |
| 61 | 91 | ECPKYVRSAKLRMVT | 83.71% |
| 62 | 92 | VRSAKLRMVTGLRNI | 75.93% |
| 63 | 93 | LRMVTGLRNIPSIQS | 75.37% |
| 64 | 94 | GLRNIPSIQSR | 76.74% |

Epitope mapping was carried out via ELISA. The synthetic peptides were diluted to 10 µg/ml in coating buffer (0.1 M sodium bicarbonate, pH 9.6), and 100 µl of diluted peptide was added into each well on 96-well Nunc Maxisorp plates (Nunc, Penfield, N.Y., USA). The plate was covered and incubated at room temperature for 1 hour before 200 µl of blocking buffer (PBS, pH 7.4, 0.05% Tween 20, 1% BSA) was added into each well for additional 1 hour incubation at room temperature. After blocking, the solution was flicked out and each well was washed with 300 µl washing buffer (PBS, pH 7.4, 0.05% Tween 20) three times. A total of 100 µl test mAb diluted to 1 µg/ml in blocking buffer was added into appropriate wells and incubated at 37° C. for 1 hour. The unbound mAb was removed after incubation and the plate was washed with 300 µl washing buffer per well three times. Appropriate diluted HRP-conjugated secondary Ab (Jackson ImmunoResearch Laboratories, Inc., West Grove, Pa., USA) was then added as 100 µl per well and incubated at 37° C. for 1 hour. Following the removal of unabsorbed secondary Ab by washing three times with washing buffer, 100 µl of SureBlue™ TMB microwell peroxidase substrate (KPL, Gaithersburg, Md., USA) was added into each well. The plate was covered and incubated at room temperature for 30 minutes before adding 100 µl TMB stop solution (KPL, Gaithersburg, Md., USA) to each well to stop the reaction. The plate was read at a wavelength of 450 nm.

The anhydrous coupling procedure was used per manufacture's recommendations. Briefly, the peptide was dissolved in at least 0.5 ml DMSO per 1 ml of Affi-Gel 10 (Bio-Rad, Hercules, Calif., USA) and A280 was measured. The gel was washed with 5× volume of cold isopropanol and after wash the moist gel was transferred into a test tube. The peptide solution was added onto the gel and the mixture was shaken overnight at room temperature. The unbound peptide was removed by washing the gel with DMSO until A280 is zero against DMSO blank. The A280 of the unbound peptide wash was measured for calculation of coupling rate. Unreacted groups of Affi-Gel were blocked by addition of 10 µl ethanolamine per 1 ml of gel.

Statistical analysis was performed using one-way analysis of variance (ANOVA) and Student's t-test. A statistical p value of 0.05 is considered significant.

Results

A. Identification and Characterization of Neutralizing Hemagglutinin (HA) Monoclonal Antibodies (mAbs) Against A/Puerto Rico/8/1934 (PR8)

1. Antigenic Specificity Characterization of Hybridoma Clones Targeting PR8 Surface Protein:

Hybridoma lines were generated from the fusion between SP2/0 myeloma cells and spleen cells from BALB/c mice that were immunized with a hemagglutinin/neuraminidase (HANA) preparation derived from the high yield vaccine donor virus, A/Puerto Rico/8/1934 (PR8). The initial screening for binding to PR8 HANA identified that a total of 114 hybridoma clones derived from 72 different parental lines were positively reactive to the ELISA plate coated with PR8 HANA preparation. The antigenic specificity was determined for all 114 hybridoma clones in Western blotting to distinguish them as either HA or NA hybridoma cell lines. With the use of hybridoma cell culture supernatants, 110 out of 114 hybridoma clones were identified as specific for PR8 HA (about 96%). Four clones (about 4%) which were derived from the same parent line, 13-2H7, are NA specific (Table E).

TABLE E

Antigenic specificity for hybridoma clones. Total 114 clones derived from 72 parental lines were tested either HA or NA positive. Hybridoma clones were named as "HANA" followed by mouse number, the well number of first screening, and the well number of subcloning.
HA: Hemagglutinin; NA: Neuraminidase

| Sample Number | Hybridoma Clone | Antigen Specificity |
|---|---|---|
| 1 | HANA 13-1D8-2E3 | HA |
| 2 | HANA 13-1G5 | HA |
| 3 | HANA 13-2A2 | HA |
| 4 | HANA 13-2H7 | NA |
| 4a | HANA 13-2H7-1E1 | NA |
| 4b | HANA 13-2H7-1F6 | NA |
| 4c | HANA 13-2H7-1G11 | NA |
| 5 | HANA 13-5G10 | HA |
| 6 | HANA 13-5G11 | HA |
| 7 | HANA 16-1G12-1B2 | HA |

TABLE E-continued

Antigenic specificity for hybridoma clones. Total 114 clones derived from 72 parental lines were tested either HA or NA positive. Hybridoma clones were named as "HANA" followed by mouse number, the well number of first screening, and the well number of subcloning.
HA: Hemagglutinin; NA: Neuraminidase

| Sample Number | Hybridoma Clone | Antigen Specificity |
| --- | --- | --- |
| 8 | HANA 16-1H9 | HA |
| 9 | HANA 16-2G12 | HA |
| 10 | HANA 16-2G8 | HA |
| 11 | HANA 16-2G9 | HA |
| 12 | HANA 16-2H5-1B11 | HA |
| 13 | HANA 16-2H7-3B9 | HA |
| 14 | HANA 17-1A3 | HA |
| 14a | HANA 17-1A3-2B5 | HA |
| 15 | HANA 39-1F2 | HA |
| 16 | HANA 39-1G4 | HA |
| 16a | HANA 39-1G4-2G6 | HA |
| 16b | HANA 39-1G4-2H2 | HA |
| 17 | HANA 39-2F6 | HA |
| 17a | HANA 39-2F6-2B5 | HA |
| 17b | HANA 39-2F6-2F9 | HA |
| 18 | HANA 39-2G12 | HA |
| 19 | HANA 39-3C9 | HA |
| 20 | HANA 39-3E4 | HA |
| 20a | HANA 39-3E4-1E3 | HA |
| 20b | HANA 39-3E4-1G12 | HA |
| 21 | HANA 39-3E5 | HA |
| 21a | HANA 39-3E5-1G12 | HA |
| 21b | HANA 39-3E5-2A5 | HA |
| 22 | HANA 39-3F2 | HA |
| 22a | HANA 39-3F2-1H6 | HA |
| 22b | HANA 39-3F2-2A6 | HA |
| 23 | HANA 39-3G10 | HA |
| 23a | HANA 39-3G10-2B9 | HA |
| 23b | HANA 39-3G10-2D10 | HA |
| 24 | HANA 39-3G3 | HA |
| 24a | HANA 39-3G3-1C3 | HA |
| 25 | HANA 39-3G9 | HA |
| 25a | HANA 39-3G9-2E7 | HA |
| 25b | HANA 39-3G9-2F5 | HA |
| 26 | HANA 39-4B11 | HA |
| 26a | HANA 39-4B11-1E8 | HA |
| 26b | HANA 39-4B11-2G7 | HA |
| 27 | HANA 39-4B9 | HA |
| 28 | HANA 39-4D12 | HA |
| 28a | HANA 39-4D12-1E11 | HA |
| 28b | HANA 39-4D12-2D11 | HA |
| 29 | HANA 39-4G1 | HA |
| 29a | HANA 39-4G1-1F7 | HA |
| 29b | HANA 39-4G1-2D2 | HA |
| 30 | HANA 39-5B7 | HA |
| 31 | HANA 39-5F2 | HA |
| 31a | HANA 39-5F2-1F6 | HA |
| 31b | HANA 39-5F2-2F4 | HA |
| 32 | HANA 41-1A2 | HA |
| 33 | HANA 41-1B8 | HA |
| 34 | HANA 41-1D5 | HA |
| 35 | HANA 41-2A4 | HA |
| 36 | HANA 41-2A8 | HA |
| 37 | HANA 41-2C1 | HA |
| 37a | HANA 41-2C1-1A5 | HA |
| 37b | HANA 41-2C1-1F7 | HA |
| 38 | HANA 41-2C5 | HA |
| 39 | HANA 41-2C7 | HA |
| 40 | HANA 41-2E9 | HA |
| 41 | HANA 41-2F11 | HA |
| 42 | HANA 41-3A6 | HA |
| 43 | HANA 41-3B4 | HA |
| 44 | HANA 41-3D10 | HA |
| 44a | HANA 41-3D10-1A9 | HA |
| 44b | HANA 41-3D10-2H3 | HA |
| 45 | HANA 41-3D5 | HA |
| 46 | HANA 41-3E3 | HA |
| 47 | HANA 41-3H5-1D7 | HA |
| 47a | HANA 41-3H5-1F11 | HA |
| 47b | HANA 41-3H5-1G10 | HA |
| 47c | HANA 41-3H5-2B10 | HA |
| 47d | HANA 41-3H5-2B8 | HA |
| 47e | HANA 41-3H5-2D3 | HA |
| 48 | HANA 41-4E4 | HA |
| 48a | HANA 41-4E4-2C12 | HA |
| 48b | HANA 41-4E4-2E1 | HA |
| 49 | HANA 41-4E9 | HA |
| 50 | HANA 41-5B3 | HA |
| 50a | HANA 41-5B3-1C8 | HA |
| 51 | HANA 41-5H10 | HA |
| 52 | HANA 56-1B9 | HA |
| 53 | HANA 56-1E12 | HA |
| 54 | HANA 56-1F1 | HA |
| 55 | HANA 56-1G3 | HA |
| 56 | HANA 56-2B5 | HA |
| 57 | HANA 56-2E12 | HA |
| 58 | HANA 56-2F7 | HA |
| 59 | HANA 56-2G9 | HA |
| 59a | HANA 56-2G9-1B3 | HA |
| 60 | HANA 56-2H10 | HA |
| 61 | HANA 56-3C4 | HA |
| 62 | HANA 56-4F6 | HA |
| 63 | HANA 56-4H3 | HA |
| 64 | HANA 56-5A11 | HA |
| 65 | HANA 56-5B2 | HA |
| 66 | HANA 56-5D1 | HA |
| 67 | HANA 56-5D8 | HA |
| 68 | HANA 61-3C3-1D8 | HA |
| 69 | HANA 61-5G10-2G6 | HA |
| 70 | HANA 66-2D6-2B5 | HA |
| 70a | HANA 66-2D6-2B7 | HA |
| 71 | HANA 66-2D9-1G4 | HA |
| 72 | HANA 66-3F3-1C4 | HA |
| 72a | HANA 66-3F3-1E6 | HA |

2. Identification of Neutralizing HA mAbs

Figure 2:
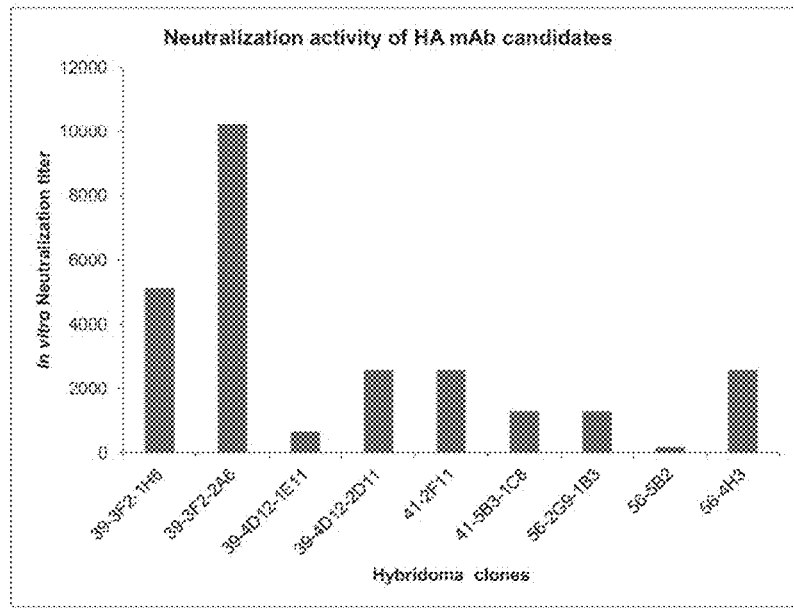
FIG. 2 shows in vitro neutralization activity of HA mAb candidates. Neutralization titers are expressed as the reciprocal of titration end-point to completely neutralize PR8.

Although all of the hybridoma clones specifically recognized either the HA or NA glycoproteins of PR8, it does not mean that they all possess the property of neutralization activity to the virus. To identify candidate mAbs which neutralize PR8 and be useful as selection reagents for classical reassortment, an in vitro plaque inhibition assay was utilized to identify those mAbs which neutralize infectivity of PR8. In principle, if the mAb can neutralize the virus, the plaque formation caused by the virus on MDCK cell monolayer would be reduced or inhibited. For the initial screening, 26 hybridoma cell supernatants were found to confer complete neutralization activity against PR8, all of which are HA-specific (Table F). In order to find the best candidate mAbs with the most potent neutralization activity, a screening by plaque inhibition assay was conducted to arrive at the neutralization titration end-point for each neutralizing mAb. From the 26 neutralizing mAbs, nine of them which have the best in vitro neutralization titer were considered as candidate selection reagents for classical reassortment (FIG. 2).

TABLE F

Hybridoma clones with neutralization activity by testing cell culture supernatants.

| Sample Number | Hybridoma Clone | Antigen Specificity |
|---|---|---|
| 1 | HANA 13-1D8-2E3 | HA |
| 16a | HANA 39-1G4-2G6 | HA |
| 16b | HANA 39-1G4-2H2 | HA |
| 21 | HANA 39-3E5 | HA |
| 21b | HANA 39-3E5-2A5 | HA |
| 22a | HANA 39-3F2-1H6 | HA |
| 22b | HANA 39-3F2-2A6 | HA |
| 24 | HANA 39-3G3 | HA |
| 24a | HANA 39-3G3-1C3 | HA |
| 28 | HANA 39-4D12 | HA |
| 28a | HANA 39-4D12-1E11 | HA |
| 28b | HANA 39-4D12-2D11 | HA |
| 36 | HANA 41-2A8 | HA |
| 37 | HANA 41-2C1 | HA |
| 41 | HANA 41-2F11 | HA |
| 44 | HANA 41-3D10 | HA |
| 50 | HANA 41-5B3 | HA |
| 50a | HANA 41-5B3-1C8 | HA |
| 52 | HANA 56-1B9 | HA |
| 53 | HANA 56-1E12 | HA |
| 59 | HANA 56-2G9 | HA |
| 59a | HANA 56-2G9-1B3 | HA |
| 61 | HANA 56-3C4 | HA |
| 63 | HANA 56-4H3 | HA |
| 65 | HANA 56-5B2 | HA |
| 67 | HANA 56-5D8 | HA |

Monoclonal antibodies with the most potent neutralization activity were screened via plaque inhibition assay, which was based on quantitation of the neutralization titration end-point for each neutralizing mAb. Through plaque inhibition assay screening, four HA mAbs: 39-3F2-1H6 (mAb-1H6), 39-3F2-2A6 (mAb-2A6), 39-4D12-2D11 (mAb-2D11), and 56-2G9-1B3 (mAb-1B3) (Table G) were found to have neutralization activity against PR8. One NA mAb-1G11 was identified with neutralization activity against PR8.

TABLE G

HI activity and isotype of neutralizing HA mAb candidates. Neutralization titers are expressed as the reciprocal of the titration end-point to completely neutralize PR8. HI titers are expressed as the reciprocal of the titration end-point to completely block the hemagglutination of chicken erythrocytes. The monoclonal antibodies are identified as indicated in the parentheses.

| Monoclonal Antibody | In vitro Neutralization Titer | HI Titer to PR8 | Isotype |
|---|---|---|---|
| 39-3F2-1H6 (mAb-1H6)* | 5120 | 80 | IgG1 |
| 39-3F2-2A6 (mAb-2A6)* | 10240 | 80 | IgG1 |
| 39-4D12-2D11 (mAb-2D11)* | 2560 | 20 | IgG1 |
| 56-2G9-1B3 (mAb-1B3)* | 1280 | 40 | IgG1 |

The mAb-1H6 and mAb-2A6 are derived from the same parent hybridoma cell line (39-3F2) and share an almost identical epitope mapping profile (seen in FIG. 6). Their epitope is composed of HA residues #158-172, #183-197, and #253-267 (H1 numbering with signal sequence). Therefore, only mAb 39-3F2-2A6 was deposited with ATCC. The epitope for mAb-2D11 is composed of HA residues #158-172, #208-222, #253-267. The epitope for mAb-1B3 is composed of HA residues #158-172 and #253-267.

3. Characterization of Neutralizing HA mAbs a) Antibody Isotype of Neutralizing HA mAbs The nine candidate HA mAbs were isotyped using Pierce Mouse Isotyping Kit (Thermo Pierce, Rockford, Ill., USA) per manufacturer protocols. All of them were characterized as mouse IgG1 mAbs (Table 1). As such, Protein G chromatography method was used to purify the candidate mAbs according to the manufacturer's recommendations.

b) Hemagglutination Inhibition (HI) Activity

All candidate HA mAbs were evaluated for HI activity as described (WHO Global Influenza Surveillance Network. 2011). RDE-treated hybridoma cell culture supernatants were used in HI assays. All the neutralizing HA mAbs, namely, 39-3F2-1H6, 39-3F2-2A6, 39-4D12-2D11, 56-2G9-1B3 had HI activity to the homologous virus, PR8, i.e., HI (+).

In addition to PR8, HI assays were also performed against two other representative influenza viruses, NYMC X-173 (H1N1) and NYMC X-175C (H3N2) to evaluate possible cross-reactivity for the HA neutralizing mAb candidates, either subtypic (to X-173) or cross-subtypic (to X-175C). X-173 (H1N1) is a high yield reassortant (HYR) incorporating six PR8 'internal' genes as backbone and HA and NA genes from wild type (WT) virus, A/South Dakota/06/2007 (H1N1). X-175C (H3N2) is a HYR which possesses HA and NA from the WT virus, A/Uruguay/716/2007 (H3N2), together with the PR8 backbone. No HI activity to X-173 (H1N1) or X-175C (H3N2) was found which indicates that the neutralizing HA mAbs specifically recognize and neutralize PR8 in vitro.

The high specificity of HI activity for the HA mAbs to PR8 suggests that they are qualified for the use as selection reagents in classical reassortment, since they are highly potent and specific to the HYR donor virus, PR8.

c) In Vitro Neutralization Activity of Purified HA mAbs

By using the plaque inhibition assay, the four Protein G chromatography purified HA mAbs were quantitatively evaluated for their in vitro neutralization activity. All HA mAb candidates that maintained potent in vitro neutralization activity after purification demonstrated complete neutralization of PR8 at 0.1 µg/ml (FIG. 3). Polynomial regression allowed for the estimation of the IC50 (50% inhibition concentration) for individual candidate antibodies. MAb-1H6 and mAb-1B3 were shown to have the highest IC50 (1.55 ng/ml and 1.54 ng/ml, respectively). MAb-2A6, though derived from the same parent cell line as mAb-1H6, had a slightly lower IC50 (1.50 ng/ml). Moreover, mAb-2D11 had the most potent in vitro neutralization activity, effectively neutralizing 50% of the plaques at IC50 of 1.40 ng/ml. Overall, the four HA mAbs had similar potency levels to achieve 100% neutralization in vitro.

d) In Ovo Neutralization Activity of Purified HA mAbs

Since the candidate mAbs will be used in embryonated chicken eggs (in ovo) to neutralize the virus with HA and NA from PR8 in the selection process, it is critical to ensure that the in vitro neutralization activity is preserved in ovo. To this end, the in ovo inhibition assay was performed to evaluate the neutralization activity of the four purified HA mAbs. As shown in FIG. 4, all four purified candidate mAbs are able to neutralize PR8 in the embryonated chicken eggs. The mAb-1H6 and mAb-2A6 which are derived from the same parent hybridoma clone also achieve similar levels of in ovo neutralization activity with 16 µg/ml for complete blocking of PR8 growth. MAb-1B3 neutralizes more efficiently than mAb-1H6 and mAb-2A6 in that it only requires 8 µg/ml to totally neutralize the in ovo growth of PR8. Among the four purified candidate HA mAbs, mAb-2D11 has the best in ovo neutralization activity with only 4 µg/ml required for complete neutralization. These results confirmed that the four purified candidate HA mAbs maintain their neutralization activity in the egg environment. Thus, all four candidates are suitable to be applied as HA selection reagents to substitute for pAbs in classical reassortment for making influenza vaccine seed viruses.

e) Specificity of HA mAb Candidates

All four purified candidate HA mAbs have strong neutralization activity to PR8 (H1N1) both in vitro and in ovo, furthermore HI activity characterization also indicated that these HI (+) mAb candidates were specific to PR8. To completely characterize the specificty of the HA mAb candidates, Western blot (WB), immunofluorescence microscopy (IFM), and in vitro plaque inhibition assay were performed using the representative viruses X-173 (H1N1) and X-175C (H3N2) as well as PR8 (H1N1). The requirement of high quality selection reagents is that the mAbs must be highly specific to their targets from the level of binding interaction as well as inhibition of biological activity. First, all four HA mAbs were individually used to blot viral proteins of PR8, X-173 and X-175C under reducing conditions which results in separation of HA1 and HA2 subunits. It was shown that all four HA mAbs were specific to the HA1 subunit of PR8, and neither subtypic (to X-173, H1N1) nor cross-subtypic (to X-175C, H3N2) recognition was detected on WB (FIG. 5). Also, they are likely have continuous epitopes rather than conformational epitopes since under reducing conditions most tertiary structure of the protein will be destroyed. Nevertheless, Western blot analysis indicates the high binding specificity of the HA mAbs to PR8.

Secondly, to further confirm the binding specificity of HA mAbs to PR8, their reactivity to HA was studied via IFM (data not shown). MDCK cells were infected with PR8, X-173 and X-175C, respectively at the multiplicity of infection (MOI) of 1. The infected cells were fixed and examined for HA recognition using candidate HA mAbs. Consistent with the high specificity of the HA candidates to PR8 HA in WB, no HA mAbs showed cross-reactivity to the other two representative viruses. The high specificity of the candidate HA mAbs to PR8 remains in the case of the 'native' form of HA, which is desirable insofar as the more specific the mAb candidates are to PR8, the better they will perform as selection reagents in developing reassortants, Finally, the biological cross-reactivity of the HA mAb candidates was investigated with plaque inhibition assay to the representative viruses, X-173 (H1N1) and X-175C (H3N2). Neither subtypic nor cross-subtypic cross-reactivity were detected.

f) Peptide Epitope Mapping for Candidate HA mAbs

To further characterize the HA mAbs, the epitope(s) of all four HA mAb candidates were mapped. Since it has been shown that HA candidate mAbs recognize the reduced HA1 subunit on Western blot suggesting a non-conformational epitope, the peptide epitope mapping method was employed to identify the epitope(s) for individual mAbs. An overlapping peptide array was synthesized to represent the linear epitopes of the HA1 subunit. Each peptide was 15 amino acids long with 10 amino acids overlapping with the successive peptide. A total of 64 peptides were synthesized without modifications and included the free amino group and carboxyl group at their N-terminus and C-terminus, respectively. The binding activity of each mAb to individual peptides was assessed by ELISA.

Within the 64 overlapping peptides (Table D), all four HA mAbs had reactivity (>2-fold normalized reactivity) to two peptides #29 and #48 corresponding to amino acids 145-159 and 240-254 in the HA1 subunit (H3 numbering) (FIG. 6a, 6b). In addition to the common reactive peptides, mAb-1H6 and mAb-2A6 also reacted with peptide #34 (HA1 170-184) (FIG. 6a), and mAb-2D11 was shown to bind to peptide #39 (HA1 195-209) as well (FIG. 6b). Although the peptides are discontinuous in primary amino acid sequence, they are all clustered together on the three-dimensional structure of HA molecule and close to the receptor-binding site (RBS) (FIG. 7). Antibody binding to these peptides will certainly interfere with the normal receptor binding at the RBS pocket, which is consistent with the HI activity data that all four neutralizing HA mAbs possess HI activity (blocking receptor binding).

For validation, the experimentally determined HA epitopes of H1N1 subtype were searched in public Immune Epitope Database [available on the World-Wide-Web at URL www(dot)iedb(dot)org] (Appendix A: Spreadsheet entitled "H1N1 HA Epitope Search"). A Total of 501 epitopes were found, within which 34 are discontinuous epitopes. The epitopes for all the four mAbs had only partially overlapped with 14 published epitopes with residues #158-172 (or #159-173) which are shown most frequently. One epitope (IEDB ID: 164527) which includes amino acids from residues #158-172, #208-222, and #253-267 may potentially represent the same epitope as mAb-2D11 (Xu et al. "Structural basis of preexisting immunity to the 2009 H1N1 pandemic influenza virus," Science, 2010); Krause et al. "An insertion mutation that distorts antibody binding site architecture enhances function of a human antibody," M Bio, 2011; and Whittle et al. "Flow cytometry reveals that H5N1 vaccination elicits cross-reactive stem-directed antibodies from multiple Ig heavy-chain lineages," Journal of Virology, 2014). However, the corresponding mAb referred therein is specific to A/South Carolina/1/1918 (1918 pandemic H1N1) and A/California/04/2009 (2009 pandemic H1N1) but not to PR8 and HAs of other influenza subtypes, as tested in enzyme-linked immunosorbent assay (ELISA). Therefore, the epitope IEDB ID-164527 is different from the epitope for mAb-2D11, which is specific to PR8. Overall the epitope search provides a solid base for the validation of the four mAbs as unique epitopes.

TABLE H

Results of H1N1 HA epitope search. Legend: H = Human; M = Mouse; F = Ferret; C = Chicken

| IEDB ID | Epitope Sequence | Peptide ID | Host |
| --- | --- | --- | --- |
| 76951 | L87, L88, V90, R91, S92, E132 | N/A: 14-15; 21-23 | M, M, M, M |
| 77529 | K171, E172 | 29 (158-172) | M |
| 94400 | K180 | N/A: 30-33 | H, H, H, H, H, H, H, H, H, H, H, H, H |
| 94401 | P200 | N/A: 35-37 | H, H, H, H, H, H, H, H, H, H, H, H |
| 133973 | K180 | N/A: 30-33 | H, H, H, H |
| 133974 | S139 | N/A; 23-25 | H, H, H |
| 159269 | G147, V148, S149, A150, W166, T168, G169, N171, G172, L173, N200, G202, D203, R205, A206, L207, K235, D238, R239, E240 | 29 (158-172) | H, H, H, H, H, H, H, H, H, H, H, H, H, H, H, H, H, H, H, H, H, H, H, H, H, H, H, H, H, H, H, H, H |

TABLE H-continued

Results of H1N1 HA epitope search. Legend: H = Human; M = Mouse; F = Ferret; C = Chicken

| IEDB ID | Epitope Sequence | Peptide ID | Host |
|---|---|---|---|
| 164527 | S138, S139, P141, N142, K171, G tralized PR8 virus in ovo at only 1 µg/ml (FIG. 11), while the best performing HA, mAb-2D11, required 4 µg/ml for complete neutralization in vitro.

Characterization of the NA mAb-1G11

As stated previously, to be qualified as a selection reagent for classical reassortment for development of influenza A vaccine seed virus, the candidate mAb must show high specificity to the target. In this case, as seen for HA mAbs, the NA mAb-1G11 must be characterized for the specificity to its ultimate target, the PR8 virus. To fulfill this objective, the following assays to characterize the specificity of mAb-1G11 were performed.

First, an NI assay was conducted to evaluate the NI activity of mAb-1G11 against PR8 NA as well as two other representative viruses X-173 (H1N1) and X-175C (H3N2). As detailed in the "Materials & Methods" section, the dilution of each virus was first optimized in NA assay. It was found that in terms of NI activity mAb-1G11 is specific to PR8 NA. For the same amount of antibody applied, 50% NA activity reduction was found for PR8 NA but not for the representative viruses, although a slight reduction (~15%) is seen for X-173 NA which belongs to the same N1 subtype as PR8 NA (FIG. 12). These results indicate that at the enzymatic level, NA mAb-1G11 is specific to the PR8 NA.

Secondly, the specificity of mAb-1G11 in terms of binding activity was evaluated in both WB and IFM. NA mAb-1G11 was used to blot the viral proteins of PR8, X-173 and X-175C under reducing conditions. It was shown that mAb-1G11 was specific to the NA of PR8, and neither subtypic (X-173, N1) nor cross-subtypic (X-175C, N2) recognition was shown on WB (FIG. 13). Similar results were observed in IFM, when mAb-1G11 was used as primary antibody to stain MDCK cells infected by the three different influenza viruses, only PR8 infected cells were positively stained but not the cells infected by either X-173 or X-175C (FIG. 14). The data from WB and IFM suggest that the NA mAb-1G11 is highly specific to PR8 NA in both denatured (WB) and non-denatured (IFM) conditions.

Thirdly, the antibody was studied via an in ovo inhibition assay. Here, although mAb-1G11 provides complete neutralization at the same minimal concentration in ovo and in vitro, due to the methodological differences between in ovo and in vitro assays the relative antibody neutralization amount per PFU virus is 20-fold lower in ovo than in vitro. This difference may be explained by NA functions, that in addition to impairing virion exodus, NA mAb-1G11 may block viral attachment by inhibiting NA enzymatic activity. In an in ovo environment a virus relies on NA activity to eliminate competing neuraminic acid receptors in order to infect the target cell. Antibodies that interfere early in the viral life cycle in ovo rather than later in vitro encounter fewer NA targets therefore are able to achieve full neutralization with lower amounts of mAb. Considering this, the in ovo assay would be expected to be more sensitive than the in vitro assay for evaluating the biological specificity of NA mAb-1G11. As shown in FIG. 15, no cross-reactivity was detected to either X-173 (N1) or X-175C (N2) viruses, which suggests that the candidate NA mAb-1G11 is highly specific to PR8 NA and would be a good candidate for use as a selection reagent in classical reassortment to develop influenza A vaccine seed viruses.

B. Development of mAb-Based Classical Reassortment

Figure 1:
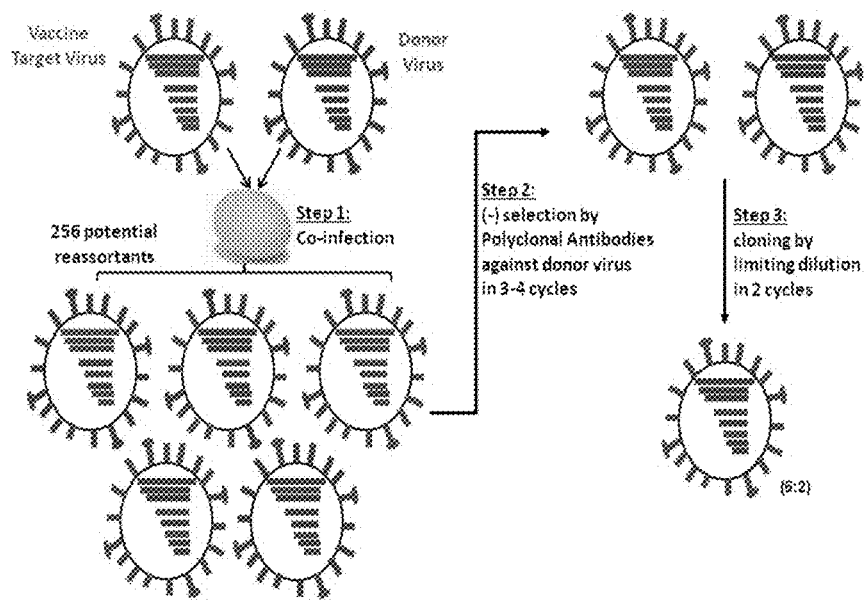
FIG. 1 shows classical reassortment procedure for generation of influenza vaccine seed virus.

As illustrated in FIG. 1, the essential concept for developing a HYR as the vaccine seed virus is to introduce 'internal' genes (all the genes except HA and NA) from the HYR donor, PR8, into a reassortant to acquire the high yield growth property while maintaining the same antigenicity as the WT virus (HA and NA genes). Since the influenza A virus (IAV) genome is composed of eight gene segments, the progeny viruses may have up to 256 (28) different gene compositions from co-infection of PR8 and WT viruses. Currently, only the progeny viruses with WT HA and NA are selected to grow by using polyclonal antibodies (pAbs) against donor virus HA and NA to eliminate any donor virus or virus progeny with PR8 HA and/or NA; subsequently the reassortant virus with the best in ovo growth property and free of PR8 HA and NA will be cloned by limiting dilution. As initially proposed, substituting the pAbs with potent neutralizing mAbs will greatly improve classical reassortment method through enhancing selection efficiency due to the high specificity and neutralizing activity of mAbs. From the panel of candidate mAbs, the PR8-specific mAb-1B3 (anti-HA) was successfully applied either alone or in combination with mAb-1G11 (anti-NA) in classical reassortment for developing influenza A vaccine seed viruses.

1. Development of H3N2 by Reassortants with mAb-1B3 and mAb-1G11

First, A/Uruguay/716/2007 (UY), an H3N2 WT virus which was the vaccine target virus for 2007-2008 flu season, was utilized as the representative WT virus. With the same dose of $10^6$ $EID_{50}$, 10-day embryonated chicken eggs were co-infected in triplicate with PR8 and UY. Allantoic fluid from each co-infected egg was processed in octuplicate for antibody negative selection at dilution ratios of $10^{-7}$, $10^{-6}$ and $10^{-5}$ respectively, meaning each selection ratio was performed in 3×8=24 different eggs. All the experiments were finished in a single round of antibody negative selection with mAb-1B3 and mAb-1G11 and a single round of cloning. No HYR virus was selected for growth at $10^{-7}$ dilution, in contrast two HYRs R-2 and R-3 were developed at $10^{-6}$ and $10^{-5}$ dilution, respectively. R-2 and R-3 both grew 8-fold better in ovo than their parental WT virus in terms of HA titer. The molecular gene analysis revealed that R-2 was a 1:7 reassortant which acquired the high yield growth property by incorporating only the M gene from PR8 (Table 4). At lower selection dilution ratio, R-3 acquired more genes from PR8 deriving its PB1, PA, NP and M genes from PR8 (Table 3).

Two candidate mAbs, mAb-1B3 (anti-HA) and mAb-1G11 (anti-NA) were successfully applied in the classical reassortment to replace the pAbs and develop HYRs Importantly, by using mAbs with guaranteed potent neutralization activity, the efficiency of the classical reassortment was significantly improved by minimizing both antibody selection and cloning cycles to one cycle, compared to the pAb-based system which requires at least three cycles of antibody negative selection and two cycles of cloning.

TABLE I

Gene constellation of hy reassortants developed in mAb-based classical reassortment.

| Gene | R-2 (H3N2) | R-3 (H3N2) | R-6 (H1N1pdm) | R-8 (H1N1) | R-15 (H3N2) |
|---|---|---|---|---|---|
| PB2 | UY | UY | CA | PR8 | UY |
| PB1 | UY | PR8 | CA | PR8 | PR8 |
| PA | UY | PR8 | CA | PR8 | PR8 |
| HA | UY | UY | CA | SD | UY |
| NP | UY | PR8 | CA | PR8 | PR8 |
| NA | UY | UY | CA | SD | UY |
| M | PR8 | PR8 | CA | PR8 | PR8 |
| NS | UY | UY | PR8 | PR8 | UY |

2. PR8 as a Universal by Donor for the Development of Influenza A Vaccine Seed Virus PR8, the best grower in embryonated chicken eggs, is widely recognized as the best HYR donor virus for developing influenza A vaccine seed viruses. However, due to the cross-reactivity of pAbs to WT viruses belonging to the same H1N1 subtype as PR8, currently two HYR donor viruses are used to provide the PR8 backbone (six 'internal' genes). PR8 (H1N1) is utilized for H3N2 subtype vaccine seeds development, whereas a H3N2 HYR, NYMC X-157, is employed for H1N1 and H1N1pdm subtypes vaccine seeds development. Although X-157 acquired all six 'internal' genes from PR8, PR8 still grows 4-fold better than X-157 in ovo. Therefore, it would be of great interest to utilize PR8 as the HYR donor for generating both H1N1 and H1N1pdm subtypes vaccine seeds as well. Considering the high specificity of the candidate mAbs, the mAb-based system makes it possible to use PR8 as the universal donor.

It was demonstrated that PR8 can be used as a universal HYR donor in the mAb-based system for all influenza A vaccine seed virus preparations. A/California/07/2009 (CA, H1N1pdm) and A/South Dakota/06/2007 (SD, H1N1) were used as representative WT viruses. Together with UY (H3N2), they represent all influenza A virus subtypes currently circulating in humans. For reassortment of both CAxPR8 and SDxPR8, the co-infection dose of both WT and donor viruses were at $10^6$ $EID_{50}$ and the dilution ratio of co-infection for mAb negative selection is $10^3$ which is the lowest possible dilution for both mAb-1B3 (HA) and mAb-1G11 (NA). Similarly as found for the reassortment of UYxPR8, only one cycle of mAb negative selection and one cycle of cloning are needed to generate the HYRs.

For reassortment of CAxPR8, 21 out of 24 selections (88%) had growth and the one with the highest HA titer was cloned. Gene analysis showed that this clone is a 1:7 reassortant (R-6, Table 3) with only NS gene derived from PR8. The growth of R-6 is 32-fold higher by HA titer (1024) than the WT virus, CA.

For reassortment of SDxPR8, 23 out of 24 selections (96%) had growth and the one with the highest HA titer was cloned. A full gene analysis of the clone revealed that it was a 6:2 reassortant (R-8, Table 3) deriving HA and NA from SD and the six 'internal' genes from PR8. The HA titer of R-8 is 8192 which is 8-fold higher than its respective WT virus, SD.

3. Development of H3N2 HYR with mAb-1B3 Only

Since the hybridoma cell line producing NA mAb-1G11 was later proven unstable, the hypothesis that developing HYR only by using HA mAb-1B3 was further tested. Through the same procedure as the development of R-3 (except inclusion of NA mAb-1G11 for selection), an HYR R-15 was developed. Further characterization has shown that R-15 is comprised of the same gene constellation as R-3 and it grows as well as R-3 in ovo. However, compared to the selection with both HA mAb-1B3 and NA mAb-1G11, the selection efficiency is discounted and more samples are required to identify the correct HYR incorporating both WT HA and NA. Although it indicates that a NA mAb is desired for a more effective/efficient selection, the data further demonstrates the utility of HA mAbs as potent selection reagents in classical reassortment for developing influenza A vaccine seed viruses.

In summary, the new mAb-based classical reassortment is a reliable and efficient method to expedite influenza A vaccine seed virus preparation. For the current pAb-based method it usually takes about 3-4 weeks to make the vaccine seed viruses. In contrast, the new mAb-based system allows us to finish the preparation in about 10 days, which can significantly reduce the time frame for developing influenza A vaccine seed viruses and reduce the overall length of time to production of the vaccine. Additionally, in the mAb-based system, PR8 can be used as the universal by donor for the development of influenza A vaccine seed viruses belonging to different subtypes. It is promising to establish a comprehensive and standardized procedure for mAb-based reassortment to develop influenza A seed viruses for vaccine production.

Example 2

Neutralizing mAbs developed and characterized in the foregoing Example 1 are compared to pAbs in the selection process of classical reassortment. In particular, selection efficiency and the time of vaccine seed virus preparation parameters are compared using routine techniques.

Compared to the current classical reassortment and reverse genetics methods which both require at least 3-4 weeks to finish the generation of vaccine seed viruses (Nicolson et al., 2005; Webby et al., 2004), the hereinbefore described mAb-based classical reassortment only needs one week to ten days to prepare the vaccine seed virus. This rapid preparation is made possible by the potent and specific neutralization activity of the mAbs employed in the system, which significantly reduced the antibody selection cycle of classical reassortment. With a single cycle of selection, reassortants with the desired surface glycoproteins, HA and NA, derived from WT virus can be cleanly selected without the contamination by reassortants deriving HA and NA from PR8. In addition, the cycle of cloning step following antibody selection was also reduced to a single cycle (FIG. 16).

Consequently, implementation of this rapid mAb-based system for generation of future vaccine seed viruses leads to earlier the public availability of the influenza vaccine. It is calculated that the vaccines would be available at least two weeks earlier, which would be highly significant in a pandemic situation. In 2009, the first dose of H1N1 pandemic influenza vaccine was delivered in the first week of October when the influenza-like illness peaked (FIG. 17). Delivery of the vaccines two to three weeks earlier would have saved additional thousands of people's lives and prevent millions of hospitalizations. These advantages, which are in part conferred by the use of monoclonal antibodies described hereinbefore, are significant and unexpected.

Ferret Challenge Experiment

The objective of this experiment is to compare the immunogenicity and the efficacy of the seed virus formulations using homologous wild-type virus challenge.

Female ferrets (*Mustela putorius furo*) (6 ferrets/group) aged about 12 months are injected with two intramuscular immunizations, 21 days apart with 500 µl of purified (e.g. split or sub-unit) seed virus compositions or antigens derived therefrom. 28 days after the second immunization, ferrets are challenged by the intratracheal route with $10^5$ Log $CCID_{50}$ of homotypic influenza strain. Nasal washes are collected at day 1 before and up to 5 days after challenge to measure viral replication. Body temperature is continuously monitored. Serum samples are collected at day 0, day 21 (post 1st immunization), 21 and 27 days after the second immunization to measure neutralizing and hemagglutinin inhibition antibody titers against homotypic and heterosubtypic strains.

From the careful consideration of the foregoing description in light of the references cited herein, one skilled in the art can ascertain the essential characteristics of this invention and, without departing from the spirit and scope thereof, can make various changes and modifications of the invention to adapt it to various usages and conditions.

REFERENCES CITED

1. Air et al. Virology. 1985; 145:237-248.
2. Ali et al. J Virol. 2000; 74:8709-8719.
3. Amano et al. J Gen Virol. 1992; 73:1969-1975.
4. Aymard et al. Bull Acad Natl Med. 1998; 182:1723-36; discussion 1736-7.
5. Barman et al. Virus Res. 2001; 77:61-69.
6. Barman et al. J Virol. 2000; 74:6538-6545.
7. Baz et al. N Engl J Med. 2009; 361:2296-2297.
8. Beaton et al. Proc Natl Acad Sci USA. 1986; 83:6282-6286.
9. Belshe R et al. N Engl J Med. 2007; 356:685-696.
10. Benne et al. Vaccine. 1997; 15:1039-1044.
11. Brewer et al. J Cell Biol. 1991; 114:413-421.
12. Bright et al. J Am Med Assoc. 2006; 295:891-894.
13. Bucher et al. J Virol. 1980; 36:586-590.
14. Burch et al. Health Technol Assess. 2009; 13:1-265.
15. Buxton et al. J Am Med Assoc. 2000; 284:1655-1663.
16. Cascino et al. Hybridoma. 1986; 5:307-318.
17. Caton et al. Cell. 1982; 31:417-427.
18. CDC Report: MMWR Morb. Mortal. Wkly. Rep. 2013; 62:119-123.
19. CDC Report: Updated CDC estimates of 2009 H1N1 influenza cases, hospitalizations and deaths in the United States, April 2009-Apr. 10, 2010.
20. Chen et al. Cell. 1998; 95:409-417.
21. Chen et al. Nat Med. 2001; 7:1306-1312.
22. Clackson et al. Science. 1995; 267:383-386.
23. Colman et al. Protein Sci. 1994; 3:1687-1696.
24. Colman et al. Nature. 1983; 303:41-44.
25. Compans et al. J Virol. 1972; 10:795-800.
26. Compans et al. J Virol. 1969; 4:528-534.
27. Connor et al. Virology. 1994; 205:17-23.
28. Couch R et al. J Infect Dis. 1986; 153:431-440.
29. Cox et al. Topley & Wilson's Microbiology and Microbial Infections. John Wiley & Sons, Ltd; 2010.
30. Das et al. Nature Structural and Molecular Biology. 2010; 17:530-538.
31. Davenport et al. Med Microbiol Immunol (Berl). 1977; 164:69-76.
32. Davies et al. Cell. 2009; 139:449-451.
33. Dawood et al. N Engl J Med. 2009; 360:2605-2615.
34. De Jong et al. N Engl J Med. 2005; 353:2667-2672.
35. Doherty et al. J Neuroimmunol. 1981; 1:227-237.
36. Doms et al. Virology. 1993; 193:545-562.
37. El Karadaghi et al. BBA—Biomembranes. 1984; 778: 269-275.
38. Enami et al. J Virol. 1996a; 70:6653-6657.
39. Erickson et al. Virology. 1980; 107:320-330.
40. Ferguson et al. Clin Chem. 1996; 42:675-684.
41. Fodor et al. J Virol. 1999; 73:9679-9682.
42. Fodor et al. J Virol. 1995; 69:4012-4019.
43. Fouchier et al. J Virol. 2005; 79:2814-2822.
44. Gamblin et al. J Biol Chem. 2010; 285:28403-28409.
45. Gerdil C. et al. Vaccine. 2003; 21:1776-1779.
46. Gerhard et al. J Virol. 1991; 65:364-372.
47. Ghedin et al. Nature. 2005; 437:1162-1166.
48. Glezen W P. Epidemiol Rev. 1996; 18:64-76.
49. Gog et al. Nucleic Acids Res. 2007; 35:1897-1907.
50. Gomez-Puertas et al. J Virol. 2000; 74:11538-11547.
51. Grey et al. J Exp Med. 1971; 133:289-304.
52. Gubareva et al. Lancet. 2000; 355:827-835.
53. Gubareva et al. J Virol. 1997; 71:3385-3390.
54. Hanson et al. Respir Res. 2006; 7:126.
55. Hara et al. Microbiol Immunol. 2003; 47:521-526.
56. Harper et al. MMWR. Recommendations and reports: Morbidity and mortality weekly report. Recommendations and reports/Centers for Disease Control. 2004; 53:1-40.
57. Hayden et al. N Engl J Med. 1999; 341:1336-1343.
58. Hayden et al. N Engl J Med. 2000; 343:1282-1289.
59. Hayden et al. J Am Med Assoc. 1996; 275:295-299.
60. Hirst et al. J Exp Med. 1942; 75:49-64.
61. Hocart et al. J Gen Virol. 1989a; 70:809-818.
62. Hocart et al. J Gen Virol. 1989b; 70:2439-2448.
63. Hoffmann et al. Vaccine. 2002; 20:3165-3170.
64. Hoffmann et al. Proc Natl Acad Sci USA. 2000; 97:6108-6113.
65. Hogue et al. Virology. 1992; 188:510-517.
66. Hsu et al. Proc Natl Acad Sci USA. 1987; 84:8140-8144.
67. Imai et al. Virus Res. 1998; 53:129-139.
68. Jin et al. EMBO J. 1997; 16:1236-1247.
69. Johannsson et al. Proc Natl Acad Sci USA. 1987; 84:6869-6873.
70. Johansson et al. J Virol. 1989; 63:1239-1246.
71. Johnson et al. Bull Hist Med. 2002; 76:105-115.
72. Karagouni et al. Scand J Immunol. 1990; 31:745-754.
73. Kawakami et al. J Biochem. 1983; 93:989-996.
74. Kawaoka et al. J Virol. 1989; 63:4603-4608.
75. Kemler et al. Virology. 1994; 202:1028-1033.
76. Kida et al. Arch Virol. 1983; 76:91-99.
77. Kilbourne Influenza. New York: Plenum Press; 1987: 157-218.
78. Kilbourne Bull World Health Organ. 1969; 41:643-645.
79. Kilbourne et al. Journal of Immunology. 1987; 138: 3010-3013.
80. Kilbourne et al. J Exp Med. 1960; 111:387-406.
81. Kilbourne et al. J Infect Dis. 2004; 189:459-461.
82. Kilbourne et al. J Infect Dis. 1971; 124:449-462.
83. Kiso et al. Lancet. 2004; 364:759-765.
84. Klenk et al. Virology. 1975; 68:426-439.
85. Knossow et al. Immunology. 2006; 119:1-7.
86. Kohler et al. Nature. 1975; 256:495-497.
87. Kovari et al. Structure. 1995; 3:1291-1293.
88. Krug et al. Cell. 1979; 18:329-334.
89. Lakadamyali et al. Microb Infect. 2004; 6:929-936.
90. Lamb et al. Trends in Genetics. 1991; 7:261-266.
91. Larson et al. Cancer Res. 1995; 55:5756s-5758s.
92. Lazarowitz et al. Virology. 1975; 68:440-454.
93. Lentz et al. Biochemistry (N Y). 1987; 26:5351-5358.
94. Lin et al. J Cell Biol. 1998; 142:51-57.
95. Lipatov et al. Acta Virol. 1997; 41:337-340.
96. Lipatov et al. J Virol. 2004; 78:8951-8959.
97. Lipman et al. ILAR Journal. 2005; 46:258-267.
98. Luytjes et al. Cell. 1989; 59:1107-1113.
99. Marasco et al. Nat Biotechnol. 2007; 25:1421-1434.
100. Marquet et al. Clin Chem. 1996; 42:258-262.
101. Masurel et al. J Hyg. 1983; 90:397-402.
102. Masurel et al. Am J Epidemiol. 1973; 97:44-49.
103. Matrosovich et al. J Virol. 2004; 78:12665-12667.
104. Mazanec et al. J Virol. 1995; 69:1339-1343.
105. Melkonian et al. J Biol Chem. 1999; 274:3910-3917.
106. Monto et al. Drugs and Aging. 1996; 8:445-451.
107. Mozdzanowska et al. Virology. 1999; 254:138-146.
108. Murti et al. Virology. 1992; 186:294-299.
109. Murti et al. Virology. 1986; 149:36-43.
110. Nayak et al. Virus Res. 2004; 106:147-165.
111. Ndifon et al. Proc Natl Acad Sci USA. 2009; 106:8701-8706.

112. Neumann et al. Proc Natl Acad Sci USA. 2005; 102:16825-16829.
113. Neumann et al. EMBO J. 2000; 19:6751-6758.
114. Neumann et al. Virus Res. 2002; 82:153-158.
115. Neumann et al. Proc Natl Acad Sci USA. 1999; 96:9345-9350.
116. Nicasio et al. Viruses. 2012; 4:1731-1752.
117. Nichol et al. N Engl J Med. 1995; 333:889-893.
118. Nicholls et al. Nat Med. 2007; 13:147-149.
119. Nicholson K G. Clinical features of influenza. Semin Respir Infect. 1992; 7:26-37.
120. Nicolson et al. Vaccine. 2005; 23:2943-2952.
121. Noble G R, ed. Epidemiological and Clinical Aspects of Influenza. Boca Raton: CRC Press; 1982. Beare A. S., ed.
122. Nuss et al. Proteins: Structure, Function and Genetics. 1993; 15:121-132.
123. Ohmit et al. J Am Geriatr Soc. 1999; 47:165-171.
124. Ortega et al. J Virol. 2000; 74:156-163.
125. Outlaw M et al. Virology. 1993; 195:413-421.
126. Palese et al. J Gen Virol. 1976; 33:159-163.
127. Palese et al. Virology. 1974; 61:397-410.
128. Palladino et al. J Virol. 1995; 69:2075-2081.
129. Parren et al. The Antiviral Activity of Antibodies in Vitro and in Vivo. 2001. Advances in Immunology; No. 77.
130. Parvin et al. J Virol. 1989; 63:5142-5152.
131. Patriarca et al. J Am Med Assoc. 1985; 253:1136-1139.
132. Palese et al. Fields Virology. Vol 2. Fifth ed. Philadelphia, Pa. 19106 USA: Lippincott Williams & Wilkins; 2007: 1655.
133. Pinto et al. Cell. 1992; 69:517-528.
134. Porter et al. Nature. 1979; 282:471-477.
135. Possee et al. J Gen Virol. 1982; 58:373-386.
136. Ramanunninair et al. PLoS One, 2013 Jun. 11; 8(6)
137. Reichelderfer et al. Current Topics in Medical Mycology. Singapore: World Scientific; 1989: 412-444.
138. Rekart et al. Am J Epidemiol. 1982; 115:587-597.
139. Richardson et al. Arch Virol. 1991; 116:69-80.
140. Robertson et al. Vaccine. 2011; 29:1836-1843.
141. Ruigrok et al. Virology. 2000; 267:289-298.
142. Russell et al. Nature. 2006; 443:45-49.
143. Schmitt et al. Adv Virus Res. 2005; 64:383-416.
144. Schünemann et al. Lancet Infectious Diseases. 2007; 7:21-31.
145. Schwarzmann et al. Arch Intern Med. 1971; 127:1037-1041.
146. Shimizu et al. Vaccine. 1985; 3:207-210.
147. Siegel et al. Transfus Clin Biol. 2002; 9:15-22.
148. Skehel et al. Proc Natl Acad Sci USA. 1982; 79:968-972.
149. Skehel et al. Proc Natl Acad Sci USA. 1984; 81:1779-1783.
150. Skehel et al. Annu Rev Biochem. 2000; 69:531-569.
151. Smith et al. Morbidity and mortality weekly report. Recommendations and reports/Centers for Disease Control. 2006; 55:1-42.
152. Stegmann T. Membrane fusion mechanisms: The influenza hemagglutinin paradigm and its implications for intracellular fusion. Traffic. 2000; 1:598-604.
153. Stevens et al. Science. 2004; 303:1866-1870.
154. Subbarao et al. Nature Reviews Immunology. 2007; 7:267-278.
155. Sugrue et al. Virology. 1990; 179:51-56.
156. Sui et al. Nat Struct Mol Biol. 2009; 16:265-273.
157. Suzuki et al. Mol Biol Evol. 2002; 19:501-509.
158. Takeda et al. Proc Natl Acad Sci USA. 2003; 100:14610-14617.
159. Takeuchi et al. J Virol. 1994; 68:911-919.
160. Taubenberger et al. The Pathology of Influenza Virus Infections. 2008 Annual Review of Pathology: Mechanisms of Disease; No. 3.
161. Thompson et al. J Am Med Assoc. 2004; 292:1333-1340.
162. Thompson et al. J Am Med Assoc. 2003; 289:179-186.
163. Tong et al. Proc Natl Acad Sci USA. 2012; 109:4269-4274.
164. Treanor et al. Vaccine. 1998; 16:1756-1760.
165. Trifonov et al. N Engl J Med. 2009; 361:115-119.
166. Vanlandschoot et al. J Gen Virol. 1998; 79 (Pt 7):1781-1791.
167. von Itzstein Nature Reviews Drug Discovery. 2007; 6:967-974.
168. Vreede et al. J Virol. 2004; 78:9568-9572.
169. W.H.O. Report: Bull World Health Organ. 1980; 58:585-591.
170. W.H.O. Influenza (Seasonal) Fact sheet 211. Available at: world-wide-web URL who.int/mediacentre/factsheets/fs211/en/ Accessed Oct. 22, 2010.
171. Waldmann et al. Nat Med. 2003; 9:269-277.
172. Wang et al. PLoS Pathog. 2010; 6:e1000796.
173. Wanitchang et al. Virus Res. 2010; 147:145-148.
174. Webby et al. Lancet. 2004; 363:1099-1103.
175. Webster et al. Microbiol Rev. 1992; 56:152-179.
176. Webster et al. Antigenic and biological characterization of influenza virus neuraminidase (N2) with monoclonal antibodies. Virology. 1984; 135:30-42.
177. Webster et al. Virology. 1988; 164:230-237.
178. Welliver et al. J Am Med Assoc. 2001; 285:748-754.
179. WHO Global Influenza Surveillance Network. Manual for the Laboratory Diagnosis and Virological Surveillance of Influenza; 2011.
180. Wiley et al. Annu Rev Biochem. 1987; 56:365-394.
181. Wiley et al. Nature. 1981; 289:373-378.
182. Wise et al. J Virol. 2009; 83:8021-8031.
183. Wright et al. Fields Virology. Vol 2. Fifth ed. Philadelphia, Pa. 19106 USA: Lippincott Williams & Wilkins; 2007a: 1701.
184. Wright et al. Fields Virology. Vol 2. Fifth ed. Philadelphia, Pa. 19106 USA: Lippincott Williams & Wilkins; 2007b: 1694.
185. Wrigley et al. Virology. 1983; 131:308-314.
186. Ye et al. Clin Vaccine Immunol. 2010; 17:1363-1370.
187. Zhirnov O P. Virology. 1990; 176:274-279.

All publications and patents cited above, including the enclosed Excel spreadsheet (Appendix A) entitled "Results of H1N1 HA Epitope Search," the entire contents of the doctoral dissertation entitled "Rapid development of influenza vaccines with neutralizing monoclonal antibodies" [available on the World-Wide-Web at URL http (://)search (dot)proquest(dot)com/docview/1468453235), identified by the 2013 ABSTRACT (Appendix B); and the entire contents of the Monoclonal Antibody Sequencing Reports (Appendix C), are incorporated herein by reference in their entirety.

What is claimed is:

1. A monoclonal antibody that binds to a discontinuous epitope of hemagglutinin (HA) polypeptide of an influenza A virus, which is expressed by a hybridoma selected from the group consisting of 39-3F2-2A6 (ATCC Patent Deposit Designation PTA-122858, 39-4D12-2D11 (ATCC Patent Deposit Designation PTA-122859) and 56-2G9-1B3 (ATCC Patent Deposit Designation PTA-122860).

2. The antibody of claim 1 which is monoclonal antibody mAb-2A6 expressed by hybridoma 39-3F2-2A6 (ATCC Patent Deposit Designation PTA-122858), which antibody binds to an epitope comprising HA residues 158-172, 183-197, and 253-267 of SEQ ID NO: 95.

3. The antibody of claim 1 which is monoclonal antibody mAb-2D11 expressed by hybridoma 39-4D12-2D11 (ATCC Patent Deposit Designation PTA-122859), which antibody binds to an epitope comprising HA residues 158-172, 208-222 and 253-267 of SEQ ID NO: 95.

4. The antibody of claim 1 which is monoclonal antibody mAb-1B3 expressed by hybridoma 56-2G9-1B3 (ATCC Patent Deposit Designation PTA-122860) which antibody binds to an epitope comprising HA residues 158-172 and 253-267 of SEQ ID NO: 95.

* * * * *